United States Patent
Kennedy et al.

(10) Patent No.: US 12,006,532 B2
(45) Date of Patent: *Jun. 11, 2024

(54) METHODS FOR TARGETED NUCLEIC ACID SEQUENCE ENRICHMENT WITH APPLICATIONS TO ERROR CORRECTED NUCLEIC ACID SEQUENCING

(71) Applicant: UNIVERSITY OF WASHINGTON, Seattle, WA (US)

(72) Inventors: Scott R. Kennedy, Seattle, WA (US); Jesse J. Salk, Seattle, WA (US); Michael Hipp, Seattle, WA (US); Elizabeth Schmidt, Seattle, WA (US); Rosa Ana Risques, Seattle, WA (US); Daniela Nachmanson, Seattle, WA (US)

(73) Assignee: UNIVERSITY OF WASHINGTON, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/933,058

(22) Filed: Sep. 16, 2022

(65) Prior Publication Data

US 2023/0295686 A1 Sep. 21, 2023

Related U.S. Application Data

(63) Continuation of application No. 16/496,936, filed as application No. PCT/US2018/024194 on Mar. 23, 2018, now Pat. No. 11,479,807.

(60) Provisional application No. 62/475,682, filed on Mar. 23, 2017, provisional application No. 62/575,958, filed on Oct. 23, 2017.

(51) Int. Cl.
*C12Q 1/6806* (2018.01)
*C12Q 1/6855* (2018.01)
*C12Q 1/686* (2018.01)

(52) U.S. Cl.
CPC ......... *C12Q 1/6806* (2013.01); *C12Q 1/6855* (2013.01); *C12Q 1/686* (2013.01); *C12Q 2521/501* (2013.01); *C12Q 2525/191* (2013.01); *C12Q 2531/113* (2013.01); *C12Q 2535/119* (2013.01); *C12Q 2535/122* (2013.01)

(58) Field of Classification Search
CPC ........................... C12Q 1/6806; C12Q 1/6855
See application file for complete search history.

(56) References Cited

U.S. PATENT DOCUMENTS

| | | | |
|---|---|---|---|
| 9,752,188 B2 | 9/2017 | Schmitt et al. | |
| 2010/0331204 A1 | 12/2010 | Jeddeloh et al. | |
| 2013/0303461 A1 | 11/2013 | Iafrate et al. | |
| 2015/0044687 A1 | 2/2015 | Schmitt et al. | |
| 2015/0197786 A1 | 7/2015 | Osborne et al. | |
| 2016/0153039 A1 | 6/2016 | Amorese et al. | |
| 2016/0362751 A1 | 12/2016 | Shin et al. | |
| 2017/0107560 A1 | 4/2017 | Peter et al. | |
| 2017/0211140 A1 | 7/2017 | Schmitt et al. | |

FOREIGN PATENT DOCUMENTS

| | | |
|---|---|---|
| GB | 2533882 B | 10/2016 |
| WO | 2011021102 A2 | 2/2011 |
| WO | 2013142389 A1 | 9/2013 |
| WO | 2015100427 A1 | 7/2015 |
| WO | 2015117040 A1 | 8/2015 |
| WO | 2017037656 A1 | 3/2017 |
| WO | 2017100441 A1 | 6/2017 |
| WO | 2018013598 A1 | 1/2018 |
| WO | 2018031588 A1 | 2/2018 |

OTHER PUBLICATIONS

Ahn et al., "Decreased Mitochondrial Mutagenesis during Transformation of Human Breast Stem Cells into Tumorigenic Cells", Cancer Research 76 (15), 4569-4578, Aug. 2016.
Akogwu et al., "A comparative study of k-spectrum-based error correction methods for next-generation sequencing data analysis", Human Genomics, 10-Suppl2(20), 50-59, Jul. 2016.
Bettegowda et al., "Detection of Circulating Tumor DNA in Early- and Late-Stage Human Malignancies. Science Translational Medicine", Feb. 19, 2014:vol. 6, Issue 224, pp. 224ra24 DOI: 10.1126/scitranslmed.3007094.
Chen et al., "DNA damage is a pervasive cause of sequencing errors, directly confounding variant identification", Science, 355, 752-756, Feb. 2017.
EPO, "Examination Report", for European Patent Application No. 18772308.5, Jun. 30, 2021, 4 pages.
EPO, "Extended European Search Report", for European Patent Application No. 18772308.5. Mail Date: Nov. 19, 2020. 7 pages.
Goodwin et al., "Coming of age: ten years of next-generation sequencing technologies", Nature Reviews: Genetics, 17, 333-351, Jun. 2016.
Havens et al., "The technology and clinical applications of hybrid capture NGS", Medical Laboratory Observer, Jul. 2016, 5 pages.
Hiatt et al., "Single molecule molecular inversion probes for targeted, high-accuracy detection of low-frequency variation", Genome Research, 23, 843-854, May 2013.

(Continued)

*Primary Examiner* — Samuel C Woolwine
*Assistant Examiner* — Carolyn L Greene
(74) *Attorney, Agent, or Firm* — Perkins Coie LLP

(57) ABSTRACT

The present technology relates generally to methods and compositions for targeted nucleic acid sequence enrichment, as well as uses of such enrichment for error-corrected nucleic acid sequencing applications. In some embodiments, highly accurate, error corrected and massively parallel sequencing of nucleic acid material is possible using a combination of uniquely labeled strands in a double-stranded nucleic acid complex in such a way that each strand can be informatically related to its complementary strand, but also distinguished from it following sequencing of each strand or an amplified product derived therefrom. In various embodiments, this information can be used for the purpose of error correction of the determined sequence.

22 Claims, 34 Drawing Sheets

Specification includes a Sequence Listing.

(56) References Cited

OTHER PUBLICATIONS

IP Office China, "First Office Action", for Chinese Application No. 201880020286.6, Nov. 2, 2022, 5 pages.

IP Office Japan, "Office Action", for Japanese Application No. 2019-552077, mail date Apr. 25, 2022, 5 pages with English translation.

Jung et al., "The DNA Integrity Number (DIN) Provided by the Genomic DNA ScreenTape Assay Allows for Streamlining of NGS of FFPE Tisue Samples", Application Note Nucleic Acid Analysis, 4 pages, Dec. 2015.

Kebschull et al., "Sources of PCR-induced distortions in high-throughput sequencing data sets", Nucleic Acids Research, 43(21), Jul. 2015, 15 pages.

Kennedy et al., "Detecting ultralow-frequency mutations by Duplex Sequencing", Nature Protocols, 9(11), 2586-2606, Oct. 2014.

Kennedy et al., "Ultra-Sensitive Sequencing Reveals an Age-Related Increase in Somatic Mitochondrial Mutations That are Inconsistent with Oxidative Damage", PLOS Genetics, 9(9), Sep. 2013, 10 pages.

Kinde et al., "Detection and quantification of rare mutations with massively parallel sequencing", PNAS, 108(23), 9350-9535, Jun. 2011.

Krimmel et al., "Ultra-deep sequencing detects ovarian cancer cells in peritoneal fluid and reveals somatic TP53 mutations in noncancerous tissues", PNAS, 113(21), 6005-6010, May 2016.

Li et al., "Fast and accurate long-read alignment with Burrows-Wheeler transform", Bioinformatics, 26 (5), 589-595, Jan. 2010.

Lou et al., "High-throughput DNA sequencing errors are deduced by orders of magnitude using circle sequencing", PNAS, 110(49), 19872-19877, Dec. 2013.

Makarova et al., ""Annotation and Classification of CRISPR-Cas Systems"", Methods Mol Biol. 2015; 1311: 47-75.

Mertes et al., "Targeted enrichment of genomic DNA regions for next-generation sequencing", Briefings in Functional Genomics, 10(6), 374-386, Nov. 2011.

Nachmanson et al., "Targeted genome fragmentation with CRISPR/Cas9 improves hybridization capture, reduces PCR bias, and enables efficient high-accuracy sequencing of small targets", bioRxiv, 207027, Oct. 2017, 38 pages.

Park et al., "Characterization of background noise in capture-based targeted sequencing data", Genome Biology, 18(136), 13 pages, Jul. 2017.

Pecuchet et al., "Analysis of Base-Position Error Rate of Next-Generation Sequencing to Detect Tumor Mutations in Circulating DNA", Clinical Chemistry, 62(11), 1492-1503, Nov. 2016.

Ran et al., "Genome engineering using hte CRISPR-Cas9 system", Nature Protocols, 8(11), 2281-2308, Oct. 2013.

Robinson et al., "Integrative genomics viewer", Nature Biotechnology, 29(1), 24-26, Jan. 2011.

Salk et al., "Enhancing the accuracy of next-generation sequencing for detecting rare and subclonal mutation", Nature Reviews Genetics, 19, pp. 269-285, May 2018.

Schmitt et al., "Detection of ultra-rare mutations by next-generation sequencing", PNAS, 109(36), 14508-14513, Sep. 2012.

Schmitt et al., "Sequencing small genomic targets with high efficiency and extreme accuracy", Nature Methods, 12 (5), 423-425, May 2015.

Schweiger et al., "Genome-Wide Massively Parallel Sequencing of Formaldehyde Fixed- Paraffin Embedded (FFPE) Tumor Tissues for Copy-Number- and Mutation-Analysis", PLoS One, 2009, vol. 4, No. 5, e5548.

Shendure et al., "Next-generation DNA sequencing", Nature Biotechnology, 26 (10), 1135-1145, Oct. 2008.

Shin et al., "CRISPR-Cas9-targeted fragmentation and selective sequencing enable massively parallel microsatellite analysis", Nature Communications, 8:14291, Feb. 2017, 13 pages.

Summerer, "Enabling technologies of genomic-scale sequence enrichment for targeted high-throughput sequencing", Genomics, 94, 363-368, Dec. 2009.

USPTO, "International Search Report and Written Opinion", for PCT/US2018/024194. Mail Date: Jul. 7, 2018. 10 pages.

Winters et al., "Are we fishing or catching? Evaluating the efficiency of bait capture of CODIS fragments", Forensic Science International: Genetics, 29, 61-70, Jul. 2017.

Zheng et al., "Anchored multiplex PCR for targeted next-generation sequencing", Nature Medicine, 20 (12), 1479-1484, Dec. 2014.

EPO, European Search Report for European Application No. 22186070.3, mail date: Dec. 15, 2022. 9 pages.

IP Office Israel, Office Action for Application No. 269431, mail date Dec. 8, 2022, 4 pages.

IP Office China, Second Office Action for Chinese Application No. 201880020286.6, Mail Date Sep. 29, 2023, 6 pages with English summary.

IP Office Australia , "Exam Report No. 1", for Application No. 2018240559, Mail Date: Jan. 31, 2024, 4 pages.

CODIS Genotype
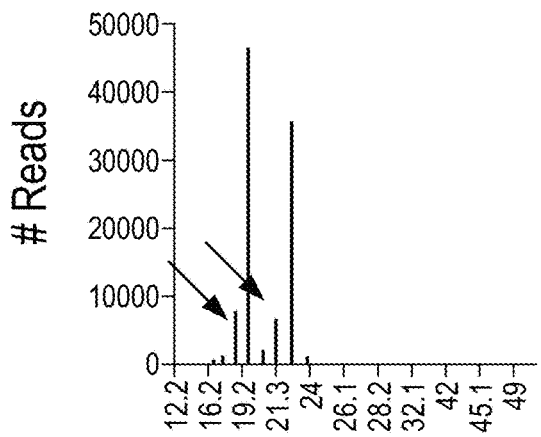
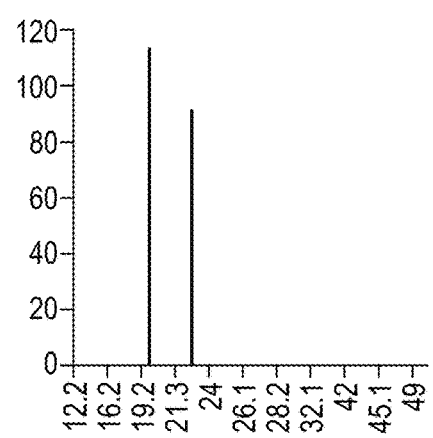
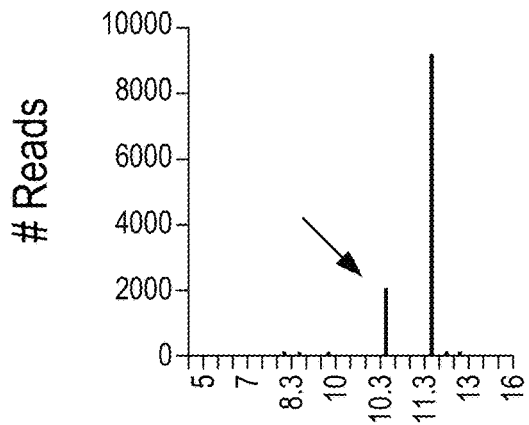
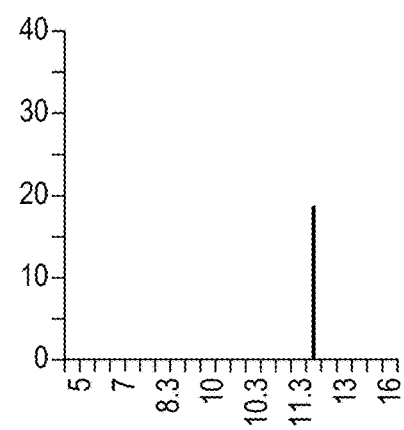
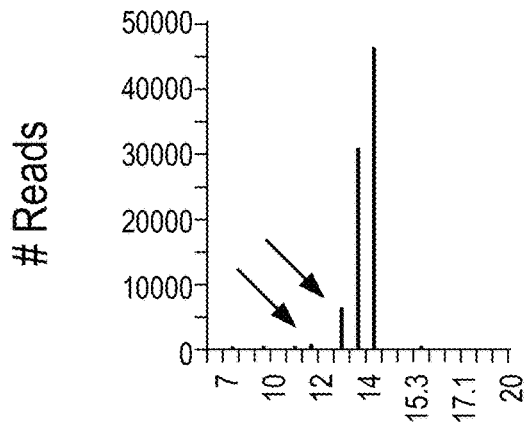
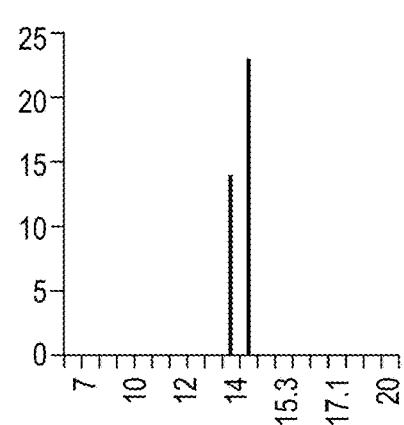
FIG. 3A      FIG. 3B

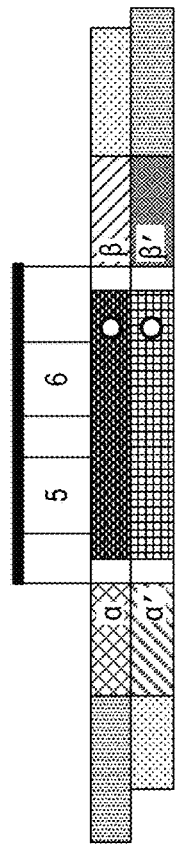
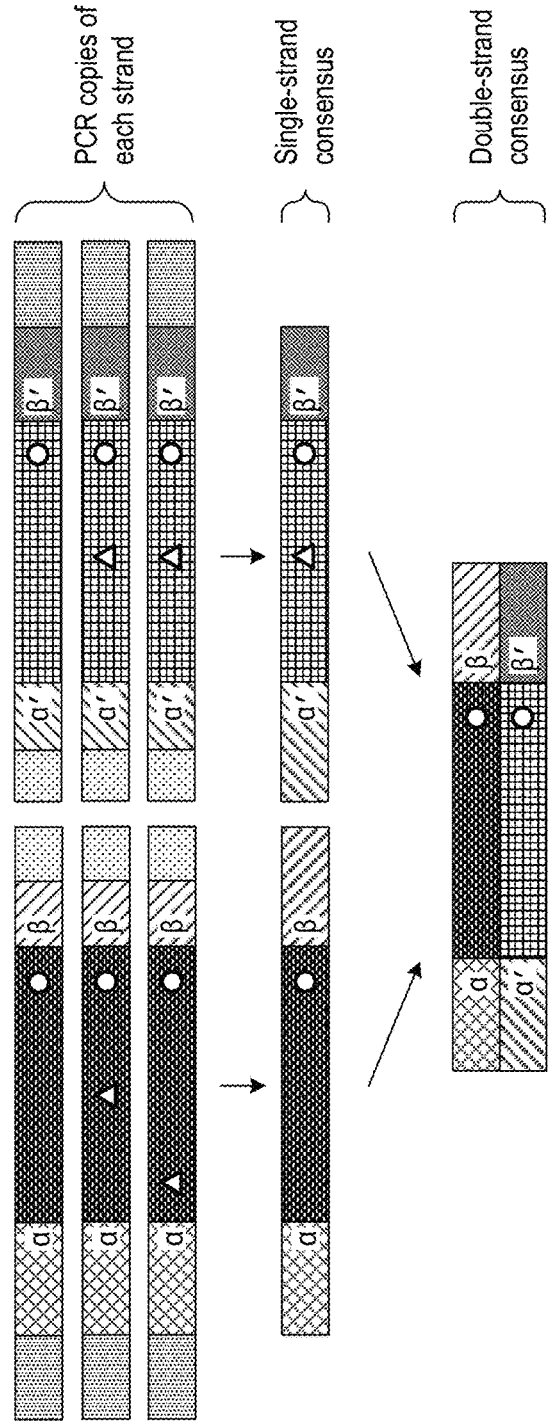
FIG. 12C
FIG. 12D

TP53 tumor protein p53 [ Homo sapiens (human) ]
NC_000017.11 Chromosome 17 Reference GRCh38.p2 Primary Assembly
Positive Strand, exons only (not entire sequence)

Key:
Bold: Coding region. Exon names are indicated in right margin and boxed together when they are cut in the same fragment
Double Underline: Cas9 cut site, PAM sequence are underlined with double line
Underline: Biotinylated probes. Probes name are indicated in left margin ...
```
                    ATACAAGAGATGAAATCCTCCAGGGTGTGGGATGGGGTGAGATTTCCTTTTAGGTACTAAGGTTCACCAAGAGGTTGTCAGA
                    CAGGGTTTGGCTGGGCCAGCAGAGACTTGACAACTCCCTCTACCTAACCAGCTGCCCAACTGTAGAAACTACCAACCCACCG
                    ACCAACAGGGAGAGGGAACAAGCACCCTCAAGGGGGTCAAGTTCTAGACCCCATGTAATAAAAGGTGGTTTCAAGGCCAGAT
                    GTACATTATTTCATTAACCCTCACAATGCACTCTGTGAGGTAGGTGCAAATGCCAGCATTTCACAGATATGGGCCTTGAAGT
                    TAGAGAAAATTCAACAGTGAGGGACAGCTTCCCTGGTTAGTACGGTGAAGTGGGCCCCTACCTAGAATGTGGCTGATTGTAA
                    ACTAACCCTTAACTGCAAGAACATTTCTTACATCTCCCAAACATCCCTCACAGTAAAAACCTTAAAATCTAAGCTGGTATGT
                    CCTACTCCCCATCCTCCTCCCCACAACAAAACACCAGTGCAGGCCAACTTGTTCAGTGGAGCCCCGGGACAAAGCAAATGGA
TP53_e11.A.2        AGTCCTGGGTGCTTCTGACGCACACCTATTGCAAGCAAGGGTTCAAAGACCCAAAACCCAAAATGGCAGGGGAGGGAGAGAT
TP53_e11.A.1        GGGGGTGGGAGGGCTGTCAGTGGGGAACAAGAAGTGGAGAATGTCAGTCTGAGTCAGGCCCTTCTGTCTTGAACATGAGTTTT  ┌────────┐
                    TTATGGCGGGAGGTAGACTGACCCTTTTTGGACTTCAGGTGGCTGTAGGAGACAGAAGCAGGGAGGAGAGATGACATCACAT  │Exon 11 │
                    GAGTGAGAGGGTCTCTGCCCCTTTTCCCTGACCAATGCTTTGAAGGGCCTAAGGCTGGGACAACGGGAATTCAAATCAAGAT  └────────┘
                    GGTGGCCACACCCCATGCAAATATGTTTACTGAGCACCTCAGAGTATTAGTGTGTATTAGTCTCGTAATCTTCCCTTACCCC
                    ATTTTACTTTATTTATCTTTTTTGAGACGGAGTTTCACTCTTGTTGCCCAGGCTGGAGTGTAATGGTGAGATCTCAGCTCAC
                    CGCAACCTCTGCCTCCCGGGTTCAAGCGATTCTCCTGCCTCAGCCTCCCGAGTAGGTAGCTGGGATTACAGGCATGCATCAC
                    CACGCCCGGCTACTTTTGTATTTTTAGTAGAGATGGGGTTTCTCCATGTTGGTCAGGCTGGGCTCAAACTCCCGACCTCAGG
                    TGATCCACTCGCCTTGGCCTCCCAGAGTGTGGGATTCGTGAGCCACCGCCCCCTTACCCCATTTTATATATAAGG
                    AAACTGAGTTTGACGGGGGTCACCTAGGACCTGCCGGTGCATGGCAGGAGTGAGTATATGACCTGAAACTCTGGCTGTATTC
                    AGTATTACACAATTATTAGGCCCCTCCTTGAGACCCTCCAGCTCTGGGCTGGGAGTTGCGGAGAATGGCAAAGAAGTATCCA
                    CACTCGTCCCTGGGTTTGGATGTTCTGTGGATACACTGAGGCAAGAATGTGGTTATAGGATTCAACCGGAGGAAGACTAAAA
                    AAATGTCTGTGCAGGGCTGGGACCCAATGAGATGGGGTCAGCTGCCTTTGACCATGAAGGCAGGATGAGAATGGAATCCTAT
TP53_e10.1_1        GGCTTTCCAACCTAGGAAGGCAGGGGAGTAGGGCCAGGAAGGGGCTGAGGTCACTCACCTGGAGTGAGCCCTGCTCCCCCT  ┌────────┐
TP53_e10.1          GGCTCCTTCCCAGCCTGGGCATCCTTGAGTTCCAAGGCCTCATTCAGCTCTCGGAACATCTCGAAGCGCTCACGCCCACGGA  │Exon 10 │
TP53_e10.1_2        TCTGCAGCAACAGAGGAGGGGGAGAAGTAAGTATATACACAGTACCTGAGTTAAAAGATGGTTCAAGTTACAATTGTTTGAC  └────────┘
                    TTTATGACGGTACAAAAGCAACATGCATTTAGTAGAAACTGCACTTCAAGTACCTATACAGCTGACTTTTAAAAATATTTAT
                    TTATTTATTTTGAGATGGGGTCTCACTCTGTTGCCCAGGCGGGAGTGCAATGGTGCAATCTTGGCTGATTGCAATCTCCGCC
                    TCTGGGGTTCAAGTGATTCTTGTGCCTCAGCCTCCCGAGTAGCTGGGACTACAGGCGTGTGCTACCACACCTGGCTAATTTT
                    TGTGTTTTTAGTAGAGATGGGGCTTCACCATGTTAGCCAGGCTGGTTTCCAACTCCTGACGTCAGGTGATCTACCCACCTCC
                    ACCTCCCAAAGTGCTGGGATTACAGGTGTGAGCCACTGTGCCCGGCCCTTTTTAAATTTTAGAGATGATGTCTTGCTATGT
                    TGTTCAGGCTGGACTCAAACTCTTGGGCTCAAGAGATCCTCCTGCCTTAGCCTCTCAAGTAACTGGGACTACATGTGCATGC
                    GACTGTGCCTCGTTTCTTTTCTTTTTTTCTGAGACGGAGTCTCACTCTATCGCCCAGGCTGGAGTGCAGTGGCGCCATCTT
                    GGCTCCCTGCAACCTCCGCCTCCTGGTTCAAGCGATTCTCCTGCCTCAGCCTCCCAAGTAGCTGGGATTACAGGCACCTGCC
                    ATCACGCCCGGTTAATTTTTGTATTTTTAGTAGAGACGGGGTTTCACCATGTTGGCTAGGCTGGTCTTGAACTCCTGACCTCA
                    GGTGATCCACCCGCCTCAGCCTCCCGAAATGCTGGGATTACAGGCGTGAGCCAGTGCGCCTGGCCTTTTCTTTTTTTGAGTC
                    TCGCTCTGCGCCCAGGCTGTGCCTGGCTCGACTGTGCCTCCTTTCATGCAACCATGCTGTTTCTCACTTTCAGTAACAATAT
                    TCAATAAATCACATGAGATATACAACATTTTATTACTATAAAAAGGGCTTTGTGTTAGATGACTTTGCCCAACTGTAGGGTA
                    ACTTAAATGCTCTGAACACGTTTCAAGTAGGCTAGGGCTGAGTGTGGTAGCTCATGCCTGTAACCCCAATACTTGGGGAGGC
                    TGAGGTGGAAGGATTGATTGAGCCCAGGGGTTTGATACCAGCATGGGCAACGTAGCAAGACCTTGACTTCACAGAAAATAAA
                    AAATTAGCTGGGTGTCGTGGCATGTGCCTGTAGTCCTAGCTACTTGGGAGGGTGAAATCACCGGGAGCCAGGGAGGTCAAGG
                    CTGCAGTGAGCTGAGATGTGCCACTGCACTCTAGCCTGAGTGACAGAGTGAGACTCTGTCTTTAAATAAATAAATAAAAAT
                    TAGCCGGGCGTGGTGGCTCACACCTGTAATCCCAGCACTTTGGGAGGCCGAGGCGGGCGGATCACATGGTCAGAAGTTCGAG
                    ACCAGCCTGGCCAACATGGTGAAACCCTGTCTCTACTAAAAATACAAAAATTAGCTGGGCGTGGTAGCAGGCGCTTGTAGTC
                    CTAGCTATTCGGGAGGCTGAGGCAGGAGAATCACTTGAACCCAGGAGGCAGAGGTTGCAGTGAGCCGAGATCATGCCACTGC
                    ACTCCAGCCTGGGCGACAGAGTGAGACTGAGTCTCAAAAAATAAAATAAAATAAAAATAAATAAATAAAAATTAGC
                    CAGGCATGGTGGTGCAGGCCTGTAGTTGAAGCAACTTGGGAGGCTGAGCTGGGAGGATGGATGGAGCCTGGGAGGTGGAGGC
                    TGCAGTGAGCTGTGACTGCACTACTGCACTCTATCCAGCCTGGGTGACAGAGCAAGACCTTGTCTCAAAAAAGTAGGCTAGA
                    GACCAGCCTGGGCAACATAGTGAGACTCTATCTATCTACAAAAAATTTTAAAAATTAGCTGGGTATGGTGGTGTATGCCTGT
                    GGTCCTAGCTACTGGGGAGGCAGAGTTAGGGGGATTGCTTGAGCCCAGGAGGGTATAATGAGCTATGATCACATCACTGTAA
                    TCCAGCCTGGGCAACAGAGCAAGATGCTGTCTCCATTAAAAATAAAATAAAAGTAGGCTAGGCAGGCCGGGTGCGGTGGCTC
                    ACGCCTGTAATCCCAGCACTTTGGGAGGCCAAGGCAGGCAGATCACAAGGTCAGGAGTTCGAGACTAGCCTGGCCAACATGG
                    TGAAACCTCATCTCTACTAAAAAAAAATAAATAACAAAAATTAGCTGGGCGTGGGGCAGGTGCCTGTAATCCCA
                    GCTACTCAGTGGGCTGAGGCAGGAGAATCGCTTGAACCCAGAAGGCGGAGGTTGCAGTGAGCCGAGATCCGCCACTGCACT
                    CCAGCCTGGGTGACAGAGTGAGACTCTGTCTCAAAAAAAAAAAAAAAAAGCAGGCTAGGCTAAGCTATGATGTTCCTTA
                    GATTAGGTGTATTAAATCCATTTTCAACTTACAATATTTTCAACTTACGACGAGTTTATCAGGAAGTAACACCATCGTAAGT
```

FIG. 17A
(SEQ ID NO: 3)

TP53 tumor protein p53 [ Homo sapiens (human) ]
NC_000017.11 Chromosome 17 Reference GRCh38.p2 Primary Assembly
Positive Strand, exons only (not entire sequence)

```
              CAAGTAGCATCTGTATCAGGCAAAGTCATAGAACCATTTTCATGCTCTCTTTAACAATTTTCTTTTTGAAAGCTGGTCTGGT
              CCTTTAAAATATATATTATGGTATAAGTTGGTGTTCTGAAGTTAGTTAGCTACAACCAGGAGCCATTGTCTTTGAGGCATCA
              CTGCCCCTGATGGCAAATGCCCCAATTGCAGGTAAAACAGTCAAGAAGAAAACGGCATTTTGAGTGTTAGACTGGAAACTT
              TCCACTTGATAAGAGGTCCCAAGACTTAGTACCTGAAGGGTGAAATATTCTCCATCCAGTGGTTTCTTCTTTGGCTGGGGAG      Exon 9
TP53_e7.2     AGGAGCTGGTGTTGTTGGGCAGTGCTAGGAAAGAGGCAAGGAAAGGTGATAAAAGTGAATCTGAGGCATAACTGCACCCTTG
TP53_e7.1     GTCTCCTCCACCGCTTCTTGTCCTGCTTGCTTACCTCGCTTAGTGCTCCCTGGGGGCAGCTCGTGGTGAGGCTCCCCTTTCT    Exon 8
              TGCGGAGATTCTCTTCCTCTGTGCGCCGGTCTCTCCCAGGACAGGCACAAACACGCACCTCAAAGCTGTTCCGTCCCAGTAG
              ATTACCACTACTCAGGATAGGAAAGAGAAGCAAGAGGCAGTAAGGAAATCAGGTCCTACCTGTCCCATTTAAAAAACCAGG
              CTCCATCTACTCCCAACCACCCTTGTCCTTTCTGGAGCCTAAGCTCCAGCTCCAGGTAGGTGGAGGAGAAGCCACAGGTTAA
TP53_e6.2     GAGGTCCCAAAGCCAGAGAAAAGAAAACTGAGTGGGAGCAGTAAGGAGATTCCCCGCCGGGGATGTGATGAGAGGTGGATGG
              GTAGTAGTATGGAAGAAATCGGTAAGAGGTGGGCCCAGGGGTCAGAGGCAAGCAGAGGCTGGGGCACAGCAGGCCAGTGTGC     Exon 7
              AGGGTGGCAAGTGGCTCCTGACCTGGAGTCTTCCAGTGTGATGATGGTGAGGATGGGCCTCCGGTTCATGCCGCCCATGCAG
TP53_e6.1     GAACTGTTACACATGTAGTTGTAGTGGATGGTGGTACAGTCAGAGCCAACCTAGGAGTAACACAGGCCCAAGATGAGGCCA
              GTGCGCCTTGGGGAGACCTGTGGCAAGCAGGGGAGGCCTTTTTTTTTTTTTTGAGATGGAATCTCGCTCTGTCGCCCAGG
              CTGGAGTGCAGTGGCGTGATCTCAGCTCACTGCAAGCTCCACCGCCCAGGTTCACGCGCATTCTCCTTCCTCAGCCTCCCGAG
              TAGCTGGGACTACAGGTGCCCAGCACCACGCCCGGCTAATTTTTTTTTGTATTTTTCAGTAGAGACGGGGTTTCACCGTTAG
              CCAGGATGGTCTCGATCTCCCAACCTCGTGATCCGCCTGCCTTGGCCTCCCAAAGTGCTGGGATTACAGGCATGAGCCACTG
              CGCCCAGCCAAGCAGGGGAGGCCCTTAGCCTCTGTAAGCTTCAGTTTTTTCAACTGTGCAATAGTTAAACCCATTTACTTTG
TP53_e5.1_1   CACATCTCATGGGGTTATAGGGAGGTCAAATAAGCAGCAGGAGAAAGCCCCCCTACTGCTCACCTGGAGGGCCACTGACAAC
TP53_e5.1     CACCCTTAACCCCTCCTCCCAGAGACCCCAGTTGCAAACCAGACCTCAGGCGGCTCATAGGGCACCACCACACTATGTCGAA    Exon 6
              AAGTGTTTCTGTCATCCAAATACTCCACACGCAAATTTCCTTCCACTCGGATAAGATGCTGAGGAGGGGCCAGACCTAAGAG
TP53_e4.3_1   CAATCAGTGAGGAATCAGAGGCCTGGGGACCCTGGGCAACCAGCCCTGTCGTCTCTCCAGCCCAGCTGCTCACCATCGCTA   Exon 5
TP53_e4.3     TCTGAGCAGCGCTCATGGTGGGGGCAGCGCCTCACAGCCTCCGTCATGTGCTGTGACTGCTTGTAGATGGCCATGGCGCGGA
TP53_e4.2     CGCGGGTGCCGGGCGGGGTGTGGAATCAACCCAGCAGGCAGGTCTTGGCCAGTTGGCAAAACATCTTGTTGAG
              GGCAGGGGAGTACTGTAGGAAGAGGAAGGAGACAGAGTTGAAAGTCAGGGCACAAGTGAACAGATAAAGCAACTGGAAGACG
              GCAGCAAAGAAACAAACATGCGTAAGCACCTCCTGCAACCCACTAGCGAGCTAGAGAGAGTTGGCGTCTACACCTCAGGAGC
              TTTTCTTTTTTTTTTTTTTTTGAGATAGGGTCTTGCTCTGTCACTCAGGCTGGAGCACAGTGGTGTGATCACAGCTCACT
              GCAGCCTCCATCTCCTGGCCTCAAGTGATCTTCCCACCTCAGCCTCCTAAGTGGCTGGGACTATAGGTGTGCACCACCATGC
              CTGGCTAATTTTTTGTATTTTTTGTAGAGACGAGGTTTCATCATGTTACCCAGGCTGGTCTTGAACTCCTGGGCTCAGGTG
              ATCTGCCTGCCTTGGCCTCTTTGAGAGTGCTGGGATTGCAGGTGTGAGCCACCAAGCCTGGTCAGGAGCTTATTTTCAAAAG
              CCAAGGAATACACGTGGATGAAGAAAAAGAAAAGTTCTGCATCCCAGGAGAGATGCTGAGGGTGTGATGGGATGGATAAAA
              GCCCAAATTCAAGGGGGGAATATTCAACTTTGGGACAGGAGTCAGAGATCACACATTAAGTGGGTAAACTATAAAAAACAC
TP53_e3.3     TGACAGGAAGCCAAAGGGTGAAGAGGAATCCCAAAGTTCCAAACAAAAGAAATGCAGGGGATACGGCAGGCATTGAAGTC
              TCATGGAAGCCAGCCCCTCAGGGCAACTCAGGCTGCAAGTGCAACATTTGGCTGTCCCAGAATGCAAGAAGCCCAGACGGAA
TP53_e3.2     ACCGTAGCTGCCCTGGTAGGTTTTCTGGGAAGGGACAGAAGATGACAGGGGCCAGGAGGGGCTGGTCAGGGGCCGCCGGT    Exon 4
TP53_e3.1     GTAGGAGCTGCTGGTGCAGGGGCCACGGGGGAGCAGCCTCTGGCATTCTGGGAGCTTCATCTGGACCTGGGTCTTCAGTGA
TP53_e2.3     ACCATTGTTCAATATCGTCCGGGGACAGCATCAAATCATCCATTGCTTGGGACGGCAAGGGGGACTGTAGATGGGTGAAAAG   Exon 3
              AGCAGTCAGAGGACCAGGTCCTCAGCCCCCCAGCCCCCAGCCCTCCAGGTCCCAGCCCTCCAGGTCCCCAGCCCAACCCT
              TGTCCTTACCAGAACGTTGTTTTCAGGAAGTCTGAAAGACAAGAGCAGAAAGTCAGTCCCATGGAATTTTCGGCTTCCCACAG   Exon 2
TP53_e2.2     GTCTCTGCTAGGGGGCTGGGGTTGGGTGGGGGGTGGGCCTGCCCTTCCAATGGATCCACTCACAGTTTCCATAGGTCTG
TP53_e2.1     AAAATGTTTCCTGACTCAGAGGGGGCTCGACGCTAGGATCTGACTGCGGCTCCTCCATGGCAGTGACCCGGAAGGCAGTCTG
              GCTGCTGCAAGAGGAAAAGTGGGGATCCAGCATGAGACACTTCCAACCCTGGGTCACCTGGGCCTGCAGAGAAGGAACCCCC
              TCCCCCAACACCATGCCAGTGTCTGAGACAGCTCGGCTTCCTGTGGAGCAGGAAAAGAATGGCTGCTTCACATTCTCTCTT
              CAATGTTTCACCACAACCCAAGCACTCCTGCCCCACCCCTCACCAGCCATGCACTTCTTTGAGGAAAAGACAATCAGAGAGG
              GACTTCCAAACCTCCCACACTAAATCCCCAAGACTTCCTAAATGTGCACCCTATTCCCATCCCTTCCTGTATTTTTTTT
              TTTTTTGAGATGGAGTCTCTCTCTGTCACCTAGGCTGGAGCAGGTGGCACGATCTCAGCTCACTGCAACCTCTACCTTC
              CGGGTTCAAGCCATTCTCCTGCCTCAGTCTCCCGAGTAGCTGGGATTACAGGCGAGTACCACCACACCCAGCTAATTTTTGT
              ATTTTTAGTAGAGACAGGGCTTTGCATGTTGGCCAGGCTGGTCTCGAACTCCTTACTTCAGGTGATCGGCCCGCCTCAGCCT
              CCTAAAGTGCCAAGATTACAGGTGTGAGCTACCGTGCCCTGCTCCCACCTCCTGTTAACAAGGATATAGTCATTCTCAGCCT
              GCAATCTCTGTATGGGAAGGACACCCCCTTGGCCCCCACCCTTCCCCACCTGATACACGGCTCCATTTCTTTGATTCCTTT
              CACTGCAAAGCTTCTGGAAGAACAACTGTCTCACCGCTCACCTGCCCATTCTCTTCGGACACTCCTCAGCCCTGCATTACAA
              ACCCCTCACGAATGGCCCGTCTCGGCTTCTTTAATCTCATCTCTTAACAACCACTCCCTCTTCCCAAAAGCTCTAGCTAGA
              CTGGCTGCCCTTCTCTGCTAATCAACTGGTGGTTCCTTGGCTAGCCAGGAACATGGGGGTAGGCTCCTCCCGTGCAGACTT
              ...
```

FIG. 17B
(SEQ ID NO: 3 continued)

gRNA
Target
TP53
Exon: 11-US 11-DS 10-US 10-DS 9/8-US 9/8-DS 7-DS 5/6-US 5/6-DS 4/3-US 4/3-DS 2-DS
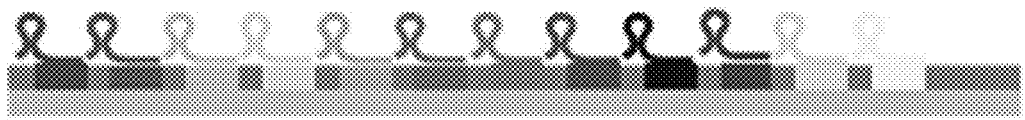
SYNTHETIC DNA WITH TP53 gRNA SEQUENCES
FIG. 21A
| TP53 guide RNA | TP53 Exon(s) Targeted | Left Fragment (bp) | Right Fragment (bp) |
|---|---|---|---|
| TP5e11_US | 11 | 24 | 476 |
| TP5e11_DS | 11 | 64 | 436 |
| TP5e10_US | 10 | 104 | 396 |
| TP5e10_DS | 10 | 144 | 356 |
| TP5e9-8_US | 9,8 | 184 | 316 |
| TP5e9-8_DS | 9,8 | 224 | 276 |
| TP5e7_DS.v2 | 7 | 264 | 236 |
| TP5e6-5_US | 5,6 | 304 | 196 |
| TP5e6-5_DS | 5,6 | 344 | 156 |
| TP5e4-3_US.v2 | 4,3 | 384 | 116 |
| TP5e4-3_DS | 4,3 | 424 | 76 |
| TP5e2_DS | 2 | 464 | 36 |
FIG. 21B
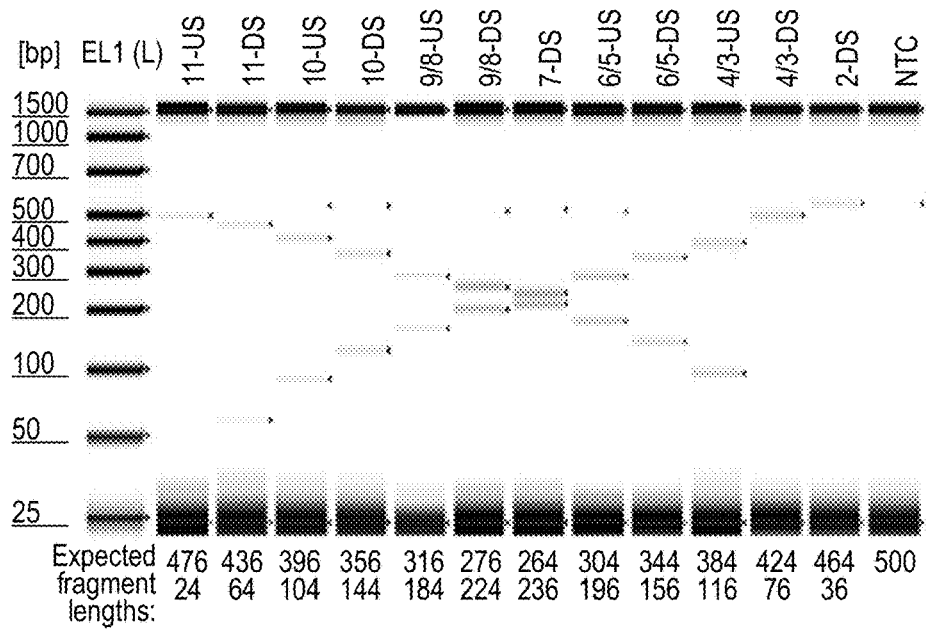
FIG. 21C

| Sample | DNA input (ng) | % Reads On Target After Size Selection | Enrichment After Size Selection |
|---|---|---|---|
| B9 | 25 | 0.76% | 7,527 |
| B9 | 100 | 0.25% | 2,452 |
| B9 | 250 | 0.21% | 2,037 |
| PF1 | 10 | 2.85% | 28,139 |
| PF1 | 25 | 1.99% | 19,583 |
| PF1 | 100 | 0.68% | 6,667 |
| PF1 | 250 | 0.70% | 6,878 |
| PF5 | 10 | 5.05% | 49,794 |
| PF5 | 25 | 0.96% | 9,456 |
| PF5 | 100 | 0.34% | 3,321 |
| PF5 | 250 | 0.22% | 2,217 |

SEQUENCE LISTING

```
Sequence total quantity: 50
SEQ ID NO: 1           moltype =    length =
SEQUENCE: 1
000

SEQ ID NO: 2           moltype =    length =
SEQUENCE: 2
000

SEQ ID NO: 3           moltype = DNA  length = 8692
FEATURE                Location/Qualifiers
misc_feature           1..8692
                       note = TP53 - tumor protein p53
source                 1..8692
                       mol_type = genomic DNA
                       organism = Homo sapiens
SEQUENCE: 3
atacaagaga tgaaatcctc cagggtgtgg gatggggtga gatttccttt taggtactaa    60
ggttcaccaa gaggttgtca gacagggttt ggctgggcca gcagagactt gacaactccc   120
tctacctaac cagctgccca actgtagaaa ctaccaaccc accgaccaac agggagaggg   180
aacaagcacc ctcaagggggg tcaagttcta gaccccatgt aataaaaggt ggtttcaagg   240
ccagatgtac attatttcat taaccctcac aatgcactct gtgaggtagg tgcaaatgcc   300
agcatttcac agatatgggc cttgaagtta gagaaaattc aacagtgagg gacagcttcc   360
ctggttagta cggtgaagtg ggcccctacc tagaatgtgg ctgattgtaa actaaccctt   420
aactgcaaga acatttctta catctcccaa acatccctca cagtaaaaac cttaaaatct   480
aagctggtat gtcctactcc ccatcctcct ccccacaaca aaacaccagt gcaggccaac   540
ttgttcagtg gagcccccggg acaaagcaaa tggaagtcct gggtgcttct gacgcacacc   600
tattgcaagc aagggttcaa agacccaaaa cccaaaatgg caggggaggg agagatgggg   660
gtgggaggct gtcagtgggg aacaagaagt ggagaatgtc agtctgagtc aggcccttct   720
gtcttgaaca tgagtttttt atggcgggag gtagactgac ccttttttgga cttcaggtgg   780
ctgtaggaga cagaagcagg gaggagagat gacatcacat gagtgagagg gtctgtgccc   840
cttttccctg accaatgctt tgaagggcct aaggctggga caacgggaat tcaaatcaag   900
atggtggcca caccccatgc aaatatgttt actgagcacc tcagagtatt agtgtgtatt   960
agtctcgtaa tcttcccctta ccccattttta ctttattttat cttttttgag acggagttc   1020
actcttgttg cccaggctgg agtgtaatgg tgagatctca gctcaccgca acctctgcct   1080
cccgggttca agcgattctc ctgcctcagc ctcccgagta ggtagctggg attacaggca   1140
tgcatcacca cgcccggcta cttttgtatt tttagtagag atgggggttc tccatgttgg   1200
tcaggctggg ctcaaactcc cgacctcagg tgatccactc gccttggcct cccagagtgt   1260
gggattcgtg agccactgcg cccggccccc ttaccccatt ttatatataa ggaaactgag   1320
tttgacgggg gtcacctagg acctgccggt gcatggcagg gctgagtata tgacctgaaa   1380
ctctggctgt attcagtatt acacaattat taggcccctc cttgagaccc tccagctctg   1440
ggctgggagt tgcggagaat ggcaaagaag tatccacact cgtccctggg tttggatgtt   1500
```

```
ctgtggatac actgaggcaa gaatgtggtt ataggattca accggaggaa gactaaaaaa    1560
atgtctgtgc agggctggga cccaatgaga tggggtcagc tgcctttgac catgaaggca    1620
ggatgagaat ggaatcctat ggcttttccaa cctaggaagg caggggagta gggccaggaa    1680
ggggctgagg tcactcacct ggagtgagcc ctgctccccc ctggctcctt cccagcctgg    1740
gcatccttga gttccaaggc ctcattcagc tctcggaaca tctcgaagcg ctcacgccca    1800
cggatctgca gcaacagagg aggggagaa gtaagtatat acacagtacc tgagttaaaa    1860
gatggttcaa gttacaattg tttgacttta tgacggtaca aaagcaacat gcatttagta    1920
gaaactgcac ttcaagtacc tatacagctg acttttaaaa atatttattt atttattttg    1980
agatggggtc tcactctgtt gcccaggcgg gagtgcaatg gtgcaatctt ggctgattgc    2040
aatctccgcc tctggggttc aagtgattct tgtgcctcag cctcccgagt agctgggact    2100
acaggcgtgt gctaccacac ctggctaatt tttgtgtttt tagtagagat ggggcttcac    2160
catgttagcc aggctggttt ccaactcctg acgtcaggtg atctacccac ctccacctcc    2220
caaagtgctg ggattacagg tgtgagccac tgtgcccggc cctttttaa attttagaga    2280
tgatgtcttg ctatgttgtt caggctggac tcaaactctt gggctcaaga gatcctcctg    2340
ccttagcctc tcaagtaact gggactacat gtgcatgcga ctgtgcctcg tttcttttct    2400
tttttttctg agacggagtc tcactctatc gcccaggctg gagtgcagtg gcgccatctt    2460
ggctccctgc aacctccgcc tcctggttca agcgattctc ctgcctcagc ctcccaagta    2520
gctgggatta caggcacctg ccatcacgcc cggttaattt ttgtatttta gtagagacgg    2580
ggtttcacca tgttggctag gctggtcttg aactcctgac ctcaggtgat ccacccgcct    2640
cagcctcccg aaatgctggg attacaggcg tgagccagtg cgcctggcct tttctttttt    2700
tgagtctcgc tctgcgccca ggctgtgcct ggctcgactg tgcctccttt catgcaacca    2760
tgctgtttct cactttcagt aacaatattc aataaatcac atgagatata caacattta    2820
ttactataaa aagggctttg tgttagatga ctttgcccaa ctgtagggta acttaaatgc    2880
tctgaacacg tttcaagtag gctagggctg agtgtggtag ctcatgcctg taaccccaat    2940
acttggggag gctgaggtgg aaggattgat tgagcccagg gtttgatac cagcatgggc    3000
aacgtagcaa gaccttgact tcacagaaaa taaaaaatta gctgggtgtc gtggcatgtg    3060
cctgtagtcc tagctacttg ggagggtgaa atcaccggag cccagggagg tcaaggctgc    3120
agtgagctga gatggtgcca ctgcactcta gcctgagtga cagagtgaga ctctgtcttt    3180
aaataaataa ataaaaatta gccgggcgtg gtggctcaca cctgtaatcc cagcactttg    3240
ggaggccgag gcgggcggat cacatggtca gaagttcgag accagcctgg ccaacatggt    3300
gaaaccctgt ctctactaaa aatacaaaaa ttagctgggc gtggtagcag gcgcttgtag    3360
tcctagctat tcgggaggct gaggcaggag aatcacttga acccaggagg cagaggttgc    3420
agtgagccga gatcatgcca ctgcactcca gcctgggcga cagagtgaga ctgagtctca    3480
aaaaaataaa ataaaataaa ataaaaataa ataaataaaa attagccagg catggtggtg    3540
caggcctgta gttaagcaa cttgggaggc tgagctggga ggatggatgg agcctgggag    3600
gtggaggctg cagtgagctg tgactgcact actgcactct atccagcctg ggtgacagag    3660
caagaccttg tctcaaaaaa gtaggctaga accagcctg gcaacatag tgagactcta    3720
tctatctaca aaaattttta aaattagct gggtatggtg gtgtatgcct gtggtcctag    3780
ctactgggga ggcagagtta ggggattgc ttgagcccag gagggtataa tgagctatga    3840
tcacatcact gtaatccagc ctgggcaaca gagcaagatg ctgtctccat taaaaataaa    3900
ataaaagtag gctaggcagg ccgggtgcgg tggctcacgc ctgtaatccc agcactttgg    3960
gaggccaagg caggcagatc acaaggtcag gagttcgaga ctagcctggc caacatggtg    4020
aaaacctcatc tctactaaaa aaaaaaataa ataaataaca aaaaattagc tgggcgtgga    4080
ggcaggtgcc tgtaatccca gctactcagt gggctgaggc aggagaatcg cttgaaccca    4140
gaaggcggag gttgcagtga gccgagatcc cgccactgca ctccagcctg ggtgacagag    4200
tgagactctg tctccaaaaa aaaaaaaaaa aaagcaggc taggctaagc tatgatgttc    4260
cttagattag gtgtattaaa tccatttttca acttacaata ttttcaactt acgacgagtt    4320
tatcaggaag taacaccatc gtaagtcaag tagcatctgt atcaggcaaa gtcatagaac    4380
cattttcatg ctctctttaa caattttctt tttgaaagct ggtctggtcc tttaaaaatat    4440
atattatggt ataagttggt gttctgaagt tagttagcta caaccaggag ccattgtctt    4500
tgaggcatca ctgcccctg atggcaaatg cccccaattgc aggtaaaaca gtcaagaaga    4560
aaacggcatt ttgagtgtta gactggaaac tttccacttg ataagaggtc ccaagactta    4620
gtacctgaag ggtgaaatat tctccatcca gtggtttctt ctttggctgg ggagaggagc    4680
tggtgttgtt gggcagtgct aggaaagagg caaggaaagg tgataaaagt gaatctgagg    4740
cataactgca cccttggtct cctccaccgc ttcttgtcct gcttgcttac ctcgcttagt    4800
gctccctggg ggcagctcgt ggtgaggctc ccctttcttg cggagattct cttcctctgt    4860
gcgccggtct ctcccaggac aggcacaaac acgcacctca aagctgttcc gtcccagtag    4920
attaccacta ctcaggatag gaaaagaaa gcaagaggca gtaaggaaat caggtcctac    4980
ctgtcccatt taaaaaacca ggctccatct actcccaacc acccttgtcc tttctggagc    5040
ctaagctcca gctccaggta ggtggaggag aagccacagg ttaaggagtc ccaaagccag    5100
agaaaagaaa actgagtggg agcagtaagg agattccccg ccggggatgt gatgagaggt    5160
ggatgggtag tagtatggaa gaaatcggta agaggtgggc caggggtca gaggcaagca    5220
gaggctgggg cacagcaggc cagtgtgcag ggtggcaagt ggctcctgac ctggagtctt    5280
ccagtgtgat gatggtgagg atgggcctcc ggttcatgc gcccatgcag gaactgttac    5340
acatagtagtt gtagtggatg gtggtacagt cagagccaac ctaggagata acacaggccc    5400
aagatgaggc cagtgcgcct tggggagacc tgtggcaagc aggggaggcc ttttttttt    5460
ttttttgaga tggaatctcg ctctgtcgcc caggctggag tgcagtggcg tgatctcagc    5520
tcactgcaag ctccaccgcc caggttcacg ccattctcct tcctcagcct cccgagtagc    5580
tgggactaca ggtgcccagc accacgcccg gctaattttt ttttgtattt tcagtagag    5640
acggggtttc accgttagcc aggatggtct cgatctccca acctcgtgat ccgcctgcct    5700
tggcctccca aagtgctggg attacaggca tgagccactg cgcccagcca agcagggag    5760
gcccttagcc tctgtaagct tcagtttttt caactgtgca atagttaaac ccatttactt    5820
tgcacatctc atgggttat agggaggtca aataagcagc aggagaaagc cccctactg    5880
ctcacctgga gggccactga caaccaccct taacccctcc tcccagaca cccagttgca    5940
aaccagacct caggcggctc atagggcacc accacactat gtcgaaaagt gtttctgtca    6000
tccaaatact ccacacgcaa atttccttcc actcggataa gatgctgagg aggggccaga    6060
cctaagcaga atcagtgagg aatcagaggc ctggggaccc tggcaacca gccctgtcgt    6120
ctctccagcc ccagctgctc accatcgcta tctgagcagc gctcatggtg ggggcagcgc    6180
ctcacaacct ccgtcatgtg ctgtgactgc ttgtagatgg ccatgcgcgc gacgcgggtg    6240
```

-continued

```
ccgggcgggg gtgtggaatc aacccacagc tgcacagggc aggtcttggc cagttggcaa    6300
aacatcttgt tgagggcagg ggagtactgt aggaagagga aggagacaga gttgaaagtc    6360
agggcacaag tgaacagata aagcaactgg aagacggcag caaagaaaca aacatgcgta    6420
agcacctcct gcaacccact agcgagctag agagagttgg cgtctacacc tcaggagctt    6480
ttcttttttt tttttttttt tgagataggg tcttgctctg tcactcaggc tggagcacag    6540
tggtgtgatc acagctcact gcagcctcca tctcctggcc tcaagtgatc ttcccacctc    6600
agcctcctaa gtggctggga ctataggtgt gcaccaccat gcctggctaa ttttttgtat    6660
tttttgtag agacgaggtt tcatcatgtt acccaggctg tcttgaact cctgggctca    6720
ggtgatctgc ctgccttggc ctctttgaga gtgctgggat tgcaggtgtg agccaccaag    6780
cctggtcagg agcttatttt caaaagcaa ggaatacacg tggatgaaga aaaagaaaag    6840
ttctgcatcc ccaggagaga tgctgagggt gtgatgggat ggataaaagc ccaaattcaa    6900
gggggaata ttcaactttg gacaggagt cagagatcac acattaagtg ggtaaactat    6960
aaaaaaacac tgacaggaag ccaaagggtg aagaggaatc ccaagttcc aaacaaaaga    7020
aatgcagggg gatacggcca ggcattgaag tctcatgaa gccagcccct cagggcaact    7080
gaccgtgcaa gtcacagact tggctgtccc agaatgcaag aagcccagac ggaaaccgta    7140
gctgccctgg taggttttct gggaagggac agaagatgac aggggccagg aggggggctgg   7200
tgcaggggcc gccggtgtag gagctgctgg tgcaggggcc acggggggag cagcctctgg    7260
cattctgagga gcttcatctg gacctgggtc ttcagtgaac cattgttcaa tatcgtccgg    7320
ggacagcatc aaatcatcca ttgcttggga cggcaagggg gactgtagat gggtgaaaag    7380
agcagtcaga ggaccaggtc ctcagccccc cagcccccca gccctccagg tccccagccc    7440
tccaggtccc cagccccaacc cttgtcctta ccagaacgtt gttttcagga agtctgaaag    7500
acaagagcag aaagtcagtc ccatggaatt ttcgcttccc acaggtctct gctaggggc    7560
tggggttggg gtggggtgg tgggcctgcc cttccaatgg atccactcac agttccata     7620
ggtctgaaaa tgtttcctga ctcagagggg gctcgacgct aggatctgac tcggctcct    7680
ccatggcagt gacccggaag gcagtctggc tgctgcaaga ggaaaagtgg ggatccagca    7740
tgagacactt ccaaccctgg gtcacctggg cctgcagaga aggaaccccc tcccccaaca    7800
ccatgccagt gtctgagaca gctcggcttc ctgtggagca ggaaaagaat ggctgcttca    7860
cattctctct tccaatgttt caccacaacc caagcactcc tgccccaccc ctcaccagcc    7920
atgcacttct tgaggaaaa acaatcaga gagggactc caaccttccc accactaaat       7980
ccccaagact tcctaaatgt gcaccctatt cccaactccc ttcctgtatt ttttttttt    8040
tttttgagatg gagtctctct ctgtcaccta ggctggagca cagtggcatg atctcagctc   8100
actgcaacct ctaccttccg ggttcaagcc attctcctgc ctcagtctcc cgagtagctg    8160
ggattacagg cgagtaccac cacacccagc taattttttg attttttagta gagacagggc    8220
tttgcatgtt ggccaggctg gtctcgaact ccttacttca ggtgatcggc ccgcctcagc    8280
ctcctaaagt gccaagatta caggtgtgag ctaccgtgcc tgctcccac tcctctgttaa    8340
caaggatata gtcattctca gcctgcaatc tctgtatggg gaaggacacc cccttggccc    8400
ccaccccttcc ccacctgata cacggctcca tttctttgat tcctttcact gcaaagcttc    8460
tggaagaaca actgtctcac cgctcacctg cccattctct tcggacactc ctcagccctg    8520
cattacaaac ccctcacgaa tggcccgtct cggcttcttt aatctcatct cttaacaacc    8580
actccctctt ccccaaaagc tctagctaga ctggctgccc ttctctgcta atcaactggt    8640
ggttccttgg ctagccagga acatggggt aggctccttc ccgtgcagac tt            8692

SEQ ID NO: 4          moltype = DNA   length = 23
FEATURE               Location/Qualifiers
misc_feature          1..23
                      note = Synthetic
source                1..23
                      mol_type = other DNA
                      organism = synthetic construct
SEQUENCE: 4
gtgggcccct acctagaatg tgg                                             23

SEQ ID NO: 5          moltype = DNA   length = 23
FEATURE               Location/Qualifiers
misc_feature          1..23
                      note = Synthetic
source                1..23
                      mol_type = other DNA
                      organism = synthetic construct
SEQUENCE: 5
attcccgttg tcccagcctt agg                                             23

SEQ ID NO: 6          moltype = DNA   length = 23
FEATURE               Location/Qualifiers
misc_feature          1..23
                      note = Synthetic
source                1..23
                      mol_type = other DNA
                      organism = synthetic construct
SEQUENCE: 6
tggttatagg attcaaccgg agg                                             23

SEQ ID NO: 7          moltype = DNA   length = 23
FEATURE               Location/Qualifiers
misc_feature          1..23
                      note = Synthetic
source                1..23
                      mol_type = other DNA
                      organism = synthetic construct
```

```
SEQUENCE: 7
ctgattgcaa tctccgcctc tgg                                              23

SEQ ID NO: 8              moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 8
cggcattttg agtgttagac tgg                                              23

SEQ ID NO: 9              moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 9
ctttgggacc tcttaacctg tgg                                              23

SEQ ID NO: 10             moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 10
caggtctccc caaggcgcac tgg                                              23

SEQ ID NO: 11             moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 11
gcacatctca tggggttata ggg                                              23

SEQ ID NO: 12             moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 12
cagggagta ctgtaggaag agg                                               23

SEQ ID NO: 13             moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 13
tgcacggtca gttgccctga ggg                                              23

SEQ ID NO: 14             moltype = DNA   length = 23
FEATURE                   Location/Qualifiers
misc_feature              1..23
                          note = Synthetic
source                    1..23
                          mol_type = other DNA
                          organism = synthetic construct
SEQUENCE: 14
atggaatttt cgcttcccac agg                                              23

SEQ ID NO: 15             moltype = DNA   length = 23
FEATURE                   Location/Qualifiers
misc_feature              1..23
                          note = Synthetic
source                    1..23
                          mol_type = other DNA
```

SEQUENCE: 15
tgggaatagg gtgcacattt agg                                                     23

SEQ ID NO: 16          moltype = DNA   length = 120
FEATURE                Location/Qualifiers
misc_feature           1..120
                       note = Synthetic
source                 1..120
                       mol_type = other DNA
                       organism = synthetic construct
SEQUENCE: 16
ccccgggaca aagcaaatgg aagtcctggg tgcttctgac gcacacctat tgcaagcaag        60
ggttcaaaga cccaaaaccc aaaatggcag gggagggaga gatgggggtg ggaggctgtc       120

SEQ ID NO: 17          moltype = DNA   length = 120
FEATURE                Location/Qualifiers
misc_feature           1..120
                       note = Synthetic
source                 1..120
                       mol_type = other DNA
                       organism = synthetic construct
SEQUENCE: 17
agtggggaac aagaagtgga gaatgtcagt ctgagtcagg cccttctgtc ttgaacatga        60
gttttttatg gcgggaggta gactgacect ttttggactt caggtggctg taggagacag       120

SEQ ID NO: 18          moltype = DNA   length = 120
FEATURE                Location/Qualifiers
misc_feature           1..120
                       note = Synthetic
source                 1..120
                       mol_type = other DNA
                       organism = synthetic construct
SEQUENCE: 18
actcacctgg agtgagccct gctcccccct ggctccttcc cagcctgggc atccttgagt        60
tccaaggcct cattcagctc tcggaacatc tcgaagcgct cacgcccacg gatctgcagc       120

SEQ ID NO: 19          moltype = DNA   length = 120
FEATURE                Location/Qualifiers
misc_feature           1..120
                       note = Synthetic
source                 1..120
                       mol_type = other DNA
                       organism = synthetic construct
SEQUENCE: 19
aatcctatgg ctttccaacc taggaaggca ggggagtagg gccaggaagg ggctgaggtc        60
actcacctgg agtgagccct gctcccccct ggctccttcc cagcctgggc atccttgagt       120

SEQ ID NO: 20          moltype = DNA   length = 120
FEATURE                Location/Qualifiers
misc_feature           1..120
                       note = Synthetic
source                 1..120
                       mol_type = other DNA
                       organism = synthetic construct
SEQUENCE: 20
tccaaggcct cattcagctc tcggaacatc tcgaagcgct cacgcccacg gatctgcagc        60
aacagaggag ggggagaagt aagtatatac acagtacctg agttaaaaga tggttcaagt       120

SEQ ID NO: 21          moltype = DNA   length = 120
FEATURE                Location/Qualifiers
misc_feature           1..120
                       note = Synthetic
source                 1..120
                       mol_type = other DNA
                       organism = synthetic construct
SEQUENCE: 21
aagaggtccc aagacttagt acctgaaggg tgaaatattc tccatccagt ggtttcttct        60
ttggctgggg agaggagctg gtgttgttgg gcagtgctag gaaagaggca aggaaaggtg       120

SEQ ID NO: 22          moltype = DNA   length = 120
FEATURE                Location/Qualifiers
misc_feature           1..120
                       note = Synthetic
source                 1..120
                       mol_type = other DNA
                       organism = synthetic construct
SEQUENCE: 22
gcataactgc acccttggtc tcctccaccg cttcttgtcc tgcttgctta cctcgcttag        60
tgctccctgg gggcagctcg tggtgaggct cccctttctt gcggagattc tcttcctctg   120

```
SEQ ID NO: 23          moltype = DNA   length = 120
FEATURE                Location/Qualifiers
misc_feature           1..120
                       note = Synthetic
source                 1..120
                       mol_type = other DNA
                       organism = synthetic construct
SEQUENCE: 23
```
tgcgccggtc tctcccagga caggcacaaa cacgcacctc aaagctgttc cgtcccagta   60
gattaccact actcaggata ggaaaagaga agcaagaggc agtaaggaaa tcaggtccta   120

```
SEQ ID NO: 24          moltype = DNA   length = 120
FEATURE                Location/Qualifiers
misc_feature           1..120
                       note = Synthetic
source                 1..120
                       mol_type = other DNA
                       organism = synthetic construct
SEQUENCE: 24
```
tgacctggag tcttccagtg tgatgatggt gaggatgggc ctccggttca tgccgcccat   60
gcaggaactg ttacacatgt agttgtagtg gatggtggta cagtcagagc caacctagga   120

```
SEQ ID NO: 25          moltype = DNA   length = 120
FEATURE                Location/Qualifiers
misc_feature           1..120
                       note = Synthetic
source                 1..120
                       mol_type = other DNA
                       organism = synthetic construct
SEQUENCE: 25
```
atgtgatgag aggtggatgg gtagtagtat ggaagaaatc ggtaagaggt gggcccaggg   60
gtcagaggca agcagaggct ggggcacagc aggccagtgt gcagggtggc aagtggctcc   120

```
SEQ ID NO: 26          moltype = DNA   length = 120
FEATURE                Location/Qualifiers
misc_feature           1..120
                       note = Synthetic
source                 1..120
                       mol_type = other DNA
                       organism = synthetic construct
SEQUENCE: 26
```
gacctcaggc ggctcatagg gcaccaccac actatgtcga aaagtgtttc tgtcatccaa   60
atactccaca cgcaaatttc cttccactcg gataagatgc tgaggagggg ccagacctaa   120

```
SEQ ID NO: 27          moltype = DNA   length = 120
FEATURE                Location/Qualifiers
misc_feature           1..120
                       note = Synthetic
source                 1..120
                       mol_type = other DNA
                       organism = synthetic construct
SEQUENCE: 27
```
ctggagggcc actgacaacc acccttaacc cctcctccca gagacccag ttgcaaacca   60
gacctcaggc ggctcatagg gcaccaccac actatgtcga aaagtgtttc tgtcatccaa   120

```
SEQ ID NO: 28          moltype = DNA   length = 120
FEATURE                Location/Qualifiers
misc_feature           1..120
                       note = Synthetic
source                 1..120
                       mol_type = other DNA
                       organism = synthetic construct
SEQUENCE: 28
```
caccatcgct atctgagcag cgctcatggt gggggcagcg cctcacaacc tccgtcatgt   60
gctgtgactg cttgtagatg gccatggcgc ggacgcgggt gccgggcggg ggtgtggaat   120

```
SEQ ID NO: 29          moltype = DNA   length = 120
FEATURE                Location/Qualifiers
misc_feature           1..120
                       note = Synthetic
source                 1..120
                       mol_type = other DNA
                       organism = synthetic construct
SEQUENCE: 29
```
gaatcagagg cctggggacc ctgggcaacc agccctgtcg tctctccagc ccagctgct   60
caccatcgct atctgagcag cgctcatggt gggggcagcg cctcacaacc tccgtcatgt   120

```
SEQ ID NO: 30           moltype = DNA   length = 120
FEATURE                 Location/Qualifiers
misc_feature            1..120
                        note = Synthetic
source                  1..120
                        mol_type = other DNA
                        organism = synthetic construct
SEQUENCE: 30
caacccacag ctgcacaggg caggtcttgg ccagttggca aaacatcttg ttgagggcag    60
gggagtactg taggaagagg aaggagacag agttgaaagt cagggcacaa gtgaacagat   120

SEQ ID NO: 31           moltype = DNA   length = 120
FEATURE                 Location/Qualifiers
misc_feature            1..120
                        note = Synthetic
source                  1..120
                        mol_type = other DNA
                        organism = synthetic construct
SEQUENCE: 31
attgaagtct catggaagcc agccctcag ggcaactgac cgtgcaagtc acagacttgg     60
ctgtcccaga atgcaagaag cccagacgga aaccgtagct gccctggtag gttttctggg   120

SEQ ID NO: 32           moltype = DNA   length = 120
FEATURE                 Location/Qualifiers
misc_feature            1..120
                        note = Synthetic
source                  1..120
                        mol_type = other DNA
                        organism = synthetic construct
SEQUENCE: 32
aagggacaga agatgacagg ggccaggagg gggctggtgc aggggccgcc ggtgtaggag    60
ctgctggtgc aggggccacg gggggagcag cctctggcat tctgggagct tcatctggac   120

SEQ ID NO: 33           moltype = DNA   length = 120
FEATURE                 Location/Qualifiers
misc_feature            1..120
                        note = Synthetic
source                  1..120
                        mol_type = other DNA
                        organism = synthetic construct
SEQUENCE: 33
ctgggtcttc agtgaaccat tgttcaatat cgtccgggga cagcatcaaa tcatccattg    60
cttgggacgg caagggggac tgtagatggg tgaaaagagc agtcagagga ccaggtcctc   120

SEQ ID NO: 34           moltype = DNA   length = 120
FEATURE                 Location/Qualifiers
misc_feature            1..120
                        note = Synthetic
source                  1..120
                        mol_type = other DNA
                        organism = synthetic construct
SEQUENCE: 34
gccccccagc cctccaggtc cccagccctc caggtcccca gcccaaccct tgtccttacc    60
agaacgttgt tttcaggaag tctgaaagac aagagcagaa agtcagtccc atggaatttt   120

SEQ ID NO: 35           moltype = DNA   length = 120
FEATURE                 Location/Qualifiers
misc_feature            1..120
                        note = Synthetic
source                  1..120
                        mol_type = other DNA
                        organism = synthetic construct
SEQUENCE: 35
cgcttcccac aggtctctgc taggggctg gggttgggt gggggtggtg ggcctgccct      60
tccaatggat ccactcacag tttccatagg tctgaaaatg tttcctgact cagaggggc    120

SEQ ID NO: 36           moltype = DNA   length = 120
FEATURE                 Location/Qualifiers
misc_feature            1..120
                        note = Synthetic
source                  1..120
                        mol_type = other DNA
                        organism = synthetic construct
SEQUENCE: 36
tcgacgctag gatctgactg cggctcctcc atggcagtga cccggaaggc agtctggctg    60
ctgcaagagg aaaagtgggg atccagcatg agacacttcc aaccctgggt cacctgggcc   120

SEQ ID NO: 37           moltype = DNA   length = 500
FEATURE                 Location/Qualifiers
```

```
misc_feature          1..500
                      note = Synthetic
source                1..500
                      mol_type = other DNA
                      organism = synthetic construct
SEQUENCE: 37
gctgagtgtg ggcccctacc tagaatgtgg gacggagtct cactctaatt cccgttgtcc    60
cagccttagg cccaggctgg agtgcagtgg ttataggatt caaccggagg cgccatcttg   120
gctccctctg attgcaatct ccgcctctgg acctccgcct cctggttcgg cattttgagt   180
gttagactgg gattctcctg cctcagcctt tgggacctct taacctgtgg ccaagtagct   240
gggattacag gtctcccaa ggcgcactgg gcacctgcca tcacgccgca catctcatgg    300
ggttataggg gtagagacgg ggtttcacag gggagtactg taggaagagg tgttggctag   360
gctggtctgc acggtcagtt gccctgaggg aactcctgac ctcaggtatg gaattttcgc   420
ttcccacagg tcagcctccc gaaatgctgg gaataggggtg cacatttagg gtggtagctc   480
atgcctgtaa ccccaatgtc                                               500

SEQ ID NO: 38         moltype = DNA  length = 17
FEATURE               Location/Qualifiers
misc_feature          1..17
                      note = Synthetic
source                1..17
                      mol_type = other DNA
                      organism = synthetic construct
SEQUENCE: 38
gacggagtct cactcta                                                   17

SEQ ID NO: 39         moltype = DNA  length = 17
FEATURE               Location/Qualifiers
misc_feature          1..17
                      note = Synthetic
source                1..17
                      mol_type = other DNA
                      organism = synthetic construct
SEQUENCE: 39
cccaggctgg agtgcag                                                   17

SEQ ID NO: 40         moltype = DNA  length = 17
FEATURE               Location/Qualifiers
misc_feature          1..17
                      note = Synthetic
source                1..17
                      mol_type = other DNA
                      organism = synthetic construct
SEQUENCE: 40
cgccatcttg gctccct                                                   17

SEQ ID NO: 41         moltype = DNA  length = 17
FEATURE               Location/Qualifiers
misc_feature          1..17
                      note = Synthetic
source                1..17
                      mol_type = other DNA
                      organism = synthetic construct
SEQUENCE: 41
acctccgcct cctggtt                                                   17

SEQ ID NO: 42         moltype = DNA  length = 17
FEATURE               Location/Qualifiers
misc_feature          1..17
                      note = Synthetic
source                1..17
                      mol_type = other DNA
                      organism = synthetic construct
SEQUENCE: 42
gattctcctg cctcagc                                                   17

SEQ ID NO: 43         moltype = DNA  length = 17
FEATURE               Location/Qualifiers
misc_feature          1..17
                      note = Synthetic
source                1..17
                      mol_type = other DNA
                      organism = synthetic construct
SEQUENCE: 43
ccaagtagct gggatta                                                   17

SEQ ID NO: 44         moltype = DNA  length = 17
FEATURE               Location/Qualifiers
misc_feature          1..17
```

```
                       note = Synthetic
source                 1..17
                       mol_type = other DNA
                       organism = synthetic construct
SEQUENCE: 44
gcacctgcca tcacgcc                                                          17

SEQ ID NO: 45          moltype = DNA  length = 17
FEATURE                Location/Qualifiers
misc_feature           1..17
                       note = Synthetic
source                 1..17
                       mol_type = other DNA
                       organism = synthetic construct
SEQUENCE: 45
gtagagacgg ggtttca                                                          17

SEQ ID NO: 46          moltype = DNA  length = 17
FEATURE                Location/Qualifiers
misc_feature           1..17
                       note = Synthetic
source                 1..17
                       mol_type = other DNA
                       organism = synthetic construct
SEQUENCE: 46
tgttggctag gctggtc                                                          17

SEQ ID NO: 47          moltype = DNA  length = 17
FEATURE                Location/Qualifiers
misc_feature           1..17
                       note = Synthetic
source                 1..17
                       mol_type = other DNA
                       organism = synthetic construct
SEQUENCE: 47
aactcctgac ctcaggt                                                          17

SEQ ID NO: 48          moltype = DNA  length = 17
FEATURE                Location/Qualifiers
misc_feature           1..17
                       note = Synthetic
source                 1..17
                       mol_type = other DNA
                       organism = synthetic construct
SEQUENCE: 48
tcagcctccc gaaatgc                                                          17

SEQ ID NO: 49          moltype =      length =
SEQUENCE: 49
000

SEQ ID NO: 50          moltype = DNA  length = 30
FEATURE                Location/Qualifiers
misc_feature           1..30
                       note = Synthetic
source                 1..30
                       mol_type = other DNA
                       organism = synthetic construct
SEQUENCE: 50
gtggtagctc atgcctgtaa ccccaatgtc                                            30
```

METHODS FOR TARGETED NUCLEIC ACID SEQUENCE ENRICHMENT WITH APPLICATIONS TO ERROR CORRECTED NUCLEIC ACID SEQUENCING

CROSS-REFERENCE TO RELATED APPLICATIONS

This application is a continuation of U.S. patent application Ser. No. 16/496,936, filed Sep. 23, 2019, now U.S. Pat. No. 11,479,807, which is the U.S. national stage of International Patent Application No. PCT/US2018/024194, filed Mar. 23, 2018, which claims priority to U.S. Provisional Patent Application No. 62/475,682, filed Mar. 23, 2017, and U.S. Provisional Patent Application No. 62/575,958, filed Oct. 23, 2017, the disclosures of all of which are hereby incorporated by reference in their entirety.

STATEMENT OF GOVERNMENT INTEREST

This invention was made with government support under Grant Nos. R01 CA160674 and R01 CA181308, awarded by the National Institutes of Health, and Grant No. W911NF-15-2-0127, awarded by the U.S. Army Research Office. The government has certain rights in the invention.

SEQUENCE LISTING

This application contains an ST.26 compliant Sequence Listing, which is submitted concurrently in xml format via EFS-Web or Patent Center and is hereby incorporated by reference in its entirety. The .xml copy, created on Sep. 16, 2022, is named 0722278137U504 Sequence Listing.xml and is 71 KB in size.

BACKGROUND

Previous approaches to certain types of genetic analysis, for example, forensic DNA analysis, rely on capillary electrophoretic (CE) separation of PCR amplicons (PCR-CE) to identify length polymorphisms in short tandem repeat sequences. This type of analysis has proven to be extremely valuable since its introduction in about 1991. Since that time, several publications have introduced standardized protocols, validated their use in laboratories worldwide, as well as detailed its use on many different population groups and introduced more efficient approaches, such as miniSTRs.

While this approach has proven to be extremely successful, the technology has a number of drawbacks that limit its utility. For example, current approaches to STR genotyping often give rise to background signal resulting from PCR stutter, caused by slippage of the polymerase on the template DNA, and resulting in a mixture of different length PCR amplicons in the final completed reaction. This issue is especially important in samples with more than one contributor (for example, a mixture of DNA derived from different specific individuals with a specific genetic makeup carrying different STR length variants), due to the difficulty in distinguishing the stutter alleles from genuine alleles. Another issue arises when analyzing degraded DNA samples. Damaged DNA can worsen the extent of stutter and PCR errors. Variation in fragment length often results in significantly lower, or even absent, longer PCR fragments. As a consequence, capillary electropherogram profiles from degraded DNA often have lower power of discrimination.

The introduction of massively parallel sequencing (MPS, also sometimes known as next generation DNA sequencing, NGS) systems has the potential to address several challenging issues in forensics analysis. For example, these platforms offer previously unparalleled capacity to allow for the simultaneous analysis of STRs and single nucleotide polymorphisms (SNPs) in nuclear and mitochondrial DNA (mtDNA), which will dramatically increase the power of discrimination between individuals and offers the possibility to determine ethnicity and even physical attributes (phenotypes). Furthermore, unlike PCR-CE, which simply reports the average genotype of an aggregate population of molecules, MPS technology digitally tabulates the full nucleotide sequence of many individual DNA molecules, thus offering the unique ability to detect minor allele frequencies (MAFs) within a heterogeneous DNA mixture. Because forensics specimens comprising two or more contributors remains one of the most problematic issues in forensics, the impact of MPS on the field of forensics could be enormous.

The publication of the human genome highlighted the immense power of MPS platforms. However, until fairly recently, the full power of these platforms was of limited use to forensics due to the read lengths being significantly shorter than the short tandem repeat (STR) loci, precluding the ability to call length-based genotypes. Initially, pyrosequencers, such as the MPS Roche 454 platform, were the only platforms with sufficient read length to sequence the core standard STR loci. However, read lengths in competing technologies have increased, thus bringing their utility for forensics applications into play. Overall, the general outcome of all these studies, regardless of the platform, is that STRs can be successfully typed, producing genotypes comparable with CE analyses, even from compromised forensic samples.

While many studies show concordance with traditional PCR-CE approaches, and even indicate additional benefits like the detection of intra-STR SNPs (single nucleotide polymorphisms), they have also highlighted a number of current issues with the technology. For example, current MPS approaches to STR genotyping rely on multiplex PCR to both provide enough DNA to sequence and introduce PCR primers. However, because multiplex PCR kits were designed for PCR-CE, they contain primers for various sized amplicons. This variation results in coverage imbalance with a bias toward amplification of smaller fragments, which can result in allele drop-out. Indeed, recent studies have shown that differences in PCR efficiency can affect mixture components, especially at low MAFs.

Like PCR-CE, MPS is not immune to the occurrence of PCR stutter. The vast majority of MPS studies on STR report the occurrence of artifactual drop-in alleles. Recently, systematic MPS studies report that most stutter events appear as shorter length polymorphisms that differ from the true allele in four base-pair units, with the most common being n−4, but with n−8 and n−12 positions also being observed. The percent stutter typically occurred in ~1% of reads but can be as high as 3% at some loci, indicating that MPS can exhibit stutter at higher rates than PCR-CE.

A variety of approaches at the level of protocol development, chemistry/biochemistry and data processing have been developed to mitigate the impact of PCR-based errors in MPS applications. In addition, techniques whereby PCR duplicates arising from individual DNA fragments can be resolved on the basis of unique random shear points or via exogenous tagging (i.e. using molecular bar codes, also known as molecular tags, unique molecular identifiers [UMIs] and single molecule identifiers [SMIs]), before or during amplification are in common use. This approach has been used to improve counting accuracy of DNA and RNA templates. Because all amplicons derived from a single starting molecule can be explicitly identified, any variation in the sequence of identically tagged sequencing reads can be used to correct base errors arising during PCR or sequencing. For instance, Kinde, et al. (Proc Natl Acad Sci USA 108, 9530-9535, 2011) introduced SafeSeqS, which uses single-stranded molecular barcoding to reduce the error rate of sequencing by grouping PCR copies sharing the barcode sequencing and forming a consensus. This approach leads to an average detection limit of 0.5% for point mutations, but its effectiveness on STR loci has not been widely evaluated.

Another recently described approach, MIPSTR, uses targeted capture of STR loci by single-molecule Molecular Inversion Probes (smMIPs) to specifically anneal to the sequences flanking the STR loci. After polymerase extension of the 3'-end of the smMIP, the ends are ligated and subjected to PCR amplification and sequencing. The use of MIPs specific to the flanking regions of the STR loci significantly increases the target specificity and increases the accuracy of genotyping STR loci. However, much like Safe-SeqS, the incorporation of a single-stranded molecular barcode cannot fully eliminate PCR artifacts arising in the first round of amplification that get carried onto derivative copies as a "jackpot" event.

Methods for higher accuracy genotyping of STR loci, single nucleotide polymorphism (SNP) loci and many other forms of mutations and genetic variants are desirable in a variety of applications in forensics, medicine, science industry. A challenge, however, is how to most efficiently generate sequence information from as many relevant copies of genetic material being sequenced as possible with the highest confidence but at a reasonable cost. Various consensus sequencing methods (both molecular barcode-based and not) have been used successfully for error correction to help better identify variants in mixtures (see J. Salk et al, *Enhancing the accuracy of next-generation sequencing for detecting rare and subclonal mutations*, Nature Reviews Genetics, 2018 for detailed discussion), but with various tradeoffs in performance. We have previously described Duplex Sequencing, an ultra-high accuracy sequencing method that relies on genotyping and comparing the independent strand sequenced of double stranded nucleic acid molecules for the purpose of error correction. The technology articulated herein describes methods for improving cost efficiency, recovery efficiency, and other performance metrics as well as overall process speed for Duplex Sequencing and related MPS sequencing methods.

SUMMARY

The present technology relates generally to methods for targeted nucleic acid sequence enrichment and uses of such enrichment for error-corrected nucleic acid sequencing applications. In some embodiments, highly accurate, error-corrected and massively parallel sequencing of nucleic acid material is possible using a combination of uniquely labeled strands in a double-stranded nucleic acid complex in such a way that each strand can be informatically related to its complementary strand, but also distinguished from it following sequencing of each strand or an amplified product derived therefrom and this information can be used for the purpose of error correction of the determined sequence. Some aspects of the present technology provide methods and compositions for improving the cost, conversion of molecules sequenced and the time efficiency of generating labeled molecules for targeted ultra-high accuracy sequencing. In some embodiments, provided methods and compositions allow for the accurate analysis of very small amounts of nucleic acid material (e.g., from a sample taken from a crime scene or from a small clinical sample or DNA floating freely in blood). In some embodiments, provided methods and compositions allow for the detection of mutations in a sample of a nucleic acid material that are present at a frequency less than one in one hundred cells or molecules (e.g., less than one in one thousand cells or molecules, less than one in ten thousand cells or molecules, less than one in one hundred thousand cells or molecules).

In some embodiments, the present disclosure provides methods including the steps of providing double-stranded nucleic acid material wherein the nucleic acid material comprises a single molecule identifier sequence on each strand of the nucleic acid material and an adapter sequence on at least one of the 5' and 3' ends of each strand of the nucleic acid material, wherein a first adapter sequence is located on one of the 5' end or 3' end of a first strand of the nucleic acid material, and a second adapter sequence is located on an opposite end of a second strand of the nucleic acid material, and wherein the first strand and the second strand originated from the same double-stranded nucleic acid molecule, amplifying the nucleic acid material, separating the amplified nucleic acid material into a first sample and a second sample, amplifying the first strand in the first sample through use of a primer specific to the first adapter sequence to provide a first nucleic acid product, amplifying the second strand in the second sample through use of a primer specific to the second adapter sequence to provide a second nucleic acid product, sequencing each of the first nucleic acid product and second nucleic acid product, and comparing the sequence of the first nucleic acid product to the sequence of the second nucleic acid product. In some embodiments, a nucleic acid material comprises an adapter sequence on each of the 5' and 3' ends of each strand of the nucleic acid material.

In some embodiments, the present disclosure provides methods including the steps of providing double-stranded nucleic acid material comprising one or more double-stranded nucleic acid molecules, wherein each double-stranded nucleic acid molecule comprises a single molecule identifier sequence on each strand and an adapter on at least one of the 5' and/or 3' ends of the nucleic acid molecule, and wherein, for each nucleic acid molecule, a first adapter sequence is associated with a first strand and a second adapter sequence is associated with a second strand of the nucleic acid molecule; amplifying the nucleic acid material, separating the amplified nucleic acid material into a first sample and a second sample, amplifying the first strand in the first sample through use of a primer specific to the first adapter sequence to provide a first nucleic acid product, amplifying the second strand in the second sample through use of a primer specific to the second adapter sequence to provide a second nucleic acid product, sequencing each of the first nucleic acid product and second nucleic acid product, and comparing the sequence of the first nucleic acid product to the sequence of the second nucleic acid product. In some embodiments, a nucleic acid material comprises an adapter sequence on each of the 5' and 3' ends of each strand of the nucleic acid material.

In some embodiments, the present disclosure also provides methods including the steps of providing double-stranded nucleic acid material, wherein the nucleic acid material is has been cut to provide strands of nucleic acid material of a substantially similar length (e.g., between about 1 and 1,000,000 bases, between 10 and 1,000 bases, or between about 100 and 500 bases) as a result of cutting with a targeted endonuclease (e.g., a CRISPR-associated (Cas) enzyme/guideRNA complex, for example Cas9 or Cpf1, meganucleases, transcription activator-like effector-based nucleases (TALENs), zinc-finger nucleases, an argonaute nuclease, etc.), and wherein the nucleic acid material comprises a single molecule identifier sequence on each strand of the nucleic acid material and an adapter sequence on at least one of the 5' and 3' ends of each strand of the nucleic acid material, wherein a first adapter sequence is located on one of the 5' end or 3' end of a first strand of the nucleic acid material, and a second adapter sequence is located on an opposite end of a second strand of the nucleic acid material, and wherein the first strand and the second strand originated from the same double-stranded nucleic acid molecule, amplifying the nucleic acid material, separating the amplified nucleic acid material into a first sample and a second sample, amplifying the first strand in the first sample through use of a primer specific to the first adapter sequence to provide a first nucleic acid product, amplifying the second strand in the second sample through use of a primer specific to the second adapter sequence to provide a second nucleic acid product, sequencing each of the first nucleic acid product and second nucleic acid product, and comparing the sequence of the first nucleic acid product to the sequence of the second nucleic acid product. In some embodiments, a nucleic acid material comprises an adapter sequence on each of the 5' and 3' ends of each strand of the nucleic acid material.

In some embodiments, sequencing each of the first nucleic acid product and second nucleic acid product includes the steps of sequencing at least one of the first strand to determine a first strand sequence read, sequencing at least one of the second strand to determine a second strand sequence read, and comparing the first strand sequence read and the second strand sequence read to generate an error-corrected sequence read. In some embodiments, an error-corrected sequence read comprises nucleotide bases that agree between the first strand sequence read and the second strand sequence read. In some embodiments, a variation occurring at a particular position in the error-corrected sequence read is identified as a true variant. In some embodiments, a variation that occurs at a particular position in only one of the first strand sequence read or the second strand sequence read is identified as a potential artifact.

In some embodiments, an error-corrected sequence read is used to identify or characterize a cancer, a cancer risk, a cancer mutation, a cancer metabolic state, a mutator phenotype, a carcinogen exposure, a toxin exposure, a chronic inflammation exposure, an age, a neurodegenerative disease, a pathogen, a drug resistant variant, a fetal molecule, a forensically relevant molecule, an immunologically relevant molecule, a mutated T-cell receptor, a mutated B-cell receptor, a mutated immunoglobulin locus, a kategis site in a genome, a hypermutable site in a genome, a low frequency variant, a subclonal variant, a minority population of molecules, a source of contamination, a nucleic acid synthesis error, an enzymatic modification error, a chemical modification error, a gene editing error, a gene therapy error, a piece of nucleic acid information storage, a microbial quasispecies, a viral quasispecies, an organ transplant, an organ transplant rejection, a cancer relapse, residual cancer after treatment, a preneoplastic state, a dysplastic state, a microchimerism state, a stem cell transplant state, a cellular therapy state, a nucleic acid label affixed to another molecule, or a combination thereof in an organism or subject from which the double-stranded target nucleic acid molecule is derived. In some embodiments, an error-corrected sequence read is used to identify a carcinogenic compound or exposure. In some embodiments, an error-corrected sequence read is used to identify a mutagenic compound or exposure. In some embodiments, a nucleic acid material is derived from a forensics sample, and the error-corrected sequence read is used in a forensic analysis.

In some embodiments, a single molecule identifier sequence comprises an endogenous shear point or an endogenous sequence that can be positionally related to the shear point. In some embodiments, a single molecule identifier sequence is at least of one of a degenerate or semi-degenerate barcode sequence, one or more nucleic acid fragment ends of the nucleic acid material, or a combination thereof that uniquely labels the double-stranded nucleic acid molecule. In some embodiments, the adapter and/or an adapter sequence comprises at least one nucleotide position that is at least partially non-complimentary or comprises at least one non-standard base. In some embodiments, an adapter comprises a single "U-shaped" oligonucleotide sequence formed by about 5 or more self-complementary nucleotides.

In accordance with various embodiments, any of a variety of nucleic acid material may be used. In some embodiments, nucleic acid material may comprise at least one modification to a polynucleotide within the canonical sugar-phosphate backbone. In some embodiments, nucleic acid material may comprise at least one modification within any base in the nucleic acid material. For example, by way of non-limiting example, in some embodiments, the nucleic acid material is or comprises at least one of double-stranded DNA, double-stranded RNA, peptide nucleic acids (PNAs), locked nucleic acids (LNAs).

In some embodiments a providing step includes ligating a double-stranded nucleic acid material to at least one double-stranded degenerate barcode sequence to form a double-stranded nucleic acid molecule barcode complex, wherein the double-stranded degenerate barcode sequence comprises the single molecule identifier sequence in each strand.

In some embodiments, amplifying the nucleic acid material in a first sample includes amplifying the first strand in the first sample through use of a primer specific to the first adapter sequence and a second primer specific to a non-adapter portion of the first strand to provide a first nucleic acid product. In some embodiments, amplifying the second strand in the second sample through use of a primer specific to the second adapter sequence and a second primer specific to a non-adapter portion of the second strand to provide a second nucleic acid product.

In some embodiments, amplifying the nucleic acid material in a first sample includes amplifying nucleic acid material derived from a single nucleic acid strand from an original double-stranded nucleic acid molecule using at least one single-stranded oligonucleotide at least partially complementary to a sequence present in the first adapter sequence and at least one single-stranded oligonucleotide at least partially complementary to a target sequence of interest such that the single molecule identifier sequence is at least partially maintained.

In some embodiments, amplifying the nucleic acid material in a second sample includes amplifying nucleic acid material derived from a single nucleic acid strand from an original double-stranded nucleic acid molecule using at least one single-stranded oligonucleotide at least partially complementary to a sequence present in the second adapter sequence and at least one single-stranded oligonucleotide at least partially complementary to a target sequence of interest such that the single molecule identifier sequence is at least partially maintained.

In some embodiments, amplifying the nucleic acid material includes generating a plurality of amplicons derived from the first strand and a plurality of amplicons derived from the second strand.

In some embodiments, provided methods further comprise, before the providing step, the steps of cutting the nucleic acid material with one or more targeted endonucleases such that a target nucleic acid fragment of a substantially known length is formed, and isolating the target nucleic acid fragment based on the substantially known length. In some embodiments, provided methods further comprise, before the providing step, ligating an adapter (e.g., an adapter sequence) to a target nucleic acid (e.g., a target nucleic acid fragment).

In some embodiments, a nucleic acid material may be or comprise one or more target nucleic acid fragments. In some embodiments, one or more target nucleic acid fragments each comprise a genomic sequence of interest from one or more locations in a genome. In some embodiments, one or more target nucleic acid fragments comprise a targeted sequence from a substantially known region within a nucleic acid material. In some embodiments, isolating a target nucleic acid fragment based on a substantially known length includes enriching for the target nucleic acid fragment by gel electrophoresis, gel purification, liquid chromatography, size exclusion purification, filtration or SPRI bead purification.

In accordance with various embodiments, some provided methods may be useful in sequencing any of a variety of suboptimal (e.g., damaged or degraded) samples of nucleic acid material. For example, in some embodiments at least some of the nucleic acid material is damaged. In some embodiments, the damage is or comprises at least one of oxidation, alkylation, deamination, methylation, hydrolysis, hydroxylation, nicking, intra-strand crosslinks, inter-strand cross links, blunt end strand breakage, staggered end double strand breakage, phosphorylation, dephosphorylation, sumoylation, glycosylation, deglycosylation, putrescinylation, carboxylation, halogenation, formylation, single-stranded gaps, damage from heat, damage from desiccation, damage from UV exposure, damage from gamma radiation damage from X-radiation, damage from ionizing radiation, damage from non-ionizing radiation, damage from heavy particle radiation, damage from nuclear decay, damage from beta-radiation, damage from alpha radiation, damage from neutron radiation, damage from proton radiation, damage from cosmic radiation, damage from high pH, damage from low pH, damage from reactive oxidative species, damage from free radicals, damage from peroxide, damage from hypochlorite, damage from tissue fixation such formalin or formaldehyde, damage from reactive iron, damage from low ionic conditions, damage from high ionic conditions, damage from unbuffered conditions, damage from nucleases, damage from environmental exposure, damage from fire, damage from mechanical stress, damage from enzymatic degradation, damage from microorganisms, damage from preparative mechanical shearing, damage from preparative enzymatic fragmentation, damage having naturally occurred in vivo, damage having occurred during nucleic acid extraction, damage having occurred during sequencing library preparation, damage having been introduced by a polymerase, damage having been introduced during nucleic acid repair, damage having occurred during nucleic acid end-tailing, damage having occurred during nucleic acid ligation, damage having occurred during sequencing, damage having occurred from mechanical handling of DNA, damage having occurred during passage through a nanopore, damage having occurred as part of aging in an organism, damage having occurred as a result if chemical exposure of an individual, damage having occurred by a mutagen, damage having occurred by a carcinogen, damage having occurred by a clastogen, damage having occurred from in vivo inflammation damage due to oxygen exposure, damage due to one or more strand breaks, and any combination thereof.

It is contemplated that nucleic acid material may come from a variety of sources. For example, in some embodiments, nucleic acid material (e.g., comprising one or more double-stranded nucleic acid molecules) is provided from a sample from a human subject, an animal, a plant, a fungi, a virus, a bacterium, a protozoan or any other life form. In other embodiments, the sample comprises nucleic acid material that has been at least partially artificially synthesized. In some embodiments, a sample is or comprises a body tissue, a biopsy, a skin sample, blood, serum, plasma, sweat, saliva, cerebrospinal fluid, mucus, uterine lavage fluid, a vaginal swab, a pap smear, a nasal swab, an oral swab, a tissue scraping, hair, a finger print, urine, stool, vitreous humor, peritoneal wash, sputum, bronchial lavage, oral lavage, pleural lavage, gastric lavage, gastric juice, bile, pancreatic duct lavage, bile duct lavage, common bile duct lavage, gall bladder fluid, synovial fluid, an infected wound, a non-infected wound, an archaeological sample, a forensic sample, a water sample, a tissue sample, a food sample, a bioreactor sample, a plant sample, a bacterial sample, a protozoan sample, a fungal sample, an animal sample, a viral sample, a multi-organism sample, a fingernail scraping, semen, prostatic fluid, vaginal fluid, a vaginal swab, a fallopian tube lavage, a cell free nucleic acid, a nucleic acid within a cell, a metagenomics sample, a lavage or a swab of an implanted foreign body, a nasal lavage, intestinal fluid, epithelial brushing, epithelial lavage, tissue biopsy, an autopsy sample, a necropsy sample, an organ sample, a human identification sample, a non-human identification sample, an artificially produced nucleic acid sample, a synthetic gene sample, a banked or stored nucleic acid sample, tumor tissue, a fetal sample, an organ transplant sample, a microbial culture sample, a nuclear DNA sample, a mitochondrial DNA sample, a chloroplast DNA sample, an apicoplast DNA sample, an organelle sample, and any combination thereof. In some embodiments, the nucleic acid material is derived from more than one source.

As described herein, in some embodiments, it is advantageous to process nucleic acid material so as to improve the efficiency, accuracy, and/or speed of a sequencing process. In some embodiments, the nucleic acid material comprises nucleic acid molecules of a substantially uniform length and/or a substantially known length. In some embodiments, a substantially uniform length and/or a substantially known length is between about 1 and about 1,000,000 bases). For example, in some embodiments, a substantially uniform length and/or a substantially known length may be at least 1; 2; 3; 4; 5; 6; 7; 8; 9; 10; 15; 20; 25; 30; 35; 40; 50; 60; 70; 80; 90; 100; 120; 150; 200; 300; 400; 500; 600; 700; 800; 900; 1000; 1200; 1500; 2000; 3000; 4000; 5000; 6000; 7000; 8000; 9000; 10,000; 15,000; 20,000; 30,000; 40,000; or 50,000 bases in length. In some embodiments, a substantially uniform length and/or a substantially known length may be at most 60,000; 70,000; 80,000; 90,000; 100,000; 120,000; 150,000; 200,000; 300,000; 400,000; 500,000; 600,000; 700,000; 800,000; 900,000; or 1,000,000 bases. By way of specific, non-limiting example, in some embodiments, a substantially uniform length and/or a substantially known length is between about 100 to about 500 bases. In some embodiments, a nucleic acid material is cut into nucleic acid molecules of a substantially uniform length and/or a substantially known length via one or more targeted endonucleases. In some embodiments, a targeted endonuclease comprises at least one modification.

In some embodiments, a nucleic acid material comprises nucleic acid molecules having a length within one or more substantially known size ranges. In some embodiments, the nucleic acid molecules may be between 1 and about 1,000,000 bases, between about 10 and about 10,000 bases, between about 100 and about 1000 bases, between about 100 and about 600 bases, between about 100 and about 500 bases, or some combination thereof.

In some embodiments, a targeted endonuclease is or comprises at least one of a restriction endonuclease (i.e., restriction enzyme) that cleaves DNA at or near recognition sites (e.g., EcoRI, BamHI, XbaI, HindIII, AluI, AvaII, BsaJI, BstNI, DsaV, Fnu4HI, HaeIII, MaeIII, N1aIV, NSiI, MspJI, FspEI, NaeI, Bsu36I, NotI, HinF1, Sau3AI, PvuII, SmaI, HgaI, AluI, EcoRV, etc.). Listings of several restriction endonucleases are available both in printed and computer readable forms, and are provided by many commercial suppliers (e.g., New England Biolabs, Ipswich, Mass.). It will be appreciated by one of ordinary skill in the art that any restriction endonuclease may be used in accordance with various embodiments of the present technology. In other embodiments, a targeted endonuclease is or comprises at least one of a ribonucleoprotein complex, such as, for example, a CRISPR-associated (Cas) enzyme/guideRNA complex (e.g., Cas9 or Cpf1) or a Cas9-like enzyme. In other embodiments, a targeted endonuclease is or comprises a homing endonuclease, a zinc-fingered nuclease, a TALEN, and/or a meganuclease (e.g., megaTAL nuclease, etc.), an argonaute nuclease or a combination thereof. In some embodiments, a targeted endonuclease comprises Cas9 or CPF1 or a derivative thereof. In some embodiments, more than one targeted endonuclease may be used (e.g., 2, 3, 4, 5, 6, 7, 8, 9, 10 or more). In some embodiments, a targeted endonuclease may be used to cut at more than one potential target region of a nucleic acid material (e.g., 2, 3, 4, 5, 6, 7, 8, 9, 10 or more). In some embodiments, where there is more than one target region of a nucleic acid material, each target region may be of the same (or substantially the same) length. In some embodiments, where there is more than one target region of a nucleic acid material, at least two of the target regions of known length differ in length (e.g., a first target region with a length of 100 bp and a second target region with a length of 1,000 bp).

In some embodiments, certain modifications are made to a portion of a sample of nucleic acid material (e.g., an adapter sequence). By way of specific example, in some embodiments, amplifying a nucleic acid material in a first sample further comprises destroying or disrupting a portion or all of a second adapter sequence found on a nucleic acid material after the separating step, and before the amplification of a first sample. By way of further example, in some embodiments, amplifying the nucleic acid material in the second sample further comprises destroying or disrupting first adapter sequences found on the nucleic acid material after the separating step, and before the amplification of the second sample. In some embodiments, destroying or disrupting may be or comprise at least one of enzymatic digestion, inclusion of at least one replication-inhibiting molecule, enzymatic cleavage, enzymatic cleavage of one strand, enzymatic cleavage of both strands, incorporation of a modified nucleic acid followed by enzymatic treatment that leads to cleavage or one or both strands, incorporation of a replication blocking nucleotide, incorporation of a chain terminator, incorporation of a photocleavable linker, incorporation of a uracil, incorporation of a ribose base, incorporation of an 8-oxo-guanine adduct, use of a restriction endonuclease, use of a ribonucleoprotein endonuclease (e.g., a Cas-enzyme, such as Cas9 or CPF1), or other programmable endonuclease (e.g., a homing endonuclease, a zinc-fingered nuclease, a TALEN, a meganuclease (e.g., megaTAL nuclease), an argonaute nuclease, etc.), and any combination thereof. In some embodiments, as an addition or alternative to primer site destruction or disruption, methods such as affinity pulldown, size selection, or any other known technique for removing and/or not amplifying undesired nucleic acid material from a sample is contemplated.

In some embodiments, at least one amplifying step includes at least one primer and/or adapter sequence that is or comprises at least one non-standard nucleotide. By way of additional example, in some embodiments, at least one adapter sequence is or comprises at least one non-standard nucleotide. In some embodiments, a non-standard nucleotide is selected from a uracil, a methylated nucleotide, an RNA nucleotide, a ribose nucleotide, an 8-oxo-guanine, a biotinylated nucleotide, a desthiobiotin nucleotide, a thiol modified nucleotide, an acrydite modified nucleotide an iso-dC, an iso dG, a 2'-O-methyl nucleotide, an inosine nucleotide Locked Nucleic Acid, a peptide nucleic acid, a 5 methyl dC, a 5-bromo deoxyuridine, a 2,6-Diaminopurine, 2-Aminopurine nucleotide, an abasic nucleotide, a 5-Nitroindole nucleotide, an adenylated nucleotide, an azide nucleotide, a digoxigenin nucleotide, an I-linker, a 5' Hexynyl modified nucleotide, an 5-Octadiynyl dU, photocleavable spacer, a non-photocleavable spacer, a click chemistry compatible modified nucleotide, a fluorescent dye, biotin, furan, BrdU, Fluoro-dU, loto-dU, and any combination thereof.

In accordance with several embodiments, any of a variety of analytical steps may be used in order to increase one or more of accuracy, speed, and efficiency of a provided process. For example, in some embodiments, sequencing each of the first nucleic acid product and second nucleic acid product includes comparing the sequence of a plurality of strands in the first nucleic acid product to determine a first strand consensus sequence, and comparing the sequence of a plurality of strands in the second nucleic acid product to determine a second strand consensus sequence. In some embodiments, comparing the sequence of the first nucleic acid product to the sequence of the second nucleic acid product comprises comparing the first strand consensus sequence and the second strand consensus sequence to provide an error-corrected consensus sequence.

It is contemplated that any of a variety of methods for amplifying nucleic acid material may be used in accordance with various embodiments. For example, in some embodiments, at least one amplifying step comprises a polymerase chain reaction (PCR), rolling circle amplification (RCA), multiple displacement amplification (MDA), isothermal amplification, polony amplification within an emulsion, bridge amplification on a surface, the surface of a bead or within a hydrogel, and any combination thereof. In some embodiments, amplifying a nucleic acid material includes use of a single-stranded oligonucleotide at least partially complementary to a region of a genomic sequence of interest and a single-stranded oligonucleotide at least partially complementary to a region of the adapter sequence. In some embodiments, amplifying a nucleic acid material includes use of single-stranded oligonucleotides at least partially complementary to regions of a first adapter sequence and a second adapter sequence (e.g., at least partially complementary to an adapter sequence on the 5' and/or 3' ends of each strand of the nucleic acid material).

One aspect provided by some embodiments, is the ability to generate high quality sequencing information from very small amounts of nucleic acid material. In some embodiments, provided methods and compositions may be used with an amount of starting nucleic acid material of at most about: 1 picogram (pg); 10 pg; 100 pg; 1 nanogram (ng); 10 ng; 100 ng; 200 ng, 300 ng, 400 ng, 500 ng, 600 ng, 700 ng, 800 ng, 900 ng, or 1000 ng. In some embodiments, provided methods and compositions may be used with an input amount of nucleic acid material of at most 1 molecular copy or genome-equivalent, 10 molecular copies or the genome-equivalent thereof, 100 molecular copies or the genome-equivalent thereof, 1,000 molecular copies or the genome-equivalent thereof, 10,000 molecular copies or the genome-equivalent thereof, 100,000 molecular copies or the genome-equivalent thereof, or 1,000,000 molecular copies or the genome-equivalent thereof, For example, in some embodiments, at most 1,000 ng of nucleic acid material is initially provided for a particular sequencing process. For example, in some embodiments, at most 100 ng of nucleic acid material is initially provided for a particular sequencing process. For example, in some embodiments, at most 10 ng of nucleic acid material is initially provided for a particular sequencing process. For example, in some embodiments, at most 1 ng of nucleic acid material is initially provided for a particular sequencing process. For example, in some embodiments, at most 100 pg of nucleic acid material is initially provided for a particular sequencing process. For example, in some embodiments, at most 1 pg of nucleic acid material is initially provided for a particular sequencing process.

As used in this application, the terms "about" and "approximately" are used as equivalents. Any citations to publications, patents, or patent applications herein are incorporated by reference in their entirety. Any numerals used in this application with or without about/approximately are meant to cover any normal fluctuations appreciated by one of ordinary skill in the relevant art.

In various embodiments, enrichment of nucleic acid material, including enrichment of nucleic acid material to region(s) of interest, is provided at a faster rate (e.g., with fewer steps) and with less cost (e.g., utilizing fewer reagents), and resulting in increased desirable data. Various aspects of the present technology have many applications in both pre-clinical and clinical testing and diagnostics as well as other applications.

Specific details of several embodiments of the technology are described below and with reference to the FIGS. 1A-24. Although many of the embodiments are described herein with respect to Duplex Sequencing, other sequencing modalities capable of generating error-corrected sequencing reads and/or other sequencing reads in addition to those described herein are within the scope of the present technology. Additionally, other nucleic acid interrogations are contemplated to benefit from the nucleic acid enrichment methods and reagents described herein. Further, other embodiments of the present technology can have different configurations, components, or procedures than those described herein. A person of ordinary skill in the art, therefore, will accordingly understand that the technology can have other embodiments with additional elements and that the technology can have other embodiments without several of the features shown and described below with reference to the FIGS. 1A-24.

BRIEF DESCRIPTION OF THE DRAWINGS

Many aspects of the present disclosure can be better understood with reference to the following drawings. The components in the drawings are not necessarily to scale. Instead, emphasis is placed on illustrating clearly the principles of the present disclosure.

FIGS. 3A and 3B show a series of graphs showing CODIS genotype versus a number of sequencing reads in the absence of error correction (FIG. 3A) and following analysis with standard DS (FIG. 3B) for three different loci in accordance with aspects of the present disclosure.

FIGS. 12A-12D are conceptual illustrations of CRISPR-DS method steps in accordance with an embodiment of the present technology. FIG. 12A shows results from CRISPR/Cas9 digestion of TP53, with seven fragments containing all TP53 coding exons that were excised via targeted cutting using gRNAs. Dark grey represents reference strand and light grey represents anti-reference strand. FIG. 12B shows size selection using 0.5×SPRI beads; uncut, genomic DNA binds beads and allows recovery of excised fragments in solution. FIG. 12C shows a schematic of a double-stranded DNA molecule fragmented and ligated with double-stranded DS-adapters, containing 10-bp of random, complementary nucleotides and a 3'-dT overhang. FIG. 12D shows a schematic for error correction by DS. Reads derived from the same strand of DNA are compared to form a single-strand consensus sequence (SSCS). Then both strands of the same starting DNA molecule are compared with one another to create a double-strand consensus sequence (DSCS), and mutations found in both SSCS reads are counted as true mutations in DSCS reads.

FIG. 12E is a comparison of library preparation steps for CRISPR-DS and standard-DS. Each box represents 1 h of time. FIG. 12F shows schematics of fragments produced using sonication, which are of shorter or longer than optimal length (corresponding to lost or redundant information, respectively) as compared to fragments products by CRISPR-DS, which are of optimal and consistent length, with full coverage of sequencing reads.

FIG. 13A is a representative gel showing insert fragment sizes prior to sequencing. FIGS. 13B and 13C are graphs showing CODIS genotype versus a number of sequencing reads in the absence of error correction (FIG. 13B) and following analysis with SPLiT-DS (FIG. 13C).

FIGS. 17A-17C (SEQ ID NO: 3) show a CRISPR/Cas9 scheme for targeted enrichment of coding regions of human TP53 in accordance with an embodiment of the present technology. TP53 tumor protein; *Homo sapiens*; NC_000017.11 Chr. 17, Ref. GRCh38.p2. Grey letters represent coding regions; exon names are indicated in the right margin and boxed together when they are in the same fragment. Grey highlighted text represent Cas9 cut sites with PAM sequences double underlines. Single underlined text represents biotinylated probes, with probe names indicated on the left margin.

FIGS. 21A-21C are a schematic illustration of a synthetic double-stranded DNA molecule (FIG. 21A) and chart of predicted fragment lengths (FIG. 21B) following CRISPR/Cas9 digestion, and a resultant TapeStation gel image of actual DNA fragment lengths following CRISPR/Cas9 digestion of the synthetic double-stranded DNA molecule (FIG. 21C) demonstrating successful cleavage using CRISPR/Cas9 digestion in accordance with an embodiment of the present technology.

FIG. 22B is a representative gel showing insert fragment sizes following adapter ligation and prior to sequencing. FIGS. 22C and 22D are electropherograms showing peaks of resultant nucleic acid library generated by CRISPR-DS (FIG. 22C) and standard DS (FIG. 22D) prior to sequencing. FIG. 22E shows duplex consensus sequence reads of TP53 generated by CRISPR-DS and standard DS protocols with Integrative Genomics Viewer. FIG. 22B shows a TapeStation gels with a ladder and samples from CRISPR-DS (A1) and standard-DS (B1). Sizes of bands correspond to CRISPR/Cas9 cut fragments with adapters. FIG. 22E shows distinct boundaries that correspond to the CRISPR/Cas9 cutting points and an even distribution of depth across positions, both within a fragment and between fragments Standard-DS shows a peak pattern generated by random shearing of fragments and hybridization capture, and uneven coverage.

FIG. 24A shows DNA samples and the enrichment achieved for each. FIG. 24B shows percent of raw reads that were "on target" as compared to amount of input DNA.

DEFINITIONS

Figure 1A:
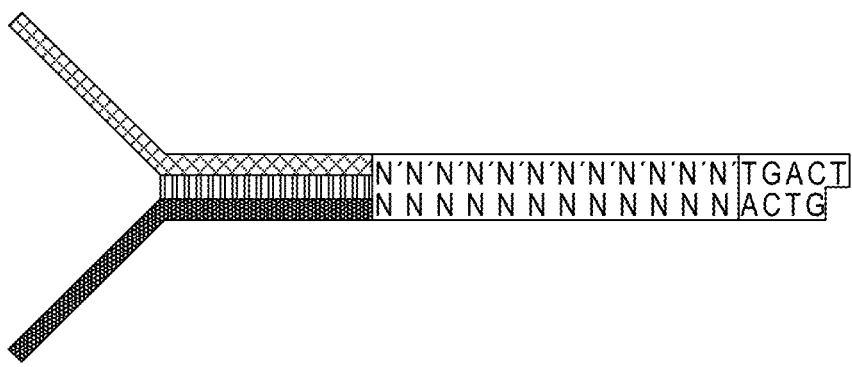
FIG. 1A illustrates a nucleic acid adapter molecule for use with some embodiments of the present technology and a double-stranded adapter-nucleic acid complex resulting from ligation of the adapter molecule to a double-stranded nucleic acid fragment (SEQ ID NOS: 1 and 2) in accordance with an embodiment of the present technology.

In order for the present disclosure to be more readily understood, certain terms are first defined below. Additional definitions for the following terms and other terms are set forth throughout the specification.

In this application, unless otherwise clear from context, the term "a" may be understood to mean "at least one." As used in this application, the term "or" may be understood to mean "and/or." In this application, the terms "comprising" and "including" may be understood to encompass itemized components or steps whether presented by themselves or together with one or more additional components or steps. Where ranges are provided herein, the endpoints are included. As used in this application, the term "comprise" and variations of the term, such as "comprising" and "comprises," are not intended to exclude other additives, components, integers or steps.

About: The term "about", when used herein in reference to a value, refers to a value that is similar, in context to the referenced value. In general, those skilled in the art, familiar with the context, will appreciate the relevant degree of variance encompassed by "about" in that context. For example, in some embodiments, the term "about" may encompass a range of values that within 25%, 20%, 19%, 18%, 17%, 16%, 15%, 14%, 13%, 12%, 11%, 10%, 9%, 8%, 7%, 6%, 5%, 4%, 3%, 2%, 1%, or less of the referred value.

Analog: As used herein, the term "analog" refers to a substance that shares one or more particular structural features, elements, components, or moieties with a reference substance. Typically, an "analog" shows significant structural similarity with the reference substance, for example sharing a core or consensus structure, but also differs in certain discrete ways. In some embodiments, an analog is a substance that can be generated from the reference substance, e.g., by chemical manipulation of the reference substance. In some embodiments, an analog is a substance that can be generated through performance of a synthetic process substantially similar to (e.g., sharing a plurality of steps with) one that generates the reference substance. In some embodiments, an analog is or can be generated through performance of a synthetic process different from that used to generate the reference substance.

Biological Sample: As used herein, the term "biological sample" or "sample" typically refers to a sample obtained or derived from a biological source (e.g., a tissue or organism or cell culture) of interest, as described herein. In some embodiments, a source of interest comprises an organism, such as an animal or human. In other embodiments, a source of interest comprises a microorganism, such as a bacterium, virus, protozoan, or fungus. In further embodiments, a source of interest may be a synthetic tissue, organism, cell culture, nucleic acid or other material. In yet further embodiments, a source of interest may be a plant-based organism. In yet another embodiment, a sample may be an environmental sample such as, for example, a water sample, soil sample, archeological sample, or other sample collected from a non-living source. In other embodiments, a sample may be a multi-organism sample (e.g., a mixed organism sample). In some embodiments, a biological sample is or comprises biological tissue or fluid. In some embodiments, a biological sample may be or comprise bone marrow; blood; blood cells; ascites; tissue or fine needle biopsy samples; cell-containing body fluids; free floating nucleic acids; sputum; saliva; urine; cerebrospinal fluid, peritoneal fluid; pleural fluid; feces; lymph; gynecological fluids; skin swabs; vaginal swabs; pap smear, oral swabs; nasal swabs; washings or lavages such as a ductal lavages or broncheoalveolar lavages; vaginal fluid, aspirates; scrapings; bone marrow specimens; tissue biopsy specimens; fetal tissue or fluids; surgical specimens; feces, other body fluids, secretions, and/or excretions; and/or cells therefrom, etc. In some embodiments, a biological sample is or comprises cells obtained from an individual. In some embodiments, obtained cells are or include cells from an individual from whom the sample is obtained. In a particular embodiment, a biological sample is a liquid biopsy obtained from a subject. In some embodiments, a sample is a "primary sample" obtained directly from a source of interest by any appropriate means. For example, in some embodiments, a primary biological sample is obtained by methods selected from the group consisting of biopsy (e.g., fine needle aspiration or tissue biopsy), surgery, collection of body fluid (e.g., blood, lymph, feces etc.), etc. In some embodiments, as will be clear from context, the term "sample" refers to a preparation that is obtained by processing (e.g., by removing one or more components of and/or by adding one or more agents to) a primary sample. For example, filtering using a semipermeable membrane. Such a "processed sample" may comprise, for example nucleic acids or proteins extracted from a sample or obtained by subjecting a primary sample to techniques such as amplification or reverse transcription of mRNA, isolation and/or purification of certain components, etc.

Determine: Many methodologies described herein include a step of "determining". Those of ordinary skill in the art, reading the present specification, will appreciate that such "determining" can utilize or be accomplished through use of any of a variety of techniques available to those skilled in the art, including for example specific techniques explicitly referred to herein. In some embodiments, determining involves manipulation of a physical sample. In some embodiments, determining involves consideration and/or manipulation of data or information, for example utilizing a computer or other processing unit adapted to perform a relevant analysis. In some embodiments, determining involves receiving relevant information and/or materials from a source. In some embodiments, determining involves comparing one or more features of a sample or entity to a comparable reference.

Expression: As used herein, "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end formation); (3) translation of an RNA into a polypeptide or protein; and/or (4) post-translational modification of a polypeptide or protein.

gRNA: As used herein, "gRNA" or "guide RNA", refers to short RNA molecules which include a scaffold sequence suitable for a targeted endonuclease (e.g., a Cas enzyme such as Cas9 or Cpf1 or another ribonucleoprotein with similar properties, etc.) binding to a substantially target-specific sequence which facilitates cutting of a specific region of DNA or RNA.

Nucleic acid: As used herein, in its broadest sense, refers to any compound and/or substance that is or can be incorporated into an oligonucleotide chain. In some embodiments, a nucleic acid is a compound and/or substance that is or can be incorporated into an oligonucleotide chain via a phosphodiester linkage. As will be clear from context, in some embodiments, "nucleic acid" refers to an individual nucleic acid residue (e.g., a nucleotide and/or nucleoside); in some embodiments, "nucleic acid" refers to an oligonucleotide chain comprising individual nucleic acid residues. In some embodiments, a "nucleic acid" is or comprises RNA; in some embodiments, a "nucleic acid" is or comprises DNA. In some embodiments, a nucleic acid is, comprises, or consists of one or more natural nucleic acid residues. In some embodiments, a nucleic acid is, comprises, or consists of one or more nucleic acid analogs. In some embodiments, a nucleic acid analog differs from a nucleic acid in that it does not utilize a phosphodiester backbone. For example, in some embodiments, a nucleic acid is, comprises, or consists of one or more "peptide nucleic acids", which are known in the art and have peptide bonds instead of phosphodiester bonds in the backbone, are considered within the scope of the present technology. Alternatively or additionally, in some embodiments, a nucleic acid has one or more phosphorothioate and/or 5'-N-phosphoramidite linkages rather than phosphodiester bonds. In some embodiments, a nucleic acid is, comprises, or consists of one or more natural nucleosides (e.g., adenosine, thymidine, guanosine, cytidine, uridine, deoxyadenosine, deoxythymidine, deoxyguanosine, and deoxycytidine). In some embodiments, a nucleic acid is, comprises, or consists of one or more nucleoside analogs (e.g., 2-aminoadenosine, 2-thiothymidine, inosine, pyrrolo-pyrimidine, 3-methyl adenosine, 5-methylcytidine, C-5 propynyl-cytidine, C-5 propynyl-uridine, 2-aminoadenosine, C5-bromouridine, C5-fluorouridine, C5-iodouridine, C5-propynyl-uridine, C5-propynyl-cytidine, C5-methylcytidine, 2-aminoadenosine, 7-deazaadenosine, 7-deazaguanosine, 8-oxoadenosine, 8-oxoguanosine, 0(6)-methylguanine, 2-thiocytidine, methylated bases, intercalated bases, and combinations thereof). In some embodiments, a nucleic acid comprises one or more modified sugars (e.g., 2'-fluororibose, ribose, 2'-deoxyribose, arabinose, and hexose) as compared with those in natural nucleic acids. In some embodiments, a nucleic acid has a nucleotide sequence that encodes a functional gene product such as an RNA or protein. In some embodiments, a nucleic acid includes one or more introns. In some embodiments, nucleic acids are prepared by one or more of isolation from a natural source, enzymatic synthesis by polymerization based on a complementary template (in vivo or in vitro), reproduction in a recombinant cell or system, and chemical synthesis. In some embodiments, a nucleic acid is at least 2, 3, 4, 5, 6, 7, 8, 9, 10, 15, 20, 25, 30, 35, 40, 45, 50, 55, 60, 65, 70, 75, 80, 85, 90, 95, 100, 110, 120, 130, 140, 150, 160, 170, 180, 190, 200, 225, 250, 275, 300, 325, 350, 375, 400, 425, 450, 475, 500, 600, 700, 800, 900, 1000, 1500, 2000, 2500, 3000, 3500, 4000, 4500, 5000 or more residues long. In some embodiments, a nucleic acid is partly or wholly single stranded; in some embodiments, a nucleic acid is partly or wholly double-stranded. In some embodiments a nucleic acid has a nucleotide sequence comprising at least one element that encodes, or is the complement of a sequence that encodes, a polypeptide. In some embodiments, a nucleic acid has enzymatic activity. In some embodiments the nucleic acid serves a mechanical function, for example in a ribonucleoprotein complex or a transfer RNA.

Reference: As used herein describes a standard or control relative to which a comparison is performed. For example, in some embodiments, an agent, animal, individual, population, sample, sequence or value of interest is compared with a reference or control agent, animal, individual, population, sample, sequence or value. In some embodiments, a reference or control is tested and/or determined substantially simultaneously with the testing or determination of interest. In some embodiments, a reference or control is a historical reference or control, optionally embodied in a tangible medium. Typically, as would be understood by those skilled in the art, a reference or control is determined or characterized under comparable conditions or circumstances to those under assessment. Those skilled in the art will appreciate when sufficient similarities are present to justify reliance on and/or comparison to a particular possible reference or control.

Single Molecule Identifier (SMI): As used herein, the term "single molecule identifier" or "SMI", (which may be referred to as a "tag" a "barcode", a "Molecular bar code", a "Unique Molecular Identifier", or "UMI", among other names) refers to any material (e.g., a nucleotide sequence, a nucleic acid molecule feature) that is capable of distinguishing an individual molecule in a large heterogeneous population of molecules. In some embodiments, a SMI can be or comprise an exogenously applied SMI. In some embodiments, an exogenously applied SMI may be or comprise a degenerate or semi-degenerate sequence. In some embodiments substantially degenerate SMIs may be known as Random Unique Molecular Identifiers (R-UMIs). In some embodiments an SMI may comprise a code (for example a nucleic acid sequence) from within a pool of known codes. In some embodiments pre-defined SMI codes are known as Defined Unique Molecular Identifiers (D-UMIs). In some embodiments, a SMI can be or comprise an endogenous SMI. In some embodiments, an endogenous SMI may be or comprise information related to specific shear-points of a target sequence, or features relating to the terminal ends of individual molecules comprising a target sequence. In some embodiments an SMI may relate to a sequence variation in a nucleic acid molecule cause by random or semi-random damage, chemical modification, enzymatic modification or other modification to the nucleic acid molecule. In some embodiments the modification may be deamination of methylcytosine. In some embodiments the modification may entail sites of nucleic acid nicks. In some embodiments, an SMI may comprise both exogenous and endogenous elements. In some embodiments an SMI may comprise physically adjacent SMI elements. In some embodiments SMI elements may be spatially distinct in a molecule. In some embodiments an SMI may be a non-nucleic acid. In some embodiments an SMI may comprise two or more different types of SMI information. Various embodiments of SMIs are further disclosed in International Patent Publication No. WO2017/100441, which is incorporated by reference herein in its entirety.

Strand Defining Element (SDE): As used herein, the term "Strand Defining Element" or "SDE", refers to any material which allows for the identification of a specific strand of a double-stranded nucleic acid material and thus differentiation from the other/complementary strand (e.g., any material that renders the amplification products of each of the two single stranded nucleic acids resulting from a target double-stranded nucleic acid substantially distinguishable from each other after sequencing or other nucleic acid interrogation). In some embodiments, an SDE may be or comprise one or more segments of substantially non-complementary sequence within an adapter sequence. In particular embodiments, a segment of substantially non-complementary sequence within an adapter sequence can be provided by an adapter molecule comprising a Y-shape or a "loop" shape. In other embodiments, a segment of substantially non-complementary sequence within an adapter sequence may form an unpaired "bubble" in the middle of adjacent complementary sequences within an adapter sequence. In other embodiments an SDE may encompass a nucleic acid modification. In some embodiments an SDE may comprise physical separation of paired strands into physically separated reaction compartments. In some embodiments an SDE may comprise a chemical modification. In some embodiments an SDE may comprise a modified nucleic acid. In some embodiments an SDE may relate to a sequence variation in a nucleic acid molecule caused by random or semi-random damage, chemical modification, enzymatic modification or other modification to the nucleic acid molecule. In some embodiments the modification may be deamination of methylcytosine. In some embodiments the modification may entail sites of nucleic acid nicks. Various embodiments of SDEs are further disclosed in International Patent Publication No. WO2017/100441, which is incorporated by reference herein in its entirety.

Subject: As used herein, the term "subject" refers an organism, typically a mammal (e.g., a human, in some embodiments including prenatal human forms). In some embodiments, a subject is suffering from a relevant disease, disorder or condition. In some embodiments, a subject is susceptible to a disease, disorder, or condition. In some embodiments, a subject displays one or more symptoms or characteristics of a disease, disorder or condition. In some embodiments, a subject does not display any symptom or characteristic of a disease, disorder, or condition. In some embodiments, a subject is someone with one or more features characteristic of susceptibility to or risk of a disease, disorder, or condition. In some embodiments, a subject is a patient. In some embodiments, a subject is an individual to whom diagnosis and/or therapy is and/or has been administered.

Substantially: As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

DETAILED DESCRIPTION

Figure 1B:
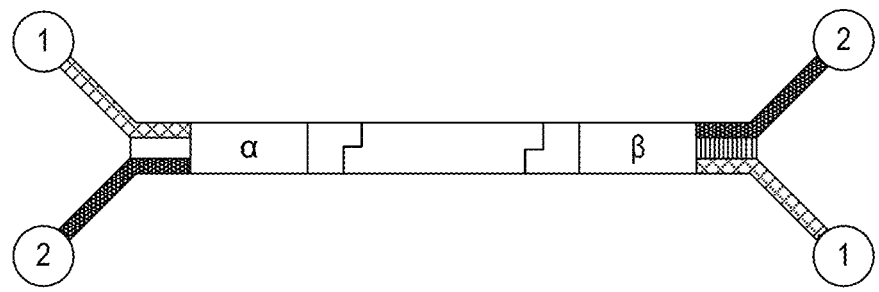
FIGS. 1B and 1C are conceptual illustrations of various Duplex Sequencing method steps in accordance with an embodiment of the present technology.
Figure 1C:
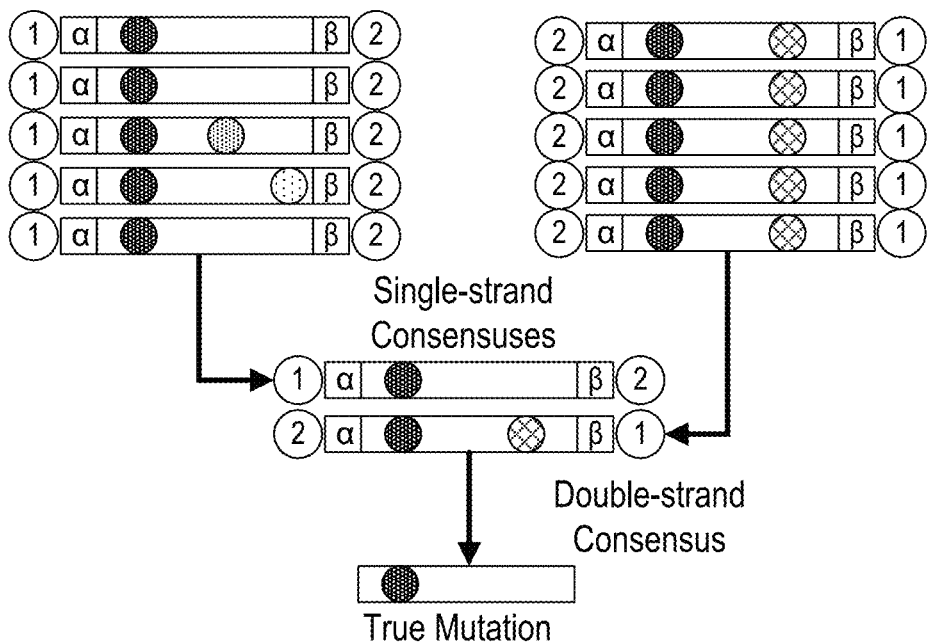

Selected Embodiments of Duplex Sequencing Methods and Associated Adapters and Reagents Duplex Sequencing (DS) is a method for producing error-corrected DNA sequences from double-stranded nucleic acid molecules, and which was originally described in International Patent Publication No. WO 2013/142389 and in U.S. Pat. No. 9,752,188, both of which are incorporated by reference in their entireties. As illustrated in FIGS. 1A-1C, and in certain aspects of the technology, DS can be used to independently sequence both strands of individual DNA molecules in such a way that the derivative sequence reads can be recognized as having originated from the same double-stranded nucleic acid parent molecule during MPS, but also differentiated from each other as distinguishable entities following sequencing. The resulting sequence reads from each strand are then compared for the purpose of obtaining an error-corrected sequence of the original double-stranded nucleic acid molecule known as a Duplex Consensus Sequence (DCS). The process of DS makes it possible to confirm whether one or both strands of an original double stranded nucleic acid molecule are represented in the generated sequencing data used to form a DCS.

In certain embodiments, methods incorporating DS may include ligation of one or more sequencing adapters to a target double-stranded nucleic acid molecule, comprising a first strand target nucleic acid sequence and a second strand target nucleic sequence, to produce a double-stranded target nucleic acid complex (e.g. FIG. 1A).

In various embodiments, a resulting target nucleic acid complex can include at least one SMI sequence, which may entail an exogenously applied degenerate or semi-degenerate sequence, endogenous information related to the specific shear-points of the target double-stranded nucleic acid molecule, or a combination thereof. The SMI can render the target-nucleic acid molecule substantially distinguishable from the plurality of other molecules in a population being sequenced. The SMI element's substantially distinguishable feature can be independently carried by each of the single strands that form the double-stranded nucleic acid molecule such that the derivative amplification products of each strand can be recognized as having come from the same original substantially unique double-stranded nucleic acid molecule after sequencing. In other embodiments the SMI may include additional information and/or may be used in other methods for which such molecule distinguishing functionality is useful, such as those described in the above-referenced publications. In another embodiment, the SMI element may be incorporated after adapter ligation. In some embodiments the SMI is double stranded in nature. In other embodiments it is single stranded in nature. In other embodiments it is a combination of single stranded and double stranded in nature.

In some embodiments, each double-stranded target nucleic acid sequence complex can further include an element (e.g., an SDE) that renders the amplification products of the two single stranded nucleic acids that form the target double-stranded nucleic acid molecule substantially distinguishable from each other after sequencing. In one embodiment, an SDE may comprise asymmetric primer sites comprised within the sequencing adapters, or, in other arrangements, sequence asymmetries may be introduced into the adapter molecules not within the primer sequences, such that at least one position in the nucleotide sequences of the first strand target nucleic acid sequence complex and the second stand of the target nucleic acid sequence complex are different from each other following amplification and sequencing. In other embodiments, the SMI may comprise another biochemical asymmetry between the two strands that differs from the canonical nucleotide sequences A, T, C, G or U, but is converted into at least one canonical nucleotide sequence difference in the two amplified and sequenced molecules. In yet another embodiment, the SDE may be a means of physically separating the two strands before amplification, such that the derivative amplification products from the first strand target nucleic acid sequence and the second strand target nucleic acid sequence are maintained in substantial physical isolation from one and other for the purposes of maintaining a distinction between the two. Other such arrangements or methodologies for providing an SDE function that allows for distinguishing the first and second strands may be utilized, such as those described in the above-referenced publications, or other methods that serves the functional purpose described.

After generating the double-stranded target nucleic acid complex comprising at least one SMI and at least one SDE, or where one or both of these elements will be subsequently introduced, the complex can be subjected to DNA amplification, such as with PCR, or any other biochemical method of DNA amplification (e.g., rolling circle amplification, multiple displacement amplification, isothermal amplification, bridge amplification or surface-bound amplification, such that one or more copies of the first strand target nucleic acid sequence and one or more copies of the second strand target nucleic acid sequence are produced (e.g., FIG. 1B). The one or more amplification copies of the first strand target nucleic acid molecule and the one or more amplification copies of the second target nucleic acid molecule can then be subjected to DNA sequencing, preferably using a "Next-Generation" massively parallel DNA sequencing platform (e.g., FIG. 1B).

The sequence reads produced from either the first strand target nucleic acid molecule and the second strand target nucleic acid molecule derived from the original double-stranded target nucleic acid molecule can be identified based on sharing a related substantially unique SMI and distinguished from the opposite strand target nucleic acid molecule by virtue of an SDE. In some embodiments the SMI may be a sequence based on a mathematically-based error correction code (for example, a Hamming code), whereby certain amplification errors, sequencing errors or SMI synthesis errors can be tolerated for the purpose of relating the sequences of the SMI sequences on complementary strands of an original Duplex (e.g., a double-stranded nucleic acid molecule). For example, with a double stranded exogenous SMI where the SMI comprises 15 base pairs of fully degenerate sequence of canonical DNA bases, an estimated 4^15=1,073,741,824 SMI variants will exist in a population of the fully degenerate SMIs. If two SMIs are recovered from reads of sequencing data that differ by only one nucleotide within the SMI sequence out of a population of 10,000 sampled SMIs, it can be mathematically calculated the probability of this occurring by random chance and a decision made whether it is more probable that the single base pair difference reflects one of the aforementioned types of errors and the SMI sequences could be determined to have in fact derived from the same original duplex molecule. In some embodiments where the SMI is, at least in part, an exogenously applied sequence where the sequence variants are not fully degenerate to each other and are, at least in part, known sequences, the identity of the known sequences can in some embodiments be designed in such a way that one or more errors of the aforementioned types will not convert the identity of one known SMI sequence to that of another SMI sequence, such that the probability of one SMI being misinterpreted as that of another SMI is reduced. In some embodiments this SMI design strategy comprises a Hamming Code approach or derivative thereof. Once identified, one or more sequence reads produced from the first strand target nucleic acid molecule are compared with one or more sequence reads produced from the second strand target nucleic acid molecule to produce an error-corrected target nucleic acid molecule sequence (e.g., FIG. 1C). For example, nucleotide positions where the bases from both the first and second strand target nucleic acid sequences agree are deemed to be true sequences, whereas nucleotide positions that disagree between the two strands are recognized as potential sites of technical errors that may be discounted. An error-corrected sequence of the original double-stranded target nucleic acid molecule can thus be produced (shown in FIG. 1C).

Alternatively, in some embodiments, sites of sequence disagreement between the two strands can be recognized as potential sites of biologically-derived mismatches in the original double stranded target nucleic acid molecule. Alternatively, in some embodiments sites of sequence disagreement between the two strands can be recognized as potential sites of DNA synthesis-derived mismatches in the original double stranded target nucleic acid molecule. Alternatively, in some embodiments sites of sequence disagreement between the two strands can be recognized as potential sites where a damaged or modified nucleotide base was present on one or both strands and was converted to a mismatch by an enzymatic process (for example a DNA polymerase, a DNA glycosylase or another nucleic acid modifying enzyme or chemical process). In some embodiments, this latter finding can be used to infer the presence of nucleic acid damage or nucleotide modification prior to the enzymatic process or chemical treatment.

Figure 2:
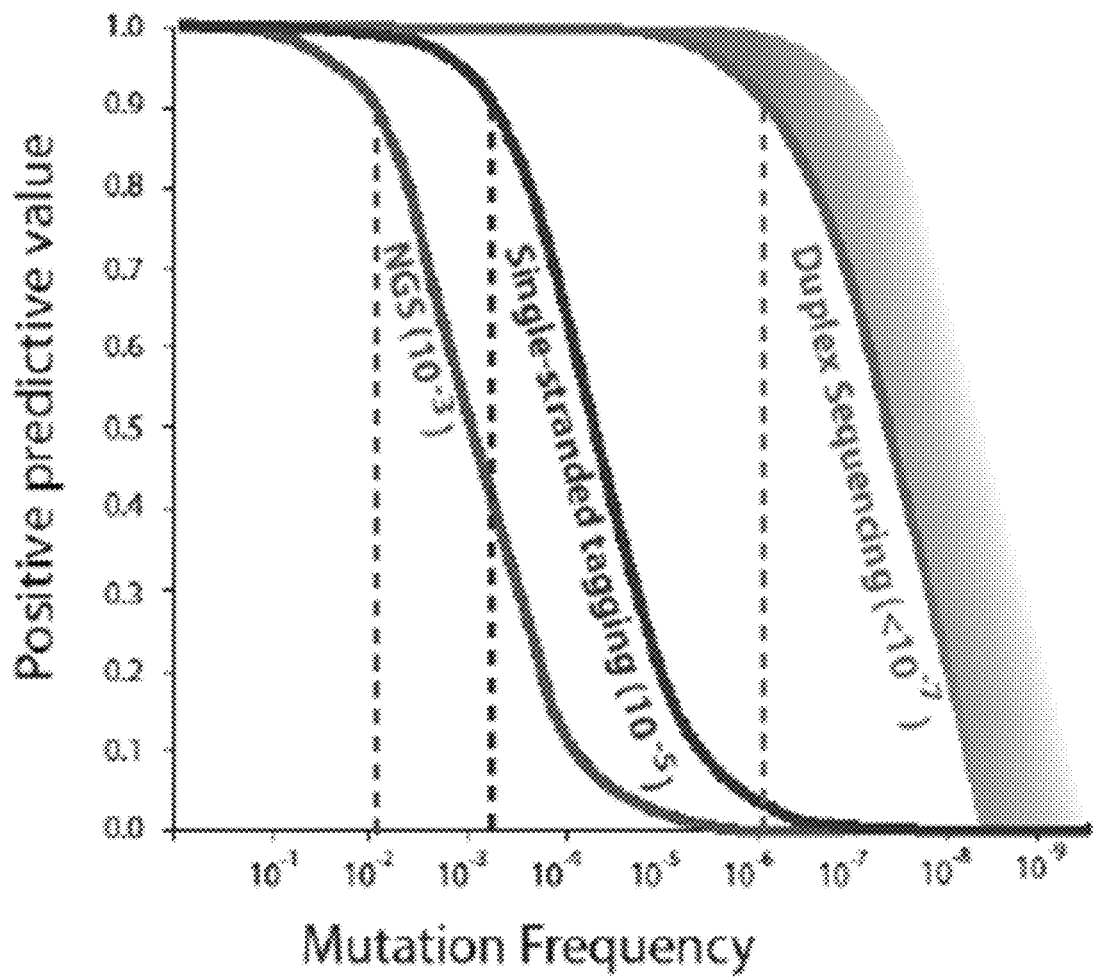
FIG. 2 is a graph plotting positive predictive value as a function of variant allele frequency in a molecular population for Next Generation Sequencing (NGS), single-stranded tag-based error correction, and duplex sequencing error correction in accordance with certain aspects of the present disclosure.

FIG. 2 is a graph plotting theoretical positive predictive value as a function of variant allele frequency in a molecular population for Next Generation Sequencing (NGS), single-stranded tag-based error correction, and duplex sequencing error correction in accordance with certain aspects of the present disclosure. Referring to FIG. 2, the positive predicted value (e.g., the expected number of correct positive calls divided by the total number of positive calls) is plotted as a function of the variant allele frequency in a molecular population for Next Generation Sequencing (NGS), single-stranded tag-based error correction, and DS error correction of a specified error rate. As seen by curve overlap, nearly all mutant calls will be correct using any method if the frequency of detected variants is greater than 1 per 10. However, the error rates of standard Illumina sequencing and single-stranded tag-based error correction result in critical losses in positive predictive value at variant frequencies of ~1 per 100 and 1 per 1,000, respectively. The extremely low error rate conferred by DS enables confident identification of variants below 1 per 100,000 (dotted line).

In some embodiments, and in accordance with aspects of the present technology, sequencing reads generated from the DS steps discussed herein can be further filtered to eliminate sequencing reads from DNA-damaged molecules (e.g., damaged during storage, shipping, during or following tissue or blood extraction, during or following library preparation, etc.). For example, DNA repair enzymes, such as Uracil-DNA Glycosylase (UDG), Formamidopyrimidine DNA glycosylase (FPG), and 8-oxoguanine DNA glycosylase (OGG1), can be utilized to eliminate or correct DNA damage (e.g., in vitro DNA damage or in vivo damage). These DNA repair enzymes, for example, are glycoslyases that remove damaged bases from DNA. For example, UDG removes uracil that results from cytosine deamination (caused by spontaneous hydrolysis of cytosine) and FPG removes 8-oxo-guanine (e.g., a common DNA lesion that results from reactive oxygen species). FPG also has lyase activity that can generate a 1 base gap at abasic sites. Such abasic sites will generally subsequently fail to amplify by PCR, for example, because the polymerase fails to copy the template. Accordingly, the use of such DNA damage repair/ elimination enzymes can effectively remove damaged DNA that doesn't have a true mutation, but might otherwise be undetected as an error following sequencing and duplex sequence analysis. Although an error due to a damaged base can often be corrected by DS in rare cases a complementary error could theoretically occur at the same position on both strands, thus, reducing error-increasing damage can reduce the probability of artifacts. Furthermore, during library preparation certain fragments of DNA to be sequenced may be single-stranded from their source or from processing steps (for example, mechanical DNS shearing). These regions are typically converted to double stranded DNA during an "end repair" step known in the art, whereby a DNA polymerase and nucleoside substrates are added to a DNA sample to extend 5' recessed ends. A mutagenic site of DNA damage in the single-stranded portion of the DNA being copied (i.e. single-stranded 5' overhang at one or both ends of the DNA duplex or internal single-stranded nicks or gaps) can cause an error during the fill-in reaction that could render a single-stranded mutation, synthesis error or site of nucleic acid damage into a double stranded form that could be misinterpreted in the final duplex consensus sequence as a true mutation whereby the true mutation was present in the original double stranded nucleic acid molecule, when, in fact, it was not. This scenario, termed "pseudo-duplex", can be reduced or prevented by use of such damage destroying/ repair enzymes. In other embodiments this occurrence can be reduced or eliminated through use of strategies to destroy or prevent single-stranded portions of the original duplex molecule to form (e.g. use of certain enzymes being used to fragment the original double stranded nucleic acid material rather than mechanical shearing or certain other enzymes that may leave nicks or gaps). In other embodiments use of processes to eliminate single-stranded portions of original double stranded nucleic acids (e.g. single-stand specific nucleases such as Si nuclease or mung bean nuclease) can be utilized for a similar purpose.

In further embodiments, sequencing reads generated from the DS steps discussed herein can be further filtered to eliminate false mutations by trimming ends of the reads most prone to pseudoduplex artifacts. For example, DNA fragmentation can generate single strand portions at the terminal ends of double-stranded molecule. These single-stranded portions can be filled in (e.g., by Klenow or T4 polymerase) during end repair. In some instances, polymerases make copy mistakes in these end repaired regions leading to the generation of "pseudoduplex molecules." These artifacts of library preparation can incorrectly appear to be true mutations once sequenced. These errors, as a result of end repair mechanisms, can be eliminated or reduced from analysis post-sequencing by trimming the ends of the sequencing reads to exclude any mutations that may have occurred in higher risk regions, thereby reducing the number of false mutations. In one embodiment, such trimming of sequencing reads can be accomplished automatically (e.g., a normal process step). In another embodiment, a mutation frequency can be assessed for fragment end regions and if a threshold level of mutations are observed in the fragment end regions, sequencing read trimming can be performed before generating a double-strand consensus sequence read of the DNA fragments.

The high degree of error correction provided by the strand-comparison technology of DS reduces sequencing errors of double-stranded nucleic acid molecules by multiple orders of magnitude as compared with standard next-generation sequencing methods. This reduction in errors improves the accuracy of sequencing in nearly all types of sequences, but can be particularly well suited to biochemically challenging sequences that are well known in the art to be particularly error prone. One non-limiting example of such type of sequence is homopolymers or other microsatellites/short-tandem repeats. Another non-limiting example of error prone sequences that benefit from DS error correction are molecules that have been damaged, for example, by heating, radiation, mechanical stress, or a variety of chemical exposures which creates chemical adducts that are error prone during copying by one or more nucleotide polymerases. In further embodiments, DS can also be used for the accurate detection of minority sequence variants among a population of double-stranded nucleic acid molecules. One non-limiting example of this application is detection of a small number of DNA molecules derived from a cancer, among a larger number of unmutated molecules from non-cancerous tissues within a subject. Another non-limiting application for rare variant detection by DS is forensic detection of the DNA from one individual intermixed at low abundance with the DNA of another individual of a different genotype.

DS has been shown to be highly successful at removing both amplification and sequencing/sequencer derived artifacts in mitochondrial and nuclear DNA. However, certain prior studies have focused on the detection of somatic point mutations and small (e.g., <5 bp) insertions and deletions. In addressing some of the challenges associated with forensic analysis (e.g., removal of PCR stutter, low levels of DNA, intermixed samples, etc.), DS holds significant promise to the forensics community. For example, and in reference to FIGS. 3A and 3B, DS has demonstrated the ability to remove PCR stutter when compared to conventional MPS. In this example, three representative CODIS loci from 10 ng Promega 2800M standard reference material DNA were sequenced using conventional MPS (FIG. 3A) and DS (FIG. 3B) on an Illumina MiSeq platform with 300 bp paired-end reads, and data were visualized with STRait-Razor STR allele-calling tool. FIG. 3A show three graphs showing CODIS genotype for each of the three CODIS loci versus a number of sequencing reads in the absence of error correction (e.g., conventional MPS) and show several stutter events (black arrows). In comparison, and as shown in FIG. 3B, DS eliminated the stutter events for the same three CODIS loci Similar results are seen at all original CODIS 13 loci. Accordingly, various aspects of DS technology can overcome some of the limitations experienced by conventional methodologies with respect to forensic analysis. Other aspects of forensic analysis, in addition to other applications of DS, may also benefit from any improvements to various aspects of conversion efficiency, or the percentage of input DNA that is converted to error-corrected sequence data. Forensic analysis may refer to applications related to human crime, natural disasters, mass casualty incidents, animal or other life-kingdom poaching, trafficking or misuse, human or animal remains identification, assault identification, missing persons identification, sexual assault identification, paleontological applications, and archeological applications among others.

With regard to the efficiency of a DS process, two types of efficiency are further described herein: conversion efficiency and workflow efficiency. For the purposes of discussing efficiency of DS, conversion efficiency can be defined as the fraction of unique nucleic acid molecules inputted into a sequencing library preparation reaction from which at least one duplex consensus sequence read is produced. Workflow efficiency may relate to relative inefficiencies with the amount of time, relative number of steps and/or financial cost of reagents/materials needed to carry out these steps to produce a Duplex Sequencing library and/or carry out targeted enrichment for sequences of interest.

In some instances, either or both conversion efficiency and workflow efficiency limitations may limit the utility of high-accuracy DS for some applications where it would otherwise be very well suited. For example, a low conversion efficiency would result in a situation where the number of copies of a target double-stranded nucleic acid is limited, which may result in a less than desired amount of sequence information produced. Non-limiting examples of this concept include DNA from circulating tumor cells or cell-free DNA derived from tumors, or prenatal infants that are shed into body fluids such as plasma and intermixed with an excess of DNA from other tissues. Although DS typically has the accuracy to be able to resolve one mutant molecule among more than one hundred thousand unmutated molecules, if only 10,000 molecules are available in a sample, for example, and even with the ideal efficiency of converting these to duplex consensus sequence reads being 100%, the lowest mutation frequency that could be measured would be 1/(10,000*100%)=1/10,000. As a clinical diagnostic, having maximum sensitivity to detect the low level signal of a cancer or a therapeutically-relevant mutation can be important and so a relatively low conversion efficiency would be undesirable in this context. Similarly, in forensic applications, often very little DNA is available for testing. When only nanogram or picogram quantities can be recovered from a crime scene or site of a natural disaster, and where the DNA from multiple individuals is mixed together, having maximum conversion efficiency can be important in being able to detect the presence of the DNA of all individuals within the mixture.

In some instances, workflow inefficiencies can be similarly challenging for certain nucleic acid interrogation applications. One non-limiting example of this is in clinical microbiology testing. Sometimes it is desired to rapidly detect the nature of one or more infectious organisms, for example, a microbial or polymicrobial bloodstream infection where some organisms are resistant to particular antibiotics based on a unique genetic variant they carry, but the time it takes to culture and empirically determine antibiotic sensitivity of the infectious organisms is much longer than the time within which a therapeutic decision about antibiotics to be used for treatment must be made. DNA sequencing of DNA from the blood (or other infected tissue or body fluid) has the potential to be more rapid, and DS among other high accuracy sequencing methods, for example, could very accurately detect therapeutically important minority variants in the infectious population based on DNA signature. As workflow turn-around time to data generation can be critical for determining treatment options (e.g., as in the example used herein), applications to increase the speed to arrive at data output would also be desirable.

Disclosed further herein are methods and compositions for targeted nucleic acid sequence enrichment and uses of such enrichment for error-corrected nucleic acid sequencing applications that provide improvement in the cost, conversion of molecules sequenced and the time efficiency of generating labeled molecules for targeted ultra-high accuracy sequencing.

Figure 4:
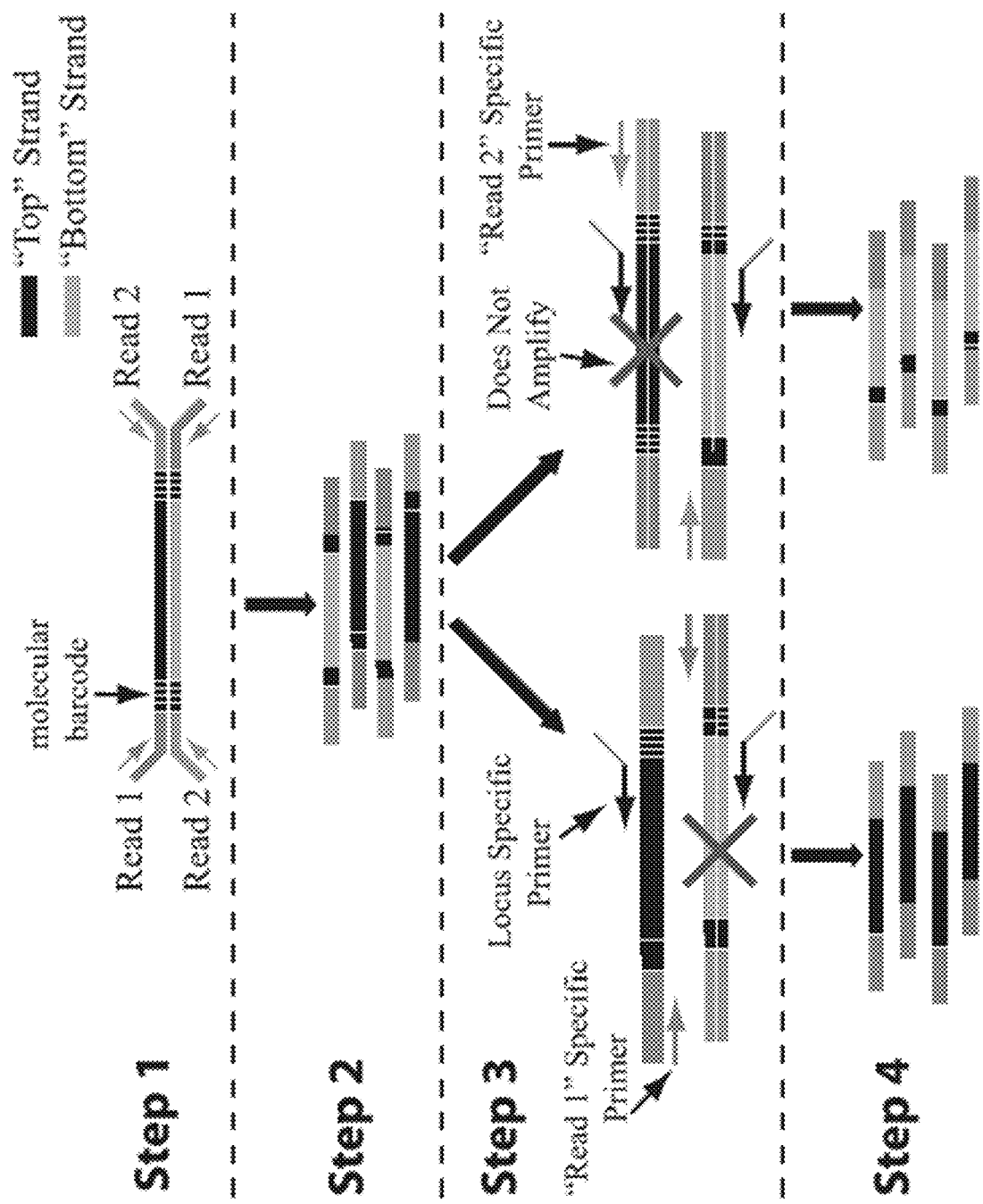
FIG. 4 is a conceptual illustration of SPLiT-DS method steps in accordance with an embodiment of the present technology.

SPLiT-DS in some embodiments, provided methods provide PCR-based targeted enrichment strategies compatible with the use of molecular barcodes for error correction. FIG. 4 is a conceptual illustration of a sequencing enrichment strategy utilizing Separated PCRs of Linked Templates for sequencing ("SPLiT-DS") method steps in accordance with an embodiment of the present technology. Referring to FIG. 4, and in one embodiment, a SPLiT-DS approach can begin with labelling (e.g., tagging) fragmented double-stranded nucleic acid material (e.g., from a DNA sample) with molecular barcodes in a similar manner as described above and with respect to a standard DS library construction protocol (e.g., as illustrated in FIG. 1B). In some embodiments, the double-stranded nucleic acid material may be fragmented (e.g., such as with cell free DNA, damaged DNA, etc.); however, in other embodiments, various steps can include fragmentation of the nucleic acid material using mechanical shearing such as sonication or other DNA cutting methods, such as described further herein. Aspects of labelling the fragmented double-stranded nucleic acid material can include end-repair and 3'-dA-tailing, if required in a particular application, followed by ligation of the double-stranded nucleic acid fragments with DS adapters containing an SMI (FIG. 4, Step 1). In other embodiments, the SMI can be endogenous or a combination of exogenous and endogenous sequence for uniquely relating information from both strands of an original nucleic acid molecule. Following ligation of adapter molecules to the double-stranded nucleic acid material, the method can continue with amplification (e.g., PCR amplification, rolling circle amplification, multiple displacement amplification, isothermal amplification, bridge amplification, surface-bound amplification, etc.) (FIG. 4, Step 2).

In certain embodiments, primers specific to, for example, one or more adapter sequences, can be used to amplify each strand of the nucleic acid material resulting in multiple copies of nucleic acid amplicons derived from each strand of an original double strand nucleic acid molecule, with each amplicon retaining the originally associated SMI (FIG. 4, Step 2). After amplification and associated steps to remove reaction byproducts, the sample can be split (preferably, but not necessarily, substantially evenly) into two or mom separate samples (e.g., in tubes, in emulsion droplets, in microchambers, isolated droplets on a surface, or other known vessels, collectively referred to as "tube(s)") (FIG. 4, Step 3). Alternately, the amplified products of the amplification may be split in a way that does not require them to be in solution, for example, binding to microbeads followed by dividing the population of microbeads into two chambers or affixing the divided amplified products to two or more distinct physical locations on a surface. Herein, we similarly term any of these latter such divided populations as functionally equivalent and being in distinct "tubes". In the example shown in FIG. 4, this step results in an average of half of the copies of any given strand/barcode amplicon being found in each tube. In other embodiments in which the original sample is split into more than two separate samples, such allocation of nucleic acid material will result in relatively comparable reduced numbers of amplicons. It should be noted that the random nature in which amplicons are split results in a variance about this mean. To take this variance into account, the hypergeometric distribution (i.e. probability of picking k barcode copies without replacement) can be used as a model to determine the minimum number of amplicons (e.g., PCR copies) of a SMI (e.g., barcode) that are needed to maximize the chance that each tube contains at least one copy derived from both strands. Without wishing to be held to a particular theory, it is contemplated that ≥4 PCR cycles (i.e. $2^4$=16 copies/barcode) during Step 2 ensures a >99% probability that each barcode copy derived from each strand will be represented at least once in each tube. In some embodiments it may be preferable to split the amplified products non-evenly. If the nucleic acid material is divided among more than two tubes, additional amplification cycles may be used to generate additional copies to accommodate the further division. After splitting the sample into two tubes, target nucleic acid region(s) (e.g., regions of interest, loci, etc.) can be enriched with multiplex PCR using primer(s) specific for an adapter sequence and primer(s) specific to the target nucleic acid region(s) of interest (FIG. 4, Step 3). In another embodiment, a linear amplification step may be added prior to the subsequent additional of second primer that allows for exponential amplification of the target region of interest.

In certain embodiments, the multiplexed target-specific PCRs are performed such that the resulting PCR products in each tube are derived from only one of the two strands (e.g., "top strand" or "bottom strand"). As shown in FIG. 4 (Step 3), this is achieved, in some embodiments, as follows: In a first tube (shown on the left), a primer at least partially complementary to "Read 1" (e.g., Illumina P5) of the adapter sequence (FIG. 4, Step 3; grey arrow), and a primer at least partially complementary to the nucleic acid region of interest and containing a "Read 2" (i.e. Illumina P7, black arrow w/grey tail) adapter sequence are used to specifically amplify (e.g., enrich) the "top strand" of the original nucleic acid molecule (FIG. 4, Steps 3 and 4). In this first sample, and because of the nature of the SDE (e.g., in this case unique adapter sequence orientation with respect to the target nucleic acid insert), the "bottom strand" does not amplify properly. Likewise, in a second tube (shown on the right), a primer at least partially complementary to "Read 2" (e.g., Illumina P5) of the adapter sequence (FIG. 4, Step 3, grey arrow) and a primer at least partially complementary to the nucleic acid region of interest and containing a "Read 1" (i.e. Illumina P7, black arrow w/grey tail) adapter sequence are used to specifically amplify (e.g., enrich) the "bottom strand" of the original nucleic acid molecule (FIG. 4, Steps 3 and 4). In this second sample, the "top strand" does not amplify properly. Following PCR, or other amplification method, a plurality of copies of the "top strand" are generated in the first tube and a plurality of copies of the "bottom strand" are generated in the second tube. As each of these resultant target-specific copies have both adapter sequences available on each end of the nucleic acid amplicon (e.g., Illumina P5 and Illumina P7 adapter sequences), these target enriched products can be sequenced using standard MPS methods.

Figure 5:
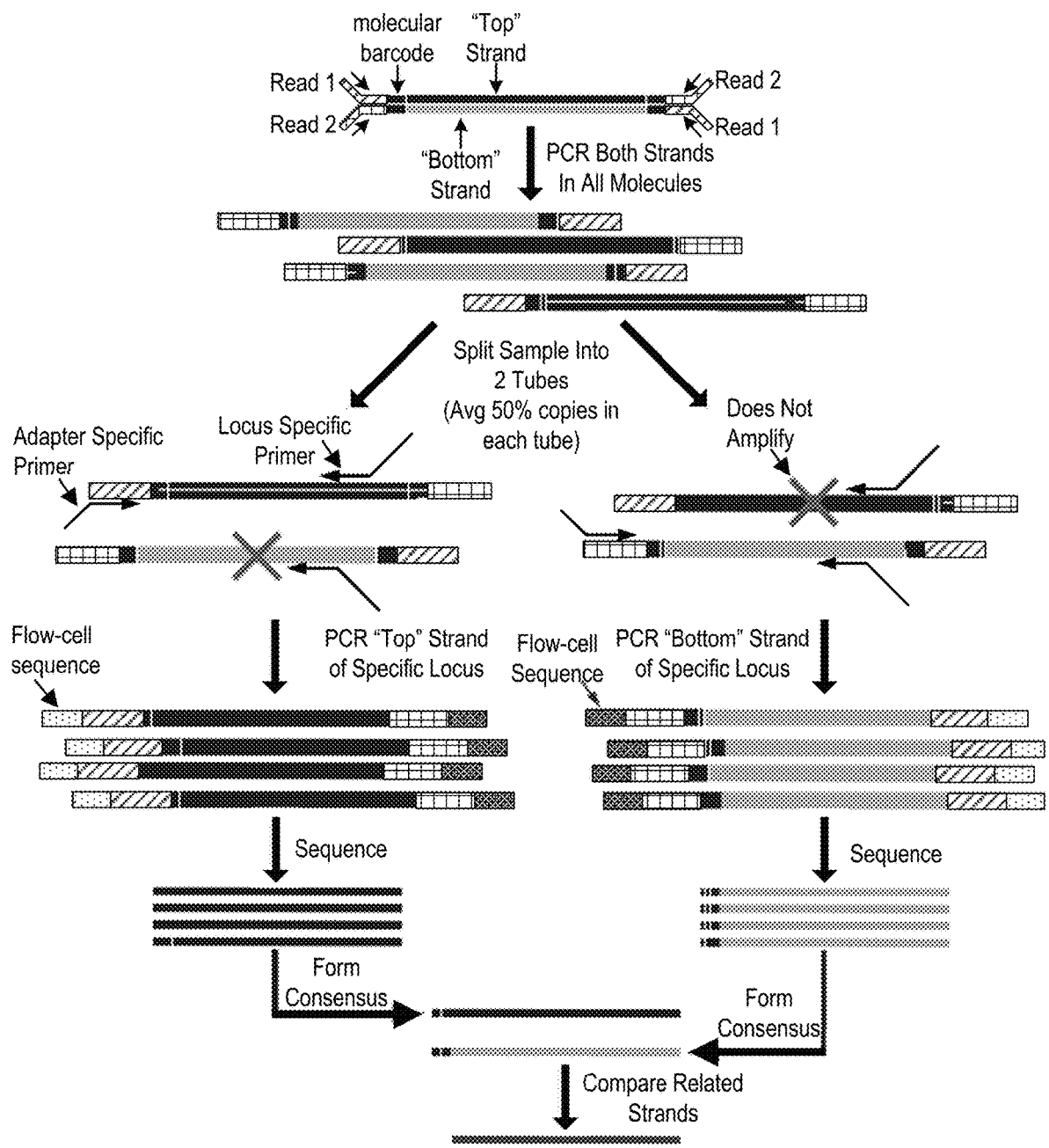
FIG. 5 is a conceptual illustration of SPLiT-DS method steps and showing steps for generating a duplex consensus sequence in accordance with an embodiment of the present technology.
Figure 6:
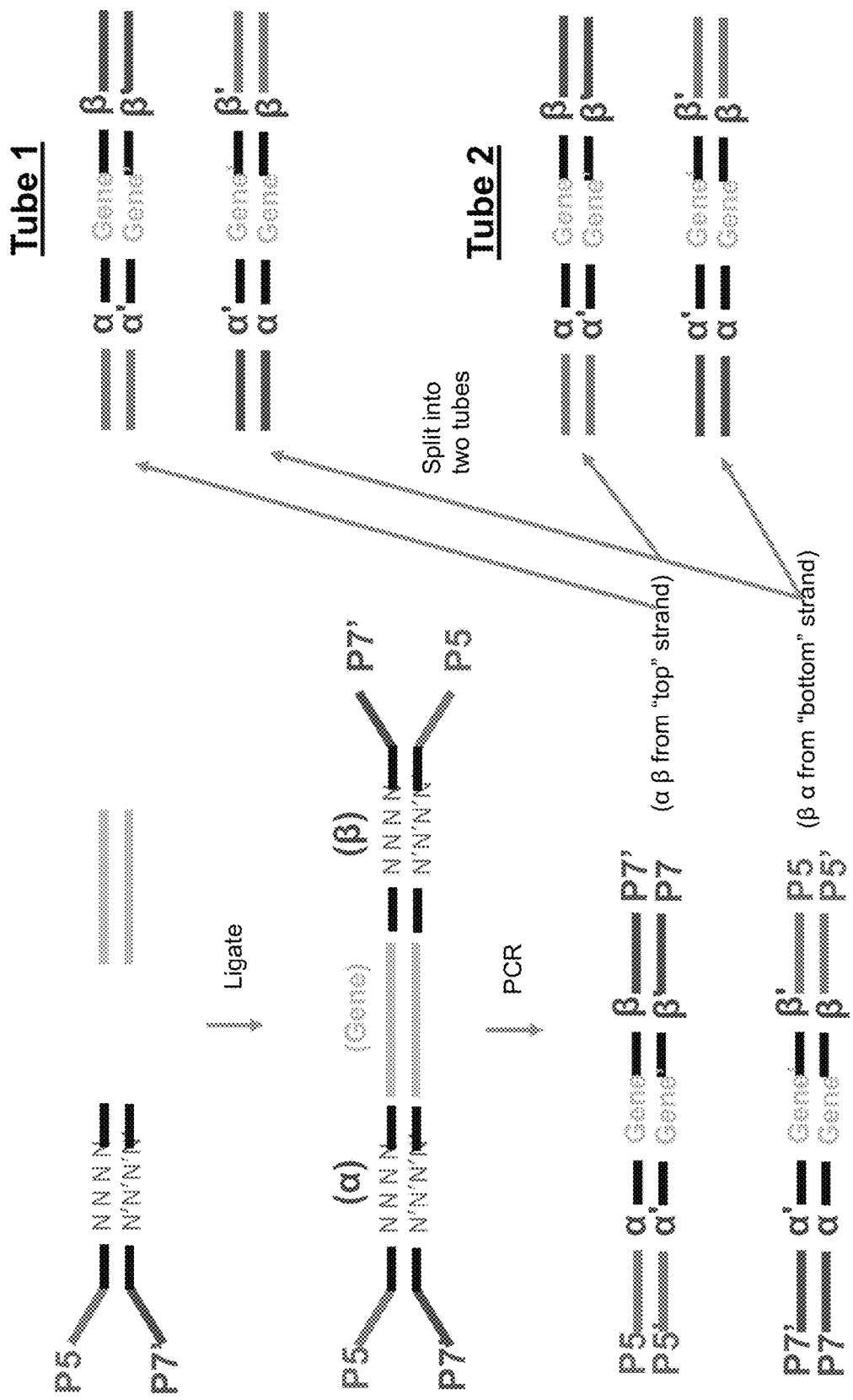
FIG. 6 is a conceptual illustration of various SPLiT-DS method steps in accordance with an embodiment of the present technology.

FIG. 5 is a conceptual illustration of SPLiT-DS method steps as shown and discussed with respect to FIG. 4, and further showing steps for sequencing the multiple copies of each PCR enriched target region and generating a duplex consensus sequence in accordance with an embodiment of the present technology. Following sequencing of the multiple copies of the "top strand" from the first tube and the multiple copies of the "bottom strand" from the second tube, sequencing data can be analyzed in an approach similar to DS, whereby sequencing reads sharing the same molecular barcode that are derived from the 'top' or 'bottom' strand of the original double stranded target nucleic acid molecule (which are found in the first tube and second tube, respectively) are separately grouped. In some embodiments, the grouped sequencing reads from the "top strand" are used to form a top strand consensus sequence (e.g., a single-strand consensus sequence (SSCS)) and the grouped sequencing reads from the "bottom strand" are used to form a bottom strand consensus sequence (e.g., SSCS). Referring to FIG. 5, the top and bottom SSCSs can then be compared to generate a duplex consensus sequence (DCS) having nucleotides that are in agreement between the two strands (e.g., variants or mutations are considered to be true if they appear in sequencing reads derived from both strands (see, e.g., FIG. 1C).

By way of specific example, in some embodiments, provided herein are methods of generating an error-corrected sequence read of a double-stranded target nucleic acid material, including the step of ligating a double-stranded target nucleic acid material to at least one adapter sequence, to form an adapter-target nucleic acid material complex, wherein the at least one adapter sequence comprises (a) a degenerate or semi-degenerate single molecule identifier (SMI) sequence that uniquely labels each molecule of the double-stranded target nucleic acid material, and (b) a first nucleotide adapter sequence that tags a first strand of the adapter-target nucleic acid material complex, and a second nucleotide adapter sequence that is at least partially non-complimentary to the first nucleotide sequence that tags a second strand of the adapter-target nucleic acid material complex such that each strand of the adapter-target nucleic acid material complex has a distinctly identifiable nucleotide sequence relative to its complementary strand. The method can next include the steps of amplifying each strand of the adapter-target nucleic acid material complex to produce a plurality of first strand adapter-target nucleic acid complex amplicons and a plurality of second strand adapter-target nucleic acid complex amplicons, and separating the adapter-target nucleic acid complex amplicons into a first sample and a second sample. The method can further include the steps of amplifying the first strand in the first sample through use of a first primer at least partially complimentary to the first nucleotide adapter sequence and a primer at least partially complimentary to a target sequence of interest to provide a first nucleic acid product, and amplifying the second strand in the second sample through use of a second primer at least partially complimentary to the second nucleotide adapter sequence and a primer at least partially complimentary to the target sequence of interest to provide a second nucleic acid product. The method may also include the steps of sequencing each of the first nucleic acid product and second nucleic acid product to produce a plurality of first strand sequence reads and plurality of second strand sequence reads, and confirming the presence of at least one first strand sequence read and at least one second strand sequence read. The method may further include comparing the at least one first strand sequence read with the at least one second strand sequence read, and generating an error-corrected sequence read of the double-stranded target nucleic acid material by discounting nucleotide positions that do not agree, or alternatively removing compared first and second strand sequence reads having one or more nucleotide positions where the compared first and second strand sequence reads are non-complementary.

By way of additional specific example, in some embodiments, provided herein are methods of identifying a DNA variant from a sample including the steps of ligating both strands of a nucleic acid material (e.g., a double-stranded target DNA molecule) to at least one asymmetric adapter molecule to form an adapter-target nucleic acid material complex having a first nucleotide sequence associated with a top strand of a double-stranded target DNA molecule and a second nucleotide sequence that is at least partially non-complementary to the first nucleotide sequence associated with a bottom strand of the double-stranded target DNA molecule, and amplifying each strand of the adapter-target nucleic acid material, resulting in each strand generating a distinct yet related set of amplified adapter-target DNA products. The method can also include the steps of separating the adapter-target DNA products into a first sample and a second sample, amplifying the top strand of the adapter-target DNA products in the first sample through use of a first primer specific (e.g., at least partially complimentary) to the first nucleotide sequence and a primer at least partially complimentary to a target sequence of interest to provide a top strand adapter-target nucleic acid complex amplicon, and amplifying the bottom strand in the second sample through use of a second primer specific (e.g., at least partially complimentary) to the second nucleotide sequence and the second primer to provide a bottom strand adapter-target nucleic acid complex amplicon. The method can further include the steps of sequencing each of the top strand adapter-target nucleic acid complex amplicon and bottom strand adapter-target nucleic acid complex amplicon, confirming the presence of at least one amplified sequence read from each strand of the adapter-target DNA complex, and comparing the at least one amplified sequence read obtained from the top strand with the at least one amplified sequence read obtained from the bottom strand to form a consensus sequence read of the nucleic acid material (e.g., a double-stranded target DNA molecule) having only nucleotide bases at which the sequence of both strands of the nucleic acid material (e.g., a double-stranded target DNA molecule) are in agreement, such that a variant occurring at a particular position in the consensus sequence read is identified as a true DNA variant.

In some embodiments, provided herein are methods of generating an error-corrected double-stranded consensus sequence from a double-stranded nucleic acid material, including the steps of tagging individual duplex DNA molecules with an adapter molecule to form tagged DNA material, wherein each adapter molecule comprises (a) a degenerate or semi-degenerate single molecule identifier (SMI) that uniquely labels the duplex DNA molecule, and (b) first and second non-complementary nucleotide adapter sequences that distinguishes an original top strand from an original bottom strand of each individual DNA molecule within the tagged DNA material, for each tagged DNA molecule, and generating a set of duplicates of the original top strand of the tagged DNA molecule and a set of duplicates of the original bottom strand of the tagged DNA molecule to form amplified DNA material. The method can also include the steps of separating the amplified DNA material into a first sample and a second sample, generating additional duplicates of the original top strand in the first sample through use of a primer specific to a first nucleotide adapter sequence and a primer at least partially complimentary to a target sequence of interest to provide a first nucleic acid product, and generating additional duplicates of the original bottom strand in the second sample through use of a primer specific to a second nucleotide adapter sequence and the (same or different) primer at least partially compli-mentary to the target sequence of interest to provide a second nucleic acid product. The method can further include the steps of creating a first single strand consensus sequence (SSCS) from the additional duplicates of the original top strand and a second single strand consensus sequence (SSCS) from the additional duplicates of the original bottom strand, comparing the first SSCS of the original top strand to the second SSCS of the original bottom strand, and generating an error-corrected double-stranded consensus sequence having only nucleotide bases at which the sequence of both the first SSCS of the original top strand and the second SSCS of the original bottom strand are complimentary.

Single Molecule Identifier Sequences (SMIs)

In accordance with various embodiments, provided methods and compositions include one or more SMI sequences on each strand of a nucleic acid material. The SMI can be independently carried by each of the single strands that result from a double-stranded nucleic acid molecule such that the derivative amplification products of each strand can be recognized as having come from the same original substantially unique double-stranded nucleic acid molecule after sequencing. In some embodiments, the SMI may include additional information and/or may be used in other methods for which such molecule distinguishing functionality is useful, as will be recognized by one of skill in the art. In some embodiments, an SMI element may be incorporated before, substantially simultaneously, or after adapter sequence ligation to a nucleic acid material.

In some embodiments, an SMI sequence may include at least one degenerate or semi-degenerate nucleic acid. In other embodiments, an SMI sequence may be non-degenerate. In some embodiments, the SMI can be the sequence associated with or near a fragment end of the nucleic acid molecule (e.g., randomly or semi-randomly sheared ends of ligated nucleic acid material). In some embodiments, an exogenous sequence may be considered in conjunction with the sequence corresponding to randomly or semi-randomly sheared ends of ligated nucleic acid material (e.g., DNA) to obtain an SMI sequence capable of distinguishing, for example, single DNA molecules from one another. In some embodiments, a SMI sequence is a portion of an adapter sequence that is ligated to a double-strand nucleic acid molecule. In certain embodiments, the adapter sequence comprising a SMI sequence is double-stranded such that each strand of the double-stranded nucleic acid molecule includes an SMI following ligation to the adapter sequence. In another embodiment, the SMI sequence is single-stranded before or after ligation to a double-stranded nucleic acid molecule and a complimentary SMI sequence can be generated by extending the opposite strand with a DNA polymerase to yield a complementary double-stranded SMI sequence. In some embodiments, each SMI sequence may include between about 1 to about 30 nucleic acids (e.g., 1, 2, 3, 4, 5, 8, 10, 12, 14, 16, 18, 20, or more degenerate or semi-degenerate nucleic acids).

In some embodiments, a SMI is capable of being ligated to one or both of a nucleic acid material and an adapter sequence. In some embodiments, a SMI may be ligated to at least one of a T-overhang, an A-overhang, a CG-overhang, a dehydroxylated base, and a blunt end of a nucleic acid material.

In some embodiments, a sequence of a SMI may be considered in conjunction with (or designed in accordance with) the sequence corresponding to, for example, randomly or semi-randomly sheared ends of a nucleic acid material (e.g., a ligated nucleic acid material), to obtain a SMI sequence capable of distinguishing single nucleic acid molecules from one another.

In some embodiments, at least one SMI may be an endogenous SMI (e.g., an SMI related to a shear point, for example, using the shear point itself or using a defined number of nucleotides in the nucleic acid material immediately adjacent to the shear point [e.g., 2, 3, 4, 5, 6, 7, 8, 9, 10 nucleotides from the shear point]). In some embodiments, at least one SMI may be an exogenous SMI (e.g., an SMI comprising a sequence that is not found on a target nucleic acid material).

In some embodiments, a SMI may be or comprise an imaging moiety (e.g., a fluorescent or otherwise optically detectable moiety). In some embodiments, such SMIs allow for detection and/or quantitation without the need for an amplification step.

In some embodiments a SMI element may comprise two or more distinct SMI elements that are located at different locations on the adapter-target nucleic acid complex.

Various embodiments of SMIs are further disclosed in International Patent Publication No. WO2017/100441, which is incorporated by reference herein in its entirety.

Strand-Defining Element (SDE)

In some embodiments, each strand of a double-stranded nucleic acid material may further include an element that renders the amplification products of the two single stranded nucleic acids that form the target double-stranded nucleic acid material substantially distinguishable from each other after sequencing. In some embodiments, a SDE may be or comprise asymmetric primer sites comprised within a sequencing adapter, or, in other arrangements, sequence asymmetries may be introduced into the adapter sequences and not within the primer sequences, such that at least one position in the nucleotide sequences of a first strand target nucleic acid sequence complex and a second stand of the target nucleic acid sequence complex are different from each other following amplification and sequencing. In other embodiments, the SDE may comprise another biochemical asymmetry between the two strands that differs from the canonical nucleotide sequences A, T, C, G or U, but is converted into at least one canonical nucleotide sequence difference in the two amplified and sequenced molecules. In yet another embodiment, the SDE may be or comprise a means of physically separating the two strands before amplification, such that the derivative amplification products from the first strand target nucleic acid sequence and the second strand target nucleic acid sequence are maintained in substantial physical isolation from one another for the purposes of maintaining a distinction between the two derivative amplification products. Other such arrangements or methodologies for providing an SDE function that allows for distinguishing the first and second strands may be utilized.

In some embodiments, an SDE may be capable of forming a loop (e.g., a hairpin loop). In some embodiments, a loop may comprise at least one endonuclease recognition site. In some embodiments the target nucleic acid complex may contain an endonuclease recognition site that facilitates a cleavage event within the loop. In some embodiments a loop may comprise a non-canonical nucleotide sequence. In some embodiments the contained non-canonical nucleotide may be recognizable by one or more enzyme that facilitates strand cleavage. In some embodiments the contained non-canonical nucleotide may be targeted by one or more chemical process facilitates strand cleavage in the loop. In some embodiments the loop may contain a modified nucleic acid linker that may be targeted by one or more enzymatic, chemical or physical process that facilitates strand cleavage in the loop. In some embodiments this modified linker is a photocleavable linker.

A variety of other molecular tools could serve as SMIs and SDEs. Other than shear points and DNA-based tags, single-molecule compartmentalization methods that keep paired strands in physical proximity or other non-nucleic acid tagging methods could serve the strand-relating function. Similarly, asymmetric chemical labelling of the adapter strands in a way that they can be physically separated can serve an SDE role. A recently described variation of DS uses bisulfite conversion to transform naturally occurring strand asymmetries in the form of cytosine methylation into sequence differences that distinguish the two strands. Although this implementation limits the types of mutations that can be detected, the concept of capitalizing on native asymmetry is noteworthy in the context of emerging sequencing technologies that can directly detect modified nucleotides. Various embodiments of SDEs are further disclosed in International Patent Publication No. WO2017/100441, which is incorporated by reference in its entirety.

Adapters and Adapter Sequences

In various arrangements, adapter molecules that comprise SMIs (e.g., molecular barcodes), SDEs, primer sites, flow cell sequences and/or other features are contemplated for use with many of the embodiments disclosed herein. In some embodiments, provided adapters may be or comprise one or more sequences complimentary or at least partially complimentary to PCR primers (e.g., primer sites) that have at least one of the following properties: 1) high target specificity; 2) capable of being multiplexed; and 3) exhibit robust and minimally biased amplification.

In some embodiments, adapter molecules can be "Y"-shaped, "U"-shaped, "hairpin" shaped, have a bubble (e.g., a portion of sequence that is non-complimentary), or other features. In other embodiments, adapter molecules can comprise a "Y"-shape, a "U"-shaped, a "hairpin" shaped, or a bubble. Certain adapters may comprise modified or non-standard nucleotides, restriction sites, or other features for manipulation of structure or function in vitro. Adapter molecules may ligate to a variety of nucleic acid material having a terminal end. For example, adapter molecules can be suited to ligate to a T-overhang, an A-overhang, a CG-overhang, a multiple nucleotide overhang, a dehydroxylated base, a blunt end of a nucleic acid material and the end of a molecule were the 5' of the target is dephosphorylated or otherwise blocked from traditional ligation. In other embodiments the adapter molecule can contain a dephosphorylated or otherwise ligation-preventing modification on the 5' strand at the ligation site. In the latter two embodiments such strategies may be useful for preventing dimerization of library fragments or adapter molecules.

An adapter sequence can mean a single strand sequence, a double-strand sequence, a complimentary sequence, a non-complimentary sequence, a partial complimentary sequence, an asymmetric sequence, a primer binding sequence, a flow-cell sequence, a ligation sequence or other sequence provided by an adapter molecule. In particular embodiments, an adapter sequence can mean a sequence used for amplification by way of compliment to an oligonucleotide.

In some embodiments, provided methods and compositions include at least one adapter sequence (e.g., two adapter sequences, one on each of the 5' and 3' ends of a nucleic acid material). In some embodiments, provided methods and compositions may comprise 2 or more adapter sequences (e.g., 3, 4, 5, 6, 7, 8, 9, 10 or more). In some embodiments, at least two of the adapter sequences differ from one another (e.g., by sequence). In some embodiments, each adapter sequence differs from each other adapter sequence (e.g., by sequence). In some embodiments, at least one adapter sequence is at least partially non-complementary to at least a portion of at least one other adapter sequence (e.g., is non-complementary by at least one nucleotide).

In some embodiments, an adapter sequence comprises at least one non-standard nucleotide. In some embodiments, a non-standard nucleotide is selected from an abasic site, a uracil, tetrahydrofuran, 8-oxo-7,8-dihydro-2'deoxyadenosine (8-oxo-A), 8-oxo-7,8-dihydro-2'-deoxyguanosine (8-oxo-G), deoxyinosine, 5'nitroindole, 5-Hydroxymethyl-2'-deoxycytidine, iso-cytosine, 5'-methyl-isocytosine, or isoguanosine, a methylated nucleotide, an RNA nucleotide, a ribose nucleotide, an 8-oxo-guanine, a photocleavable linker, a biotinylated nucleotide, a desthiobiotin nucleotide, a thiol modified nucleotide, an acrydite modified nucleotide an iso-dC, an iso dG, a 2'-O-methyl nucleotide, an inosine nucleotide Locked Nucleic Acid, a peptide nucleic acid, a 5 methyl dC, a 5-bromo deoxyuridine, a 2,6-Diaminopurine, 2-Aminopurine nucleotide, an abasic nucleotide, a 5-Nitroindole nucleotide, an adenylated nucleotide, an azide nucleotide, a digoxigenin nucleotide, an I-linker, an 5' Hexynyl modified nucleotide, an 5-Octadiynyl dU, photocleavable spacer, a non-photocleavable spacer, a click chemistry compatible modified nucleotide, and any combination thereof.

In some embodiments, an adapter sequence comprises a moiety having a magnetic property (i.e., a magnetic moiety). In some embodiments this magnetic property is paramagnetic. In some embodiments where an adapter sequence comprises a magnetic moiety (e.g., a nucleic acid material ligated to an adapter sequence comprising a magnetic moiety), when a magnetic field is applied, an adapter sequence comprising a magnetic moiety is substantially separated from adapter sequences that do not comprise a magnetic moiety (e.g., a nucleic acid material ligated to an adapter sequence that does not comprise a magnetic moiety).

In some embodiments, at least one adapter sequence is located 5' to a SMI. In some embodiments, at least one adapter sequence is located 3' to a SMI.

In some embodiments, an adapter sequence may be linked to at least one of a SMI and a nucleic acid material via one or more linker domains. In some embodiments, a linker domain may be comprised of nucleotides. In some embodiments, a linker domain may include at least one modified nucleotide or non-nucleotide molecules (for example, as described elsewhere in this disclosure). In some embodiments, a linker domain may be or comprise a loop.

In some embodiments, an adapter sequence on either or both ends of each strand of a double-stranded nucleic acid material may further include one or more elements that that provide a SDE. In some embodiments, a SDE may be or comprise asymmetric primer sites comprised within the adapter sequences.

In some embodiments, an adapter sequence may be or comprise at least one SDE and at least one ligation domain (i.e., a domain amendable to the activity of at least one ligase, for example, a domain suitable to ligating to a nucleic acid material through the activity of a ligase). In some embodiments, from 5' to 3', an adapter sequence may be or comprise a primer binding site, a SDE, and a ligation domain.

Various methods for synthesizing DS adapters have been previously described in, e.g., U.S. Pat. No. 9,752,188 and International Patent Publication No. WO2017/100441, which are both incorporated by reference herein in their entireties.

Primers

In some embodiments, one or more PCR primers that have at least one of the following properties: 1) high target specificity; 2) capable of being multiplexed; and 3) exhibit robust and minimally biased amplification are contemplated for use in various embodiments in accordance with aspects of the present technology. A number of prior studies and commercial products have designed primer mixtures satisfying certain of these criteria for conventional PCR-CE. However, it has been noted that these primer mixtures are not always optimal for use with MPS. Indeed, developing highly multiplexed primer mixtures can be a challenging and time consuming process. Conveniently, both Illumina and Promega have recently developed multiplex compatible primer mixtures for the Illumina platform that show robust and efficient amplification of a variety of standard and non-standard STR and SNP loci. Because these kits use PCR to amplify their target regions prior to sequencing, the 5'-end of each read in paired-end sequencing data corresponds to the 5'-end of the PCR primers used to amplify the DNA. In some embodiments, provided methods and compositions include primers designed to ensure uniform amplification, which may entail varying reaction concentrations, melting temperatures, and minimizing secondary structure and intra/inter-primer interactions. Many techniques have been described for highly multiplexed primer optimization for MPS applications. In particular, these techniques are often known as ampliseq methods, as well described in the art.

Amplification

Provided methods and compositions, in various embodiments, make use of, or are of use in, at least one amplification step wherein a nucleic acid material (or portion thereof, for example, a specific target region or locus) is amplified to form an amplified nucleic acid material (e.g., some number of amplicon products). In some embodiments, provided methods include a step of separating an amplified nucleic acid material into, for example, a first and second sample.

In some embodiments, amplifying a nucleic acid material in a first sample includes a step of amplifying nucleic acid material derived from a single nucleic acid strand from an original double-stranded nucleic acid material using at least one single-stranded oligonucleotide at least partially complementary to a sequence present in a first adapter sequence and at least one single-stranded oligonucleotide at least partially complementary to a target sequence of interest such that a SMI sequence is at least partially maintained.

In some embodiments, amplifying a nucleic acid material in a second sample includes a step of amplifying the nucleic acid material in a second sample includes amplifying nucleic acid material derived from a single nucleic acid strand from an original double-stranded nucleic acid material using at least one single-stranded oligonucleotide at least partially complementary to a sequence present in the second adapter sequence and at least one single-stranded oligonucleotide at least partially complementary to a target sequence of interest such that the SMI sequence is at least partially maintained.

In some embodiments, an amplified nucleic acid material may be separated into 3 or more samples (e.g., 4, 5, 6, 7, 8, 9, 20, 20, 30, 40, 50 or more samples) prior to a second amplification step. In some embodiments, each sample includes substantially the same amount of amplified nucleic acid material as each other sample. In some embodiments, at least two samples include substantially different amounts of amplified nucleic acid material.

In some embodiments, amplifying nucleic acid material in a first sample or a second sample can include amplifying samples in "tubes" (e.g., PCR tubes), in emulsion droplets, microchambers, and other examples described above or other known vessels.

In some embodiments, at least one amplifying step includes at least one primer that is or comprises at least one non-standard nucleotide. In some embodiments, a non-standard nucleotide is selected from a uracil, a methylated nucleotide, an RNA nucleotide, a ribose nucleotide, an 8-oxo-guanine, a biotinylated nucleotide, a locked nucleic acid, a peptide nucleic acid, a high-Tm nucleic acid variant, an allele discriminating nucleic acid variant, any other nucleotide or linker variant described elsewhere herein and any combination thereof.

While any application-appropriate amplification reaction is contemplated as compatible with some embodiments, by way of specific example, in some embodiments, an amplification step may be or comprise a polymerase chain reaction (PCR), rolling circle amplification (RCA), multiple displacement amplification (MDA), isothermal amplification, polony amplification within an emulsion, bridge amplification on a surface, the surface of a bead or within a hydrogel, and any combination thereof.

In some embodiments, certain modifications may be made to a portion of a sample of nucleic acid material (e.g., an adapter sequence). By way of specific example, in some embodiments, amplifying a nucleic acid material in a first sample may further comprise destroying or disrupting a portion or all of a second adapter sequences found on a nucleic acid material after the separating step, and before the amplification of a first sample. By way of additional specific example, in some embodiments, amplifying the nucleic acid material in the second sample may further comprise destroying or disrupting at least a portion of the first adapter sequences found on the nucleic acid material after the separating step, and before the amplification of the second sample. In some embodiments, destroying or disrupting may be or comprise at least one of enzymatic digestion (e.g., via an endonuclease and/or an exonuclease), inclusion of at least one replication-inhibiting molecule, enzymatic cleavage, enzymatic cleavage of one strand, enzymatic cleavage of both strands, incorporation of a modified nucleic acid followed by enzymatic treatment that leads to cleavage or one or both strands, incorporation of a replication blocking nucleotide, incorporation of a chain terminator, incorporation of a photocleavable linker, incorporation of a uracil, incorporation of a ribose base, incorporation of an 8-oxo-guanine adduct, use of a sequence-specific restriction endonuclease, use of a targeted endonuclease (e.g., a Cas-enzyme such as Cas9 or CPF1), and any combination thereof. In some embodiments, as an addition or alternative to primer site destruction or disruption, methods such as affinity pulldown, size selection, or any other known technique for removing and/or not amplifying undesired nucleic acid material from a sample is contemplated.

In some embodiments non-desirable first amplification products targeted for at least partial destruction would lead to a second amplification product following a second amplification with a targeted primer that would ultimately contain two similar primer binding sites on each end of the molecule rather than two distinct primer binding sites. In some embodiments such a structure can be problematic for MPS DNA sequence performance or efficiency.

In some embodiments, amplifying a nucleic acid material includes use of at least one single-stranded oligonucleotide at least partially complementary to a target region or a target sequence of interest (e.g., a genomic sequence, a mitochondrial sequence, a plasmid sequence, a synthetically produced target nucleic acid, etc.) and a single-stranded oligonucleotide at least partially complementary to a region of the adapter sequence (e.g., a primer site). In some embodiments, amplifying a nucleic acid material includes use of single-stranded oligonucleotides at least partially complementary to regions of the adapter sequences on the 5' and 3' ends of each strand of the nucleic acid material.

In general, robust amplification, for example PCR amplification, can be highly dependent on the reaction conditions. Multiplex PCR, for example, can be sensitive to buffer composition, monovalent or divalent cation concentration, detergent concentration, crowding agent (i.e. PEG, glycerol, etc.) concentration, primer concentrations, primer Tms, primer designs, primer GC content, primer modified nucleotide properties, and cycling conditions (i.e. temperature and extension times and rate of temperature changes). Optimization of buffer conditions can be a difficult and time consuming process. In some embodiments, an amplification reaction may use at least one of a buffer, primer pool concentration, and PCR conditions in accordance with a previously known amplification protocol. In some embodiments, a new amplification protocol may be created, and/or an amplification reaction optimization may be used. By way of specific example, in some embodiments, a PCR optimization kit may be used, such as a PCR Optimization Kit from Promega®, which contains a number of pre-formulated buffers that are partially optimized for a variety of PCR applications, such as multiplex, real-time, GC-rich, and inhibitor-resistant amplifications. These pre-formulated buffers can be rapidly supplemented with different $Mg^+$ and primer concentrations, as well as primer pool ratios. In addition, in some embodiments, a variety of cycling conditions (e.g., thermal cycling) may be assessed and/or used. In assessing whether or not a particular embodiment is appropriate for a particular desired application, one or more of specificity, allele coverage ratio for heterozygous loci, interlocus balance, and depth, among other aspects may be assessed. Measurements of amplification success may include DNA sequencing of the products, evaluation of products by gel or capillary electrophoresis or HPLC or other size separation methods followed by fragment visualization, melt curve analysis using double stranded nucleic acid binding dyes or fluorescent probes, mass spectrometry or other methods known in the art.

In accordance with various embodiments, any of a variety of factors may influence the length of a particular amplification step (e.g., the number of cycles in a PCR reaction, etc.). For example, in some embodiments, a provided nucleic acid material may be compromised or otherwise suboptimal (e g degraded and/or contaminated). In such case, a longer amplification step may be helpful in ensuring a desired product is amplified to an acceptable degree. In some embodiments an amplification step may provide an average of 3 to 10 sequenced PCR copies from each starting DNA molecule, though in other embodiments, only a single copy of each of a top strand and bottom strand are required. Without wishing to be held to a particular theory, it is possible that too many or too few PCR copies could result in reduced assay efficiency and, ultimately, reduced depth. Generally, the number of nucleic acid (e.g., DNA) fragments used in an amplification (e.g., PCR) reaction is a primary adjustable variable that can dictate the number of reads that share the same SMI/barcode sequence. Because SPLiT-DS makes use of additional PCR steps and does not require use hybridization-based targeted capture as some previously described methods do, any double stranded nucleic acid input amount requirements reported using prior methods are unlikely to be directly translatable to presently provided methods, which are likely to be more efficient.

Primer Site Destruction

Figure 7:
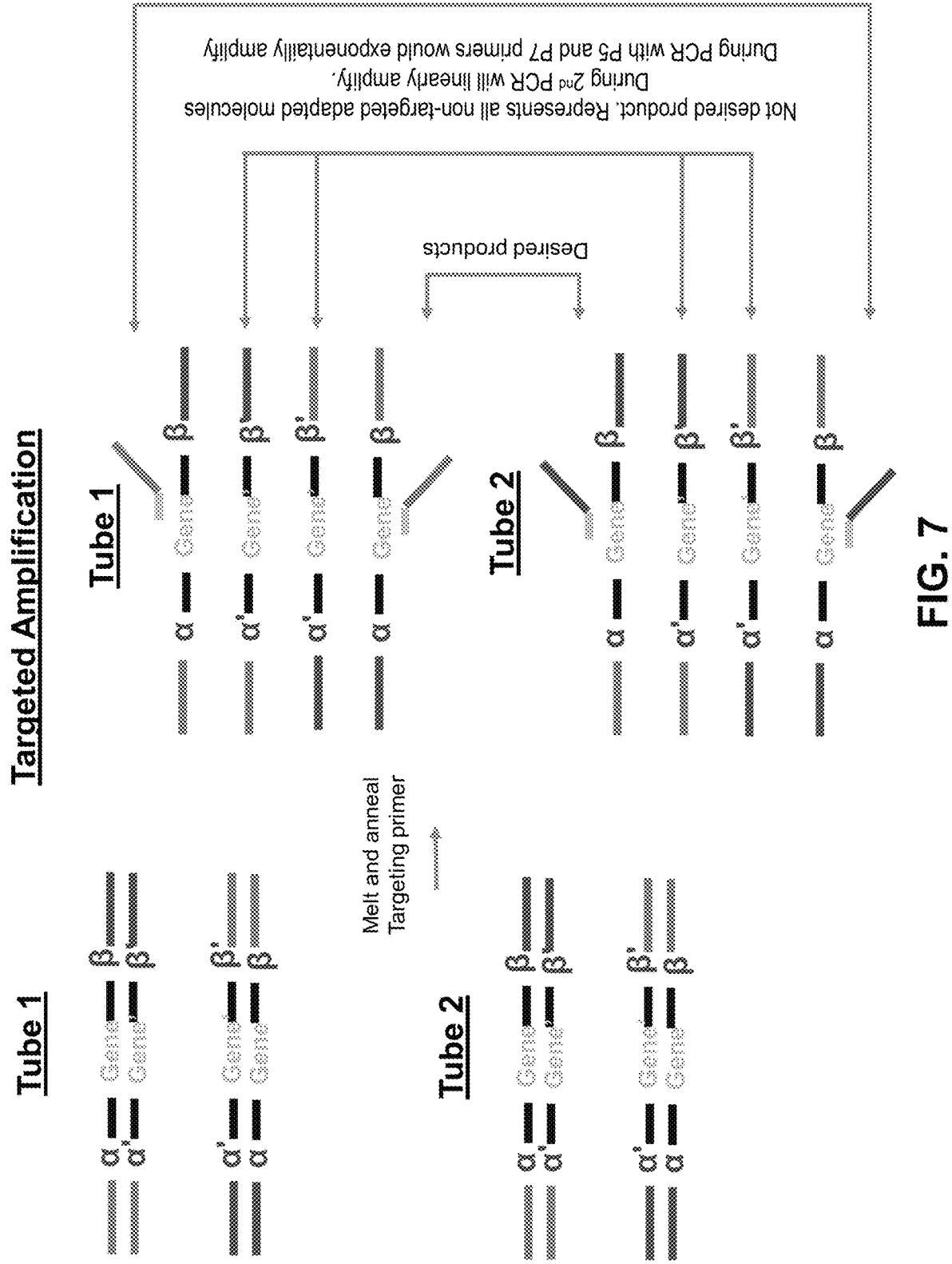
FIG. 7 is a conceptual illustration of further SPLiT-DS method steps in accordance with an embodiment of the present technology.

FIGS. 6-9B are conceptual illustrations of a variety of SPLiT-DS method steps in accordance with additional embodiments of the present technology. As discussed above, and with reference to FIGS. 4-6, method steps associated with SPLiT-DS, provide amplified nucleic acid material having first and second strand amplicons tagged with SMIs (e.g., α, α', β, β', FIG. 6) and additional adapter sequence comprising asymmetric primer sites (e.g., for Illumina P5 and P7 primers, FIG. 6) after a first round of amplification that can be separated into multiple samples. FIG. 7 illustrates subsequent steps wherein nested PCR reactions can provide enriched amplification of top and bottom strands of an original nucleic acid molecule in separate reaction samples (e.g., tubes). As shown in FIG. 7, some non-desirable amplification products and subsequent sequencing reads may be generated in addition to enrichment of the desired amplified products. Accordingly, and in some embodiments, efficiency may be reduced (e.g. percent of desired products for use in SPLiT-DS may be low relative to those that are not useful in a SPLiT-DS protocol).

Figure 8A:
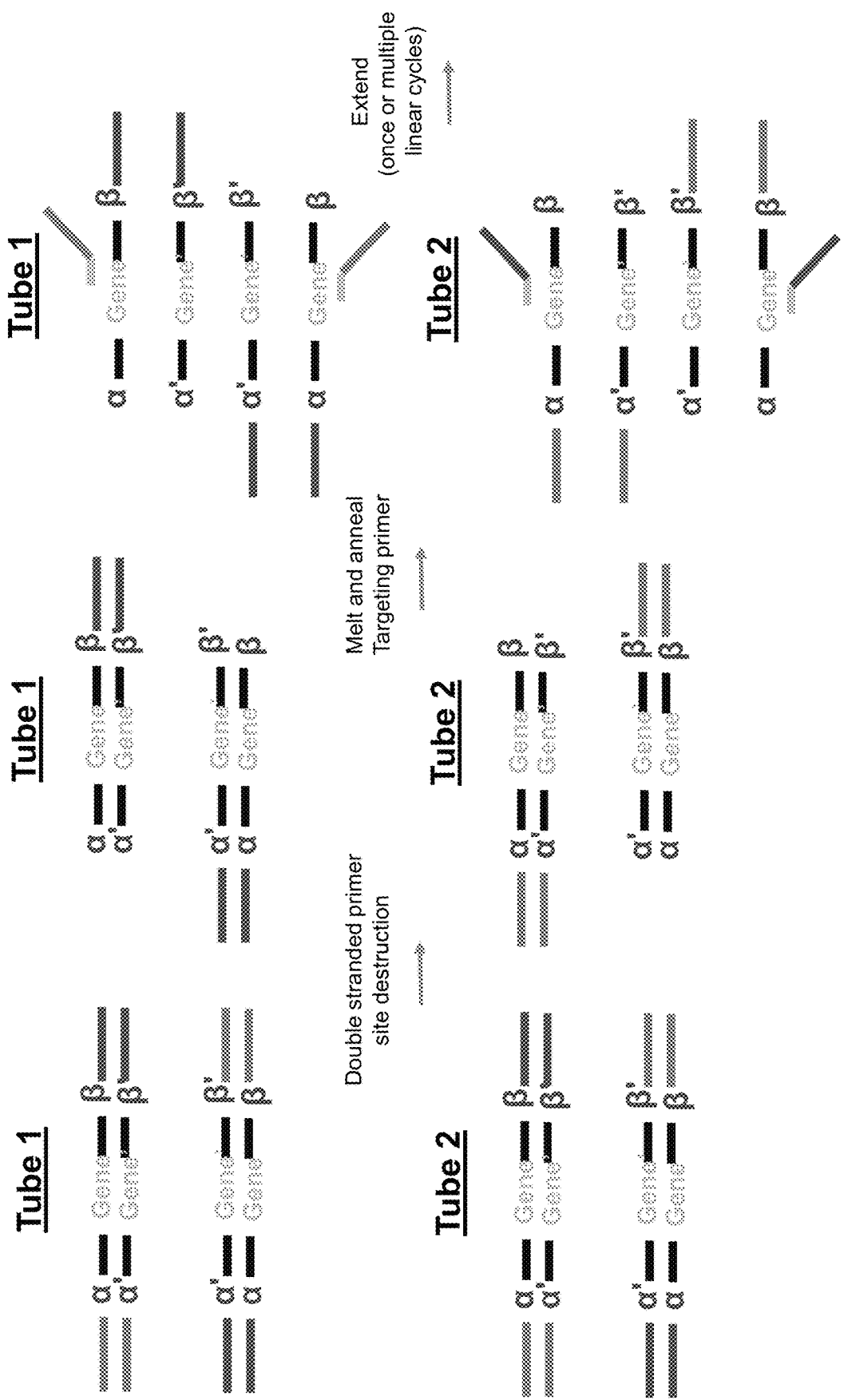
FIG. 8A is a conceptual illustration of SPLiT-DS method steps incorporating double-stranded primer site destruction schemes in accordance with an additional embodiment of the present technology.
Figure 8B:
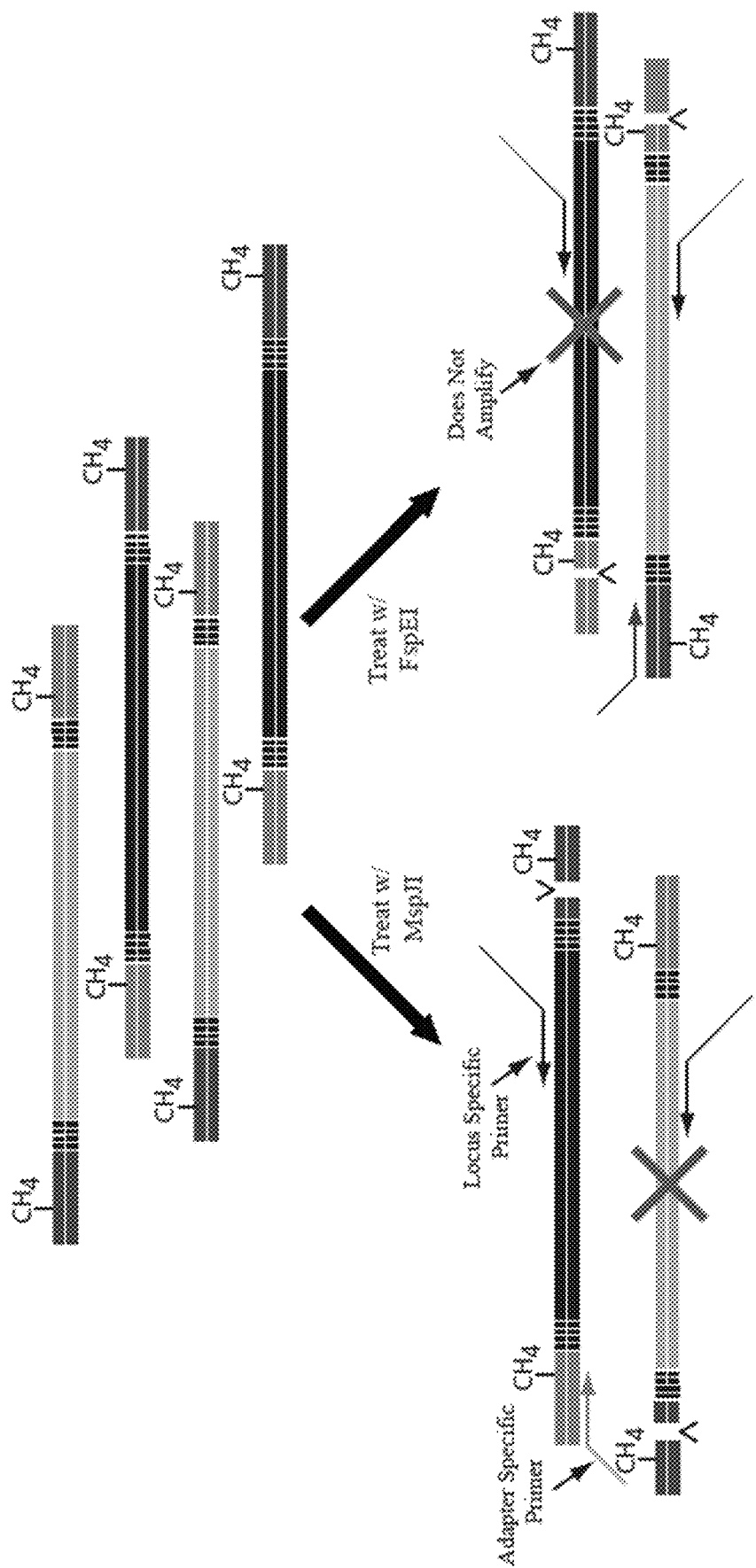
FIG. 8B is a conceptual illustration of an example of the SPLiT-DS method steps illustrated in FIG. 8A and in accordance with an embodiment of the present technology.

In accordance with additional aspects of the present technology, various aspects of conversion efficiency and workflow efficiency may increase by employing one or more strategies for reducing and/or eliminating amplification and sequencing of non-desirable amplification products. In some embodiments, primer site destruction or disruption (e.g., destruction of a primer site within an adapter sequence) may be used as a way of enriching for certain nucleic acid products after a first round of amplification and separation of the amplified nucleic acid material into multiple samples (as in, e.g. FIG. 8A). In some embodiments, provided methods may include use of double-stranded primer site destruction. Several methods of primer site destruction are contemplated herein. FIGS. 8A-8D are conceptual illustrations of SPLiT-DS method steps incorporating double-stranded primer site destruction schemes. Double-stranded primer site destruction may be achievable through a variety of means including through introduction of primer site modifications in targeted strands via modified primers used in a first amplification step (e.g., FIG. 6). In some embodiments, primers in a first PCR can have modifications including uracil, methylation, RNA bases, 8-oxo-guanine or other modifications that may be targeted in later steps. In some embodiments, primer site destruction may be or comprise restriction enzyme or other targeted endonuclease (such as Cas9, CPF1 etc) digestion of a sequence present, for example, in an adapter sequence wherein it has been determined that the chance of the restriction site has a low chance of occurring in the sequence of interest. In certain embodiments, an oligonucleotide complimentary to the primer sequence to be destroyed could be added to a particular sample followed by interrogation with a targeted endonuclease specific to double-stranded DNA. In another specific embodiment, a hybridizing oligo having a methyl group could be used to recruit a methylation-specific restriction endonuclease to a complimentary primer site. As illustrated in FIG. 8A, double-stranded primer site destruction (e.g., destruction of primer sites on both copies of a non-targeted strand in a sample), can be used to destroy, cripple or remove the "P5" primer sequence from both "top strand" and "bottom strand" copies in tube 1. Likewise, in tube 2, the "P7" primer sequence can be selectively destroyed, crippled or removed from both "top strand" and "bottom strand" copies. FIG. 8B is a conceptual illustration of one example for selectively destroying a primer sequence in a sample. As shown in FIG. 8B, a first sample can be treated with a first restriction endonuclease (e.g., MspJI) that selectively cleaves a site found in a first primer sequence (e.g., Illumina "P5"), thereby destroying the first primer site in all nucleic acid material in the first sample. Likewise, a second sample can be treated with a second restriction endonuclease (e.g., FspEI) that selectively cleaves a site found in a second primer sequence (e.g., Illumina "P7"), thereby destroying the second primer site in all nucleic acid material in the second sample.

Figure 8C:
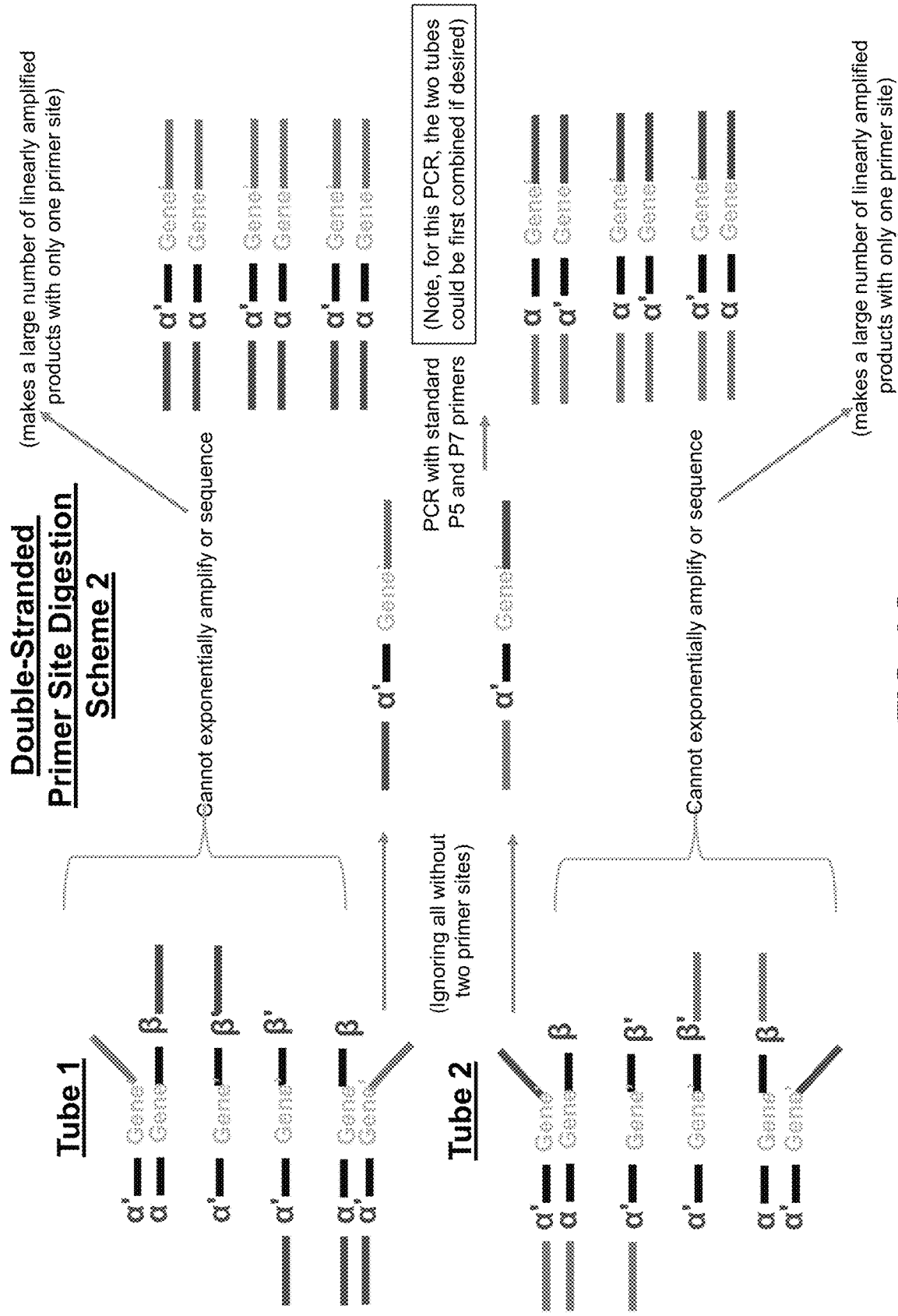
FIG. 8C is a conceptual illustration of an embodiment of SPLiT-DS method steps following the method steps illustrated in FIG. 8A in accordance with additional aspects of the present technology.

In reference to FIGS. 8A and 8C together, by selectively amplifying (extending once or multiple linear cycles) products in tube 1 using a "P7" primer and a target sequence primer (e.g., gene-specific primer) having a "P5" primer site tail, only "bottom strand" species are generated incorporating both "P7" and "P5" primer sites (see, e.g., FIG. 8C) while other nucleic acid species in tube 1 cannot exponentially amplify or sequence (e.g., are lacking the "P5" primer site). Likewise, by selectively amplifying (extending once or multiple linear cycles) products in tube 2 using a "P5" primer and a target sequence primer (e.g., gene-specific primer) having a "P7" primer site tail, only "top strand" species are generated incorporating both "P5" and "P7" primer sites (see, e.g., FIG. 8C) while other nucleic acid species in tube 2 cannot exponentially amplify or sequence (e.g., are lacking the "P5" primer site). It will be understood, that while non-desired linear products won't sequence or exponentially amplify, they may consume primers and dNTPs, which may have some impact on efficiency such reactions.

Figure 8D:
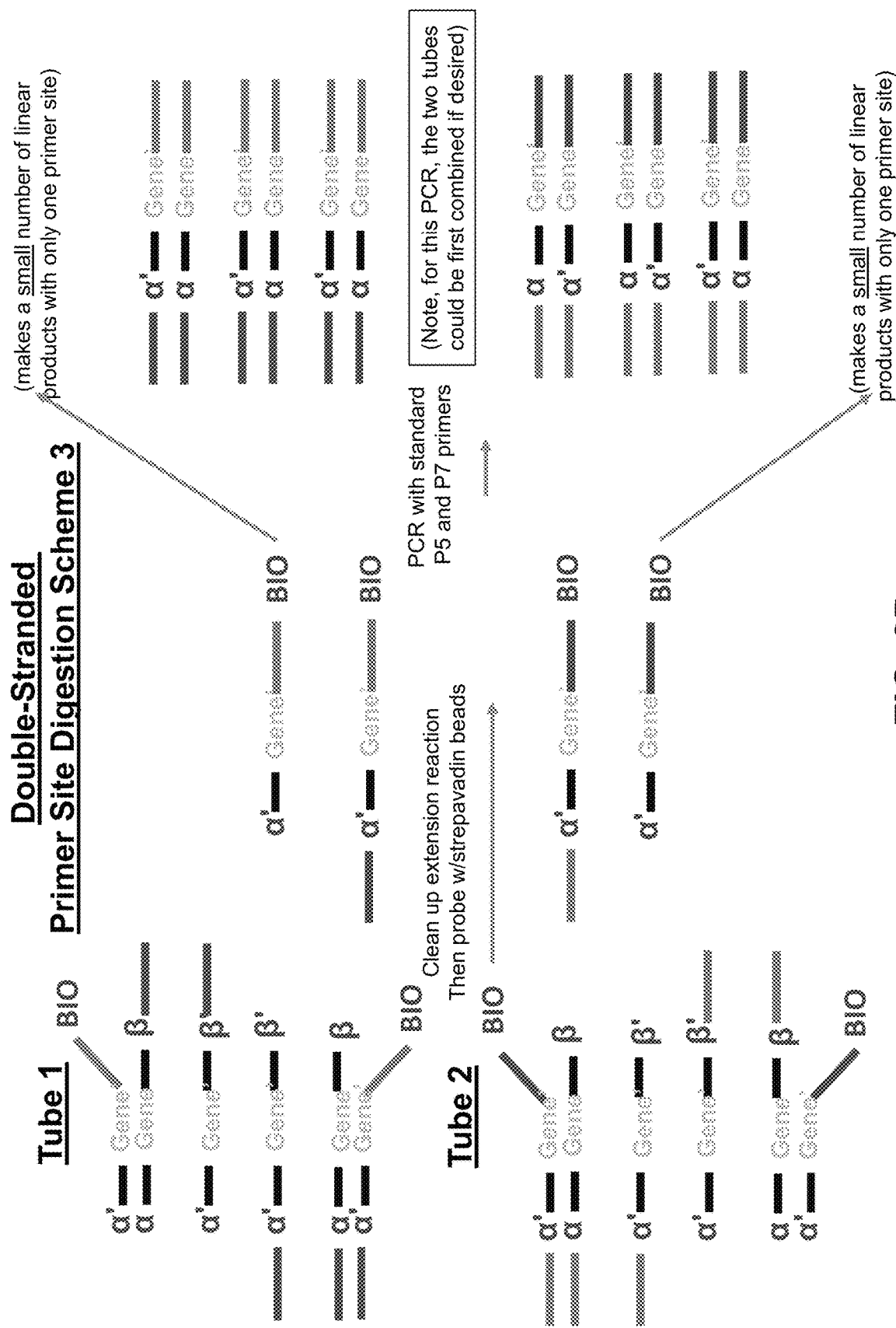
FIG. 8D is a conceptual illustration of SPLiT-DS method steps incorporating double-stranded primer site destruction schemes in accordance with another embodiment of the present technology.

In some embodiments, methods including primer site destruction may also use one or more biotinylated or other targeting primers. FIG. 8D is a conceptual illustration of SPLiT-DS method steps incorporating double-stranded primer site destruction schemes in accordance with another embodiment of the present technology. In the embodiment illustrated in FIG. 8D, target sequence primers having a "P5" primer site tail or a "P7" primer site tail are biotinylated. Referring to FIG. 8D, and following the extension step with the biotinylated targeting primers, streptavidin bead or hydrogel-enrichment may be used to enrich for products having two primers sites, thereby eliminating the majority of nucleic acid species having only one primer site. It is contemplated that in some such embodiments, such enrichment may improve PCR efficiency and/or facilitate multiplexing approaches and/or improve cluster amplification efficiency on an MPS DNA sequencer and/or generate more usable sequencing data on an MPS DNA sequencer.

To further limit off-target enrichment of species captured by biotin/streptavidin enrichment, further amplification with nested primers (e.g., "P5" or "P7" primers and an internally nested second targeting primer having the opposite flow cell sequence) can be used to further enrich for on-target species and reduce non-desired amplification products. In a particular embodiment, selective linear amplification using, for example, a primer specific to the target sequence of interest, can further enrich for the desired species prior to addition of paired nested primers for exponential amplification.

Figure 9A:
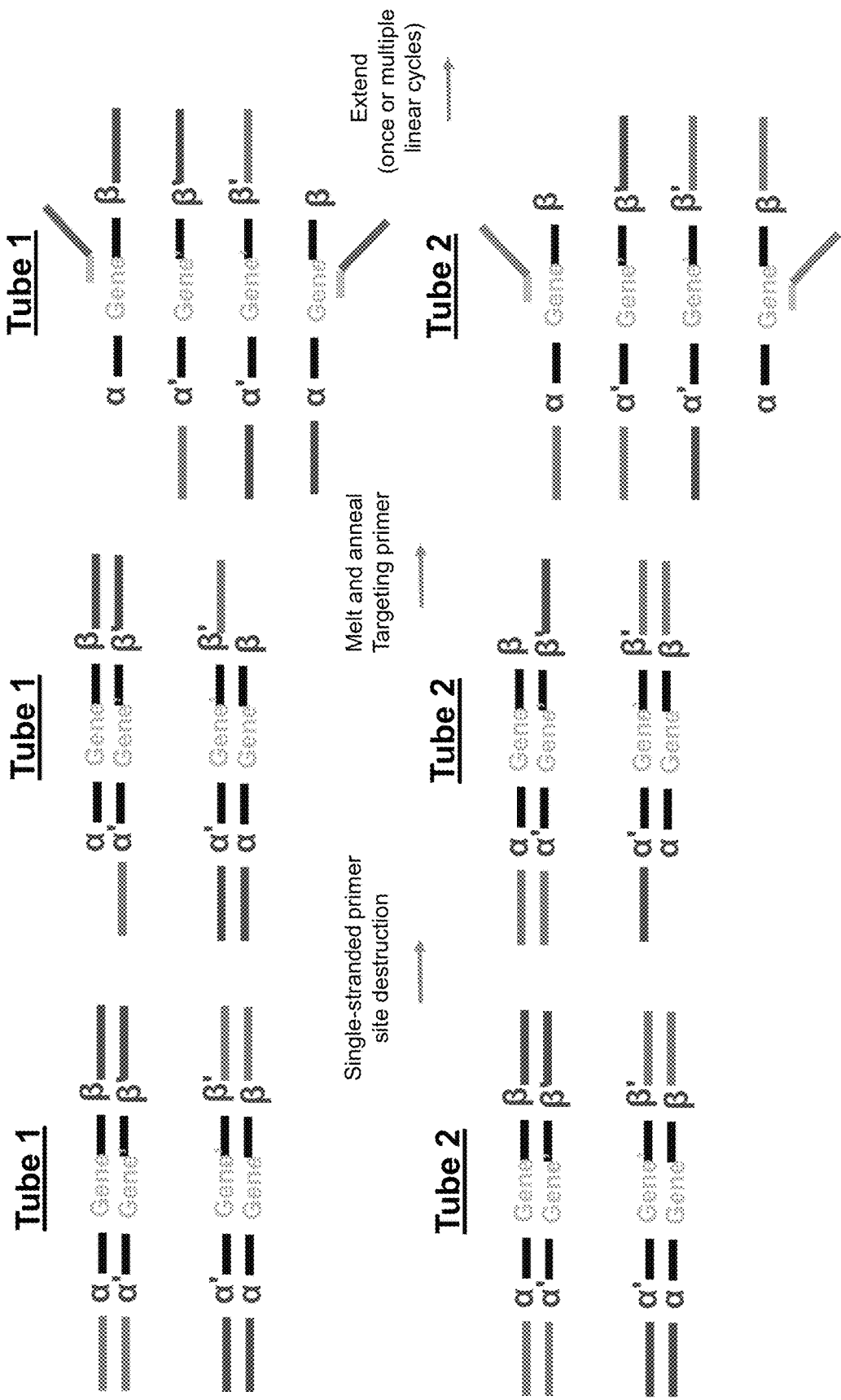
FIGS. 9A and 9B are conceptual illustrations of various embodiments of SPLiT-DS method steps incorporating single-stranded primer site destruction schemes in accordance with further aspects of the present technology.
Figure 9B:
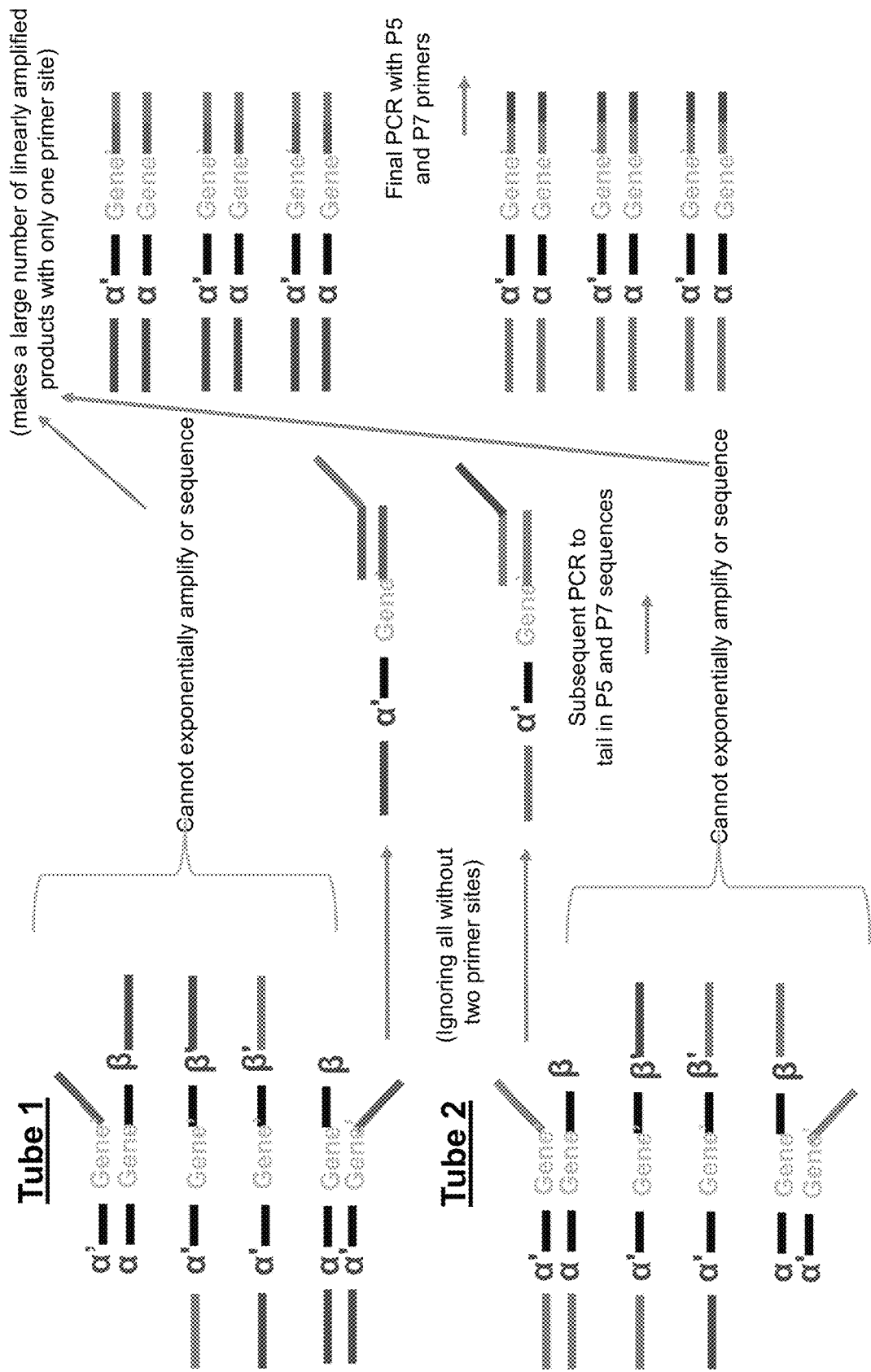

In some embodiments, single-stranded primer site destruction may be used. FIGS. 9A and 9B are conceptual illustrations of various embodiments of SPLiT-DS method steps incorporating single-stranded primer site destruction schemes in accordance with further aspects of the present technology. By way of non-limiting example, and as illustrated in FIG. 9A, a primer site may be destroyed in one strand of a double-stranded molecule by use of a modified primer (not shown) during the first amplification step of SPLiT-DS (see, e.g., FIG. 6). The modified primer can include a chemical modification (e.g., uracil, methylation, RNA bases, 8-oxo-guanine, etc.) or the like that can be subsequently targeted for destruction or crippling of the primer site on the affected strand. Subsequent amplification (extending once or multiple linear cycles) of desired targets in tube 1 using a "P7" primer and a target sequence primer (e.g., gene-specific primer) specially labelled (e.g., biotin, different flow cell adapter tail having, etc.), only "bottom strand" species are generated incorporating both "P7" and the special label (e.g., biotin, different primer site, etc.) (see, e.g., FIG. 9A) while other nucleic acid species in tube 1 will not exponentially amplify. Non-desired products are further selected against in a next step by streptavidin bead enrichment (not shown) or via further amplification with "P7" primer and modified primer with different primer site compliment and flow cell adapter tail with "P5" primer site (FIG. 9B). A final amplification reaction with "P7" and "P5" primers yield enriched "bottom strand" products in the tube 1 sample (FIG. 9B). The compliment steps in the sample in tube 2 can be made to enrich for "top strand" products (FIG. 9B). Without wishing to be bound by any particular theory, it is contemplated that if an option for double-stranded primer site digestion is available, such an option may be preferred over single-strand digestion.

In further embodiments, one or more of the schemes described with respect to FIGS. 6-9B, may be combined or certain steps may be eliminated while still achieving certain efficiency improvements. For example, in one embodiment, biotinylated targeting primers can be used during an extension step (e.g., following method steps shown in FIG. 6), and subsequent streptavidin probing can be used to recover the strands of interest. In this embodiment (e.g., without primer site destruction), species having two of the same primer sites (e.g., two "P5" primer sites, two "P7" primer sites), will also be recovered.

Multiple PCRs Per Captured Molecule

Figure 10:
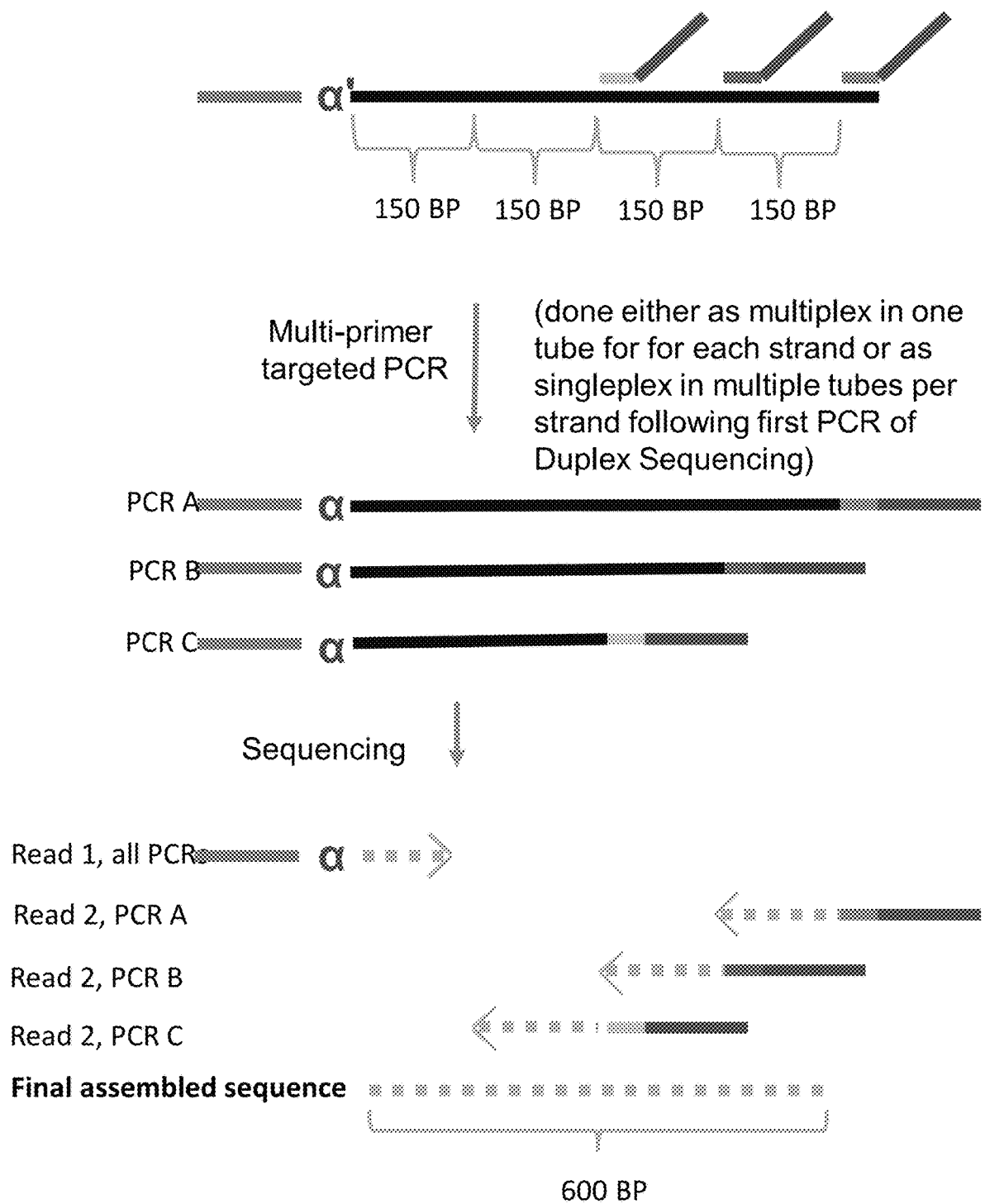
FIG. 10 is a conceptual illustration of SPLiT-DS method steps using multiple targeted primers for generating duplex consensus sequences for longer nucleic acid molecules in accordance with yet another embodiment of the present technology.

In certain applications, targeted regions or sequences may be challenging to sequence because nucleic acid breakpoints may fall close to target specific primers resulting in short fragments or entirely missed regions. For example, randomly sheared DNA or circulating cell free DNA (cfDNA), such as circulating tumor DNA or circulating fetal DNA, samples may have targeted sequences that cannot be retrieved (e.g., detected/covered in a sequencing read). In some embodiments, provided methods may overcome such challenges by targeting multiple regions within a target sequence, such as with the use of multiple target primers complimentary to staggered portions of the target sequence (e.g., each primer targeted to a different region of the target sequence). To avoid challenges associated with short fragments, and in one embodiment, DNA may be sheared into larger pieces than may be typically desirable for optimal sequencing. FIG. 10 is a conceptual illustration of SPLiT-DS method steps using multiple targeted primers for generating duplex consensus sequences for longer nucleic acid molecules in accordance with yet another embodiment of the present technology.

Referring to FIG. 10, a provided method may include the use of multiple amplification primers, for example, multiple primers each targeted to a region (e.g., ~100 BP apart) of a target sequence of interest. In accordance with various embodiments, such an approach could be performed in a single reaction (e.g., tube), or in other embodiments, in multiple reactions (e.g., tubes), for example, to avoid nearby or adjacent primers from interacting with one other. In some embodiments, preventing interactions of multiple staggered primers in the same tube may be mitigated by performing extension with a strand-displacing polymerase so that primers that prime from downstream don't block primers that prime from further upstream. In some embodiments, extension may be performed for several linear cycles with a first primer, followed by cleanup, and another set of extensions for a second primer, etc. As shown in FIG. 10, each nested primer set generates amplification products of different lengths which can be subsequently sequenced. Read 1 of all amplification products will yield the same sequence information, while paired-end sequence reads from each of the amplification products A, B and C will yield staggered sequencing information that together with Read 1 sequencing information provides an assembled sequence of greater length than previously possible with MPS or standard DS protocols.

In some embodiments, analyses of multi-primer data are conducted with methods non-standard to other DS methods. As will be appreciated by one of skill in the art, duplex assembly of multi-primer sequence reads is not possible with an SMI tag alone, as multiplexed samples may include products of varying lengths with the same tag. To address this challenge, some embodiments include assembly of duplexes by a tag that is a combination of SMI and the sequence (e.g., genomic) position of a targeted primer start site. In some embodiments, after duplex assembly, data may be evaluated for duplex reads with a common SMI but different lengths. In some embodiments, individual duplex families may be assembled into an aggregate "multi-read duplex family". It is contemplated that some such embodiments may facilitate subassembly of DS targeted regions into longer single-molecule reads which may be advantageous for certain applications and increase the effective genotyping length of target nucleic acid molecules with short read sequencing platforms.

As is known to those of skill in the art, the longest contiguous read that can currently be obtained by an Illumina NextSeq is ~300 BP: paired-end 150 BP reads that meet in middle, as long as enzymatic targeting and primers are carefully designed to produce fragments of substantially near to this length. Accordingly, embodiments incorporating multi-primer approaches, as described herein, may, in some embodiments, achieve longer whole molecule DS sequences.

In some aspects, provided methods reflect the insight that, in some embodiments, multiple targeted primers combined with SPLiT-DS may achieve, among other things, (i) contiguous sequence(s) of long single molecules and, optionally, with (ii) high specificity and/or (ii) DS accuracy. It is considered more likely than not that methods provided herein may be useful in applications such as, e.g.: those that require long, accurate continuous reads; de novo genome assembly; performing assays in repetitive regions (i.e. regions of genome with repetitive sequence) where unique mapping is difficult; sequencing regions that are considered particularly challenging (e.g. HLA locus, cancer pseudogenes, microsatellites); assaying for co-incidence of variants in, e.g. cancer (e.g. drug sensitizing mutations, resistance mutations), haplotype analysis (e.g., evaluating origin of a mutation in circulating fetal DNA (e.g. maternal, paternal, or fetal origin)), metagenomics (e.g. antibiotic resistance); overcoming limitations of certain enzymes (e.g. Cas9 and limitations on how far apart particular regions need to be based on location of enzyme recognition sites); large structural rearrangements; and/or indels, etc.

Additional Embodiments for Processing Nucleic Acid Material

Figure 11C:
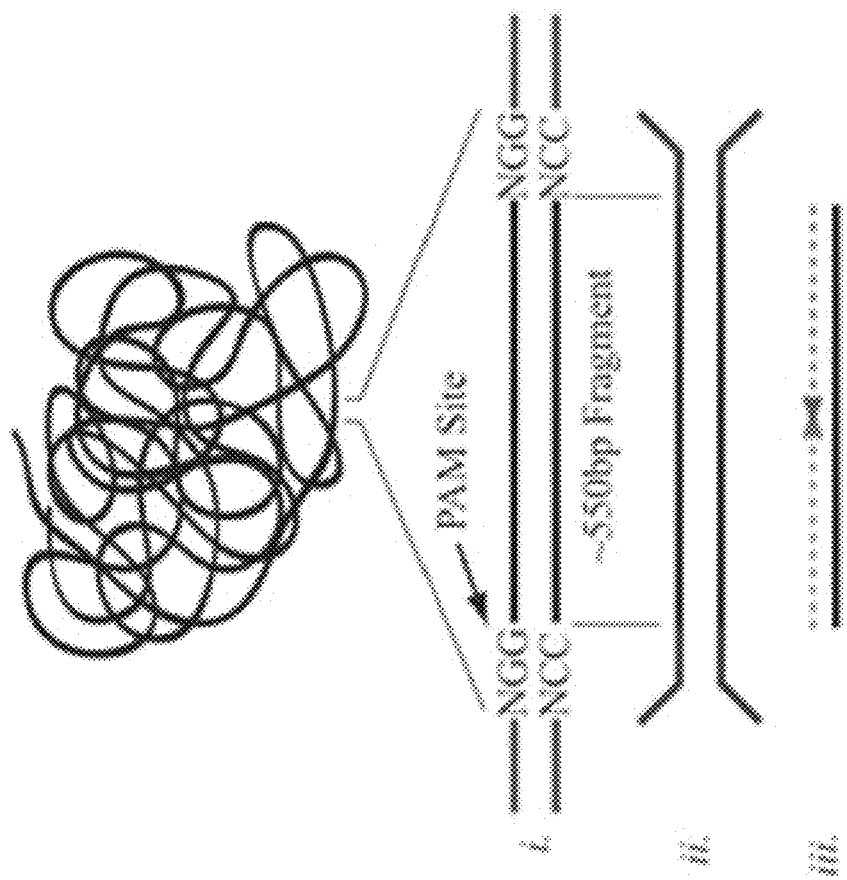
FIG. 11C is a schematic illustrating steps of a method for generating targeted fragment sizing with CRISPR/Cas9 for generating sequencing information in accordance with an embodiment of the present technology.
Figure 11A:
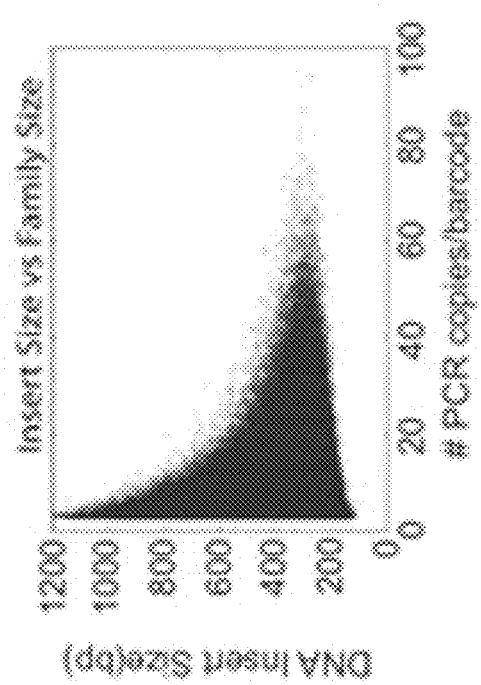
FIG. 11A is a graph plotting a relationship between nucleic acid insert size and resulting family size following amplification in accordance with an embodiment of the present technology.
Figure 11B:
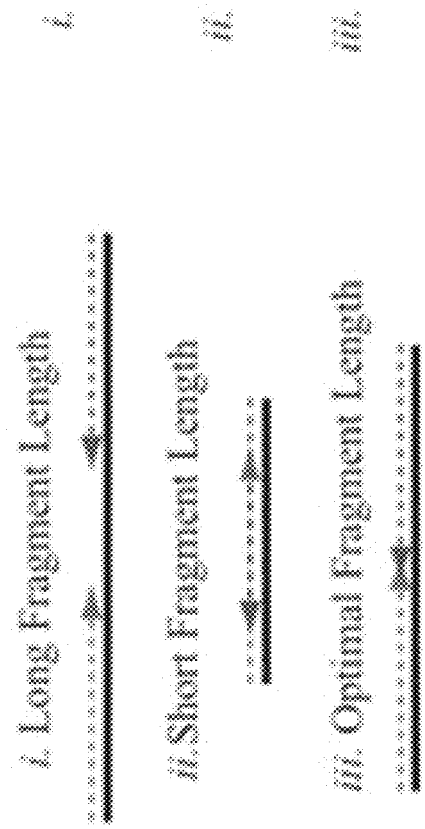
FIG. 11B is a schematic illustrating sequencing data generated for different nucleic acid insert sizes in accordance with aspects of the present technology.

In some embodiments, it is advantageous to process nucleic acid material so as to improve the efficiency, accuracy, and/or speed of a sequencing process. In accordance with further aspects of the present technology, the efficiency of, for example, DS and/or SPLiT-DS can be enhanced by targeted nucleic acid fragmentation. Classically, nucleic acid (e.g., genome, mitochondrial, plasmid, etc.) fragmentation is achieved either by physical shearing (e.g., sonication) or somewhat non-sequence-specific enzymatic approaches that utilize an enzyme cocktail to cleave DNA phosphodiester bonds. The result of either of the above methods is a sample where the intact nucleic acid material (e.g., genomic DNA (gDNA)) is reduced to a mixture of randomly or semi-randomly sized nucleic acid fragments. While effective, these approaches generate variable sized nucleic acid fragments which may result in amplification bias (e.g., short fragments tend to PCR amplify more than longer fragments and cluster amplify more easily during polony formation) and uneven depth of sequencing. For example, FIG. 11A is a graph plotting a relationship between nucleic acid insert size and resulting family size following amplification. As shown in FIG. 11A, because shorter fragments tend to preferentially amplify, a greater number of copies of each of these shorter fragments are generated and sequenced, providing a disproportionate level of sequencing depth of these regions. Further, with longer fragments, a portion of DNA between the limit of a sequencing read (or between the ends of paired end sequencing reads) cannot be interrogated and is "dark" despite being successfully ligated, amplified and captured (FIG. 11B). Likewise, with short reads, and when using paired-end sequencing, reading the same sequence in the middle of a molecule from both reads provides redundant information and is cost-inefficient (FIG. 11B). Random or semi-random nucleic acid fragmentation may also result in unpredictable break points in target molecules that yield fragments that may not have complementarity or reduced complementarity to a bait strand for hybrid capture, thereby decreasing a target capture efficiency. Random or semi-random fragmentation can also break sequences of interest and or lead to very small or very large fragments that are lost during other stages of library preparation and can decrease data yield and efficiency.

One other problem with many methods of random fragmentation, particularly mechanical or acoustic methods, is that they introduce damage beyond double-stranded breaks that can render portions of double-stranded DNA no longer double-stranded. For example, mechanical shearing can create 3' or 5' overhangs at the ends of molecules and single-stranded nicks in the middle of molecules. These single-stranded portions amenable to adapter ligation, such as a cocktail of "end repair" enzymes, are used to artificially render it double-stranded once again, and which can be a source of artificial errors (such as described above with respect to "pseudoduplex molecules"). In many embodiments, maximizing the amount of double-stranded nucleic acid of interest that remains in native double-stranded form during handling is optimal.

Accordingly, in some embodiments, provided methods and compositions take advantage of a targeted endonuclease (e.g., a ribonucleoprotein complex (CRISPR-associated endonuclease such as Cas9, Cpf1), a homing endonuclease, a zinc-fingered nuclease, a TALEN, an argonaute nuclease, and/or a meganuclease (e.g., megaTAL nuclease, etc.), or a combination thereof) or other technology capable of cutting a nucleic acid material (e.g., one or more restriction enzymes) to excise a target sequence of interest in an optimal fragment size for sequencing. In some embodiments, targeted endonucleases have the ability to specifically and selectively excise precise sequence regions of interest. FIG. 11C is a schematic illustrating steps of a method for generating targeted fragment sizing with CRISPR/Cas9 and for generating sequencing information in accordance with an embodiment of the present technology. By pre-selecting cut sites, for example with a programmable endonuclease (e.g., CRISPR-associated (Cas) enzyme/guide-eRNA complex) that result in fragments of predetermined and substantially uniform sizes (FIG. 11C), the biases and the presence of uninformative reads can be drastically reduced. Furthermore, because of the size differences between the excised fragments and the remaining non-cut DNA, a size selection step (as further described below) can be performed to remove the large off-target regions, thus pre-enriching the sample prior to any further processing steps. The need for end-repair steps may be reduced or eliminated as well, thus saving time and risk of pseudoduplex challenges and, in some cases, reducing or eliminating the need for computational trimming of data near the end of molecules, thus improving efficiency.

Restriction Endonucleases

It is specifically contemplated that any of a variety of restriction endonucleases (i.e., enzymes) may be used to provide nucleic acid material of substantially uniform length. Generally, restriction enzymes are typically produced by certain bacteria/other prokaryotes and cleave at, near or between particular sequences in a given segment of DNA.

It will be apparent to one of skill in the art that a restriction enzyme is chosen to cut at a particular site or, alternatively, at a site that is generated in order to create a restriction site for cutting. In some embodiments, a restriction enzyme is a synthetic enzyme. In some embodiments, a restriction enzyme is not a synthetic enzyme. In some embodiments, a restriction enzyme as used herein has been modified to introduce one or more changes within the genome of the enzyme itself. In some embodiments, restriction enzymes produce double-stranded cuts between defined sequences within a given portion of DNA.

While any restriction enzyme may be used in accordance with some embodiments (e.g., type I, type II, type III, and/or type IV), the following represents a non-limiting list of restriction enzymes that may be used: AluI, ApoI, AspHI, BamHI, BfaI, BsaI, CfrI, DdeI, DpnI, DraI, EcoRI, EcoRII, EcoRV, HaeII, HaeIII, HgaI, HindII, HindIII, HinFI, KpnI, MamI, MseI, MstI, MstII, NcoI, NdeI, NotI, PacI, PstI, PvuI, PvuII, RcaI, RsaI, SacI, SacII, SalI, Sau3AI, ScaI, SmaI, SpeI, SphI, StuI, XbaI, XhoI, XhoII, XmaI, XmaII, and any combination thereof. An extensive, but non-exhaustive list of suitable restriction enzymes can be found in publically-available catalogues and on the internet (e.g., available at New England Biolabs, Ipswich, Mass., U.S.A.).

Targeted Endonucleases

Targeted endonucleases (e.g., a CRISPR-associated ribonucleoprotein complex, such as Cas9 or Cpf1, a homing nuclease, a zinc-fingered nuclease, a TALEN, a megaTAL nuclease, an argonaute nuclease, and/or derivatives thereof) can be used to selectively cut and excise targeted portions of nucleic acid material for purposes of enriching such targeted portions for sequencing applications. In some embodiments, a targeted endonuclease can be modified, such as having an amino acid substitution for provided, for example, enhanced thermostability, salt tolerance and/or pH tolerance. In other embodiments, a targeted endonuclease may be biotinylated, fused with streptavidin and/or incorporate other affinity-based (e.g., bait/prey) technology. In certain embodiments, a targeted endonuclease may have an altered recognition site specificity (e.g., SpCas9 variant having altered PAM site specificity). CRISPR-based targeted endonucleases are further discussed herein to provide a further detailed non-limiting example of use of a targeted endonuclease. We note that the nomenclature around such targeted nucleases remains in flux. For purposes herein, we use the term "CRISPR-based" to generally mean endonucleases comprising a nucleic acid sequence, the sequence of which can be modified to redefine a nucleic acid sequence to be cleaved. Cas9 and CPF1 are examples of such targeted endonucleases currently in use, but many more appear to exist different places in the natural world and the availability of different varieties of such targeted and easily tunable nucleases is expected to grow rapidly in the coming years. Similarly, multiple engineered variants of these enzymes to enhance or modify their properties are becoming available. Herein, we explicitly contemplate use of substantially functionally similar targeted endonucleases not explicitly described herein or not yet discovered, to achieve a similar purpose to disclosures described within.

CRISPR-DS

Figure 12A:
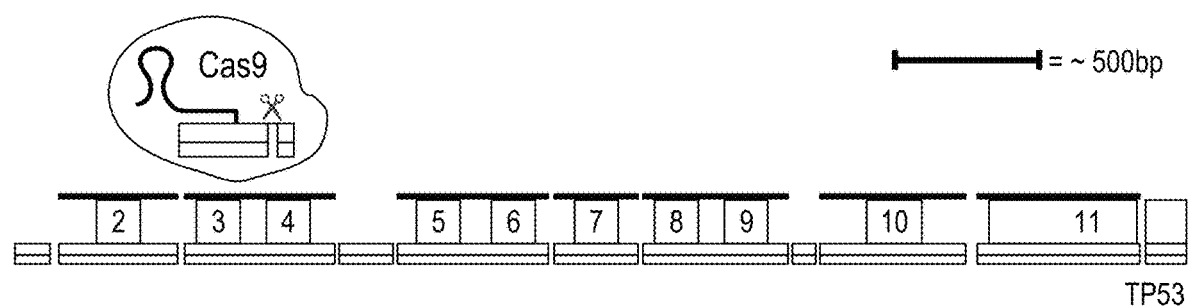
Figure 12B:
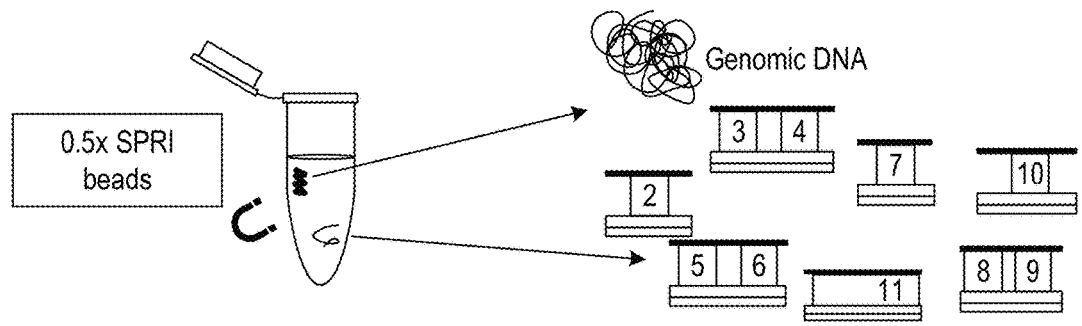
Figure 12E:
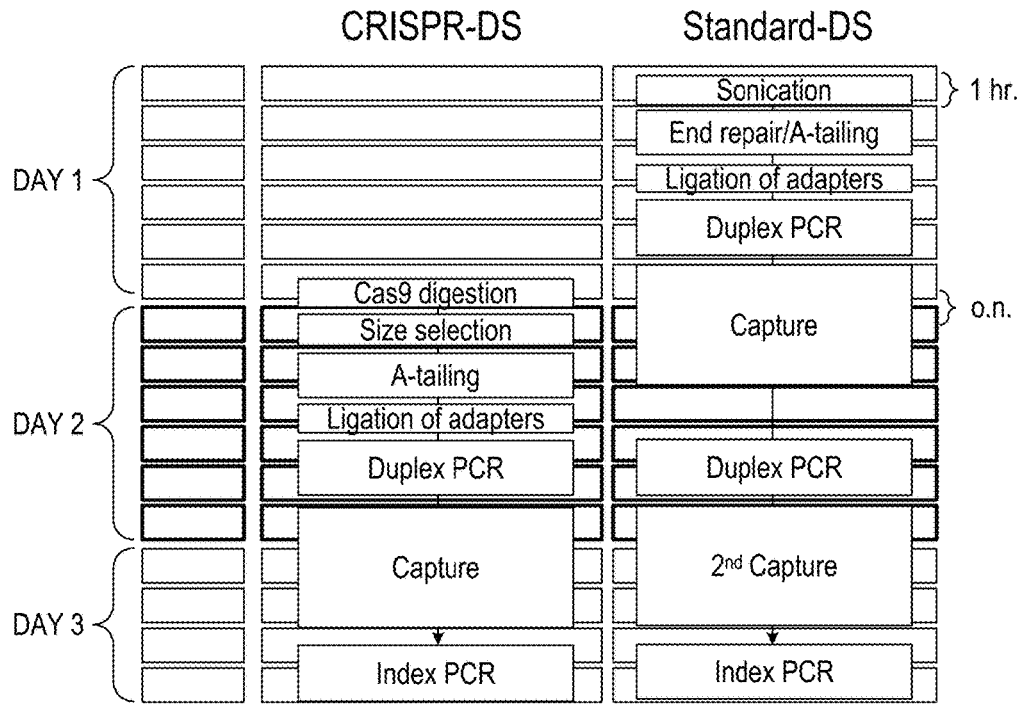
FIGS. 12E and 12F schematically compare CRISPR-DS and standard DS method steps in accordance with certain embodiments of the present technology.
Figure 12F:
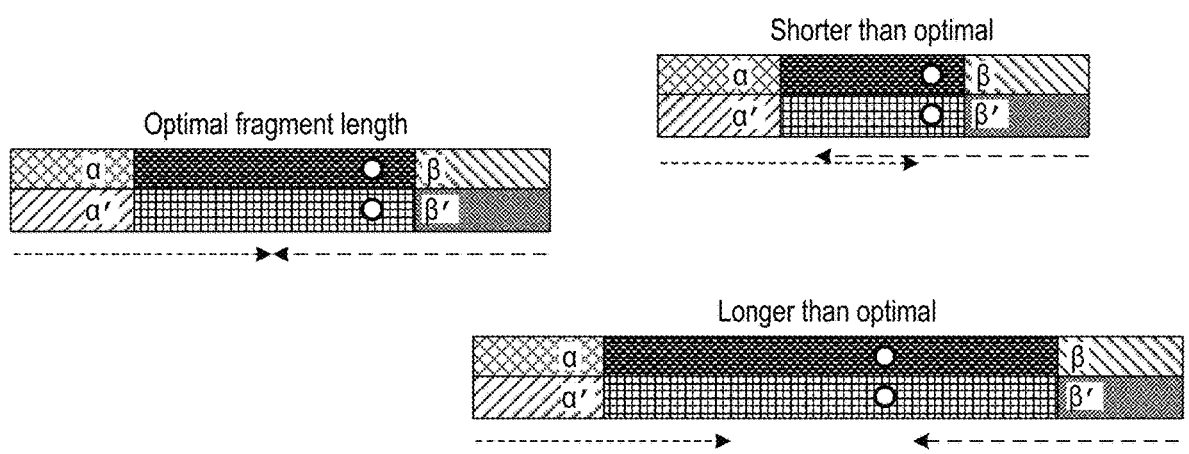

Additional aspects of the present technology are directed to methods for enriching region(s) of interest using the programmable endonuclease CRISPR/Cas9. In particular, CRISPR/Cas9 (or other programmable endonuclease) can be used to selectively excise one or more sequence regions of interest wherein the excised target region(s) are designed to be of one or more predetermined lengths, thus enabling size selection prior to library preparation for sequencing applications such as DS and SPLiT-DS. These programmable endonucleases can be used either alone or in combination with other forms of targeted nucleases, such as restriction endonucleases. This method, termed CRISPR-DS, allows for very high on-target enrichment (which may reduce need for subsequent hybrid capture steps), which can significantly decrease time and cost as well as increase conversion efficiency. FIGS. 12A-12D are conceptual illustrations of CRISPR-DS method steps in accordance with an embodiment of the present technology. For example, CRISPR/Cas9 can be used to cut at one or more specific sites (e.g., PAM sites) within a target sequence (FIG. 12A; TP53 target region in this example). FIG. 12B illustrates one method of isolating the excised target portion using SPRI/Ampure bead and magnet purification to remove high molecular weight DNA while leaving the pre-determined shorter fragment. In other embodiments, the excised portion of pre-determined length can be separated from non-desirable DNA fragments and other high molecular weight genomic DNA (if applicable) using a variety of size selection methods including, but not limited to gel electrophoresis, gel purification, liquid chromatography, size exclusion purification, and filtration purification methods. Following size selection, CRISPR-DS methods include steps consistent with DS method steps (see, e.g., FIG. 12E) including A-tailing (CRISPR/Cas9 excision leaves blunt ends), ligation of DS adapters (FIG. 12C), duplex amplification (FIG. 12D), a capture step and index amplification (e.g., PCR) before sequencing of each strand and generating a duplex consensus sequence (FIG. 12D). In addition to improvement in workflow efficiencies as evident in FIG. 12E, CRISPR-DS provides optimal fragment lengths for high efficiency amplification and sequencing steps (FIG. 12F).

In certain embodiments, CRISPR-DS solves multiple common problems associated with NGS, including, e.g. inefficient target enrichment, which may be optimized by CRISPR-based size selection; sequencing errors, which can be removed using DS methodology for generating an error-corrected duplex consensus sequence; and uneven fragment size, which is mitigated by predesigned CRISPR/Cas9 fragmentation (Table 1).

TABLE 1 crRNA sequences for TP53 CRISPR/Cas9 digestion (SEQ ID NOS: 4-15)

| Target description: | Name: | Sequence plus pam site: | Position start: | Position end: | Zhang score |
|---|---|---|---|---|---|
| TP53-upstream of exon 11 | TP53e11_US | GTGGGCCCcTACCTAGAATGTgG | 7572606 | 7572628 | 79 |
| TP53-downstream of exon 11 | TP53e11_DS | ATTCCCGTTGTCCCAGCCTTAGG | 7573118 | 7573096 | 70 |
| TP53-upstream of exon 10 | TP53e10_US | TGGTTATAGGATTCAACCGGAGG | 7573754 | 7573776 | 91 |
| TP53-downstream of exon 10 | TP53e10_DS | CTGATTGCAATCTCCGCCTCTGG | 7574261 | 7574283 | 86 |
| TP53-upstream of exons 9-8 | TP53e9-8_DS | CGGCATTTTGAGTGTTAGACTGG | 7576792 | 7576814 | 80 |
| TP53-downstream of exons 9-8 | TP53e9-8_US | CTTTGGGACCTCTTAACCTGTGG | 7577324 | 7577302 | 80 |
| TP53-downstream of exon 7 | TP53e7_DS.v2 | CAGGTCTCCCCAAGGCGCACTGG | 7577660 | 7577638 | 81 |
| TP53-upstream of exons 6-5 | TP53e6-5_US | GCACATCTCATGGGGTTATAGGG | 7578050 | 7578072 | 84 |
| TP53-downstream of exons 6-5 | TP53e6-5_DS | CAGGGGAGTACTGTAGGAAGAGG | 7578545 | 7578567 | 61 |
| TP53-upstream of exons 4-3 | TP53e4-3_US.v2 | TGCACGGTCAGTTGCCCTGAGGG | 7579317 | 7579295 | 81 |
| TP53-downstream of exons 4-3 | TP53e4-3_DS | ATGGAATTTTCGCTTCCCACAGG | 7579751 | 7579773 | 79 |
| TP53-downstream of exon 2 | TP53e2_DS | TGGGAATAGGGTGCACATTTAGG | 7580242 | 7580220 | 66 |

The in vitro digestion of DNA material with Cas9 Nuclease makes use of the formation of a ribonucleoprotein complex, which both recognizes and cleaves a pre-determined site (e.g., a PAM site, FIG. 11C). This complex is formed with guide RNAs ("gRNAs", e.g., crRNA+tracrRNA) and Cas9. For multiplex cutting, the gRNAs can be complexed by pooling all the crRNAs, then complexing with tracrRNA, or by complexing each crRNA and tracrRNA separately, then pooling. In some embodiments, the second option may be preferred because it eliminates competition between crRNAs.

As will be appreciated by one of skill in the art, as described herein, CRISPR-DS may have application for sensitive identification of mutations in situations in which samples are DNA-limited, such as forensics and early cancer detection applications.

In some embodiments, the nucleic acid material comprises nucleic acid molecules of a substantially uniform length. In some embodiments, a substantially uniform length is between about 1 and 1,000,000 bases). For example, in some embodiments, a substantially uniform length may be at least 1; 2; 3; 4; 5; 6; 7; 8; 9; 10; 15; 20; 25; 30; 35; 40; 50; 60; 70; 80; 90; 100; 120; 150; 200; 300; 400; 500; 600; 700; 800; 900; 1000; 1200; 1500; 2000; 3000; 4000; 5000; 6000; 7000; 8000; 9000; 10,000; 15,000; 20,000; 30,000; 40,000; or 50,000 bases in length. In some embodiments, a substantially uniform length may be at most 60,000; 70,000; 80,000; 90,000; 100,000; 120,000; 150,000; 200,000; 300,000; 400,000; 500,000; 600,000; 700,000; 800,000; 900,000; or 1,000,000 bases. By way of specific, non-limiting example, in some embodiments, a substantially uniform length is between about 100 to about 500 bases. In some embodiments a size selection step, such as those described herein, may be performed before any particular amplification step. In some embodiments a size selection step, such as those described herein, may be performed after any particular amplification step. In some embodiments, a size selection step such as those described herein may be followed by an additional step such as a digestion step and/or another size selection step.

In addition to use of targeted endonuclease(s), any other application appropriate method(s) of achieving nucleic acid molecules of a substantially uniform length may be used. By way of non-limiting example, such methods may be or include use of one or more of: an agarose or other gel, an affinity column, HPLC, PAGE, filtration, SPRI/Ampure type beads, or any other appropriate method as will be recognized by one of skill in the art.

In some embodiments, processing a nucleic acid material so as to produce nucleic acid molecules of substantially uniform length (or mass), may be used to recover one or more desired target region from a sample (e.g., a target sequence of interest). In some embodiments, processing a nucleic acid material so as to produce nucleic acid molecules of substantially uniform length (or mass), may be used to exclude specific portions of a sample (e.g., nucleic acid material from a non-desired species or non-desired subject of the same species). In some embodiments, nucleic acid material may be present in a variety of sizes (e.g., not as substantially uniform lengths or masses).

In some embodiments, more than one targeted endonuclease or other method for providing nucleic acid molecules of a substantially uniform length may be used (e.g., 2, 3, 4, 5, 6, 7, 8, 9, 10 or more). In some embodiments, a targeted nuclease may be used to cut at more than one potential target region of a nucleic acid material (e.g., 2, 3, 4, 5, 6, 7, 8, 9, 10 or more). In some embodiments where there is more than one target region of a nucleic acid material, each target region may be of the same (or substantially the same) length. In some embodiments where there is more than one target region of a nucleic acid material, at least two of the target regions of known length differ in length (e.g., a first target region with a length of 100 bp and a second target region with a length of 1,000 bp).

In some embodiments, multiple targeted endonucleases (e.g., programmable endonucleases) may be used in combination to fragment multiple regions of the target nucleic acid of interest. In some embodiments, one or more programmable targeted endonucleases may be used in combination with other targeted nucleases. In some embodiments one or more targeted endonucleases may be used in combination with random or semi-random nucleases. In some embodiments, one or more targeted endonucleases may be used in combination with other random or semi-random methods of nucleic acid fragmentation such as mechanical or acoustic shearing. In some embodiments, it may be advantageous to perform cleavage in sequential steps with one or more intervening size selection steps. In some embodiments where targeted fragmentation is used in combination with random or semi-random fragmentation, the random or semi-random nature of the latter may be useful for serving the purpose of a SMI. In some embodiments where targeted fragmentation is used in combination with random or semi-random fragmentation, the random or semi-random nature of the latter may be useful for facilitating sequencing of regions of a nucleic acid that are not easily cleaved in a targeted way such as long highly repetitive regions.

Additional Methods

In some embodiments, a provided method may include the steps of providing a nucleic acid material, cutting the nucleic acid material with a targeted endonuclease (e.g., a ribonucleoprotein complex) so that a target region of predetermined length is separated from the rest of the nucleic acid material, and analyzing the cut target region. In some embodiments, provided methods may further include ligating at least one SMI and/or adapter sequence to at least one of the 5' or 3' ends of the cut target region of predetermined length. In some embodiments, analyzing may be or comprise quantitation and/or sequencing.

In some embodiments quantitation may be or comprise spectrophotometric analysis, real-time PCR, and/or fluorescence-based quantitation (e.g., using fluorescent dye tagging). In some embodiments, sequencing may be or comprise Sanger sequencing, shotgun sequencing, bridge PCR, nanopore sequencing, single molecule real-time sequencing, ion torrent sequencing, pyrosequencing, digital sequencing (e.g., digital barcode-based sequencing), sequencing by ligation, polony-based sequencing, electrical current-based sequencing (e.g., tunneling currents), sequencing via mass spectroscopy, microfluidics-based sequencing, and any combination thereof.

In some embodiments, a targeted endonuclease is or comprises at least one of a CRISPR-associated (Cas) enzyme (e.g., Cas9 or Cpf1) or other ribonucleoprotein complex, a homing endonuclease, a zinc-fingered nuclease, a transcription activator-like effector nuclease (TALEN), an argonaute nuclease, and/or a megaTAL nuclease. In some embodiments, more than one targeted endonuclease may be used (e.g., 2, 3, 4, 5, 6, 7, 8, 9, 10 or more). In some embodiments, a targeted nuclease may be used to cut at more than one potential target region of predetermined length (e.g., 2, 3, 4, 5, 6, 7, 8, 9, 10 or more). In some embodiments where there is more than one target region of predetermined length, each target region may be of the same (or substantially the same) length. In some embodiments where there is more than one target region of predetermined length at least two of the target regions of predetermined length differ in length (e.g., a first target region with a length of 100 bp and a second target region with a length of 1,000 bp).

Additional Aspects

In accordance with an aspect of the present disclosure some embodiments provide high quality sequencing information from very small amounts of nucleic acid material. In some embodiments, provided methods and compositions may be used with an amount of starting nucleic acid material of at most about: 1 picogram (pg); 10 pg; 100 pg; 1 nanogram (ng); 10 ng; 100 ng; 200 ng, 300 ng, 400 ng, 500 ng, 600 ng, 700 ng, 800 ng, 900 ng, or 1000 ng. In some embodiments, provided methods and compositions may be used with an input amount of nucleic acid material of at most 1 molecular copy or genome-equivalent, 10 molecular copies or the genome-equivalent thereof, 100 molecular copies or the genome-equivalent thereof, 1,000 molecular copies or the genome-equivalent thereof, 10,000 molecular copies or the genome-equivalent thereof, 100,000 molecular copies or the genome-equivalent thereof, or 1,000,000 molecular copies or the genome-equivalent thereof. For example, in some embodiments, at most 1,000 ng of nucleic acid material is initially provided for a particular sequencing process. For example, in some embodiments, at most 100 ng of nucleic acid material is initially provided for a particular sequencing process. For example, in some embodiments, at most 10 ng of nucleic acid material is initially provided for a particular sequencing process. For example, in some embodiments, at most 1 ng of nucleic acid material is initially provided for a particular sequencing process. For example, in some embodiments, at most 100 pg of nucleic acid material is initially provided for a particular sequencing process. For example, in some embodiments, at most 1 pg of nucleic acid material is initially provided for a particular sequencing process.

In accordance with other aspects of the present technology, some provided methods may be useful in sequencing any of a variety of suboptimal (e.g., damaged or degraded) samples of nucleic acid material. For example, in some embodiments at least some of the nucleic acid material is damaged. In some embodiments, the damage is or comprises at least one of oxidation, alkylation, deamination, methylation, hydrolysis, nicking, intra-strand crosslinks, inter-strand cross links, blunt end strand breakage, staggered end double strand breakage, phosphorylation, dephosphorylation, sumoylation, glycosylation, single-stranded gaps, damage from heat, damage from desiccation, damage from UV exposure, damage from gamma radiation damage from X-radiation, damage from ionizing radiation, damage from non-ionizing radiation, damage from heavy particle radiation, damage from nuclear decay, damage from beta-radiation, damage from alpha radiation, damage from neutron radiation, damage from proton radiation, damage from cosmic radiation, damage from high pH, damage from low pH, damage from reactive oxidative species, damage from free radicals, damage from peroxide, damage from hypochlorite, damage from tissue fixation such formalin or formaldehyde, damage from reactive iron, damage from low ionic conditions, damage from high ionic conditions, damage from unbuffered conditions, damage from nucleases, damage from environmental exposure, damage from fire, damage from mechanical stress, damage from enzymatic degradation, damage from microorganisms, damage from preparative mechanical shearing, damage from preparative enzymatic fragmentation, damage having naturally occurred in vivo, damage having occurred during nucleic acid extraction, damage having occurred during sequencing library preparation, damage having been introduced by a polymerase, damage having been introduced during nucleic acid repair, damage having occurred during nucleic acid end-tailing, damage having occurred during nucleic acid ligation, damage having occurred during sequencing, damage having occurred from mechanical handling of DNA, damage having occurred during passage through a nanopore, damage having occurred as part of aging in an organism, damage having occurred as a result if chemical exposure of an individual, damage having occurred by a mutagen, damage having occurred by a carcinogen, damage having occurred by a clastogen, damage having occurred from in vivo inflammation damage due to oxygen exposure, damage due to one or more strand breaks, and any combination thereof.

Nucleic Acid Material

Types

In accordance with various embodiments, any of a variety of nucleic acid material may be used. In some embodiments, nucleic acid material may comprise at least one modification to a polynucleotide within the canonical sugar-phosphate backbone. In some embodiments, nucleic acid material may comprise at least one modification within any base in the nucleic acid material. For example, by way of non-limiting example, in some embodiments, the nucleic acid material is or comprises at least one of double-stranded DNA, single-stranded DNA, double-stranded RNA, single-stranded RNA, peptide nucleic acids (PNAs), locked nucleic acids (LNAs).

Modifications

In accordance with various embodiments, nucleic acid material may receive one or more modifications prior to, substantially simultaneously, or subsequent to, any particular step, depending upon the application for which a particular provided method or composition is used.

In some embodiments, a modification may be or comprise repair of at least a portion of the nucleic acid material. While any application-appropriate manner of nucleic acid repair is contemplated as compatible with some embodiments, certain exemplary methods and compositions therefore are described below and in the Examples.

By way of non-limiting example, in some embodiments, DNA repair enzymes, such as Uracil-DNA Glycosylase (UDG), Formamidopyrimidine DNA glycosylase (FPG), and 8-oxoguanine DNA glycosylase (OGG1), can be utilized to correct DNA damage (e.g., in vitro DNA damage). These DNA repair enzymes, for example, are glycoslyases that remove damaged bases from DNA. For example, UDG removes uracil that results from cytosine deamination (caused by spontaneous hydrolysis of cytosine) and FPG removes 8-oxo-guanine (e.g., most common DNA lesion that results from reactive oxygen species). FPG also has lyase activity that can generate 1 base gap at abasic sites. Such abasic sites will subsequently fail to amplify by PCR, for example, because the polymerase fails copy the template. Accordingly, the use of such DNA damage repair enzymes can effectively remove damaged DNA that doesn't have a true mutation, but might otherwise be undetected as an error following sequencing and duplex sequence analysis.

As discussed above, in further embodiments, sequencing reads generated from the processing steps discussed herein can be further filtered to eliminate false mutations by trimming ends of the reads most prone to artifacts. For example, DNA fragmentation can generate single strand portions at the terminal ends of double-stranded molecules. These single-stranded portions can be filled in (e.g., by Klenow) during end repair. In some instances, polymerases make copy mistakes in these end repaired regions leading to the generation of "pseudoduplex molecules." These artifacts can appear to be true mutations once sequenced. These errors, as a result of end repair mechanisms, can be eliminated from analysis post-sequencing by trimming the ends of the sequencing reads to exclude any mutations that may have occurred, thereby reducing the number of false mutations. In some embodiments, such trimming of sequencing reads can be accomplished automatically (e.g., a normal process step). In some embodiments, a mutation frequency can be assessed for fragment end regions and if a threshold level of mutations are observed in the fragment end regions, sequencing read trimming can be performed before generating a double-strand consensus sequence read of the DNA fragments.

Sources

It is contemplated that nucleic acid material may come from any of a variety of sources. For example, in some embodiments, nucleic acid material is provided from a sample from at least one subject (e.g., a human or animal subject) or other biological source. In some embodiments, a nucleic acid material is provided from a banked/stored sample. In some embodiments, a sample is or comprises at least one of blood, serum, sweat, saliva, cerebrospinal fluid, mucus, uterine lavage fluid, a vaginal swab, a nasal swab, an oral swab, a tissue scraping, hair, a finger print, urine, stool, vitreous humor, peritoneal wash, sputum, bronchial lavage, oral lavage, pleural lavage, gastric lavage, gastric juice, bile, pancreatic duct lavage, bile duct lavage, common bile duct lavage, gall bladder fluid, synovial fluid, an infected wound, a non-infected wound, an archeological sample, a forensic sample, a water sample, a tissue sample, a food sample, a bioreactor sample, a plant sample, a fingernail scraping, semen, prostatic fluid, fallopian tube lavage, a cell free nucleic acid, a nucleic acid within a cell, a metagenomics sample, a lavage of an implanted foreign body, a nasal lavage, intestinal fluid, epithelial brushing, epithelial lavage, tissue biopsy, an autopsy sample, a necropsy sample, an organ sample, a human identification ample, an artificially produced nucleic acid sample, a synthetic gene sample, a nucleic acid data storage sample, tumor tissue, and any combination thereof. In other embodiments, a sample is or comprises at least one of a microorganism, a plant-based organism, or any collected environmental sample (e.g., water, soil, archaeological, etc.).

Selected Examples of Applications

As is described herein, provided methods and compositions may be used for any of a variety of purposes and/or in any of a variety of scenarios. Below are described examples of non-limiting applications and/or scenarios for the purposes of specific illustration only.

Forensics

Previous approaches to forensic DNA analysis relied almost entirely on capillary electrophoretic separation of PCR amplicons to identify length polymorphisms in short tandem repeat sequences. This type of analysis has proven to be extremely valuable since its introduction in 1991. Since that time, several publications have introduced standardized protocols, validated their use in laboratories worldwide, detailed its use on many different population groups, and introduced more efficient approaches, such as miniSTRs.

While this approach has proven to be extremely successful, the technology has a number of drawbacks that limit its utility. For example, current approaches to STR genotyping often give rise to background signal resulting from PCR stutter, caused by slippage of the polymerase on the template DNA. This issue is especially important in samples with mom than one contributor, due to the difficulty in distinguishing the stutter alleles from genuine alleles. Another issue arises when analyzing degraded DNA samples. Variation in fragment length often results in significantly lower, or even absent, longer PCR fragments. As a consequence, profiles from degraded DNA often have lower power of discrimination.

The introduction of MPS systems has the potential to address several challenging issues in forensics analysis. For example, these platforms offer unparalleled capacity to allow for the simultaneous analysis of STRs and SNPs in nuclear and mtDNA, which will dramatically increase the power of discrimination between individuals and offers the possibility to determine ethnicity and even physical attributes. Furthermore, unlike PCR-CE, which simply reports the average genotype of an aggregate population of molecules, MPS technology digitally tabulates the full nucleotide sequence of many individual DNA molecules, thus offering the unique ability to detect MAFs within a heterogeneous DNA mixture. Because forensics specimens comprising two or more contributors remains one of the most problematic issues in forensics, the impact of MPS on the field of forensics could be enormous.

The publication of the human genome highlighted the immense power of MPS platforms. However, until fairly recently, the full power of these platforms was of limited use to forensics due to the read lengths being significantly shorter than the STR loci, precluding the ability to call length-based genotypes. Initially, pyrosequencers, such as the Roche 454 platform, were the only platforms with sufficient read length to sequence the core STR loci. However, read lengths in competing technologies have increased, thus bringing their utility for forensics applications into play. A number of studies have revealed the potential for MPS genotyping of STR loci. Overall, the general outcome of all these studies, regardless of the platform, is that STRs can be successfully typed producing genotypes comparable with CE analyses, even from compromised forensic samples.

While all of these studies show concordance with traditional PCR-CE approaches, and even indicate additional benefits like the detection of intra-STR SNPs, they have also highlighted a number of current issues with the technology. For example, current MPS approaches to STR genotyping rely on multiplex PCR to both provide enough DNA to sequence and introduce PCR primers. However, because multiplex PCR kits were designed for PCR-CE, they contain primers for various sized amplicons. This variation results in coverage imbalance with a bias toward amplification of smaller fragments, which can result in allele drop-out. Indeed, recent studies have shown that differences in PCR efficiency can affect mixture components, especially at low MAFs. To address this issue, several sequencing kits specifically designed for forensics are now commercially available and validation studies are beginning to be reported. However, due to the high level of multiplexing, amplification biases are still evident.

Like PCR-CE, MPS is not immune to the occurrence of PCR stutter. The vast majority of MPS studies on STR report the occurrence of artifactual drop-in alleles. Recently, systematic MPS studies report that most stutter events appear as shorter length polymorphisms that differ from the true allele in four base-pair units, with the most common being n−4, but with n−8 and n−12 positions also being observed. The percent stutter typically occurred in ~1% of reads, but can be as high as 3% at some loci, indicating that MPS can exhibit stutter at higher rates than PCR-CE.

In contrast, in some embodiments, provided methods and compositions allow for high quality and efficient sequencing of low quality and/or low amount samples, as described above and in the Examples below. Accordingly, in some embodiments, provided methods and/or compositions may be useful for rare variant detection of the DNA from one individual intermixed at low abundance with the DNA of another individual of a different genotype.

Forensic DNA samples commonly contain non-human DNA. Potential sources of this extraneous DNA are: the source of the DNA (e.g., microbes in saliva or buccal samples), the surface environment from which the sample was collected, and contamination from the laboratory (e.g. reagents, work area, etc.). Another aspect provided by some embodiments is that certain provided methods and compositions allow for the distinguishing of contaminating nucleic acid material from other sources (e.g., different species) and/or surface or environmental contaminants so that these materials (and/or their effects) may be removed from the final analysis and not bias the sequencing results.

In highly degraded DNA, the loci specific PCR may not work well due to the DNA fragments not containing the requisite primer annealing site, resulting in allelic dropout. This situation would limit the uniqueness of genotype calls and the confidence of matches is less assured, especially in the mixture trials. However, in some embodiments, provided methods and compositions allow for the use of single nucleotide polymorphisms (SNPs) in addition to or as an alternative to STR markers.

In fact, with ever increasing data on human genetic variation, SNPs are increasingly relevant for forensic work. As such, in some embodiments, provided methods and compositions use a primer design strategy such that multiplex primer panels may be created, for example, based on currently available sequencing kits, which virtually ensure reads traverse one or more SNP locations.

Patient Stratification

Patient stratification, which generally refers to the partitioning of patients based on one or more non-treatment-related factors, is a topic of significant interest in the medical community. Much of this interest may be due to the fact that certain therapeutic candidates have failed to receive FDA approval, in part to a previously unrecognized difference among the patients in a trial. These differences may be or include one or more genetic differences that result in a therapeutic being metabolized differently, or in side effects being present or exacerbated in one group of patients vs one or more other groups of patients. In some cases, some or all of these differences may be detected as one or more distinct genetic profile(s) in the patient(s) that result in a reaction to the therapeutic that is different from other patients that do not exhibit the same genetic profile.

Accordingly, in some embodiments, provided methods and compositions may be useful in determining which subject(s) in a particular patient population (e.g., patients suffering from a common disease, disorder or condition) may respond to a particular therapy. For example, in some embodiments, provided methods and/or compositions may be used to assess whether or not a particular subject possesses a genotype that is associated with poor response to the therapy. In some embodiments, provided methods and/or compositions may be used to assess whether or not a particular subject possesses a genotype that is associated with positive response to the therapy.

Monitoring Response to Therapies (tumor mutation, etc.)

The advent of next-generation sequencing (NGS) in genomic research has enabled the characterization of the mutational landscape of tumors with unprecedented detail and has resulted in the cataloguing of diagnostic, prognostic, and clinically actionable mutations. Collectively, these mutations hold significant promise for improved cancer outcomes through personalized medicine as well as for potential early cancer detection and screening. Prior to the present disclosure, a critical limitation in the field has been the inability to detect these mutations when they are present at low frequency. Clinical biopsies are often comprised mostly of normal cells and the detection of cancer cells based on their DNA mutations is a technological challenge even for modern NGS. The identification of tumor mutations amongst thousands of normal genomes is analogous to finding a needle in a haystack, requiring a level of sequencing accuracy beyond previously known methods.

Generally, this problem is aggravated in the case of liquid biopsies, where the challenge is not only to provide the extreme sensitivity required to find tumor mutations, but also to do so with the minimal amounts of DNA typically present in these biopsies. The term 'liquid biopsy' typically refers to blood in its ability to inform about cancer based on the presence of circulating tumor DNA (ctDNA). ctDNA is shed by cancer cells into the bloodstream and has shown great promise to monitor, detect and predict cancer as well as to enable tumor genotyping and therapy selection. These applications could revolutionize the current management of patients with cancer, however, progress has been slower than previously anticipated. A major issue is that ctDNA typically represents a very small portion of all the cell-free DNA (cfDNA) present in plasma. In metastatic cancers its frequency could be >5%, but in localized cancers is only between 1%-0.001%. In theory, DNA subpopulations of any size should be detectable by assaying a sufficient number of molecules. However, a fundamental limitation of previous methods is the high frequency with which bases are scored incorrectly. Errors often arise during cluster generation, sequencing cycles, poor cluster resolution, and template degradation. The result is that approximately 0.1-1% of sequenced bases are called incorrectly. Further issues can arise from polymerase mistakes and amplification bias during PCR that can result in skewed populations or the introduction of false mutant allele frequencies (MAF), Taken together, previously known techniques, including conventional NGS, are incapable of performing at the level required for the detection of low frequency mutations.

Several approaches have been employed to attempt to improve the accuracy of NGS, Removal of DNA damage with in vitro repair kits has been shown to reduce the number of false variant calls in NGS. However, not all mutagenic lesions are recognized by these enzymes, nor is the fidelity of repair perfect. Another approach that has gained significant traction is to take advantage of PCR duplicates arising from individual DNA fragments to form a consensus. Termed 'molecular barcoding', reads sharing unique random shear points or exogenously introduced random DNA sequences before or during PCR are grouped and the most prevalent sequence kept. Kinde, introduced this idea with SafeSeqS, which uses single-stranded molecular barcoding to reduce the error rate of sequencing by grouping PCR copies sharing the barcode sequencing and forming a consensus. This approach leads to an average detection limit of 0.5% and has been successful for the detection of ctDNA in metastatic cancers, but only in ~40% of early cancers. This detection limit can be substantially improved with digital droplet PCR (ddPCR), which can detect mutations at MAF as low as ~0.01%. The mutations, however, need to be previously known, which seriously limits multiple cancer applications. In addition, only 1-4 mutations can be tested at a time, precluding high-throughput screening (Table 2).

TABLE 2

| Feature | SPLiT-DS | Duplex-Sequencing | SafeSeqS | ddPCR |
|---|---|---|---|---|
| Sensitivity (detection of mutations) | 0.005%* | 0.005% | 0.50% | 0.01% |
| Minimum DNA input | ::10 ng | 500 ng | 10 ng | <1 ng |
| Molecular barcode | ds | ds | | na |
| Enrichment approach | PCR | Capture | PCR | PCR |
| Knowledge of tumor mutation required | no | no | no | yes |
| Number of bp screened | >10,000 bp | >10,000 bp | >10,000 bp | 1 bp × 4 multiplex |
| Scalability | High | Low | High | Very Low |

Prior to the present disclosure, the only technology with comparable sensitivity to ddPCR, but without requiring a priori knowledge of the tumor mutation is DS. DS extends the idea of molecular barcoding by using double-strand molecular barcodes to take advantage of the fact that the two strands of DNA contain complementary information. We have previously demonstrated that this approach results in an unprecedented sensitivity of <0.005% in human nuclear DNA.

Due to its high accuracy, DS, SPLIT-DS, and CRISPR-DS as well as methods for increasing conversion and workflow efficiency of these sequencing platforms hold promise in the oncology field. As is described herein, provided methods and compositions allow for an innovative approach to the DS methodology that integrates the double strand molecular tagging of DS with target sequence specific amplification (e.g., PCR) for increased efficiency and scalability while maintaining error correction.

In addition to the need for an assay that is highly accurate and efficient, the realities of the clinical laboratory also demand assays that are fast, scalable, and reasonably cost effective. Accordingly, various embodiments in accordance with aspects of the present technology that improve workflow efficiency of DS (e.g., enrichment strategy for DS) is highly desirable. Amplification-based enrichment and digestion/size selection enrichment of specific target sequences for DS applications, as described herein provide high target specificity, performance on low DNA inputs, scalability, and minimal cost (typically ~$2-3/sample).

Some embodiments of provided methods and compositions are especially significant for cancer research in general and for the field of ctDNA in particular, as the technology developed herein has the potential to identify cancer mutations with unprecedented sensitivity while minimizing DNA input, preparation time, and costs. SPLiT-DS and CRISPR-DS, among other embodiments disclosed herein, can be useful for clinical applications that could significantly increase survival through improved patient management and early cancer detection.

EXAMPLES

Example 1: SPLiT-DS

SPLiT-DS is a PCR-based targeted enrichment strategy compatible with the use of molecular barcodes on each strand for Duplex Sequencing error correction (FIG. 4A). In this exemplary embodiment, to begin a SPLiT-DS analysis, one or more DNA samples is fragmented using one or more approaches (similar to previously described Duplex Sequencing library construction as is known in the art). After fragmentation, most commonly end-repair and 3'-dA-tailing are performed, followed by ligation of each DNA fragment with T-tailed DS adapters containing degenerate or semi-degenerate double-stranded barcodes (FIG. 4, Step 1). Alternatively, other types of ligation overhangs, blunt ended ligation or adapter ligation chemistry previously described in International Patent Publication No. WO 2017/100441 and in U.S. Pat. No. 9,752,188 can be used. Substantially all duel adapted DNA molecules are PCR amplified using primers specific to the universal primer binding sites in the single-stranded adapter tails, which provides multiple barcoded copies of DNA fragments ("barcoded fragments") derived from each strand (FIG. 4, Step 2). After removing reaction byproducts, a given sample is split into two separate tubes (FIG. 4, Step 3) (i.e., the sample is split in half, with each tube containing roughly half the contents of the sample). On average, half of the copies of any given barcoded fragments will be transferred to each tube; however, due to randomness involved in splitting of samples, variance in distribution of any given barcoded fragment may occur. To account for any such variance, a hypergeometric distribution (i.e. probability of picking k barcode copies without replacement) is used as a model to determine minimum number of PCR copies of a given barcode needed to achieve a reasonably high probability that each tube contains at least one barcoded fragment derived from each of two (i.e., both) DNA strands from the original duplex. It is contemplated that in accordance with a hypergeometric model, ≥4 PCR cycles in (i.e. 2E4=16 copies/barcode) during Step 1 is more likely than not to provide a >99% probability that each barcoded fragment (from each strand) will be represented at least once in each tube. This assumes a uniform and nearly 100% PCR amplification efficiency which may not be realistic in all scenarios, but is a reasonable assumption with relatively low input high quality DNA samples (for example 10 ng human genomic DNA per 50 uL PCR). After splitting the sample into two tubes, target loci are enriched with multiplex PCR using primers specific for the adapter sequence and to the genetic loci of interest (FIG. 4, Step 4).

Multiplexed loci-specific PCRs are performed such that the resulting PCR products in each tube are derived from only one of the two original strands of a given DNA molecule sample. This is achieved according to the following procedure, using a sample that is split into two tubes (a first tube and a second tube) as described herein. In the first tube, PCR is performed using a primer specific for hybridizing to the "Read 1" (i e Illumina P5) adapter sequence (FIG. 4, Step 3; grey arrow), as well as primers specific to the genetic loci of interest, tailed with the sequence for the Read 2 (i.e. Illumina P7) adapter sequences (FIG. 4, Step 3; black arrow w/grey tail). Alternatively this tail may be shortened so as to not contain the full P7 sequence, which can instead be added via a later PCR prior to sequencing. It is proposed that this step provides that amplification products with one P5 and one P7 sequence at each termini only occurs from DNA derived from one strand of the original parental DNA molecule (i.e. initial sample DNA). Sequentially or simultaneously, a similar reaction is repeated in the second tube: amplification occurs from the amplification product derived from the opposite strand of the same genomic location as compared to the amplification of the sample in the first tube. This is achieved by using a loci-specific primer that anneals to the opposite strand orientation as in tube 1 (i.e., anti-reference versus reference sequence) and is tailed with the opposite universal primer sequence (i.e. P5 instead of P7) and an adapter primer to the opposite universal primer sequence (i.e. P7 instead of P5). Data are analyzed in an approach similar to that used in conventional Duplex Sequencing analysis/library construction, whereby reads sharing a particular barcode from the 'original first strand or the original second strand) are grouped to a single strand consensus sequence.

These single-stranded consensus sequences ("SSCSs") are then compared to the consensus computed for the other original strand (e.g., opposite strand, as described herein). The identity of a nucleotide position is retained only if the sequences obtained at the same position are complementary for the two SSCSs derived from each of the original strands of the duplex. If the identity of the positions do not match in the SSCSs, this is noted. For nucleotide positions where there is agreement between the paired SSCSs, the identity of this position is detailed in a final Duplex Consensus Sequence (i.e. form a DCS) (FIG. 1C). For positions where the sequence identity between the two SSCSs do not match, these are flagged as potential sites of error and are typically discounted by marking this position as an unknown (i.e. "N"). Alternative strategies as previously described in International Patent Publication No. WO 2017/100441 and in U.S. Pat. No. 9,752,188 include discounting the entire consensus read if mismatches are found or using statistical approaches to assign confidences to one variant versus the other and decide which is more probably as the true variant, based on the prior probability of a particular type of error and how well represented a given SSCS is in terms of the number of family members that make it up and how well these agree. Another approach is to retain uncertainty of the nucleotide position, for example, with IUPAC nomenclature (such as "K" to represent a position that may be either a G or a T). Additional information may be applied to the consensus sequence data file to reflect the relative likelihood of the identity of one nucleotide over another an uncertain position, for example, based on prior probabilities of certain types of sequencer or amplification errors in a given sequence context or the relative number of reads that support each variant at that position in each paired consensus family or read quality scores of raw reds comprising a SSCS family etc.

It should be noted that although the Duplex Consensus calling approach is substantially similar to that described in International Patent Publication No. WO 2017/100441 and in U.S. Pat. No. 9,752,188, in the case of SPLiT-DS, a single molecular identifier sequence at one end of the molecule is typically used to identify individual molecules (as opposed to one on each end) and the sequence reads that derive from copies of one of the original strands is found in one tube and the complementary original strand can be found in that of the other tube. This need not be the case, however: as described elsewhere herein, a PCR reaction of a duplex amplified library may be split into more than two tubes (for example, four tubes with one specific primer pair for each tube) and carry out the above process at both ends of the original molecule, such that two Duplex consensus sequences are made per molecule. An initial PCR reaction can similarly be split into multiple tubes (FIG. 10) and multiple reads can be generated for Duplex Sequencing error correction and/or subassembly of longer sequences with short read sequences.

It is often convenient to differentially index the products of each tube to differentiate them following multiplex sequencing. This is not mandatory, however. One benefit of SPLiT-DS is that targeted enrichment using PCR can be achieved, which speeds up the workflow of prior versions of Duplex Sequencing that are reliant on hybrid capture to enrich for regions of interest or other approaches. At the same time it allows use of Duplex adapter and tags for maximal accuracy, which cannot be achieved with traditional amplicon sequencing.

Example 2: Development of SPLiT-DS for CODIS STR Loci

The present Example is based on the insight that currently available methods of genotyping repetitive regions of DNA such as Short Tandem Repeats (STRs) would benefit from improvement of accuracy and sensitivity. This Example extends and improves upon an established protocol for DS (which itself can remove "stutter"; FIG. 3B) to create a "SPLiT-DS" assay/protocol. The current example will demonstrate (1) design of primers and subsequent selection for use in multiplex PCR; (2) methods to improve DNA library preparation; (3) evaluation of accuracy, precision, sensitivity, and specificity of provided technologies, such as, e.g. using decreasing amounts of DNA; (4) demonstrated substantially reduced stutter in the final error-corrected data.

Primer Design and Selection for Multiplex PCR

SPLiT-DS PCR primers are designed to preferably have the following properties: 1) high target specificity; 2) capable of being multiplexed; and 3) exhibit robust and minimally biased amplification. Though a number of existing primer mixtures satisfying these criteria for use in conventional PCR capillary electrophoresis (PCR-CE), the same primer mixtures are not reliable in MPS. To this end, available data (mapping coordinates from sequencing data obtained using commercially available kits that amplify target loci prior to sequencing (i.e. 5'-end of each read in paired-end sequencing data corresponds to the 5'-end of the PCR primers used to amplify the DNA)) were leveraged to develop primers for use in the present example. The insights described herein, as well as data obtained from previous Example(s), are used to inform design of an initial primer set for the Expanded CODIS Core loci (CODIS20) plus PentaD, PentaF, and SE3329 (for simplicity, unless otherwise indicated, this will collectively be referred to as simply the CODIS loci). Previously determined mapping coordinates do not provide other information about primers used in commercially (or otherwise) available kits, such as length, melting temperature, and concentrations, thus creation of primers in the present Example focus on designs that maximize the probability of achieving uniform, robust, and specific amplification prior to multiplexing any reaction.

Results can be analyzed by direct sequencing (e.g., Illumina MiSeq platform) as opposed to, e.g. gel analysis. Each sample can be evaluated on a number of metrics to design an optimal primer mixture. Metrics include: 1) specificity (i.e. number of on target reads divided by number of off target reads); 2) allele coverage ratio for heterozygous loci (i.e. lower depth allele divided by higher depth allele; ideal is 1.0); 3) interlocus balance (i.e. lowest depth locus divided by highest depth locus; ideal is 1.0); and 4) depth variation (i.e.

average depth of each locus divided by total average depth of all loci. At least one primer set can be chosen on the basis of these metrics, for further analysis and development. Alternatively and/or additionally, primer design may include use of a web-based program, such as, e.g. Primer3, for each STR marker.

Example 3: Improvement in Methods of Library Preparation

The library preparation protocol for SPLiT-DS follows standard protocols known, such as the Duplex Sequencing protocol, up until the completion of the first PCR step. The present Example improves and expands upon this protocol, by improving steps that occur after the first Duplex Sequencing PCR step, in and, in particular, on loci-specific PCRs, which are unique to the SPLiT-DS technologies provided herein.

As a point of reference, reactions will first be run using known buffers, primer pool concentrations, and PCR conditions (e.g. as in a standard DS protocol), but applied to the SPLiT-DS approach, which serves the purpose of targeted enrichment after an initial Duplex Sequencing PCR is carried out that could in some cases be followed by other forms of targeted enrichment such as hybrid capture. Efficacy of these conditions on multiplex PCRs will be determined by directly sequencing the reactions on the Illumina MiSeq platform and monitoring specificity, allele coverage ratio for heterozygous loci, interlocus balance, and depth. This assay will evaluate PCR efficacy (and not, e.g., error correction) so approximately 100,000-500,000 reads per condition will be used, allowing analysis of at least 50 PCR conditions per sequencing run.

In this particular example, an average of 3 to 10 sequenced PCR copies (i.e. barcode family) from each starting DNA molecule should be obtained for a successful analysis. In other embodiments a successful analysis might be defined as recovering one or more copies of each original DNA strand of a particular duplex molecule. It is contemplated that more than 3-10 copies could cause reduced assay efficiency in terms of use of sequencer resources without additional useful data. It is contemplated that an average of too few copes of each strand will not meet criterial for a defined successful analysis and ultimately, reduced depth. It is contemplated that in some embodiments that defining a successful analysis as achieving a minimum number of sequenced copies of each strand facilitates higher accuracy Duplex Sequencing than Duplex Sequencing with a smaller minimum required number of copies per original strand.

SPLiT-DS cannot rely on known conditions for DNA input (e.g. such as those known in other assays), as it is a unique approach as compared to other currently available technologies; therefore, DNA input amount used in the PCRs occurring after the splitting will be determined, as changes (e.g. reduction) to input amounts up until the first PCR step will necessarily impact post-processing depth.

After DNA input ranges have been determined, qPCR based assays will be will be used to quantify absolute amount of adapter ligated target DNA (similar to, e.g. Step 3 in FIG. 4).

Accuracy, Precision, Sensitivity, and Specificity with Decreasing DNA Input

Accuracy, precision, sensitivity and specificity on commonly used Standard Reference Material (SRM) DNA will be conducted as a point of reference for the improved technologies as described herein. SPLiT-DS will then be performed (e.g., evaluating accuracy and precision of approach) on decreasing amounts of input DNA (i.e. sensitivity), using serial dilutions (e.g. within a range of about 50 pg to about 10 ng). At least 6 different libraries will be independently prepared for each DNA input. After sequencing and error correction (using in-house software developed and designed specifically for the SPLiT-DS variant of Duplex Sequencing), accuracy will be assessed using STRait Razor to: (i) genotype the processed data; and/or (ii) determine percentage of reads that exhibit "correct" genotype at each CODIS locus (i.e. as known from a standardized sample). Precision will be evaluated by determining: (i) allele coverage ratio for heterozygous loci; (ii) interlocus balance; (iii) depth variation; and/or (iv) percent stutter (e.g. quantification of sample-to-sample variation).

Detection of Contaminating DNA

The present Example also focuses on improvements in currently available methods of DNA evaluation to detect contamination of a given sample with exogenous DNA (e.g. forensic DNA of human contaminated with non-human DNA). SPLiT-DS analyses will be conducted on human DNA samples in the presence of contaminating DNA (e.g. mice, dog, cow, chicken, *Candida albicans, Escherichia coli, Staphylococcus aureus*, etc.). Analyses will include sample DNA spiked with 10 ng contaminating DNA, in triplicate, at the following ratios: 50:50, 10:1, and 100:1 (contaminant:sample DNA, by mass), as well as 100:0 control (i.e. no human DNA) 0:100 (unspiked human DNA). Each successfully generated library will be sequenced and mapped onto a given contaminant corresponding reference genome and human genome (GRCh38). This mapping will be used to determine percentage of reads that exhibit the correct (e.g. aligned with reference genome) genotype at each locus and compared to values of controls. Alignments will provide information about ranges of contaminating DNA that are still permissive for successful SPLiT-DS (i.e. levels of contaminating DNA that may be present without adversely affecting precision and/or strength of SPLiT-DS).

Example 4: Validation of SPLiT-DS on Sole Source Samples

To validate SPLiT-DS as a viable high accuracy genotyping method on a representative human population, DNA purified from cells obtained from the Personal Genome Project (PGP) will be used (see, e.g., demographic summary details of the PGP in Table 3).

TABLE 3

| PGP Sample Details | | |
|---|---|---|
| Categories | Sub-Categories | # of Samples |
| Sex | Male | 95 |
| | Female | 40 |
| Race | Asian, Other | 4 |
| | Black | 1 |
| | Caucasian | 116 |
| | Chinese | 2 |
| | Hispanic/Latino | 3 |
| | Multi-racial | 4 |
| | Not reported | 5 |

Evaluate the Ability of SPLiT-DS to Correctly Genotype DNA Single-Source Samples.

SPLiT-DS will be performed, in duplicate, on DNA purified from cell lines of unrelated individuals from the PGP. DNA from approximately 110 unique individuals will be tested. SPLiT-DS will be performed using appropriate quantities of DNA as determined in previous examples (i.e. smallest quantity that reliably (e.g. >80%) produces sequencing libraries in >60× average post-processing depth for each loci). After sequencing and performing error correction using in-house SPLiT-DS software described herein, STRait Razor will be used to genotype samples.

As an interpretation guideline for genotyping our SPLiT-DS data, a modified 'consensus' approach of the two replicates will be used, as follows:

No Result: when at least one (e.g. one of the two) replicate produces low coverage (e.g., <60×);

Correct genotype: when all (e.g., two of two) replicates produce the expected genotype (i.e., matching the genotype in WGS data for a given sample).

Undefined genotype: when different genotypes are obtained at a given locus in all replicates (e.g. two of two) or when only one genotype differs from the WGS data.

Wrong genotype: when all (two of two) replicates show the same incorrect genotype.

Quantifying amount of stutter will be performed on all sample and loci by determining stutter ratio for each sequenced locus. Stutter ratio is calculated by dividing the read count of a given stutter allele by the read count of the actual sample allele. If more than one type of stutter event is observed, calculations of each stutter length will be made. To minimize bias of this analysis, a stutter ratio will only be calculated at a locus with an average depth of ≥60× (80% power to detect ≥1 post-processing read containing an alternative stutter allele occurring at 5% (1–Sample Binomial Test). In cases where consistent higher depth coverage for at least several loci is obtained, lower frequency stutter events will be examined and ratios calculated appropriately (e.g. adjusting power).

Another portion of the analysis in this example will include effect of STR length on various parameters and then comparing the results to STR length at a given locus in a reference (e.g. specificity, allele coverage ratio for heterozygous loci, interlocus balance, and/or depth). It is contemplated that evaluation of these parameters will improve interpretation of polymorphisms based on STR length (including, e.g. as SPLiT-DS samples being evaluated are taken from a generally outbred population and may, for example, have a variety of STR length polymorphisms). In addition to evaluation of effect of STR length, stutter ratios will also be determined. Finally, calculations of power of discrimination for each sample (based on loci that are correctly genotyped according to guidelines described herein, e.g. using expected allele frequencies in the US population) will be performed.

Results from the analyses described in this Example may determine the breadth of use of SPLiT-DS (as well as extent of any bias in the method) such as, for example, in various types of samples, and/or for genotyping STR.

Comparison and Concordance Studies with Capillary Electrophoresis and MPS Approaches To demonstrate superiority of SPLiT-DS as a sequencing method for forensics applications, for example, concordance studies against currently available methods will be performed. At present, the "gold standard" for forensic STR genotyping is PCR-CE. SPLiT-DS results obtained in accordance with the Examples described herein will be compared to the same DNA samples genotyped using PCR-CE analysis and 1 ng of input DNA, according to standard procedures. The two data sets (PCR-CE and SPLiT-DS, along with appropriate controls/references (e.g. WGS PGP sample data)) may determine level of concordance between the two approaches. Concordance studies will also be performed using a commercially available kit (e g Illumina FORENSEQ DNA Signature Prep Kit) that uses targeted PCR amplification of 63 STRs, including the CODIS loci, and 95 identity informative SNPs. The same samples used in the concordance studies of PCR-CE and SPLiT-DS will be used, and genotyping will be performed using STRait-Razor. PCR stutter will also be reviewed in each approach (PCR-CE, commercial kit, SPLiT-DS) and stutter will be calculated if true allele peak heights are at least 600 RFU (stochastic threshold) but not in excess of 15,000 RFU. To eliminate any additive effect of plus and minus stutter at repeat position(s) between heterozygous alleles, positions two repeat units apart will not be included. As described herein, stutter percentages will be calculated by dividing peak height of the stutter peak by peak height of the true allele. In the case of samples analyzed with a commercially available kit, all alleles with ≥60 observed reads will be called and percentage stutter calculated as described herein. Comparisons will be performed between percent stutter for each tested locus. It is contemplated that though stutter results between platforms are not directly comparable to one another, data will provide a reasonable estimate of relative abundance of stutter in each method.

Example 5: Validation of SPLiT-DS on Damaged DNA and DNA Mixtures

Highly damaged/degraded DNA and mixtures confound currently available genotyping technologies. Accordingly, the present Example will demonstrate the ability of SPLiT-DS to correctly genotype samples with damaged DNA and DNA mixtures, improving and extending currently available methodologies.

Validation of SPLiT-DS on Damaged DNA from Single Contributors

SPLiT-DS will be performed on DNA sampled exposed to three forensically-relevant categories: (i) chemical exposure; (ii) ultraviolet (UV) light; and (iii) elevated temperatures (see Table 4 for a summary of exemplary exposure methods/conditions used in previous studies/known to affect conventional STR analysis). Due to lack of SRM available for damaged DNA samples, level of damage induced will be standardized between biological replicates. DNA will first be exposed to environmental condition(s) and time points as in Table 4, and evaluation conducted using a commercially available kit (e.g., KAPA Biosystems hgDNA Quantification and QC qPCR kit (Roche/KAPA Biosystems)), used to determine DNA damage/degradation in a given sample. Only samples that exhibit comparable levels of damage (defined as within one standard deviation of our observed mean) for a particular environmental condition (as determined by the assay described herein), will be used in the analyses of the present Example.

Experiments to evaluate SPLiT-DS on damaged/degraded DNA will be performed, in triplicate, on Promega 2800M SRM DNA using the smallest input DNA amount needed to consistently (>50%) forms libraries capable of being sequenced using SPLiT-DS using the harshest possible conditions in each category of Table 4 (determination of such an amount made as described herein). It is contemplated that those conditions that do not produce consistent libraries will be considered to define limit of sensitivity of SPLiT-DS on damaged/degraded DNA. Any such libraries will not be evaluated.

TABLE 4

DNA damage conditions.

| Damaging Agent | Experimental Condition |
|---|---|
| Oxidative H$_2$O$_2$ | Purified DNA incubated for 1, 5, 10, and 24 h at 37° C. in 30 mM H$_2$O$_2$ and FeSO$_4$ |
| Bleach | Purified DNA incubated for 0.5, 1, 5, 10, 24 h at 25° C. in 5% bleach solution |
| Acid Hydrolysis | Purified DNA incubated for 12, 24, 48, 72 h at 70° C. in 0.2N HCl |
| UV radiation (λ = 254 nm) | Purified DNA incubated for 1, 5, 10, 30 min at 25° C. at a power of 0.4 µW/cm$^2$ |
| Temperature/ Desiccation | Purified DNA incubated at 25° C., 50° C., and 80° C. for 1, 10, 20, 30 days |

Samples will be also sequenced on an Illumina MiSeq platform using 300 bp paired-end reads and data processed using custom SPLiT-DS software as described herein on data genotypes determined using STRait Razor. It is contemplated that an experimental condition that results in failure to correctly genotype (as described in a previous Example), will define limit of accuracy for SPLiT-DS on damaged/degraded DNA. Calculations will also be performed to determine specificity, allele coverage ratio for heterozygous loci, and/or depth for each locus for damaged/degraded DNA, and results will be compared to undamaged controls.

Since relative performance of SPLiT-DS on high quality DNA is not necessarily directly translatable to that on damaged DNA, comparisons will also be performed using SPLiT-DS, standard PCR-CE, and MPS methods. These methods will be performed using 10 PGP samples genotyped in previous Examples further subjected to the most challenging condition (as determined by results) in each category of damage for successfully genotyped SPLiT-DS samples. Samples will be genotyped by PCR-CE and conventional MPS using appropriate commercially available kits, as described in a previous Example. Relative performance of SPLiT-DS to PCR-CE and MPS will be determined as described herein, including determination and comparison of relative amounts of stutter, allelic dropout, intra-allelic balance, and genotyping success rate between approaches. I SPLiT-DS may provide more sensitive and accurate results using smaller samples and/or more damaged/degraded samples of DNA, than is achievable with other methods.

Validation of SPLiT-DS on Mixtures.

Improved efficacy (e.g. increased accuracy and sensitivity, as compared to available methods) of SPLiT-DS analysis on DNA mixtures consisting of two genetically unrelated individuals on a wide range of MAF ratios will be demonstrated. For each mixture in Table 5, ten, two-person combinations will be selected from the PGP samples genotyped in a previous Example. Specific PGP samples used in the present Example will depend on specific genotype, as determined in either a previous Example or by their whole genome sequence (available as part of the PGP). If possible, contributor pairs that differ by at least two repeats lengths at ≥8 loci will be chosen. It is considered more likely than not that more than 10 ng of DNA from each sample will be required. Exact amount will be determined by how efficiently SPLiT-DS works on at each locus, as determined in a previous Example.

TABLE 5

DNA mixture conditions

| Mixture Type | Component Amounts (%) |
|---|---|
| Two-Person Mixture | 99.9/0.1 |
|  | 99.5/0.5 |
|  | 99/1 |
|  | 95/5 |
|  | 90/10 |
| Three-Person Mixture (Optional) | 98/1.9/0.1 |
|  | 95/4.5/0.5 |
|  | 90/9/1 |
|  | 80/15/5 |

DNA input amounts will be adjusted such that any minor contributor will be represented with at least 10 reads. It is considered that representation with at least 10 reads confers a >95% chance of detecting both alleles at all CODIS loci. Specific amount required to achieve 10 MAF reads will depend on limits of sensitivity of SPLiT-DS, as demonstrated in a previous Example.

To minimize variability between replicates, mixtures will be constructed based on triplicate DNA quantifications using the QUANTIFILER Duo DNA Quantification Kit (Thermo Fisher). As described herein, samples will be sequenced on the Illumina MiSeq platform and data processed using custom SPLiT-DS software as describe herein and genotyped using STRait Razor. Evaluating presence of stutter in these experiments contributes to evaluation of performance of SPLiT-DS on DNA mixtures. For each analyzed locus in each mixture sample, a Wilson score interval (a form of binomial proportion confidence interval) for the known MAF will be calculated. Number of stutter events that differ by one repeat length from the known MAFs in the mixture will also be counted. If a stutter read count is within the 95% Wilson score interval of one of the MAF alleles, the locus will be considered a partial match. If both MAF alleles fail this test, then the locus will be considered a failed genotype call (homozygous alleles will automatically fail if the MAF cannot be distinguished from stutter). As in previous Examples, comparison studies of SPLiT-DS to PCR-CE and MPS will also be performed and evaluated as described herein, as well as comparisons of relative amounts of stutter, allelic dropout, intra-allelic balance, and/or genotyping success rate. Results of two-person mixture experiments will then be used to conduct three-person mixture experiments (see, e.g., Table 5), using the same sample selection criteria and analyses as in two-person mixture analysis.

SPLiT-DS will also be performed using simulated casework samples of single source and two person mixtures using DNA supplied by the Washington State Patrol Forensic Laboratory Services Bureau from previously analyzed, commercially obtained forensic DNA proficiency tests. Genotyping using SPLiT-DS will be compared to the on-line posted consensus results for the samples.

Example 6: Improved Performance of SPLiT-DS on Damaged DNA Samples

Figure 13A:
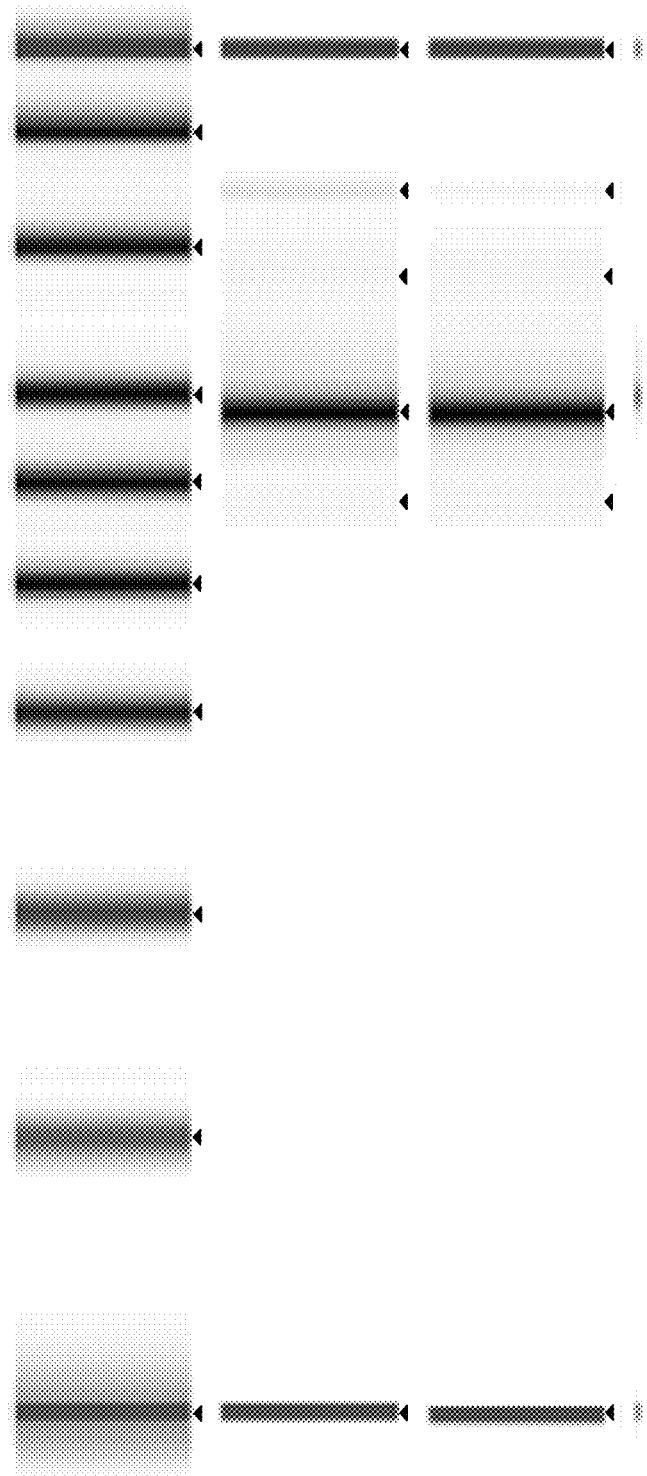
FIGS. 13A-13C show data resulting from a SPLiT-DS procedure in accordance with an embodiment of the present technology.
Figures 13B, 13C:
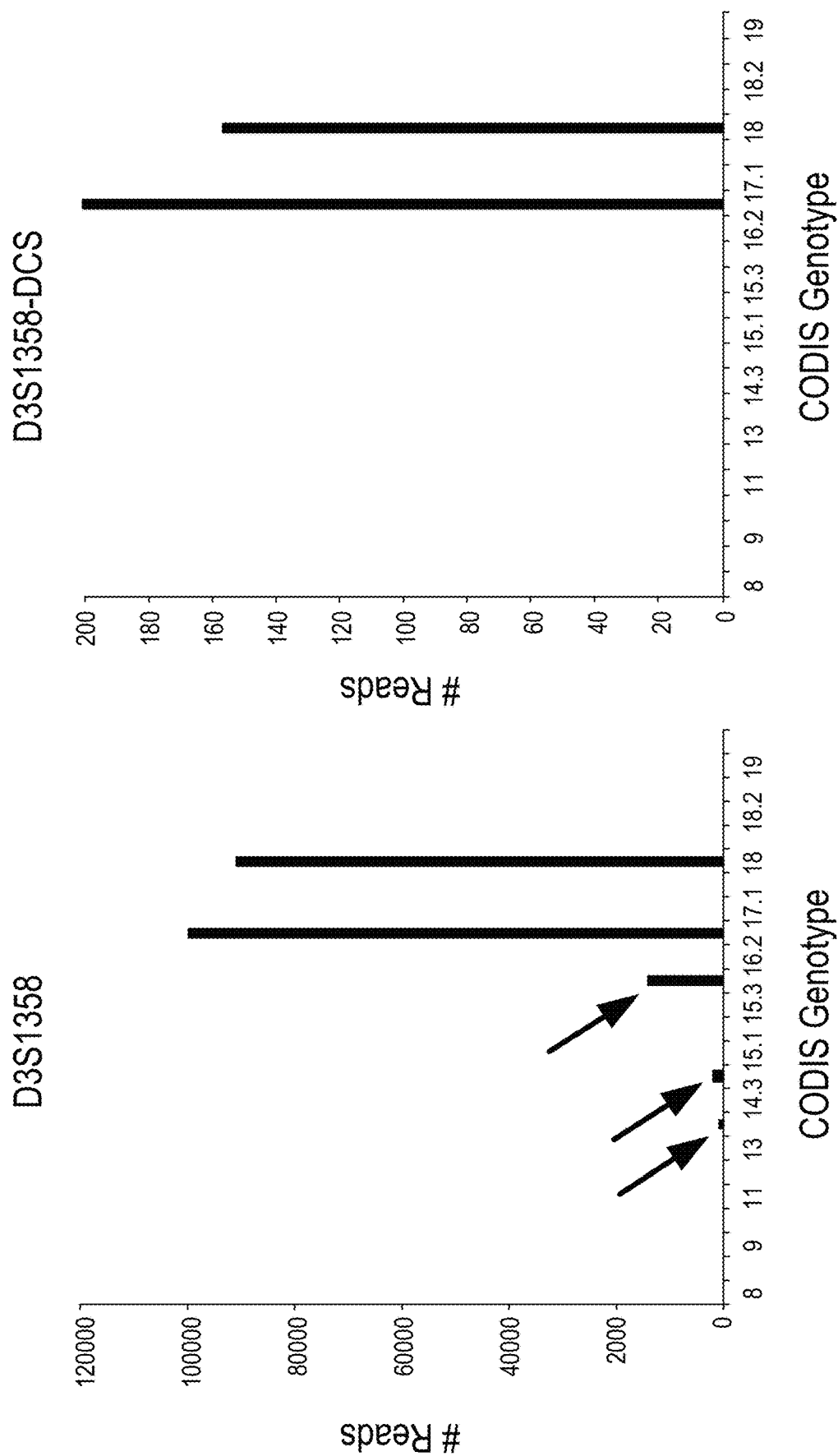

Formalin fixation causes extreme DNA damage in the form of cytidine deamination, oxidative damage, and cross-linking. To demonstrate capability of SPLiT-DS as compared to currently available methods, analyses were conducted on highly damaged DNA by sequencing nuclear DNA subjected to formalin fixation at the D3S1358 locus of Promega 2800M SRM (FIGS. 13B and 14A). FIGS. 13A-13C show data resulting from a SPLiT-DS procedure in accordance with an embodiment of the present technology. FIG. 13A is a representative gel showing insert fragment sizes prior to sequencing (Lane 1 is a ladder; lanes 2 and 3 are samples of PCR products from each tube; e.g. see Step 4 of FIG. 4). FIGS. 13B and 13C are graphs showing CODIS genotype versus a number of sequencing reads in the absence of error correction (FIG. 13B) and following analysis with SPLiT-DS (FIG. 13C). FIG. 13B shows a sample (D3S1358) with observed polymorphisms in the absence of error correction; stutter events are indicated by the black arrows. FIG. 13C shows a sample (D3S1358-DCS) that does not contain detectable stutter events after analysis with SPLiT-DS. The x-axis of each of FIGS. 13B and 13C indicates CODIS genotype and the y-axis indicates the number of reads.

Figure 14B:
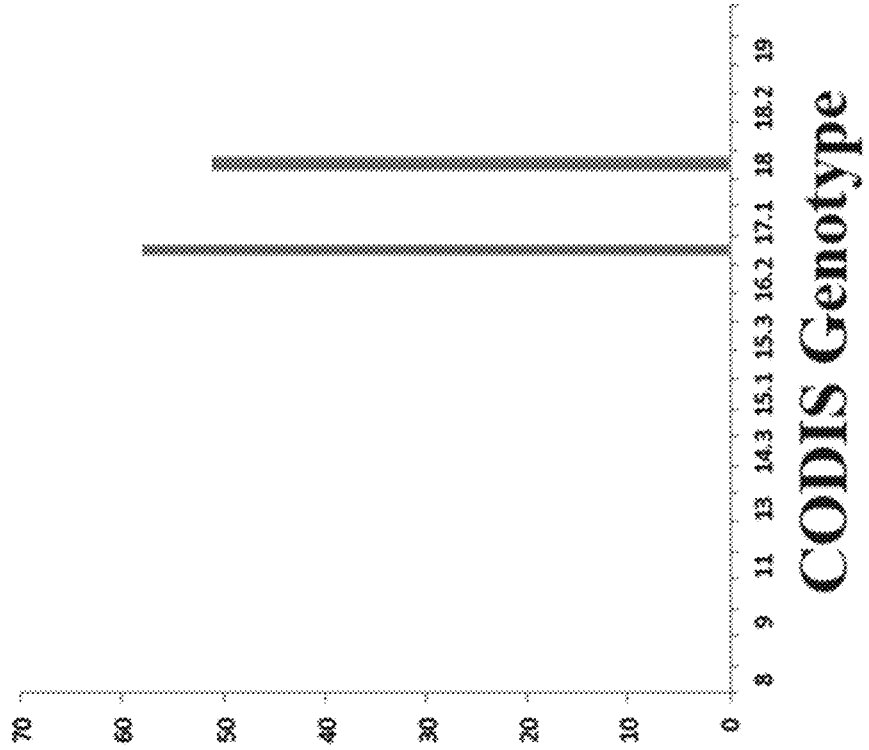
FIGS. 14A and 14B are graphs showing CODIS genotype versus a number of sequencing reads in the absence of error correction (FIG. 14A) and following analysis with SPLiT-DS (FIG. 14B) for highly damaged DNA in accordance with an embodiment of the present technology.
Figure 14A:
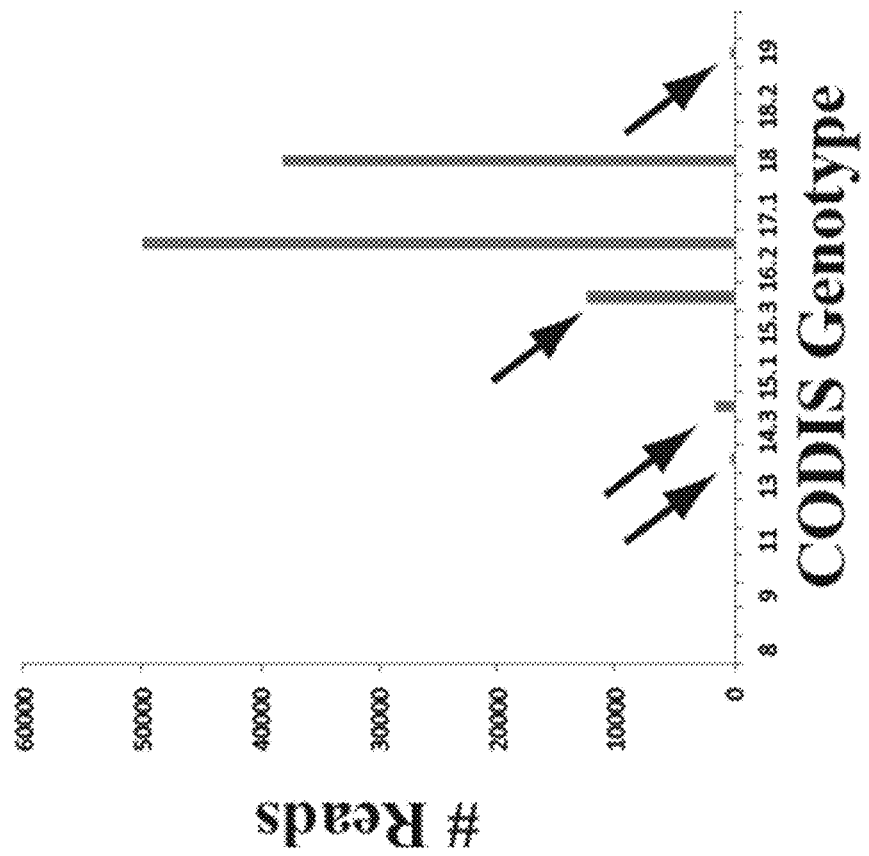

FIGS. 14A and 14B are graphs showing CODIS genotype versus a number of sequencing reads in the absence of error correction (FIG. 14A) and following analysis with SPLiT-DS (FIG. 14B) for highly damaged DNA in accordance with an embodiment of the present technology. The x-axis of each panel indicates CODIS genotype and the y-axis indicates the number of reads. FIG. 14A shows a damaged DNA sample not analyzed by SPLiT-DS (D3S1358) and demonstrating stutter events (black arrows) as well as significant amounts of apparent point mutations (not shown). FIG. 14B shows a sample (D3S1358-DCS) analyzed with SPLiT-DS error correction, and demonstrating an absence of detectable stutter events. No apparent point mutations were observed.

SPLiT-DS results demonstrated that, on formalin exposed DNA, all PCR and sequencing based artifacts that are present using standard sequencing methods were eliminated using SPLiT-DS. (FIGS. 13C and 14B). It was noted that there was a decrease in efficiency (approximately 3-fold) on these samples (see, e.g. FIG. 14B vs. FIG. 13C), however, the presence of interstrand crosslinks common in formalin fixation may have contributed to this decrease.

Example 7: Targeted Genome Fragmentation

The present Example demonstrates targeted genome fragmentation as a method of improving efficiency of sequencing of genomic DNA (gDNA). SPLiT-DS genome fragmentation is typically achieved by methods such as, e.g. physical shearing or enzymatic digestion of DNA phosphodiester bonds. Such approaches may produce a sample where the intact gDNA is reduced to a mixture of randomly sized DNA fragments. While highly robust, variable sized DNA fragments can cause PCR amplification bias (short fragments amplify more) and uneven depth of sequencing (FIG. 11A); as well as sequencing reads that do not overlap the region(s) of interest within a DNA fragment. Accordingly, the present Example will use CRISPR/Cas9 overcome these issues. Cut sites will be designed to produce fragments of predetermined and uniform sizes. A more homogenous set of fragments is considered more likely than not to overcome biases and/or presence of uninformative reads that can impact efficiency in other techniques that do not use targeted fragmentation. It is also considered likely that targeted fragmentation will facilitate pre-enrichment of a given sample prior to library preparation as removal of large off-target regions by separating fragments from gDNA is likely t to be possible due to fragment size consistency/difference.

Example 8: SPLiT-DS for Surveillance and Diagnosis of Cancer

The presence of circulating tumor DNA in blood has been recognized for decades, but requires ultra-sensitive methods for reliable development of cancer biomarkers (e.g. markers to diagnose and/or track disease presence/progress). SPLiT-DS helps to overcome pervasive challenges including low amounts of circulating tumor DNA within blood samples that contain varying amounts of cell free DNA. SPLiT-DS also improves and extends upon several highly sensitive and specific methods known in the art such as, BEAMing, SafeSeqS, TamSeq, and ddPCR, as it does not require a priori knowledge of a particular mutation. SPLiT-DS provides an approach capable of detecting cancer associated mutations with the highest level of accuracy currently available, low DNA input, and without prior knowledge of a particular tumor mutation.

The present Example will use SPLiT-DS to evaluate sequences associated with circulating tumor cell DNA. Control samples of known mutation will be used and run alongside samples from patients with diagnosed and/or suspected cancer.

SPLiT-DS and Genomic or Cell Free DNA

SPLiT-DS will be used to develop assays for accurate sequencing of low input gDNA (10-100 ng) and cfDNA (~10 ng). Genomic DNA generally occurs in large fragments (>1 Kb) and cell free DNA occurs almost exclusively as ~150 bp fragments of scarce frequency.

Low Input {10-100 ng} gDNA Rationale

The present Example demonstrates the feasibility of SPLiT-DS for low DNA input and its suitability for multiplexing. Though tissue may be available from biopsies of cancer patients, it is preferred to be conservative with use of such samples in order to complete all necessary testing. Accordingly, sequencing of gDNA would benefit from an improved platform, such as that provided by SPLiT-DS, that requires less input material.

Each target in SPLiT-DS is separately designed and optimized. The genes TP53, KRAS and BRAF will be assayed as a proof-of-principle. In particular, each gene has known target regions, where mutations associated with cancer occur. TP53 has 10 coding exons (of relatively small size), all of which will be targeted using SPLiT-DS. KRAS has known mutational hotspots at codons 12, 13, and 61 in exon 2, all of which will be targeted. BRAF has a mutation of V600E in exon 15 that will be targeted.

Material and Methods

SPLiT-DS assays will be performed on gDNA, as outlined in FIGS. 4 and 5 using DNA from de-identified tumors with known clonal mutations in TP53, KRAS and BRAF, as well as leukocyte gDNA from cancer-free individuals. Two different sets of experiments will be performed in order to perform any optimization/validation steps as well as test efficiency and sensitivity.

Efficiency

Efficiency is defined as percentage of input DNA molecules that are converted to DCS reads. Efficiency in this Example is targeted to be at least 30%, but >50%. It is considered more likely than not that 10 ng of input DNA will achieve a mean DCS depth of 1000× across loci of interest (10 ng=~3200 genomes, so 3200×0.3 efficiency=~1000 genomes sequenced). Efficiency depends, in part, on performance of the multiplex PCR. Using an in silico approach, PCR primers will be designed to have: i) high target specificity; ii) ability to be multiplexed; and iii) ability to perform robust and minimally biased amplification.

CRISPR/Cas9 systems will be used to specifically produce ~500-550 bp fragments that include a particular region of interest (see FIG. 11C). After completing design of guide RNAs and PCR primers, a combinatorial approach will be used to achieve: (i) target specificity (i.e. percentage of on target reads, acceptable >70%); and (ii) inter-locus depth balance (i.e. lowest depth locus divided by highest depth locus; acceptable >0.5). Optimized pools of guides and primers will be then applied to 10 ng as well as 100 ng of the same gDNA. These pools will be used for all subsequent experiments involving gDNA.

Sensitivity

TP53-mutated tumor gDNA will be spiked into control, non-mutated leukocyte gDNA at ratios of 1:2, 1:10, 1:100, 1:1000, 1:10,000. The same mixing experiment will be performed with two additional tumor DNAs containing known clonal mutations in each of KRAS and BRAF, for a total of 15 samples (5 dilutions for each of 3 genes). These 15 samples will be processed by SPLiT-DS as described herein, using 10 ng and 100 ng of input DNA. "Expected" and "observed" MAF will be compared (using a guideline that maximum MAF is determined by $MAF^{max}=\alpha \cdot 1N$ where N is the number of genomes and a is the efficiency of SPLiT-DS; for example with an efficiency of 30%, $MAF^{max}$ is 0.1% for 10 ng of DNA and 0.01% for 100 ng of DNA).

Based on the binomial distribution, it is considered to be more likely than not to achieve 63% probability of detecting a given mutation present at the $MAF^{max}$. Because there are 3 spiked mutations in the experiment, statistically it is more likely than not that at least one will be detected at 0.1% and 0.01%, and this probability will increase as efficiency increases above 30%.

In addition to spiked mutations, SNPs will be used to confirm sensitivity, as normal control DNA will be from a different individual than the tumor DNAs. SNPs will be examined at the same dilutions (homozygous SNPs) and at effective dilutions of 1:4, 1:20, 1:200, 1:2000 and 1:20,000 (heterozygous SNPs).

CRISPR/Cas9 was able to efficiently cut all TP53 exons and facilitate enrichment by size-selection and maximize read usage CRISPR/Cas9 guides were designed to cut TP53 exons (see FIG. 12A). 10 ng of gDNA were digested and processed using SPLiT-DS (see FIGS. 12B and 12C) as described in previous Examples with appropriate PCR primers to amplify exons 5-6 and 7 (FIGS. 12C and 12D). Both strands of DNA were properly sequenced with a high percentage of on-target reads and produced DCS reads after matching the complementary random tags for each molecule (FIG. 12D). In addition, the average depth obtained for a starting amount of DNA of 10 ng corresponds to an efficiency of 25% (that is, from the original 3000 genomes, ~800× average were sequenced), which represents a 50-fold improvement over standard DS and an unprecedented improvement as compared conventional solution hybridization approaches.

Example 9: Development of SPLiT-DS for Accurate Sequencing of cfDNA

The present Example demonstrates use of SPLiT-DS for detection of mutations in exemplary cancer-related genes: TP53, KRAS, and BRAF in cfDNA.

Material and Methods

Cell-free DNA from commercially available plasma (Conversant Bio) will be extracted using a QIAamp Circulating Nucleic Acid kit. Three different synthetic 150 bp DNA molecules encoding a known mutation for each of the three genes of interest will be used. Each of these synthetic DNA molecules will be spiked into the cfDNA at ratios of 1:2, 1:10, 1:100, 1:1000, 1:10,000. Two different sets of experiments will be performed to optimize and validate SPLiT-DS protocol parameters for cfDNA.

Efficiency

Since cfDNA is already fragmented, no cutting (e.g. CRISPR/Cas9) is required. Therefore, SPLiT-DS is performed as described in previous examples, with the addition of a nested PCR. Resultant fragments will be sequenced with a MiSeq v3 150 cycles approximately 10 samples will be multiplexed in a cartridge for a total of 2.5 million reads each.

Sensitivity

Five mixed dilutions (1:2, 1:10, 1:100, 1:1000, 1:10,000) for each of TP53, KRAS, and BRAF mutations in cfDNA will be analyzed by SPLiT-DS with the optimized primers designed in this Example, and beginning with 10 ng and 100 ng of DNA. Experiments will be run side-by-side with SafeSeqS to compare sensitivity between techniques (a known technique for accurate sequencing of ctDNA is SafeSeqS, which reduces NGS errors by using single-strand correction). It is considered more likely than not that SPLiT-DS will outperform SafeSeqS for the detection of mutations at MAF=0.1% and 0.01%. It is considered more likely than not that SPLiT-DS will be able to detect spike mutations at an estimated mean sensitivity of 0.5% (Table 2), but that Safe-SeqS will not be able to detect any spike mutation at such a low frequency.

Figure 15A:
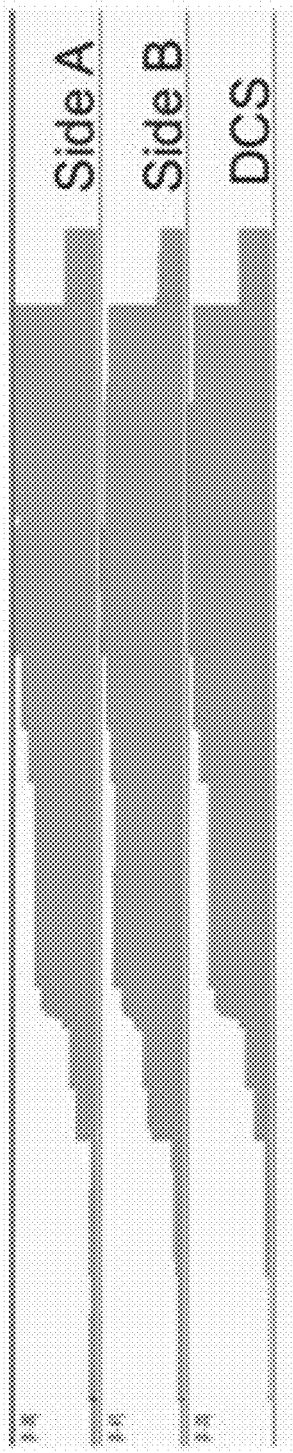
FIGS. 15A and 15B visually represent SPLiT-DS sequencing data of KRAS exon 2 generated from 10 ng (FIG. 15A) and 20 ng (FIG. 15B) of cfDNA in accordance with an embodiment of the present technology.
Figure 15B:
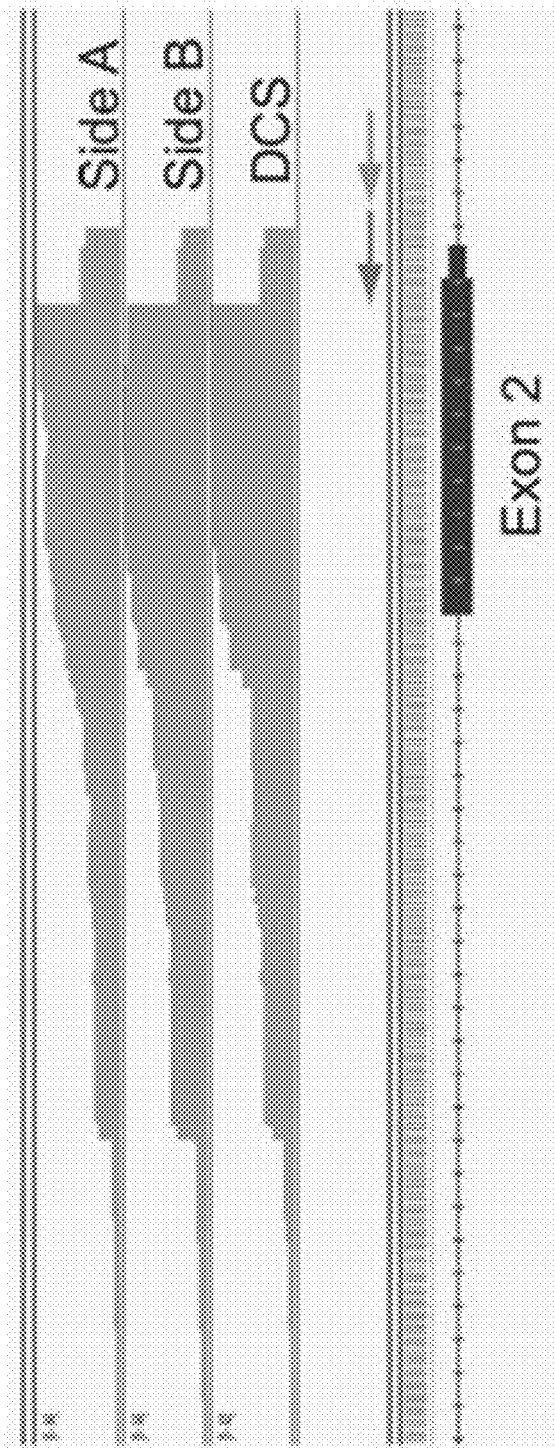

Primers (for a nested PCR approach) were designed to amplify codons 12 and 13 in KRAS exon 2. 10 ng and 20 ng of cfDNA extracted from normal plasma (Conversant Bio) were processed in parallel. FIGS. 15A and 15B visually represent SPLiT-DS sequencing data of KRAS exon 2 using nested PCR and generated from 10 ng (FIG. 15A) and 20 ng (FIG. 15B) of cfDNA in accordance with an embodiment of the present technology. In this Example, target enrichment was accomplished using SPLiT-DS and sequencing was on an Illumina MiSeq with 75 bp paired-end reads. SSCS for both 'A' and 'B' strands prior to duplex formation, as well as the final DCS reads are shown. Arrows indicate two locus specific PCR primers (grey primer=nested PCR primer).

As shown in FIGS. 15A and 15B, "Side A" and "Side B" correspond to the two different strands of DNA, which were amplified properly and found their complementary strands to form highly accurate DCS reads. Although depth obtained was modest (~50 reads), it corresponds to an efficiency of ~1%, which is the current efficiency of standard DS. Thus, at baseline (i.e. without any optimization), SPLiT-DS obtained results with the same efficiency as currently used approaches, but with as little as 10 ng of input DNA, demonstrating efficiency improvements over other available approaches for sequencing cfDNA, including at very low quantities.

Example 10: SPLiT-DS for Pancreatic Cancer Detection and Prognosis Based on ctDNA The present Example demonstrates improvements (as compared to currently available methods) upon detection of mutations in ctDNA of patients with pancreatic ductal adenocarcinoma (PDAC) using SPLiT-DS. SPLiT-DS provides improved sensitivity of ddPCR in multiple target genes including KRAS, TP53, and BRAF. It is considered more likely than not that the results of these assays will demonstrate improved sensitivity to detect one mutation in 95% of PDAC patients and two mutations in >50% of PDAC cases over current approaches.

In addition, as most DNA in circulation of a human subject (i.e. in the circulatory system (e.g. cell free DNA), is of hematopoietic origin, leukocyte DNA will be sequences and mutations compared with those found in cfDNA. It is proposed that these results will inform, with greater sensitivity and accuracy than other results, whether certain background mutations originate in leukocyte subclones.

Materials and Methods

Fully de-identified cfDNA and matching leukocyte DNA samples from 40 patients with PDAC, 20 patients with chronic pancreatitis, and 20 age-matched normal controls will be evaluated. Blood samples will be processed within two hours of extraction and samples including 2-5 ml of plasma and 500 ul of buffy coat will be provided. In addition, for PDAC patients, a piece of frozen tumor will be available to confirm tumor mutations. For all PDAC patients, blood is procured pre-operatively. All patients are followed clinically, and detailed clinico-pathological information will be available, including time to recurrence and mortality. Patient samples will include those from 20 with localized cancer and 20 with metastatic cancer.

ctDNA will be extracted with a QIAamp Circulating Nucleic Acid Kit and gDNA will be extracted with a QIAamp DNA Mini kit. 10 ng or more of cf DNA (from collected plasma), 100 ng of gDNA, and all available ctDNA (up to 100 ng) will be processed with appropriate SPLiT-DS procedures as described herein, targeting KRAS, BRAF, and TP53. Sequencing will be performed with the Illumina 150-cycle MiSeq v3 Reagent Kit for ctDNA and 600-cycle for gDNA. In the 150-cycle kit, 10 ctDNA samples will be multiplexed, and in the 600-cycle kit 15 gDNA samples will be multiplexed. Based on the experimental design, it is considered more likely than not that expected efficiency of at least 30% will be obtained with sequencing depths of at least 1,000× for 10 ng of DNA and as much as 10,000× for 100 ng of DNA. Data will be analyzed following sequencing, DCS production, and mutation identification.

Pancreatic Cancer Detection

Sensitivity and specificity of SPLiT-DS to detect KRAS, TP53, and BRAF mutations in cfDNA from patients with PDAC will be determined in the present Example. To analyze sensitivity, mutations found in cfDNA will be compared with tumor mutations (clonal and subclonal) identified by SPLiT-DS. As SPLiT-DS results provide coverage for nearly all PDAC cases with 1 mutation and >50% of cases with 2 mutations, it is considered more likely than not that at least one tumor mutation will be detected in cfDNA from all metastatic cases and about 80% of localized cases, for a combined sensitivity for all PDAC of ~90%.

Mutations found in cfDNA will be compared with those found in matched leukocytes purified from the same patient. Mutations found in cfDNA as well as matching leukocytes will be considered biological background and discounted from final mutational counts in cfDNA. Upon subtraction of shared mutations, cfDNA mutations will be compared in PDAC, pancreatitis, and controls. It is considered more likely than not that cancer mutations will have higher frequency than biological background mutations, even if biological background mutations (e.g. age-related mutations) remain in samples. Optimal threshold for mutation frequency will be determined in order to distinguish cancers and controls with maximum sensitivity and specificity using the area under the curve and age-corrected ROC models.

Pancreatic Cancer Prognosis

Due to increased sensitivity of SPLiT-DS as demonstrated in previous Examples, it is considered more likely than not that, in contrast to previously available approaches, ctDNA will be detectable in almost (90%) all PDAC patients. Instead of a binary variable (i.e. yes/no) for presence of ctDNA, ctDNA MAF will be analyzed as a quantitative variable and compare MAF scores and clinical data (e.g. to compare MAF score and prognosis). Whether a mutated gene, codon, and/or mutation type are correlated with recurrence or mortality will also be determined. Multivariate COX models, adjusted for confounders (including age and stage), will be used to test ability of these variables and their combinations to predict disease free survival and overall survival. Kaplan-Meier curves will be used to represent predictive value of categorical variables.

Example 11: SPLiT-DS for Identification of Resistance Mutations in Metastatic CRC Detection of Early Stage Cancers, and Prediction of Recurrence Using ctDNA In metastatic CRC (i.e. Stage IV), which represents about 50% of the cases at presentation, tumor genotyping is essential to guiding therapy decisions: oncogenic mutations in KRAS, NRAS, and BRAF occur in about 50% of CRC patients and predict a lack of response to EGFR monoclonal antibodies cetuximab and panitumumab Thus, these genes are routinely assessed in both fixed and unfixed tissue biopsies, but currently available approaches often result in low quality subclonal resolution, and suffer from sampling bias. Consequently, tumors with subclonal mutations might be missed and a portion of patients might be administered therapies that are certain to fail. Therefore, in the present Example, tumor genotyping with ctDNA using SPLiT-DS will demonstrate an assay with improved sensitivity over currently available techniques, which will also improve diagnostics and treatment due to detection of SPLiT-DS pre-existing resistance mutations that condition the eligibility of a patient for EGFR blockade therapy.

Detection and Prediction of CRC Presence and/or Recurrence

SPLiT-DS will be used on a panel of 5 commonly mutated CRC genes to demonstrate detection of mutations in ctDNA without prior knowledge of any particular tumor mutation. It is considered more likely than not that results from this assay will be able to inform future CRC detection using much more simplified testing (e.g. a blood test).

The present example will also demonstrate improvements upon methods used to detect and/or predict recurrence. At present, available techniques are limited by lack of sufficient sensitivity and/or specificity, or, for techniques that have sufficient sensitivity/specificity, they are cost prohibitive. Therefore, SPLiT-DS analyses of ctDNA will demonstrate improved detection and prediction of recurrence in CRC, offering improvements in accuracy (e.g. greater than 100-fold over, e.g. SafeSeqS) and ability to expand and assess multiple genes.

Materials and Methods

Samples from patients of multiple biopsy types from >300 patients that underwent surgical resection of tumors will be used in the present Example. Available biospecimens include tumor, plasma, and buffy coat. Patients from whom samples were obtained were followed longitudinally and blood samples are available at 6, 12 and 24 months after baseline resection. For all patients, detailed clinico-pathological information, including recurrence is available. All the samples and coded medical information is fully de-identified. Samples from patients with metastatic disease were previously assessed for KRAS and NRAS mutations to determine likelihood of response to cetuximab or panitumumab. If no mutations were found, targeted therapy was applied. Resistance was documented via progression with imaging studies.

Samples from 20 patients with metastatic cancer (stage IV) and 40 patients with localized cancers (stages I-III) will be evaluated. DNA will be purified from plasma (2-5 ml) and buffy coat obtained pre-operatively, as well as from frozen tumor samples. Patients categorized as having metastatic cancer will be those that tested negative for KRAS and NRAS mutations, but did not respond to EGFR inhibitor therapy. At least 10 patients with recurrence will also be included. ctDNA will be measured in blood collected at 6, 12 and 24 months after surgery. As in a previous Example, leukocyte DNA mutations will be used to identify potential biological background mutations that might be present in cfDNA.

In addition, as APC is the most commonly mutated gene in CRC and the SPLiT-DS panel used in this Example will include the most commonly mutated regions of APC such as, e.g. the mutation cluster region, which extends from codon 1,286 to codon 1,585 (299 bp), which covers about 60% of CRC mutations in APC52, as well as the additional top hits found in COSMIC for a total of ~1000 bp. NRAS codons 12, 13 and 61 will also be included. Therefore, the panel used in this Example will include APC (~1000 bp), TP53 (coding region 1182 bp), KRAS (codons 12, 13, 61), BRAF (V600E), and NRAS (codons 12, 13, 61), for a total size ~2700 bp. It is considered more likely than not that the panel described in this Example will cover all CRC samples comprising one mutation and a subset of those with two mutations.

Identification of Resistance Mutations in Metastatic CRC

SPLiT-DS will be used to evaluate samples from metastatic CRC, for clonal tumor mutations in cfDNA. All tumors will be negative for KRAS and NRAS mutations, but are likely to carry at least one clonal mutation (in APC or TP53) identified with the panel described in this Example. SPLiT-DS will also be used to determine whether presence of very low frequency (<0.1%) mutations in ctDNA are detectable that confer resistance to EGFR therapy. It is considered more likely than not that samples from patients with metastatic disease will be successfully sequenced at very high depth (~10,000×). SPLiT-DS analyses will also improve detection of low frequency KRAS, BRAF and NRAF mutations in ctDNA of patients with metastatic disease who tested negative for KRAS and NRAS by Sanger sequencing of tumor DNA, but have also failed EGFR therapy. Tumor DNA with be sequenced using SPLiT-DS at similar high depth to determine presence or absence of primary resistance mutations in ctDNA. Results will be compared between ctDNA and DNA derived from intratumor tissues.

Detection of Localized CRC

SPLiT-DS will be used to identify ctDNA using a panel of 5 CRC genes as described herein, in samples from localized (Stages I-III) cancer. Tumor DNA will also be sequence using SPLiT-DS. As described in a previous Example, presence of biological background mutations originating in leukocyte cells will also be determined.

Certain currently available methods (e.g., CEA) provide an estimated 1.5-6 months 'lead time' as compared to other methods for detection of recurrence, but it is not clear whether such an amount of time impacts survival. Other techniques may improve lead time, but require a priori knowledge of tumor genotype(s). Therefore, SPLiT-DS will be used to sequence ctDNA and demonstrate superior ability to improve of "lead" time by several months, and, as described herein, does not require prior knowledge of tumor genotype. Ability of SPLiT-DS to detect ctDNA at 6, 12, and 24 months after primary surgery in patients with localized CRC that experienced recurrence will be demonstrated in the present Example. Ten patients will be selected on bases of having recurrence in which tumor and baseline ctDNA carried at least one mutation (ideally 2) in the genes of previously-described panels. For each sample (individual), clinical history over time (chemotherapy, CT scans and other indicators of relapse) will be plotted against total ctDNA levels for each mutation at baseline, 6, 12 and 24 months. Comparisons to CEA levels and lead time to recurrence of ctDNA and CEA will also be evaluated.

Example 12: CRISPR-DS

Figure 16A:
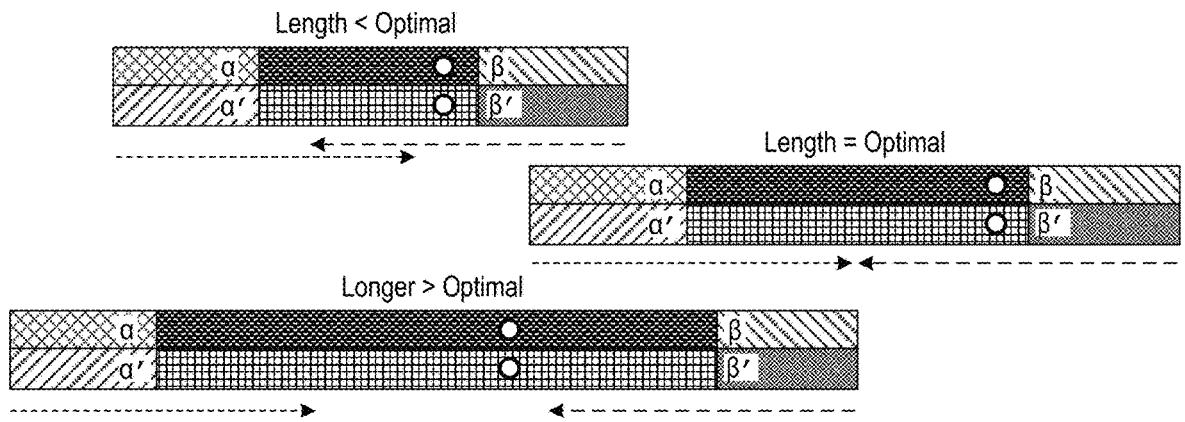
FIG. 16A is a schematic illustration of fragment lengths produced by sonication and by CRISPR/Cas9 fragmentation in accordance with an embodiment of the present technology.
Figure 16B:
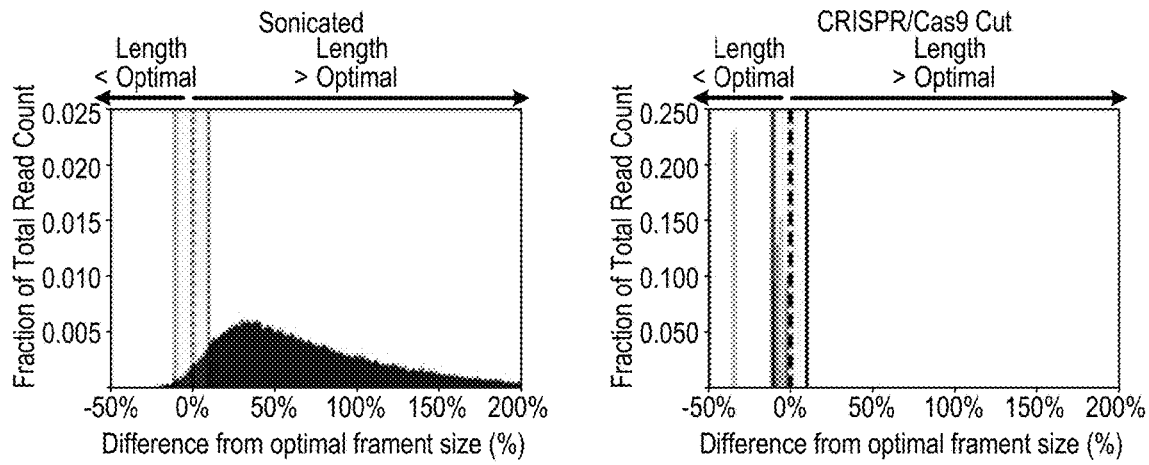
FIGS. 16B and 16C are histogram graphs showing fragment insert size of samples prepared with standard DS and CRISPR-DS protocols in accordance with embodiments of the present technology. X-axis represent percent difference from optimal fragment size, e.g. fragment size that matches the sequencing read length after adjustments for molecular barcodes and clipping. Columnar region shows range of fragment sizes which are within 10% difference from optimal size, with optimal size being designated with a vertical hashed line.
Figure 16C:
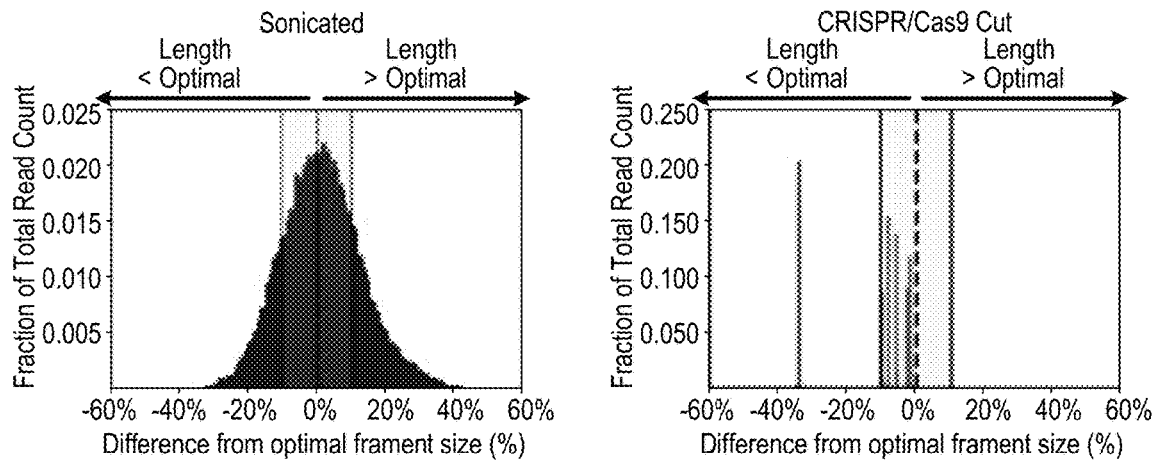

The present Example describes creation of CRISPR-DS to perform highly accurate and sensitive sequencing. CRISPR-based technology was used to excise target regions designed with predetermined, homogenous length (FIG. 12A). In the present Example, the CRISPR-compatible nuclease used was Cas9. This size control was used to facilitate size selection prior to library preparation (FIG. 12B), followed by double-stranded barcoding (FIG. 12C) to perform error removal (similar to previously described, e.g. DS methods) (FIG. 12D). Following barcoding, a single round of capture is performed (in contrast to other available methods), and results in very high, on-target enrichment, with ability to produce fragments to cover a full sequencing read (FIGS. 12F and 16A). Fragmentation for hybridization capture is usually performed with sonication, which often generates fragments that are either too long and with sequencing reads that don't overlap with a region of interest, and/or are too short and with sequencing reads that overlap with each other and re-read the same sequence (FIGS. 12F and 16A). FIGS. 16B and 16C are histogram graphs showing fragment insert size of samples prepared with standard DS and CRISPR-DS protocols in accordance with embodiments of the present technology. X-axis represent percent difference from optimal fragment size, e.g. fragment size that matches the sequencing read length after adjustments for molecular barcodes and clipping. Columnar region shows range of fragment sizes which are within 10% difference from optimal size, with optimal size being designated with a vertical hashed line. As shown in FIGS. 16B and 16C, sonication produced significant variability in the amount of deviation from the optimal fragment size (FIG. 16B) while CRISPR/Cas9 digestion yielded fragments that had the vast majority of the reads within the optimal fragment size (FIG. 16C).

The present Example demonstrates how false mutations are prevented by use of CRISPR-based fragmentation, including, e.g. because the enzyme used in this Example, Cas9, produces blunt ends, which do not require end-repair. Thus, the technologies provided herein overcome multiple common and pervasive problems of NGS, including inefficient target enrichment, sequencing errors, and uneven fragment size.

Figure 23:
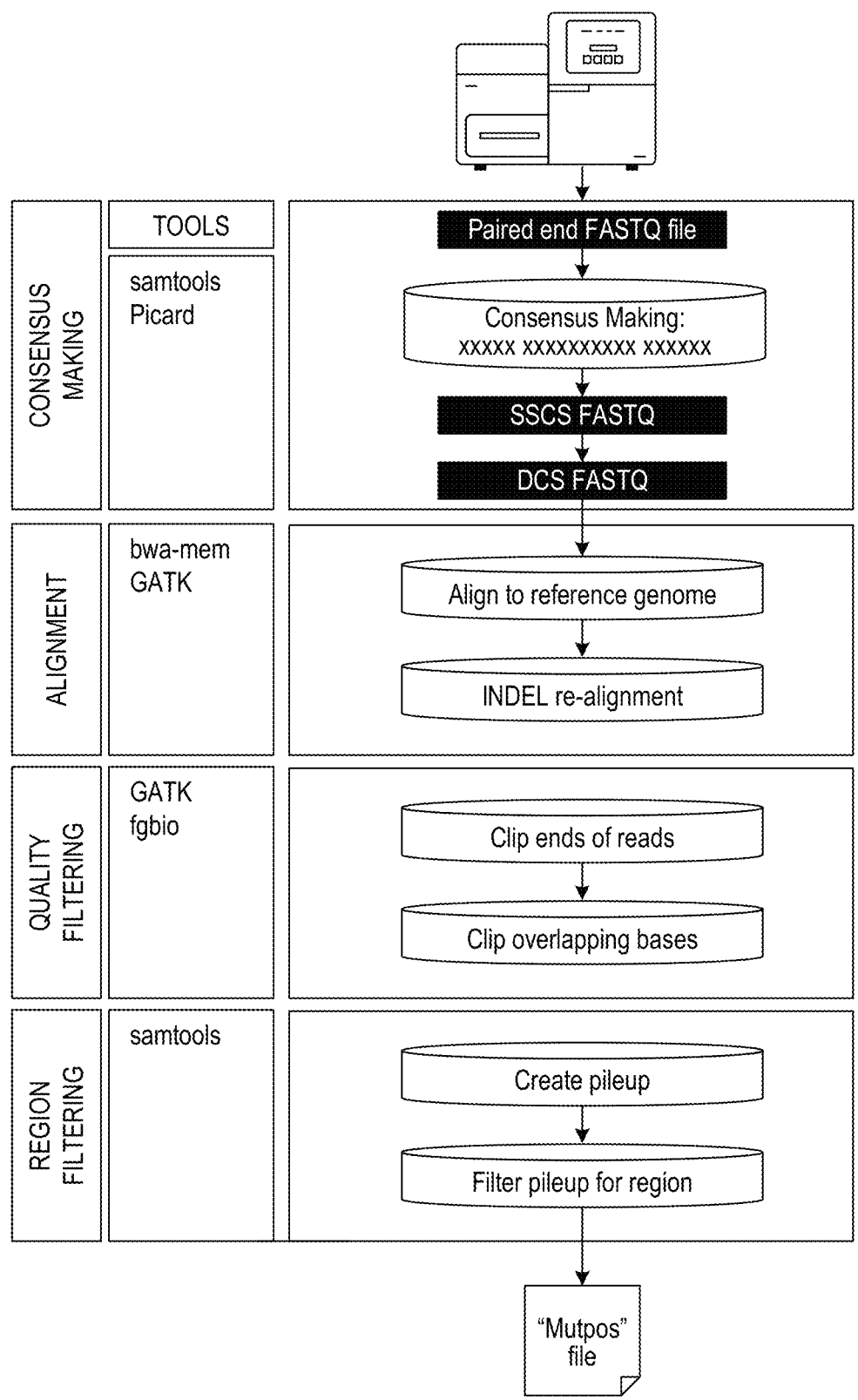
FIG. 23 is a schematic overview of CRISPR-DS data processing steps in accordance with an embodiment of the present technology.

Guide RNAs (gRNAs) were designed to excise a coding region of TP53 and flanking intronic areas (FIG. 12A). Fragment size was set at ~500 bp. gRNAs were selected based on specificity score and fragment length (Table 1, FIGS. 17A-17C,). Test samples with variable amounts of input DNA (10-250 ng) were CRISPR/Cas9 digested, followed by size selection with solid-phase reversible immobilization (SPRI) beads to remove undigested high molecular weight DNA and enrich for excised fragments containing targeted regions (FIG. 12B). Subsequent library preparation was performed according to currently available, standard protocols, but using only one round of capture and minor modifications, as described herein. DNA was A-tailed, ligated with DS adapters, amplified, purified by bead wash, and captured by hybridization with biotinylated 120 bp DNA probes targeting TP53 exons (Table 6). Captured samples were amplified with index primers and sequenced in an Illumina MiSeq v3 600 cycle kit. Analysis was performed as in standard protocols, but modified to include generation of a consensus sequence prior to alignment (FIG. 23).

TABLE 6

TP53 hybridization capture probes
(SEQ ID NOS: 16-36)

| Targeted exon: | IDT probe name: | IDT probe sequence: |
|---|---|---|
| Exon11 | TP53_e11.A.2 | CCCCGGGACAAAGCAAATGGAAGTCCTGGGTGCTTCTGACGCACACCTATTGCAAGCAAGGGTTCAAAGACCCAAAACCCAAAATGGCAGGGGAGGGAGAGATGGGGGTGGGAGGCTGTC |
| Exon11 | TP53_e11.A.1 | AGTGGGGAACAAGAAGTGGAGAATGTCAGTCTGAGTCAGGCCCTTCTGTCTTGAACATGAGTTTTTTATGGCGGGAGGTAGACTGACCCTTTTTGGACTTCAGGTGGCTGTAGGAGACAG |
| Exon10 | TP53_e10.1 | ACTCACCTGGAGTGAGCCCTGCTCCCCCCTGGCTCCTTCCCAGCCTGGGCATCCTTGAGTTCCAAGGCCTCATTCAGCTCTCGGAACATCTCGAAGCGCTCACGCCCACGGATCTGCAGC |
| Exon10 | TP53_e10.1_1 | AATCCTATGGCTTTCCAACCTAGGAAGGCAGGGGAGTAGGGCCAGGAAGGGGCTGAGGTCACTCACCTGGAGTGAGCCCTGCTCCCCCCTGGCTCCTTCCCAGCCTGGGCATCCTTGAGT |
| Exon10 | TP53_e10.1_2 | TCCAAGGCCTCATTCAGCTCTCGGAACATCTCGAAGCGCTCACGCCCACGGATCTGCAGCAACAGAGGAGGGGAGAAGTAAGTATATACACAGTACCTGAGTTAAAAGATGGTTCAAGT |
| Exon9-8 | TP53_e8.1 | AAGAGGTCCCAAGACTTAGTACCTGAAGGGTGAAATATTCTCCATCCAGTGGTTTCTTCTTTGGCTGGGGAGAGGAGCTGGTGTTGTTGGGCAGTGCTAGGAAAGAGGCAAGGAAAGGTG |
| Exon9-8 | TP53_e7.2 | GCATAACTGCACCCTTGGTCTCCTCCACCGCTTCTTGTCCTGCTTGCTTACCTCGCTTAGTGCTCCCTGGGGGCAGCTCGTGGTGAGGCTCCCCTTTCTTGCGGAGATTCTCTTCCTCTG |
| Exon9-8 | TP53_e7.1 | TGCGCCGGTCTCTCCCAGGACAGGCACAAACACGCACCTCAAAGCTGTTCCGTCCCAGTAGATTACCACTACTCAGGATAGGAAAAGAGAAGCAAGAGGCAGTAAGGAATCAGGTCCTA |
| Exon7 | TP53_e6.1 | TGACCTGGAGTCTTCCAGTGTGATGATGGTGAGGATGGGCCTCCGGTTCATGCCGCCCATGCAGGAACTGTTACACATGTAGTTGTAGTGGATGGTGGTACAGTCAGAGCCAACCTAGGA |
| Exon7 | TP53_e6.2 | ATGTGATGAGAGGTGGATGGGTAGTAGTATGGAAGAAATCGGTAAGAGGTGGGCCCAGGGGTCAGAGGCAAGCAGAGGCTGGGGCACAGCAGGCCAGTGTGCAGGGTGCAAGTGGCTCC |
| Exon6-5 | TP53_e5.1 | GACCTCAGGCGGCTCATAGGGCACCACCACACTATGTCGAAAGTGTTTCTGTCATCCAAATACTCCACACGCAAATTCCTTCCACTCGGATAAGATGCTGAGGAGGGCCAGACCTAA |

TABLE 6-continued

TP53 hybridization capture probes
(SEQ ID NOS: 16-36)

| Targeted exon: | IDT probe name: | IDT probe sequence: |
|---|---|---|
| Exon6-5 | TP53_e5.1_1 | CTGGAGGGCCACTGACAACCACCCTTAACCCCTCCTCCCAGAGACCCCAGTTGCAAACCAGACCTCAGGCGGCTCATAGGGCACCACCACACTATGTCGAAAAGTGTTTCTGTCATCCAA |
| Exon6-5 | TP53_e4.3 | CACCATCGCTATCTGAGCAGCGCTCATGGTGGGGGCAGCGCCTCACAACCTCCGTCATGTGCTGTGACTGCTTGTAGATGGCCATGGCGCGGACGCGGGTGCCGGGCGGGGGTGTGGAAT |
| Exon6-5 | TP53_e4.3_1 | GAATCAGAGGCCTGGGGACCCTGGGCAACCAGCCCTGTCGTCTCTCCAGCCCCAGCTGCTCACCATCGCTATCTGAGCAGCGCTCATGGTGGGGGCAGCGCCTCACAACCTCCGTCATGT |
| Exon6-5 | TP53_e4.2 | CACCCACAGCTGCACAGGGCAGGTCTTGGCCAGTTGGCAAAACATCTTGTTGAGGGCAGGGGAGTACTGTAGGAAGAGGAAGGAGACAGAGTTGAAAGTCAGGGCACAAGTGAACAGAT |
| Exon4-3 | TP53_e3.3 | ATTGAAGTCTCATGGAAGCCAGCCCCTCAGGGCAACTGACCGTGCAAGTCACAGACTTGGCTGTCCCAGAATGCAAGAAGCCCAGACGGAAACCGTAGCTGCCCTGGTAGGTTTTCTGGG |
| Exon4-3 | TP53_e3.2 | AAGGGACAGAAGATGACAGGGGCCAGGAGGGGGCTGGTGCAGGGGCCGCCGGTGTAGGAGCTGCTGGTGCAGGGGCCACGGGGGGAGCAGCCTCTGGCATTCTGGGAGCTTCATCTGGAC |
| Exon4-3 | TP53_e3.1 | CTGGGTCTTCAGTGAACCATTGTTCAATATCGTCCGGGGACAGCATCAAATCATCCATTGCTTGGGACGGCAAGGGGACTGTAGATGGGTGAAAAGAGCAGTCAGAGGACCAGGTCCTC |
| Exon4-3 | TP53_e2.3 | GCCCCCCAGCCCTCCAGGTCCCCAGCCCTCCAGGTCCCCAGCCCAACCCTTGTCCTTACCAGAACGTTGTTTTCAGGAAGTCTGAAAGACAAGAGCAGAAAGTCAGTCCATGGAATTTT |
| Exon2 | TP53_e2.2 | CGCTTCCCACAGGTCTCTGCTAGGGGGCTGGGGTTGGGGTGGGGGTGGTGGGCCTGCCCTTCCAATGGATCCACTCACAGTTTCCATAGGTCTGAAAATGTTTCCTGACTCAGAGGGGGC |
| Exon2 | TP53_e2.1 | TCGACGCTAGGATCTGACTGCGGCTCCTCCATGGCAGTGACCCGGAAGGCAGTCTGGCTGCTGCAAGAGGAAAAGTGGGGATCCAGCATGAGACACTTCCAACCCTGGGTCACCTGGGCC |

Figure 18A:
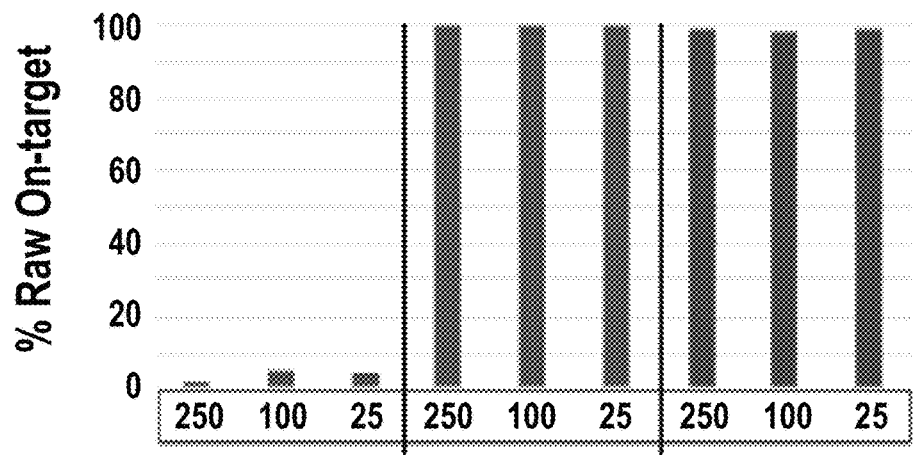
FIGS. 18A-18C are bar graphs showing percent of raw sequencing reads on-target (covering TP53) (FIG. 18A), showing percentage recovery as calculated by percentage of genomes in input DNA that produced duplex consensus sequence reads (FIG. 18B), and showing median duplex consensus sequence depth (FIG. 18C) across all targeted regions for various input amounts of DNA processed using standard DS and CRISPR-DS in accordance with an embodiment of the present technology.
Figure 18B:
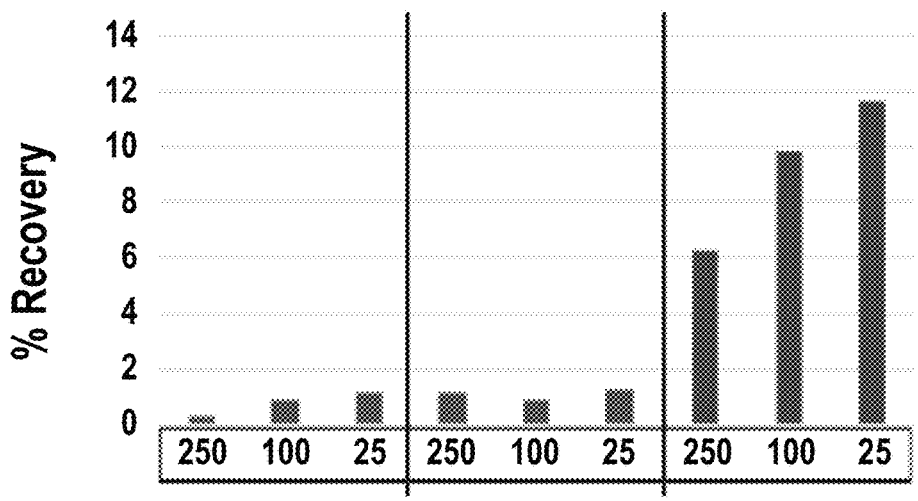
Figure 18C:
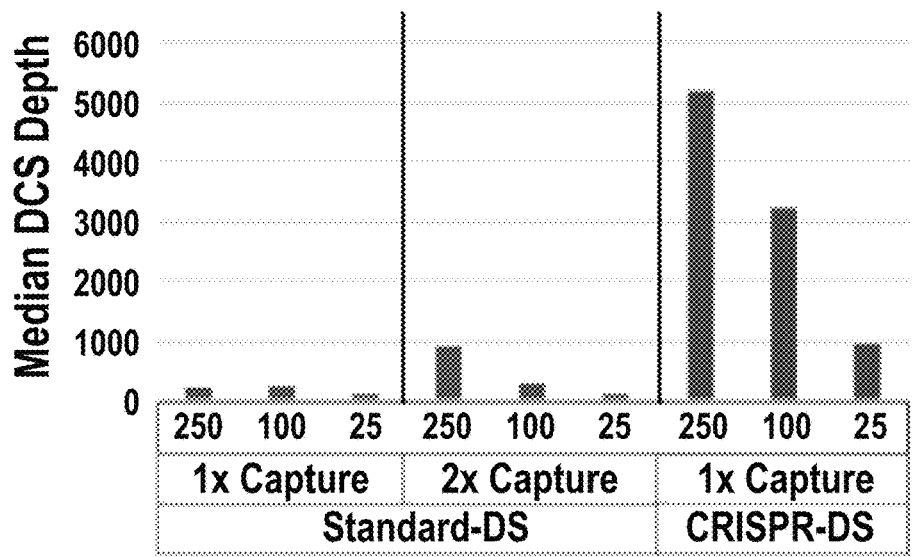
Figure 19:
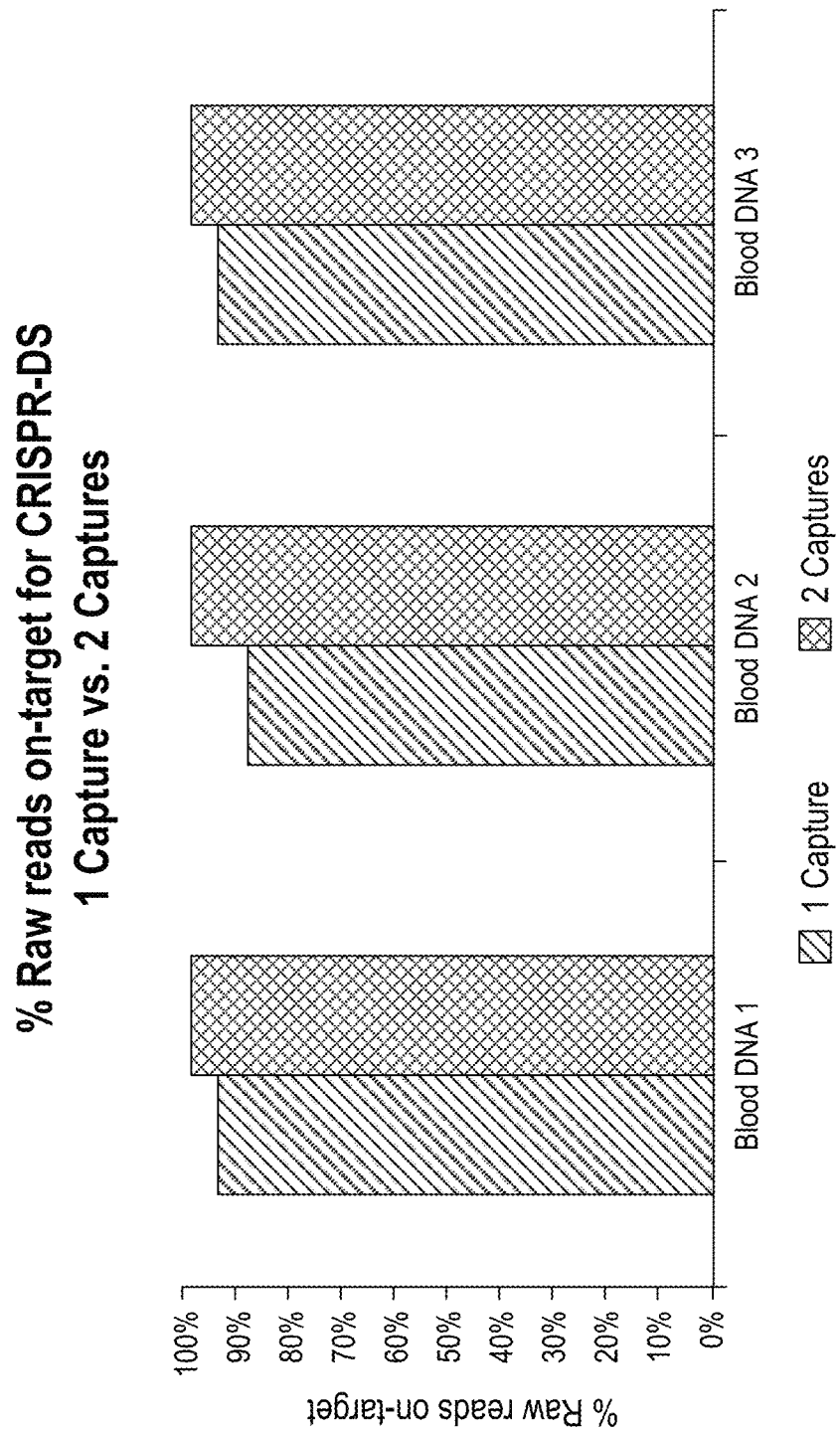
FIG. 19 is a bar graph showing target enrichment provided by CRISPR-DS with one capture step as compared to two capture steps on three different blood DNA samples in accordance with an embodiment of the present technology.
Figures 22A, 22B:
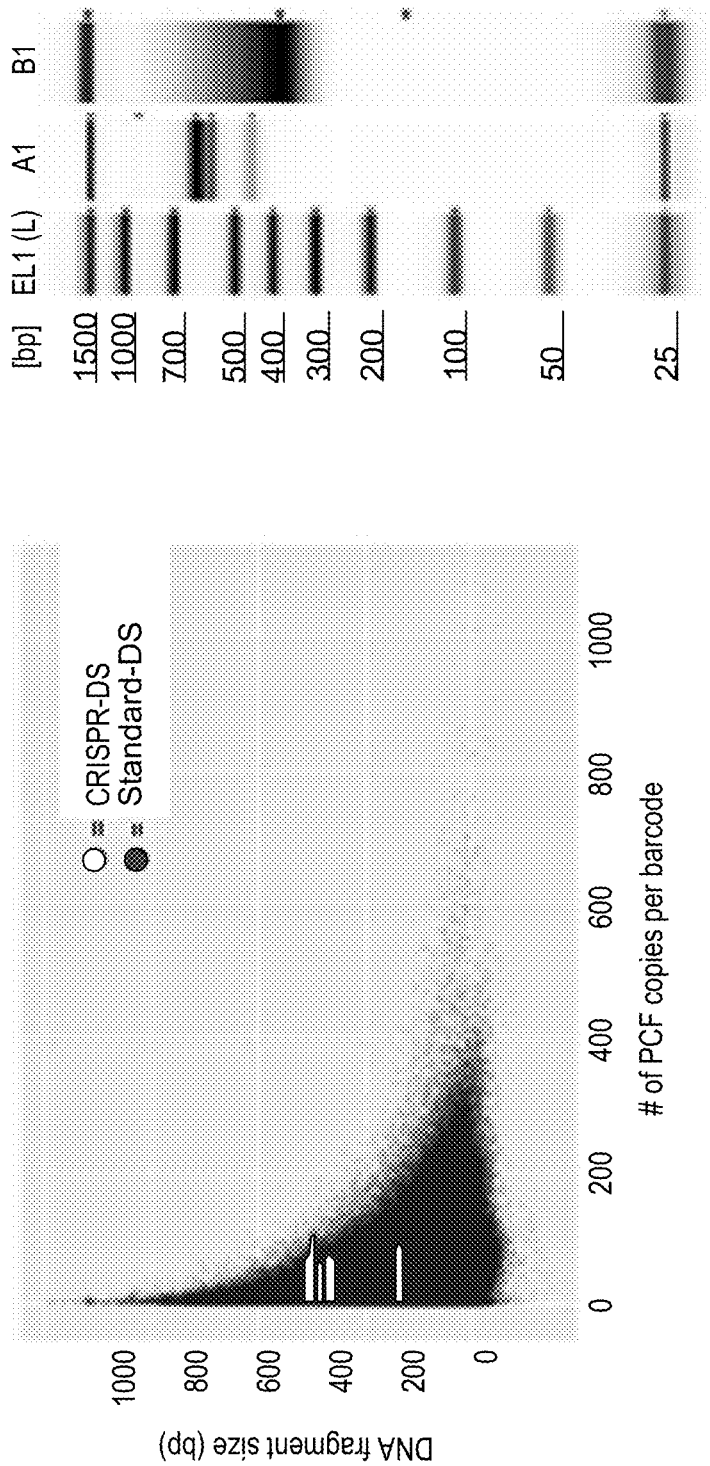
FIG. 22A is a graph plotting a relationship between nucleic acid insert size and resulting family size following amplification of TP53 using CRISPR-DS and standard DS protocols in accordance with an embodiment of the present technology. Dots represent original barcoded DNA molecules, and in CRISPR-DS, all DNA molecules (lighter dots) have preset sizes and generate similar number of PCR copies (as seen by several "band-like" clusters of lighter dots). In standard-DS (dark dots), sonication shears DNA into variable fragment lengths (dark dots, distributed more widely over plot than lighter dots). The plot shows a larger number of shorter fragments than longer fragments.
FIGS. 22B-22E show data on TP53 resulting from CRISPR-DS and standard DS method steps in accordance with an embodiment of the present technology.
Figure 22C:
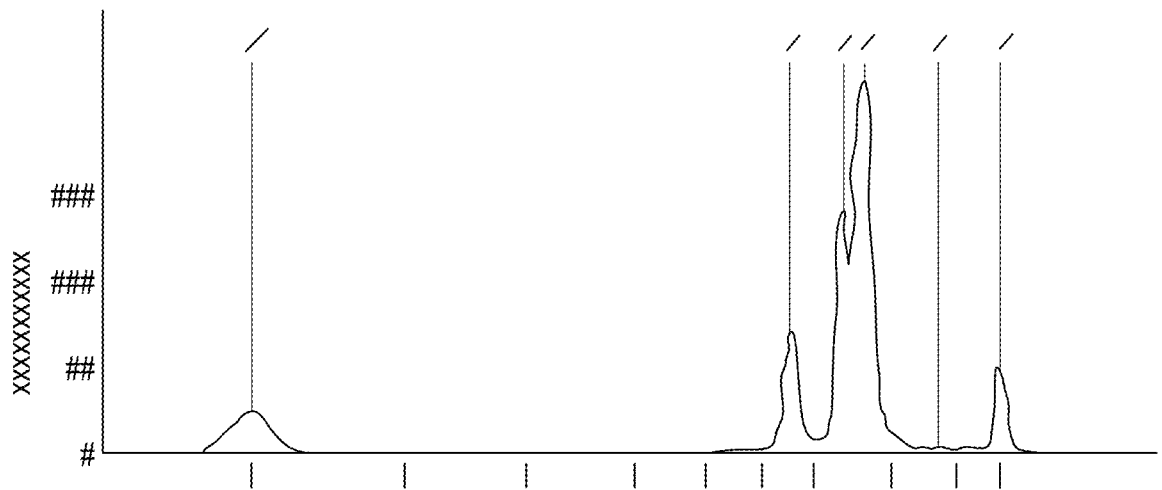
Figure 22D:
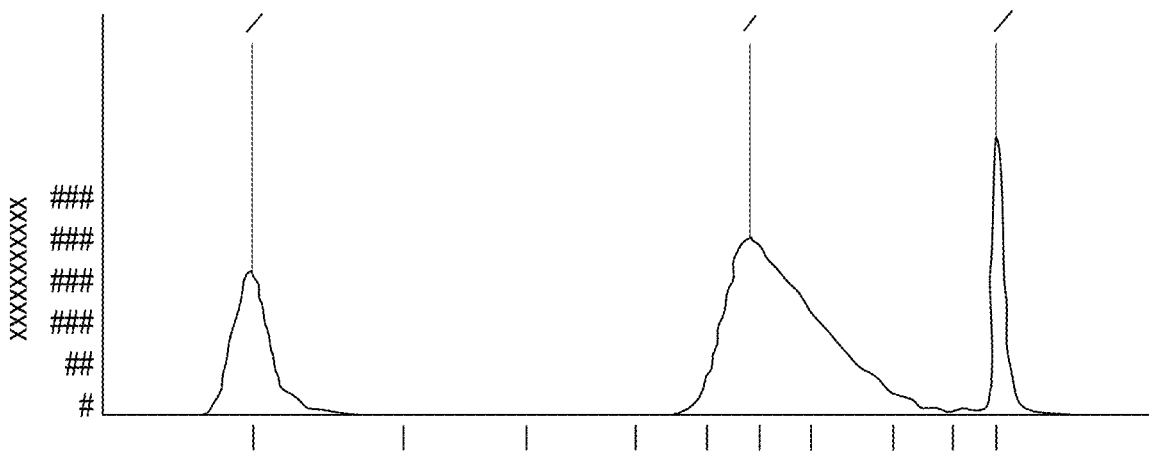
Figure 22E:
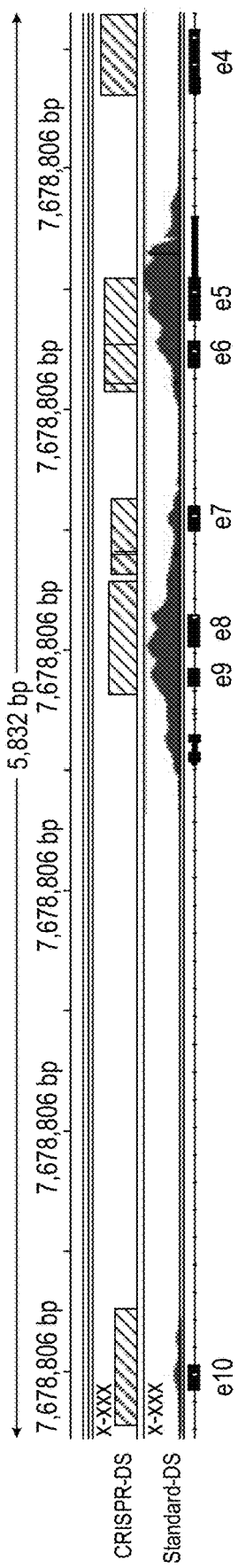

A side by side comparison of standard DS with one or two rounds of hybridization capture vs. CRISPR-DS with one round of hybridization capture is shown in FIGS. 18A-18C. FIGS. 18A-18C are bar graphs showing percent of raw sequencing reads on-target (covering TP53) (FIG. 18A), showing percentage recovery as calculated by percentage of genomes in input DNA that produced duplex consensus sequence reads (FIG. 18B), and showing median duplex consensus sequence depth (FIG. 18C) across all targeted regions for various input amounts of DNA processed using standard DS and CRISPR-DS. FIG. 18A shows percentage of raw sequencing reads on-target (covering TP53) between Standard-DS with two rounds of capture and CRISPR-DS with one round of capture. FIG. 18B shows percentage recovery as calculated by percentage of genomes in input DNA that produced DCS reads. FIG. 18C shows median DCS depth across all targeted regions was calculated for each input amount. Three input amounts (250 ng, 100 ng and 25 ng) of the same DNA extracted from normal human bladder tissue were sequenced with a standard protocol (i.e., standard-DS) as well as with CRISPR-DS. With one round of capture, CRISPR-DS achieved >90% raw reads on-target (e.g. covering TP53) (Table 8, shown below), which represents significant improvement over standard-DS (which achieved ~5% raw reads on-target with one round of capture (Table 8, shown below). A second round of capture minimally increased raw reads in CRISPR-DS (FIG. 19). Standard-DS produced a recovery rate (e.g., percentage of input genomes recovered as sequenced genomes; also known as fractional genome-equivalent recovery) of ~1% across different inputs while CRISPR-DS produced a recovery rate ranging from 6 to 12%. The recovery rate of CRISPR-DS translates to 25 ng of DNA producing a DCS depth (depth generated by DCS reads) comparable to what 250 ng of DNA produces with standard-DS. Side-by-side comparison of the two methods also demonstrated that CRISPR-DS can provide an improvement in that overrepresentation of short fragments due to PCR amplification bias does not occur/impact results (i.e., coverage of region(s) of interest is even) distinct bands/peaks provided confirmation of correct library preparation prior to sequencing, and well-defined fragments created by targeted fragmentation fully spanned desired target regions with homogeneous coverage (FIG. 22E).

Materials and Methods

Samples

Samples analyzed in the present Example included de-identified human genomic DNA from peripheral blood, bladder with and without cancer, and peritoneal fluid DNA. Patient information was available for peritoneal fluid samples and used to confirm presence of a tumor mutation. Fluid samples were obtained from the University of Washington Gynecologic Oncology Tissue Bank, which collected specimens and clinical information after informed consent under protocol number 27077 approved by the University of Washington Human Subjects Division institutional review board. De-identified frozen bladder samples were obtained from the University of Washington Genitourinary Cancer Specimen Biorepository and from not previously fixed or frozen autopsy tissue. DNA had been previously extracted with a QIAamp DNA Mini kit (Qiagen, Inc., Valencia, Calif., USA) and it had never been denatured. DNA was quantified with a Qubit HS dsDNA kit (ThermoFisher Scientific). DNA quality was assessed with Genomic TapeStation (Agilent, Santa Clara, Calif.) and DNA integrity numbers (DIN) were determined. DIN is a measure of genomic DNA quality ranging from 1 (very degraded) to 10 (not degraded). Peripheral blood DNA and peritoneal fluid DNA had DINs>7 (reflecting good quality DNA with no degradation). FIG. 19 is a bar graph showing target enrichment provided by CRISPR-DS with one capture step as compared to two capture steps on three different blood DNA samples.

Figure 20A:
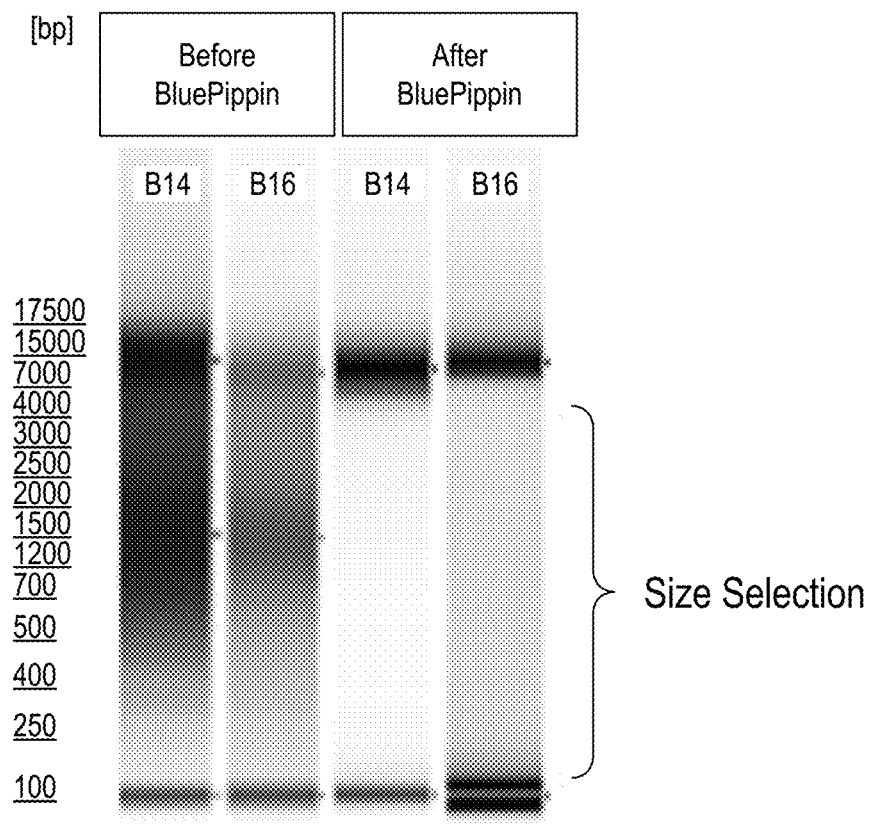
FIGS. 20A and 20B show results from pre-enrichment for high MW DNA with BluePippin on a pulse-field gel (FIG. 20A) and a bar graph (FIG. 20B) showing a comparison of percentage of on-target raw reads and duplex consensus sequence depth for the same DNA sequenced before and after BluePippin pre-enrichment in accordance with an embodiment of the present technology.
Figure 20B:
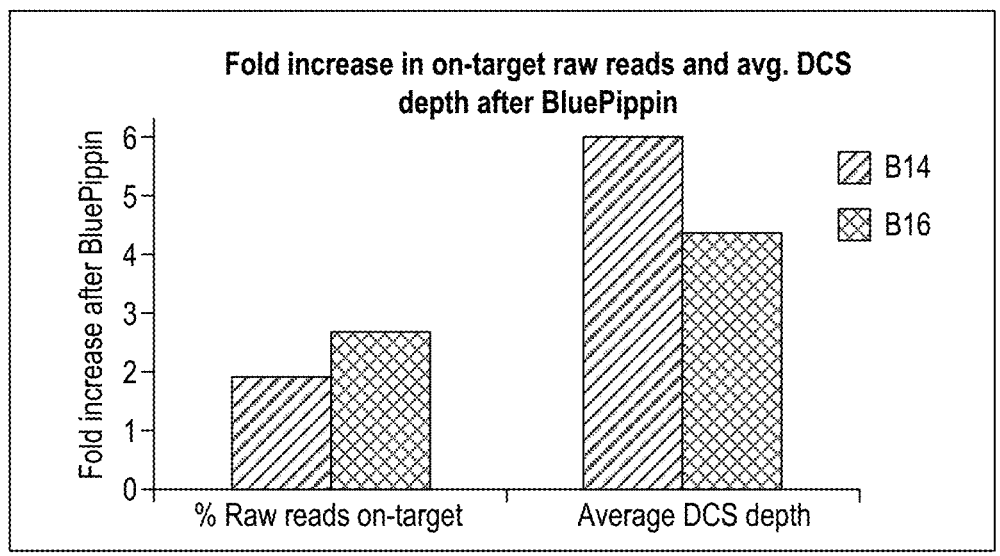

Bladder samples were purposely selected to include different levels of DNA degradation. Bladder DNA samples B1 to B13 had DINs between 6.8 and 8.9 and were successfully analyzed by CRISPR-DS (Table 10, shown below). Samples B14 and B16 had DINs of 6 and 4, respectively, and were used to demonstrate improvements made by pre-enrichment of high molecular weight DNA with the Bluepippin system (FIGS. 20A and 20B).

CRISPR Guide Design.

gRNAs to excise TP53 exons were designed to have characteristics including: ability to produce fragments of ~500 bp covering the TP53 coding region and (2) highest MIT website score ("MIT score"; CRISPR.mit.edu:8079/; Table 1 and FIGS. 17A-17C). For exon 7, guides were designed to produce a smaller size fragment in order to avoid a proximal poly-A tract within the area of interest. A total of 12 gRNAs were designed, which excised TP53 into 7 different fragments (FIG. 12A). All gRNAs had "MIT" scores >60. Quality of cuts was assessed by reviewing alignment of the final DCS reads with the Integrative Genomics Viewer. Successful guides produced a typical coverage pattern with sharp edges in region boundaries and proper DCS depth (FIG. 22E). If a guide was "unsuccessful" a drop in DCS depth was observed and as well as presence of long reads that spanned beyond the expected cutting point; such guides were redesigned as needed. A synthetic GeneBlock DNA fragment (IDT, Coralville, Iowa) that included all gRNA sequences interspaced with random DNA sequences (Table 7) was used to assess guides (FIG. 21A-21B). 3 ng of GeneBlock DNA were digested with each of the gRNAs using the CRISPR/Cas9 in vitro digestion protocol described herein. After digestion, reactions were analyzed by TapeStation 4200 (Agilent Technologies, Santa Clara, Calif., USA) (FIG. 21C). Predefined fragment lengths were present and confirmed proper gRNA assembly and ability of gRNA to cleave its target site.

TABLE 7

GeneBlock DNA Fragment (SEQ ID NOS: 37-50)

Geneblock fragment-500 bp with all of the gRNA
target sequences.
GCTGAGTGTGGGCCCCTACCTAGAATGTGGGACGGAGTCTCACTCTAATT
CCCGTTGTCCCAGCCTTAGGCCCAGGCTGGAGTGCAGTGGTTATAGGATT
CAACCGGAGGCGCCATCTTGGCTCCCTCTGATTGCAATCTCCGCCTCTGG
ACCTCCGCCTCCTGGTTCGGCATTTTGAGTGTTAGACTGGGATTCTCCTG
CCTCAGCCTTTGGGACCTCTTAACCTGTGGCCAAGTAGCTGGGATTACAG
GTCTCCCCAAGGCGCACTGGGCACCTGCCATCACGCCGCACATCTCATGG
GGTTATAGGGGTAGAGACGGGGTTTCACAGGGGAGTACTGTAGGAAGAGG
TGTTGGCTAGGCTGGTCTGCACGGTCAGTTGCCCTGAGGGAACTCCTGAC
CTCAGGTATGGAATTTTCGCTTCCCACAGGTCAGCCTCCCGAAATGCTGG
GAATAGGGTGCACATTTAGGGTGGTAGCTCATGCCTGTAACCCCAATGTC Spacer Sequences 17 bp (from intronic area DS of
TP53 exon 10)
GACGGAGTCTCACTCTA
CCCAGGCTGGAGTGCAG
CGCCATCTTGGCTCCCT
ACCTCCGCCTCCTGGTT
GATTCTCCTGCCTCAGC
CCAAGTAGCTGGGATTA
GCACCTGCCATCACGCC
GTAGAGACGGGGTTTCA
TGTTGGCTAGGCTGGTC
AACTCCTGACCTCAGGT
TCAGCCTCCCGAAATGC Beginning spacer sequence (7 bp):
GCTGAGT Ending spacer sequencer (30 bp):
GTGGTAGCTCATGCCTGTAACCCCAATGTC CRISPR/Cas9 In Vitro Digestion of Genomic DNA.

crRNAs and tracrRNAs (IDT, Coralville, Iowa) were complexed into gRNAs and then 30 nM of gRNAs were incubated with Cas9 nuclease (NEB, Ipswich, Mass.) at ~30 nM, lx NEB Cas9 reaction buffer, and water in a volume of 23-27 µL at 25° C. for 10 min. Then, 10-250 ng of DNA was added, for a final volume of 30 µL. The reaction was incubated overnight at 37° C., then heat shocked at 70° C. for 10 min for enzymatic inactivation.

Size Selection.

Size selection was used to select predetermined fragment length for target enrichment prior to library preparation. AMPure XP Beads (Beckman Coulter, Brea, Calif., USA) were used to remove off-target, un-digested high molecular weight DNA. After heat inactivation, a reaction was combined with a 0.5× ratio of beads, briefly mixed and then incubated for 3 min to allow high MW DNA to bind. Beads were then separated from the solution with a magnet and the solution (containing the targeted DNA fragment length) was transferred into a new tube Standard AMPure 1.8× ratio bead purification was performed, and eluted into 50 µL of TE Low.

Library Preparation

A-Tailing, and Ligation

Fragmented DNA was A-tailed and ligated using the NEBNext Ultra II DNA Library Prep Kit (NEB, Ipswich, Mass.) according to the manufacturer's protocol. The NEB end-repair and A-tailing (ERAT) reaction was incubated at 20° C. for 30 min and 65° C. for 30 min. End-repair is not needed for CRISPR-DS (Cas9 produces blunt ends), but the ERAT reaction was used for convenient A-tailing. The NEB ligation mastermix and 2.5 µl of DS adapters at 15 µM were then added and incubated at 20° C. for 15 min. Commercial adapter prototypes (FIG. 12C) were synthesized with the following differences from adapters used in previous studies: (1) 10 bp random, double-stranded molecular tags were used, instead of 12 bp; and (2) substitution of the previous 3' 5 bp conserved sequence by a simple 3'-dT overhang was used to ligate onto the 5'-dA-tailed DNA molecules. Upon ligation, DNA was cleaned by a 0.8× ratio AMPure Bead purification and eluted into 23 µL of nuclease free water.

PCR

Ligated DNA was amplified using KAPA Real-Time Amplification kit with fluorescent standards (KAPA Biosystems, Woburn, Mass., USA). 50 al reactions were prepared including KAPA HiFi HotStart Real-time PCR Master Mix, 23 µl of previously ligated and purified DNA and DS primers MWS13 and MWS20 at a final concentration of 2 µM. The reactions were denatured at 98° C. for 45 sec and amplified with 6-8 cycles of 98° C. for 15 sec, 65° C. for 30 sec, and 72° C. for 30 sec, followed by final extension at 72° C. for 1 min. Samples were amplified until they reached Fluorescent Standard 3 (which produces a sufficient and standardized number of DNA copies into capture across samples, prevents over-amplification, and indicates successful Cas9 cutting and ligation), which typically takes 6-8 cycles depending on the amount of DNA input. A 0.8× ratio AMPure Bead wash was performed to purify amplified fragments, which were eluted into 40 µL of nuclease free water. Compared to standard-DS at the PCR step, CRISPR-DS provides improvements including: (i) providing fragments of similar sizes (reduces amplification bias towards small fragments (FIG. 22A) (ii) production of more homogeneous coverage of regions of interest (FIG. 22E); and (iii) accurate assessment by TapeStation 4200 (Agilent Technologies, Santa Clara, Calif., USA) of successful library preparation (using predetermined fragment size characteristics). In standard-DS, PCR products are a wide range of sizes due to sonication and present as a wide smear which is difficult to compare between samples (FIG. 22A). In contrast to other approaches such as, e g standard-DS (which can produce results that are hard to compare between samples), CRISPR-DS, produces discrete peaks that are clearly indicative of successful cutting and ligation and are amenable of comparison for quality control across samples (FIGS. 22B-D).

Capture and Post-Capture PCR

TP53 xGen Lockdown Probes (IDT, Coralville, Iowa) were used to perform hybridization capture for TP53 exons in accordance with previous studies, but modified as follows: probes (from IDT TP53 Lockdown probe set) were selected to cover the entire TP53 coding region (exon 1 and part of exon 11 are not coding regions) (Table 6). Each CRISPR/Cas9 excised fragment was covered by at minimum of 2 probes and a maximum of 5 probes (FIGS. 17A-17C). To produce the capture probe pool, each of the probes for a given fragment was pooled in equimolar amounts, producing 7 different pools (one for each fragment). The 7 fragment pools were then mixed, again, in equimolar amounts (with the exception of pools for exon 7 and exons 8-9, which were represented at 40% and 90% respectively). Decrease of capture probes for those exons was implemented in cases where overrepresentation of exons was observed at sequencing. The final capture pool was diluted to 0.75 pmol/µl. Hybridization capture was performed according to a standard IDT protocol, with the following modifications: blockers MWS60 and MSW61, which are specific to DS adapters, were used; 75 µl (instead of 100 µl) of Dynabeads M-270 Streptavidin beads were used; and post-capture PCR was performed with the KAPA Hi-Fi HotStart PCR kit (KAPA Biosystems, Woburn, Mass., USA) using MWS13 and indexed primer MWS21 at a final concentration of 0.8 µM. The reaction was denatured at 98° C. for 45 sec and then amplified for 20 cycles at 98° C. for 30 sec, 60° C. for 45 sec, and 72° C. for 45 sec, followed by extension at 72° C. for 60 sec. PCR products were purified with a 0.8× AMPure Bead wash.

Sequencing

Samples were quantified using the Qubit dsDNA HS Assay Kit, diluted, and pooled for sequencing. The sample pool was then visualized on the Agilent 4200 TapeStation to confirm library quality. The TapeStation electropherogram showed sharp, distinct peaks corresponding to the fragment length of the designed CRISPR/Cas9 cut fragments (FIGS. 22B-22D). (This step can also be performed for each sample individually, prior to pooling, to verify performance of each individual sample as needed/desired). The final pool was quantified using the KAPA Library Quantification kit (KAPA Biosystems, Woburn, Mass., USA). The library was sequenced on the MiSeq Illumina platform using a v3 600 cycle kit (Illumina, San Diego, Calif., USA) in accordance with manufacturer's instructions. Each sample had ~7-10% of a lane allocated (corresponding to –2 million reads); each sequencing run was spiked with approximately 1% PhiX control DNA.

Data Processing

A custom bioinformatics pipeline was created to automate analysis from raw FASTQ files to text files (FIG. 23). This pipeline is similar to methods used for standard DS analysis, but with the following modifications: (i) retention of paired read information is achieved and (ii) consensus-making is performed prior to alignment. Paired-end reads are used in analysis of CRISPR-DS data, but also represent an improvement over standard DS analysis as they provide quality control of fragment size and removal of potential technical artifacts due to presence of short fragments. In addition, standard DS analysis performs consensus making after all reads are mapped to a reference genome, whereas CRISPR- DS analysis performs consensus as the initial step, solely reliant on the bases read by the sequencer. It is considered more likely than not that this change will improve consensus making and reduce time required for data processing. In CRISPR-DS, consensus making was executed by a custom python script called UnifiedConsensusMaker.py, which took all reads that are derived from the same tag, compared the base called at each position, and produced a single-stranded consensus (SSCS) read. The SSCS reads for each complementary pair of tags were then compared position by position to create a double-stranded consensus (DCS) read (FIG. 12D). Two FASTQ files were made containing the resulting SSCS reads and DCS reads (DCS reads correspond to original DNA molecules so the average DCS depth is an estimation of the number of genomes sequenced). Recovery rate (also called fractional genome-equivalent recovery) was calculated as average DCS depth (sequenced genomes) divided by number of input genomes (1 ng of DNA corresponds to ~330 haploid genomes). Raw reads on-target were calculated by counting number of reads whose genomic coordinates fell within upstream and downstream CRISPR/Cas9 cut sites with a 100 bp window added to either side. Paired-end, DCS FASTQ files were then aligned to the human reference genome v38, using bwa-mem v.0.7.419 with default parameters. Mapped reads were re-aligned with GATK Indel-Realigner, and low quality bases were clipped from the ends with GATK Clip-Reads. Conservative clipping of 30 bases from the 3' end and another 7 bases from 5' end was performed. In addition, overlapping areas of read-pairs, which in the TP53 design spanned ~80 bp, were trimmed back using fgbio ClipOverlappingReads. This algorithm performs even clipping from the two ends of the paired reads until they meet, which maximizes the use of sequencing bases with high PHRED quality scores. A pileup file was created from the resulting file using SAMtools mpileup. The pileup file was then filtered using a custom python script with a BED file for targeted genomic positions. The BED file can be easily created using the coordinates of the CRISPR/Cas9 gRNAs. Then the filtered pileup file is processed by a custom-made script, mut-position.1.33.py, which creates a tab delimited text file with mutation information called 'mutpos'. The mutpos includes a summary of the DCS depth and the mutations at each position sequenced (software used in CRISPR-DS analysis may be accessed at hypertext transfer protocol secure://github.com/risqueslab/CRISPR-DS).

Standard-DS

Three amounts of DNA (25 ng, 100 ng, and 250 ng) from normal human bladder sample B9 were sequenced with standard-DS with one round and two rounds of capture, and compared to results from CRISPR-DS. Standard-DS analysis was performed, but using the KAPA Hyperprep kit (KAPA Biosystems, Woburn, Mass., USA) was used for end-repair and ligation and the KAPA Hi-Fi HotStart PCR kit (KAPA Biosystems, Woburn, Mass., USA) was for PCR amplification. Hybridization capture was performed with xGen Lockdown probes that covered TP53 exons 2-11 (the same probes were used in both standard DS and CRISPR-DS). Samples were sequenced on ~10% of a HiSeq 2500 Illumina platform to accommodate shorter fragment lengths.

CRISPR-DS Target Enrichment

To characterize CRISPR-DS target enrichment, two separate analyses were performed:

The first analysis included comparison of one vs. two rounds of capture (and comparison to results of standard DS). Three DNA samples were processed for CRISPR-DS and split in half after one hybridization capture. The first half was indexed and sequenced and the second half was subject to an additional round of capture, as required in the original DS protocol. Percentage of raw reads "on-target" (i.e. covering TP53 exons) was compared for one vs. two captures. Details of comparisons between standard DS and CRISPR-DS can be seen in Table 8.

TABLE 8

Comparison of Standard-DS vs. CRISPR-DS

| Method | Sample | Input DNA (ng) | Rounds of Hybridization Capture | Raw Reads On Target (%) | Median DCS depth (TP53 exons 2-11) | Recovery Rate |
|---|---|---|---|---|---|---|
| STANDARD-DS | B9 | 250 | 2 | 99.1% | 946 | 1.1% |
| | | 100 | 2 | 99.3% | 306 | 0.9% |
| | | 2 | 2 | 99.4% | 100 | 1.2% |
| | | 250 | 1 | 1.3% | 215 | 0.3% |
| | | 100 | 1 | 5.6% | 296 | 0.9% |
| | | 25 | 1 | 5.1% | 94 | 1.1% |
| CRISPR-DS | B9 | 250 | 1 | 98.7% | 5167 | 6.3% |
| | | 100 | 1 | 98.2% | 3219 | 9.8% |
| | | 25 | 1 | 99.0% | 967 | 11.7% |

Figures 24A, 24B:
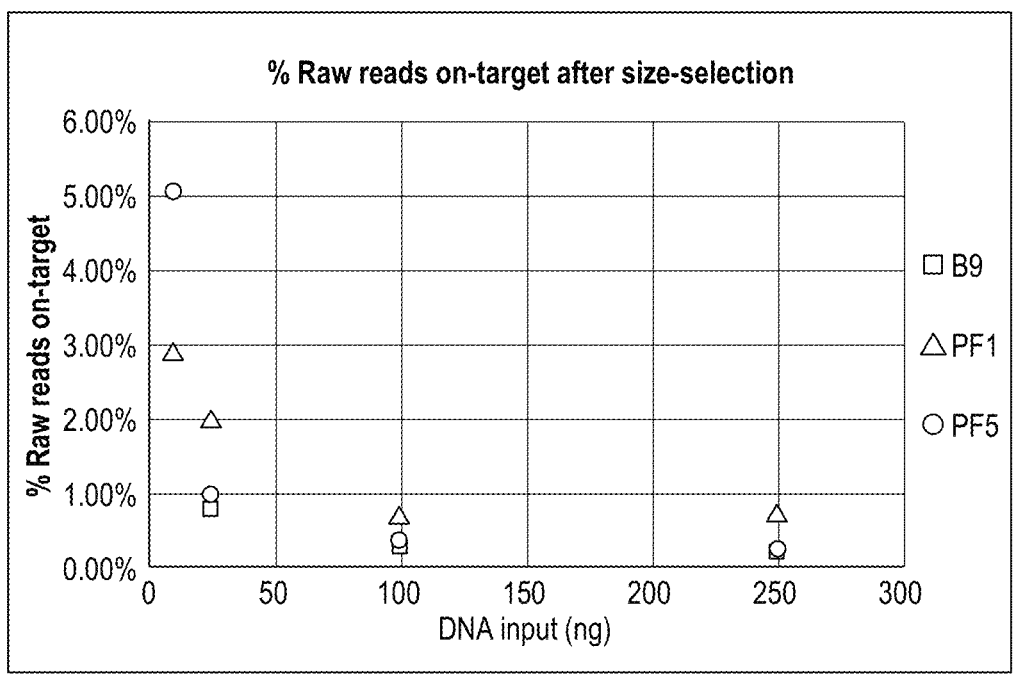
FIGS. 24A and 24B are a chart (FIG. 24A) and graph (FIG. 24B) showing results quantifying a degree of target enrichment following CRISPR/Cas9 digestion followed by size selection in accordance with an embodiment of the present technology.

The second analysis assessed percentage of raw reads on-target without performing hybridization capture and determined enrichment produced exclusively by size selecting CRISPR excised fragments. Different DNA amounts (from 10 ng to 250 ng) of three different samples were processed with the protocol described in the first analysis until the first PCR, (i.e. prior to hybridization capture). FIGS. 24A and 24B are a chart (FIG. 24A) and graph (FIG. 24B) showing results quantifying a degree of target enrichment following CRISPR/Cas9 digestion followed by size selection in accordance with an embodiment of the present technology. FIG. 24A shows DNA samples and the enrichment achieved for each. FIG. 24B shows percent of raw reads that were "on target" as compared to amount of input DNA. Then the PCR product was indexed and sequenced. Percentage of raw reads on-target was calculated and fold enrichment was estimated (taking into consideration targeted region size, in this case, 3280 bp).

Pre-Enrichment for High Molecular Weight DNA

Selection of high molecular weight DNA improves the performance of degraded DNA in CRISPR-DS. This selection was performed using a BluePippin system (Sage Science, Beverly, Mass.). Two bladder DNAs with DINs of 6 and 4 were run using a 0.75% gel cassette and high-pass setting to obtain >8 kb fragments. Size selection was confirmed w TapeStation (FIG. 20A). Then 250 ng of DNA before BluePippin and 250 ng of DNA after BluePippin were processed in parallel with CRISPR-DS. Percentage of raw reads on-target as well as average DCS depth was quantified and compared (FIG. 20B).

Example 13: CRISPR-DS in Ovarian Cancer Samples

To validate ability of CRISPR-DS to detect low-frequency mutations, four peritoneal fluid samples were collected during debulking surgery from women with ovarian cancer and analyzed. Presence of a TP53 tumor mutation in these samples was previously demonstrated by standard-DS. 100 ng of DNA (30-100 fold less than what was used for standard-DS) was used for CRISPR-DS analysis and a DCS depth comparable to standard-DS was obtain and TP53 tumor mutation was successfully identified in all cases (Table 9). Recovery rates ranged between 6 and 12%, representing an increase of 15×-200× as compared to standard-DS with the same DNA.

To test the effect of DIN on assay performance, low molecular weight DNA was removed prior to CRISPR/Cas9 digestion. The pulse-field feature of the BluePippin system was used to select high molecular weight DNA from two samples with "degraded DNA" (DINs 6 and 4). Pre-enrichment increased raw reads on-target by 2-fold and DCS depth by 5-fold (FIG. 20B). To directly quantify the degree of enrichment conferred simply by CRISPR/Cas9 digestion followed by size selection, 3 samples were sequenced without capture. 10-250 ng of DNA were digested, size-selected, ligated, amplified, and sequenced. Percentage of raw reads "on-target" ranged from 0.2% to 5%, corresponding to −2,000× to 50,000× fold enrichment (Table 11). Notably, lower DNA inputs showed highest enrichment, probably reflecting optimal removal of off-target, high molecular weight DNA fragments when they are in lower abundance.

TABLE 9

Comparison of Standard-DS vs. CRISPR-DS for 4 different samples with TP53 mutations.

| Method | Sample | Input DNA (ng) | Raw Reads On Target | Medium Final Depth* | Recovery (%) | Tumor Mutation | Mutant Allele Fraction |
|---|---|---|---|---|---|---|---|
| Standard-DS | PF1 | 9,196 | 92.4% | 2742 | 0.09% | chr17: g.7578275G > A | 68.5% |
| | PF2 | 3,000 | 92.8% | 5381 | 0.54% | chr17: g.7577548C > T | 1.2% |
| | PF3 | 10,186 | 95.9% | 1866 | 0.06% | chr17: g.7578403C > T | 1.6% |
| | PF4 | 7,436 | 95.4% | 2029 | 0.08% | chr17: g.7578526C > T | 0.6% |
| CRISPR-DS | PF1 | 100 | 76.6% | 2039 | 6.18% | chr17: g.7578275G > A | 68.4% |
| | PF2 | 100 | 94.3% | 2831 | 8.58% | chr17: g.7577548C > T | 1.0% |
| | PF3 | 100 | 87.6% | 3801 | 11.52% | chr17: g.7578403C > T | 0.4% |
| | PF4 | 100 | 96.5% | 2194 | 6.65% | chr17: g.7578526C > T | 0.1% |

*After final Duplex Sequencing data processing is performed.

Example 14: CRISPR-DS in Bladder Tissue Samples

The present Example describes use of CRISPR-DS in a set of 13 DNA samples extracted from bladder tissue of different patients (Table 10). 250 ng of DNA from each sample was used for the assay and resulted in a median DCS depth of 6,143×, corresponding to a median recovery rate of 7.4%. Reproducible performance was demonstrated with technical replicates for two samples (B2 and B4). All samples had >98% DCS reads on-target, but percentage of raw reads on-target ranged from 43% to 98%. Low target enrichment corresponded to samples with DNA Integrity Numbers (DIN)<7.

TABLE 11

Target enrichment due to size selection.

| Sample | DNA Input (ng) | Reads On Target (%) | Fold Enrichment |
|---|---|---|---|
| B9 | 25 | 0.76% | 7,527 |
| | 200 | 0.25% | 2,452 |
| | 250 | 0.21% | 2,037 |
| PF1 | 10 | 2.85% | 28,139 |
| | 25 | 1.99% | 19,583 |

TABLE 10

CRISPR-DS sequencing results for 13 samples processed with 250 ng input DNA.

| Sample ID | DIN | DNA Input (ng) | # Raw reads | % of Raw Reads on Target | # DCS reads | % of DCS Reads on target | DCS depth | Recovery rate |
|---|---|---|---|---|---|---|---|---|
| B1 | 6.8 | 250 | 7751046 | 44.0% | 68906 | 100.0% | 6143.2 | 7.4% |
| B2a | 6.9 | 250 | 4575484 | 43.0% | 37984 | 99.1% | 3386.4 | 4.1% |
| B2b | 6.9 | 250 | 4855458 | 47.5% | 42815 | 99.1% | 3817.1 | 4.6% |
| B3 | 8.2 | 250 | 4214290 | 85.8% | 30847 | 98.8% | 2750.1 | 3.3% |
| B4a | 8.8 | 250 | 4200814 | 84.4% | 85822 | 99.0% | 7651.3 | 9.3% |
| B4b | 8.8 | 250 | 4581646 | 86.6% | 84051 | 99.1% | 7493.4 | 9.1% |
| B5 | 8.5 | 250 | 3938328 | 98.4% | 101201 | 98.7% | 9022.4 | 10.9% |
| B6 | 8.7 | 250 | 4640288 | 78.0% | 69002 | 98.8% | 6151.7 | 7.5% |
| B7 | 7.6 | 250 | 4230402 | 91.2% | 60950 | 98.8% | 5433.9 | 6.6% |
| B8 | 7.0 | 250 | 3869654 | 93.6% | 38586 | 98.9% | 3440.1 | 4.2% |
| B9 | 8.9 | 250 | 4594068 | 96.6% | 75089 | 99.2% | 6694.4 | 8.1% |
| B10 | 8.6 | 250 | 5764098 | 79.0% | 61303 | 99.1% | 5465.3 | 6.6% |
| B11 | 8.5 | 250 | 5764650 | 80.9% | 71381 | 99.3% | 6363.8 | 7.7% |
| B12 | 7.9 | 250 | 5234650 | 85.9% | 40092 | 99.4% | 3574.3 | 4.3% |
| B13 | 7.0 | 250 | 3737110 | 74.0% | 71138 | 99.1% | 6284.8 | 7.6% |

TABLE 11-continued

Target enrichment due to size selection.

| Sample | DNA Input (ng) | Reads On Target (%) | Fold Enrichment |
|---|---|---|---|
| | 100 | 0.68% | 6,667 |
| | 250 | 0.70% | 6,878 |
| PF5 | 10 | 5.05% | 49,794 |
| | 25 | 0.96% | 9,456 |
| | 100 | 0.34% | 3,321 |
| | 250 | 0.22% | 2,217 |

CRISPR/Cas9 fragmentation followed by size selection successfully performed efficient target enrichment and eliminated any need for a second round of capture for small target regions. In addition, PCR bias was eliminated and homogenous coverage of areas of interest was achieved, representing a substantial improvement over currently available methods.

EQUIVALENTS AND SCOPE

The above detailed descriptions of embodiments of the technology are not intended to be exhaustive or to limit the technology to the precise form disclosed above. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments. All references cited herein are incorporated by reference as if fully set forth herein.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

Those skilled in the art will recognize, or be able to ascertain using no more than routine experimentation, many equivalents to the specific embodiments of the disclosed technology described herein. The scope of the present technology is not intended to be limited to the above Description, but rather is as set forth in the following claims.

The invention claimed is:

1. A method comprising:
(a) providing nucleic acid constructs each comprising:
a double-stranded nucleic acid fragment comprising a first strand and a second strand;
a first adapter polynucleotide attached to one end of the fragment; and
a second adapter polynucleotide attached to the other end of the fragment,
wherein the first and second adapter polynucleotides each comprise:
an end portion comprising a 5'-associated sequence and a 3'-associated sequence that are at least partially non-complementary, and
a portion between the end portion and the nucleic acid fragment comprising a double-stranded single molecule identifier (SMI), and
wherein the nucleic acid fragment of at least one of the constructs comprises a target of interest;
(b) amplifying at least a portion of the constructs to generate first and second strand amplicons, wherein a portion of the first and the second strand amplicons comprise the target of interest;
(c) separating the amplicons of (b) into a first sample and a second sample each comprising a plurality of the first strand amplicons and a plurality of the second strand amplicons;
(d) performing targeted amplification of the first sample and the second sample, wherein the targeted amplification of the first sample comprises exponentially amplifying only the first strand amplicons to generate a first nucleic acid product using a primer specific to the 5'-associated sequence and a primer specific to the target of interest, such that the SMI of the first adapter polynucleotide or second adapter polynucleotide is maintained in the first nucleic acid product, and wherein the targeted amplification of the second sample comprises exponentially amplifying only the second strand amplicons to generate a second nucleic acid product using a primer specific to the 3'-associated sequence and a primer specific to the target of interest, such that the SMI that is maintained in the first nucleic acid product is also maintained in the second nucleic acid product;

(e) sequencing the first nucleic acid product and the second nucleic acid product to obtain sequence reads each comprising an SMI sequence and a sequence of the target of interest; and (f) identifying a set of the sequence reads as deriving from a same original nucleic acid construct based at least in part on the SMI sequence of the sequence reads in the set, wherein at least one of the reads in the set is obtained from the first nucleic acid product and at least one of the reads in the set is obtained from the second nucleic acid product.

2. The method of claim 1, wherein providing the nucleic acid constructs comprises, for each of the constructs:
  ligating to the double-stranded nucleic acid fragment: a first adaptor precursor molecule and a second adaptor precursor molecule, wherein the first and second adaptor precursor molecules each comprise a single-stranded SMI; and
  generating an opposite strand of the single-stranded SMI using a polymerase, thereby generating a double-stranded SMI.

3. The method of claim 1, wherein the SMI comprises a barcode sequence that uniquely labels the individual nucleic acid fragments such that amplicons generated from a same nucleic acid fragment are distinguishable from amplicons generated from other nucleic acid fragments.

4. The method of claim 1, wherein the fragments comprise randomly or semi-randomly sheared DNA and (f) identifying a set of the sequence reads as deriving from a same original nucleic acid construct is based on the SMI sequence of each of the sequence reads in the set and based on one or more nucleotides endogenous to an end of the fragment.

5. The method of claim 1, wherein, for each of the constructs comprising a target of interest, the nucleic acid fragment originated from a subject.

6. The method of claim 5, wherein, for each of the constructs comprising a target of interest, the nucleic acid fragment originated from a liquid biopsy sample.

7. The method of claim 1, further comprising (g) comparing the set of sequence reads of step (f) and generating an error-corrected sequence from the set of sequence reads.

8. The method of claim 7, further comprising comparing the error-corrected sequence to a reference sequence and assigning a nucleotide basecall of the error-corrected sequence as a true variant if the nucleotide basecall differs from a corresponding nucleotide in the reference sequence.

9. The method of claim 7, wherein identifying the set of sequences of step (f) comprises:
  (i) generating a first strand consensus sequence from a first set of one or more sequence reads from the first nucleic acid product based at least in part on sequence read in the set having an SMI sequence derived from a same original nucleic acid construct;
  (ii) generating a second strand consensus sequence from a second set of sequence reads from the second nucleic acid product based at least in part on sequence read in the set having an SMI sequence derived from the same original nucleic acid construct of (i); and
  wherein the generating of step (g) comprises generating a duplex consensus sequence based on the first strand consensus sequence and the second strand consensus sequence.

10. The method of claim 9, wherein generating the duplex consensus sequence comprises identifying a nucleotide basecall that does not correspond between the first strand consensus sequence and the second strand consensus sequence as a sequencing artifact.

11. The method of claim 1, further comprising (g) comparing the at least one read in the set obtained from the first nucleic acid product to the at least one read in the set obtained from the second nucleic acid product to generate an error-corrected sequence.

12. A method of sequencing a target of interest, the method comprising:
  (a) providing nucleic acid constructs each comprising:
    a double-stranded nucleic acid fragment comprising a first strand and a second strand;
    a first adapter polynucleotide attached to one end of the fragment; and
    a second adapter polynucleotide attached to the other end of the fragment,
    wherein the first and second adapter polynucleotides each comprise:
      an end portion comprising a 5'-associated sequence and a 3'-associated sequence that are at least partially non-complementary, and
      a portion between the end portion and the nucleic acid fragment comprising a double-stranded single molecule identifier (SMI), and
    wherein the nucleic acid fragment of at least one of the constructs comprises a target of interest;
  (b) amplifying the constructs to generate first and second strand amplicons comprising the target of interest;
  (c) separating the amplified constructs into a first sample and a second sample each comprising a plurality of first strand amplicons and a plurality of second strand amplicons;
  (d) performing targeted amplification of the first sample and the second sample,
  wherein the targeted amplification of the first sample comprises generating a first nucleic acid product enriched for first strand amplicons comprising the target of interest using a primer specific to the 5'-associated sequence and a primer specific to the target of interest, such that the SMI of the first adapter polynucleotide or second adapter polynucleotide is maintained in the first nucleic acid product, and
  wherein the targeted amplification of the second sample comprises generating a second nucleic acid product enriched for second strand amplicons comprising the target of interest using a primer specific to the 3'-associated sequence and a primer specific to the target of interest, such that the SMI that is maintained in the first nucleic acid product is also maintained in the second nucleic acid product;
  (e) sequencing each of the first nucleic acid product and second nucleic acid product to obtain sequence reads;

(f) identifying a set of the sequence reads as deriving from a same original nucleic acid construct based at least in part on the SMI sequence of the sequence reads in the set, wherein at least one of the reads in the set is obtained from the first nucleic product and at least one of the reads in the set is obtained from the second nucleic acid product; and (g) comparing the sequence reads identified in step (f) to generate an error-corrected sequence.

13. The method of claim 12, wherein providing the nucleic acid constructs comprises, for each of the constructs:
ligating to a double-stranded nucleic acid fragment a first adaptor precursor molecule and a second adaptor precursor molecule, wherein the first and second adaptor precursor molecules each comprise a single-stranded SMI; and
generating an opposite strand of the single-stranded SMI using a polymerase, thereby generating a double-stranded SMI.

14. The method of claim 12, wherein the SMI comprises a barcode sequence that uniquely labels the individual nucleic acid fragments such that amplicons generated from a same nucleic acid fragment are distinguishable from amplicons generated from other nucleic acid fragments.

15. The method of claim 12, wherein (f) identifying a set of the sequence reads as deriving from a same original nucleic acid construct is based on the SMI sequence of the sequence reads in the set and based on one or more nucleotides endogenous to an end of a portion of the sequence read deriving from the fragment.

16. The method of claim 12, wherein, for one or more of the constructs comprising a target of interest, the nucleic acid fragment originated from a subject.

17. The method of claim 12, wherein, for one or more of the constructs comprising a target of interest, the nucleic acid fragment originated from a liquid biopsy sample.

18. The method of claim 12, wherein the end portion of each of the first and the second adapter polynucleotides are Y-shaped.

19. The method of claim 12, further comprising comparing the error-corrected sequence to a reference sequence and assigning a nucleotide basecall of the error-corrected sequence as a true variant if the nucleotide basecall differs from a corresponding nucleotide in the reference sequence.

20. The method of claim 12, wherein the identifying of step (f) comprises:
(i) generating a first strand consensus sequence from a first set of one or more sequence reads from the first nucleic acid product and each having an SMI sequence derived from a same original nucleic acid construct;
(ii) generating a second strand consensus sequence from a second set of sequence reads from the second nucleic acid product and each having an SMI sequence derived from the same original nucleic acid construct of (i); and
wherein the comparing of step (g) comprises comparing the first strand consensus sequence and the second strand consensus sequence to generate a duplex consensus sequence.

21. The method of claim 20, wherein generating the duplex consensus sequence comprises identifying a nucleotide basecall that does not correspond between the first strand consensus sequence and the second strand consensus sequence as a sequencing artifact.

22. The method of claim 12, wherein the comparing of step (g) comprises comparing the at least one read in the set obtained from the first nucleic acid product to the at least one read in the set obtained from the second nucleic acid product to generate the error-corrected sequence.

\* \* \* \* \*